United States Patent
Spencer et al.

(10) Patent No.: US 10,006,003 B2
(45) Date of Patent: Jun. 26, 2018

(54) COMPOSITIONS AND METHODS FOR FLOWABLE ALLOGRAFT AMNIOTIC TISSUE

(71) Applicant: Surgenex, LLC, Scottsdale, AZ (US)

(72) Inventors: Eliott Spencer, Sandy, UT (US); Doug Schmid, Sandy, UT (US); Abel Bullock, Scottsdale, AZ (US)

(73) Assignee: Surgenex, LLC, Scottsdale, AZ (US)

( * ) Notice: Subject to any disclaimer, the term of this patent is extended or adjusted under 35 U.S.C. 154(b) by 0 days. days.

(21) Appl. No.: 15/199,763

(22) Filed: Jun. 30, 2016

(65) Prior Publication Data

US 2017/0002312 A1    Jan. 5, 2017

Related U.S. Application Data

(60) Provisional application No. 62/187,148, filed on Jun. 30, 2015.

(51) Int. Cl.
| | |
|---|---|
| *C12N 5/00* | (2006.01) |
| *C12N 5/073* | (2010.01) |
| *A61K 35/50* | (2015.01) |
| *A61K 9/08* | (2006.01) |
| *A61K 9/00* | (2006.01) |
| *A01N 1/02* | (2006.01) |

(52) U.S. Cl.
CPC .......... *C12N 5/0605* (2013.01); *A01N 1/0221* (2013.01); *A61K 9/0019* (2013.01); *A61K 9/08* (2013.01); *A61K 35/50* (2013.01); *C12N 2500/62* (2013.01)

(58) Field of Classification Search
None
See application file for complete search history.

(56) References Cited

U.S. PATENT DOCUMENTS

| | | | |
|---|---|---|---|
| 8,834,928 B1 * | 9/2014 | Truncale | C12N 5/0663 424/484 |
| 2008/0181967 A1 * | 7/2008 | Liu | A61K 35/44 424/583 |
| 2010/0216237 A1 * | 8/2010 | Ganchas Soares | C12N 5/0605 435/366 |
| 2011/0008397 A1 | 1/2011 | Cohen | |
| 2014/0342015 A1 * | 11/2014 | Murphy | A61K 35/50 424/582 |
| 2015/0010610 A1 | 1/2015 | Cohen | |
| 2015/0037316 A1 | 2/2015 | Edinger et al. | |
| 2015/0086573 A1 | 3/2015 | Brahm | |

FOREIGN PATENT DOCUMENTS

| | | |
|---|---|---|
| CN | 103361300 B | 4/2015 |
| KR | 20150009656 A | 1/2015 |
| WO | 2009052132 A1 | 4/2009 |

* cited by examiner

*Primary Examiner* — Blaine Lankford
(74) *Attorney, Agent, or Firm* — DLA Piper LLP (US)

(57) ABSTRACT

The present technology provides methods for preparing a flowable amniotic composition derived from amniotic membrane of humans. Various embodiments of the method for preparing the amniotic composition may comprise mincing the amniotic membrane in a cryopreservation solution, cryopreservation, homogenization, filtration, centrifugation, and resuspension of a pellet in a cell solution to produce the flowable amniotic composition. The amniotic composition may comprise approximately 2.7 million viable cells per milliliter. The viability of the cells may be substantially stable for at least six months at −18° C. Some preparations of the amniotic composition may have a flowability that may be at least partially characterized by a viscosity suitable for delivery to the target site through at least a 22 gauge needle.

21 Claims, 4 Drawing Sheets

COMPOSITIONS AND METHODS FOR FLOWABLE ALLOGRAFT AMNIOTIC TISSUE

CROSS-REFERENCES TO RELATED APPLICATIONS

This application claims the benefit of U.S. Provisional Patent Application No. 62/187,148, filed on Jun. 30, 2015 and incorporates the disclosure of that application herein by reference in its entirety. To the extent that the present disclosure conflicts with any referenced application, however, the present disclosure is to be given priority.

BACKGROUND OF THE INVENTION

The placenta is a fetomaternal organ that functions to transport nutrients and gases to the fetus and facilitates waste elimination through the umbilical cord and maternal blood supply. The placenta also has endocrine and metabolic functions needed during pregnancy. The placenta comprises both maternal and embryo-derived tissue including the umbilical cord, the amniotic membrane that surrounds the fetus, and the outer chorionic membrane. The amniotic membrane is avascular and comprises an epithelial layer and an inner stromal layer.

The amniotic membrane is a rich source of stem cells, growth factors, antioxidants, compounds having antimicrobial properties, and various organic compounds that support fetal growth. The amniotic membrane is immune-privileged and does not illicit an immune response by the mother despite its fetal origin. The amniotic membrane's stem cells have the capacity to differentiate into many types of tissue and have been the subject of extensive research for their therapeutic uses.

BRIEF SUMMARY OF THE INVENTION

The present technology provides methods for preparing a flowable amniotic composition derived from amniotic membrane of humans. Various embodiments of the method for preparing the amniotic composition may comprise mincing the amniotic membrane in a cryopreservation solution, cryopreservation, homogenization, filtration, centrifugation, and resuspension of a pellet in a cell solution to produce the flowable amniotic composition. The amniotic composition may comprise approximately 2.7 million viable cells per milliliter. The viability of the cells may be substantially stable for at least six months at −18° C. Some preparations of the amniotic composition may have a flowability that may be at least partially characterized by a viscosity suitable for delivery to the target site through at least a 22 gauge needle.

BRIEF DESCRIPTION OF THE FIGURES

A more complete understanding of the present invention may be derived by referring to the detailed description when considered in connection with the following illustrative figures. In the following figures, corresponding reference numbers will refer to elements and steps throughout the figures.

Figure 1:
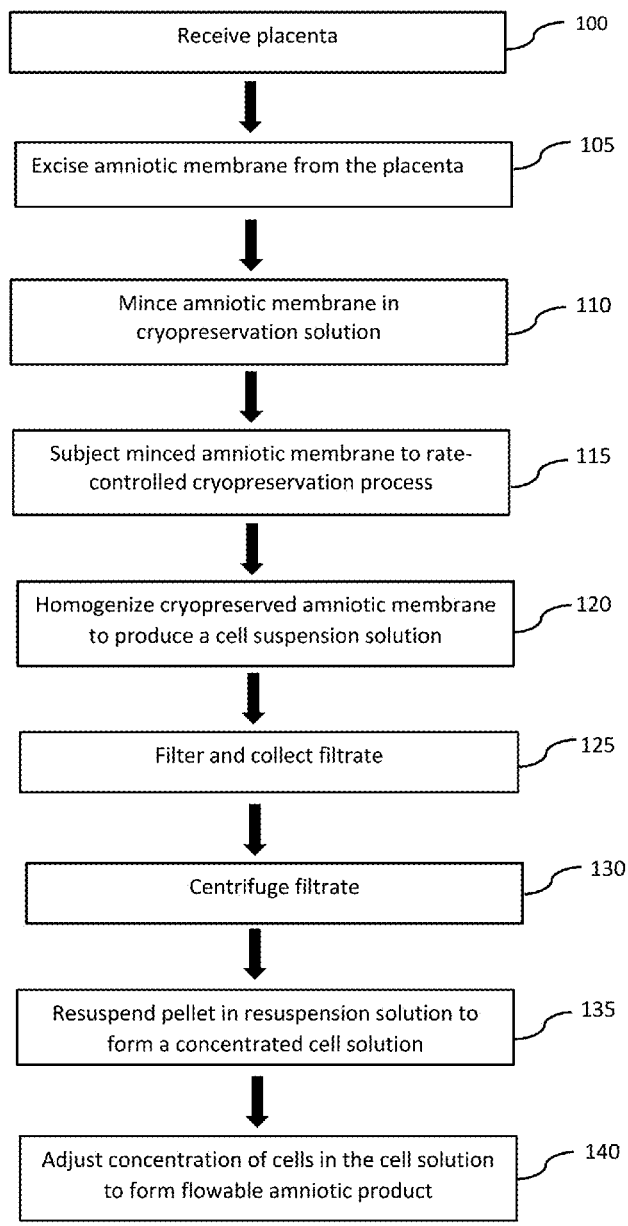
FIG. 1 is a flow chart showing an overview of an exemplary method of preparing an amniotic membrane cell suspension solution.

Elements and steps in the figures are illustrated for simplicity and clarity and have not necessarily been rendered according to any particular sequence or scale. For example, steps that may be performed concurrently or in different order are illustrated in the figures to help to improve understanding of embodiments of the present invention.

DETAILED DESCRIPTION OF THE INVENTION

The present invention may be described in terms of functional block components and various processing steps. Such functional blocks may be realized by any number of components configured to perform the specified functions and achieve the various results. For example, the present invention may employ various process steps, apparatus, systems, methods, etc. In addition, the present invention may be practiced in conjunction with any number of systems and methods for providing compositions comprising live amniotic cells, and the system described is merely one exemplary application for the invention. Further, the present invention may employ any number of conventional techniques for manufacture of biological products under good manufacturing practices (GMP) guidelines, tissue collection, tissue processing, cell culture, homogenization, filtration, and cell counting.

The particular implementations shown and described are illustrative of the invention and its best mode and are not intended to otherwise limit the scope of the present invention in any way. For the sake of brevity, conventional manufacturing, connection, preparation, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

Methods for preparing an amniotic composition comprising amniotic cells produced from a placenta with improved flowability, viable cell yield, and/or stability at −18° C. are provided. The methods include providing cells from processing of any placental components including one or more of the amniotic membrane, villus, cotyledon, basal plate, umbilical cord tissue, chorionic plate, chorionic membrane, Wharton's jelly, placental globe, and/or the blood of the umbilical cord.

Various embodiments of the amniotic composition derived from human or animal placental components may comprise an improved number and/or concentration of healthy, live cells over known methods of placental cell preparations. In various embodiments, the amniotic composition may also comprise at least one of proteins, growth factors, scaffolding, other extracellular matrix, and materials derived from processing the amniotic membrane. Referring to Appendix A, approximately 1450 proteins were identified as being present extracellularly and intracellularly in the amniotic composition. Many of the proteins present in the amniotic composition are known to promote cellular growth (ie., growth factors), structure, and/or maintenance. For example, and without limitation, the amniotic composition was found to comprise keratin (a fibrous structural protein), fibrinogen (an extracellular matrix protein that binds platelets contributing to wound healing), heat shock proteins (which, when located extracellulary, modulate immune function), and fibronectin (a glycoprotein that binds extracellular matrix proteins and promotes cell adhesion, growth, and differentiation).

Exemplary methods may provide a minimally manipulated solution comprising cells under the Food and Drug Administration's (FDA's) criterion of minimal manipulation under 21 CFR 1271.10(a)(1). Briefly, minimal manipulation refers to preparations of human cells, tissues, and cell/tissue based products that are intended for implantation, transplantation, infusion, or transfer to a human recipient. Minimal manipulation of these preparations may prevent the introduction, transmission, and spread of communicable diseases. Minimal manipulation of cells and tissues refers to processing that does not alter the original relevant biological characteristics of those cells and tissues and the tissue's utility for reconstruction, repair, or replacement.

Various embodiments of the present technology may exclude some conventional tissue disruption techniques and/or solutions that may disrupt cell membranes, cause changes in cell morphology, cause cell lysis, remove cellular surface proteins, and/or any other method that may be detrimental to cell viability or may be deemed as "more than minimal manipulation" under the FDA standards described above. For example, in various embodiments, cell treatments such as blending, sonicating, macerating, flash freezing, rinsing of a cell pellet, vortexing, lyophilizing, and the like, may be avoided throughout the exemplary methods described below. In some embodiments, solutions comprising trypsin and/or solutions that are hypertonic or hypotonic to cells may be avoided in one or more steps of the exemplary methods described below.

One embodiment of a method of preparing the cell solution from amniotic membrane is provided in the flow chart shown in FIG. 1. The method of preparing the cell solution from the amniotic membrane comprises receiving a placenta from a human birth (100). In each step of the method, the amniotic membrane and associated placental material may be handled using conventional sterile techniques to produce a sterile cell solution appropriate for later use in medical treatment in humans and animals. In each step of the method, the amniotic membrane may be handled according to prudent practices for handling infectious materials to prevent potential infectious disease transmission. The human placenta may be obtained from a seronegative maternal donor wherein the placenta may be further subjected to serological tests for any undesired infectious agents such as syphilis, retroviruses such as HIV, viral hepatitis and the like.

In some embodiments, the method of preparing the cell solution from the amniotic membrane may comprise excising the amniotic membrane from the placenta (105). The excision may be performed in a class 2 biosafety cabinet such as a laminar flow hood that has been sterilized with ultraviolet light and/or 70% isopropanol. The placenta may initially be washed in DMSO and PBS or sterile saline solution, to remove blood clots and/or coagulated blood. The placenta comprises two principal layers of fetal membranes, the outer chorionic membrane and the inner amniotic membrane. The amniotic membrane may be separated from the chorionic membrane by blunt dissection with a sterile scalpel through the boundary between these two membranes.

Once the amniotic membrane has been excised, the amniotic membrane may be minced in a cryopreservation solution (110). Mincing of the amniotic membrane may comprise manual and/or mechanical cutting of the amniotic membrane into small pieces. For example, the amniotic membrane may be minced into a flowable solution that can be injected or transplanted. The cryopreservation solution may comprise any suitable cryoprotectant in a pH balanced saline solution, cell medium, serum and/or any other liquid appropriate for sustaining the viability of live cells. For example, the cryoprotectant may comprise dimethyl sulfoxide (DMSO), polyvinylpyrrolidone (PVP), glycerol, and/or methylcellulose. In some embodiments, the cryopreservation solution may comprise a solution of 0.9% sodium chloride (NaCl) with 8% DMSO as the cryoprotectant. In another embodiment, the cryopreservation solution may comprise a solution of phosphate buffered saline (PBS) with 8% DMSO wherein the brand of DMSO is Rimso-50®. In some embodiments, the cryoprotectant may further comprise any appropriate buffer, antibacterial composition, preservative.

In various embodiments of the present technology, the minced amniotic membrane in the cryopreservation solution may be subjected to a cryopreservation process (115). The cryopreservation process may comprise placing the minced amniotic membrane in a rate-controlled freezing apparatus that gradually reduces temperature until −80° C. is reached. In various embodiments, the cryopreservation process may occur over an approximately 8-48 hour period. For example, in one embodiment, the amniotic membrane may be minced in a cold cryopreservation solution at 4° C. and then placed in the rate-controlled freezer. The freezer may be set at an initial temperature of 4° C. and gradually reduce its temperature to −80° C. over 10 hours time. Once the amniotic membrane is cryopreserved at −80° C., this tissue may then be transferred and stored indefinitely in liquid nitrogen pending further processing in the exemplary methods below or the tissue may be processed directly without liquid nitrogen storage.

In various embodiments of the present technology, the cryopreserved minced amniotic membrane may be further homogenized to form a substantially homogenized cell suspension solution (120). In some embodiments, the minced cryopreserved amniotic membrane may be sheered and/or minced prior to homogenization. Further sheering and/or mincing of the cryopreserved amniotic membrane may make the processes of homogenization more efficient, quicker, and/or less damaging to the cells in the amniotic membrane tissue. For example, in one embodiment, the minced cryopreserved amniotic membrane may be further minced and/or sheered until the resulting pieces are small enough to fit into a Dounce tissue grinder, such as a 50 mL Dounce. A large clearance pestle may then be used with the Dounce for initial reduction of larger pieces of tissue.

The cell suspension solution may be prepared by homogenization of the cryopreserved minced amniotic membrane according to any suitable method of tissue disruption that yields intact live cells that are at least partially released from extracellular tissue structures. In some embodiments, the cryopreserved minced amniotic membrane may be homogenized until it appears to have a substantially uniform consistency. For example, homogenization may comprise one or more of stirring, mixing, dispersing, grinding, shearing, enzymatic digestion to release cells from extracellular matrix structures, and combinations thereof. Homogenization techniques may comprise mechanical homogenizers such as a Dounce homogenizer, French press, French pressure cell, gentle vortex bead beating, and/or mortar and pestle. In one embodiment, homogenization may be performed by applying a smaller clearance pestle to the Dounce containing the further minced amniotic membrane that has been processed with the larger clearance pestle, as described above. The smaller clearance pestle may further disrupt the resulting smaller pieces of tissue formed by the larger clearance pestle to form the final homogenized cell suspension solution.

The cell suspension solution may be filtered to remove any remaining large particles (125). For example, in some embodiments, the cell suspension solution may be passed through a filter having a pore size of 200 µm. In one embodiment, the filter may have a pore size of approximately 200 µm. The filter may comprise any suitable sterile or sterilizable filter and/or filter system for at least partially removing detritus and particulates. For example, the filter may comprise a stainless steel mesh, nylon mesh, polyester felt, and/or any other suitable material.

In various embodiments of the present invention, the filtered cell suspension solution may be gently centrifuged to concentrate the cells and extracellular material therein (130). Centrifugation may be performed to at least partially separate the cells, including stem cells, with the extracellular material from the cryopreservation solution. The RCF may be chosen to produce a cell pellet without enough force to cause lysis or a change in cellular morphology. For example, in various embodiments, the Relative Centrifugal Force (RCF) may be 200-300×g until a cell pellet forms. In one embodiment, centrifugation may be performed on the filtered cell suspension solution at approximately 235×g for approximately 20 minutes. In some embodiments, the centrifuge tube used in the rotor may be selected for reducing the pressure on the cells in the filtered cell suspension solution. For example, a round bottom or flat bottom centrifuge tube may be used instead of a conical bottom centrifuge tube.

In various embodiments of the present technology, the pellet comprising the cells and extracellular material may be resuspended in a resuspension solution to form a concentrated cell solution (135). The resuspension solution may comprise any pH balanced saline solution, cell medium, and/or any other liquid appropriate for sustaining the viability of live cells. For example, in one embodiment, the resuspension solution may comprise PBS, 0.9% NaCl solution, Plasma Lyte-A, Minimum Essential Medium, Dulbecco's Modified Eagle's Medium (DMEM), and/or human albumin 25% solution. In some embodiments, the resuspension solution may be appropriate for delivery onto the target area.

In some embodiments, the pellet may be resuspended in a minimal volume of the resuspension solution to maximize the concentration of the cells and extracellular material. The concentration of the cells in the concentrated cell solution may be measured using any conventional method of cell counting method such as flow cytometry or visually using a hemocytometer and microscope. The concentration of the cells in the concentrated cell solution may be adjusted to any desired concentration by adding a requisite amount of the resuspension solution, resulting in the amniotic composition suitable for delivery onto the target wound (140).

The amniotic composition produced according to the exemplary methods may have beneficial characteristics to allow particular therapeutic applications and improved efficacy. In some embodiments, the amniotic composition may exhibit marked stability in cell viability when stored at −18° C. In some embodiments, the amniotic composition may have a significantly higher percentage of viable cells, as compared to other amniotic membrane preparations. In some embodiments, the amniotic composition may comprise a viscosity sufficiently low to allow it to move through a small gauge needle, such as a 22-gauge needle.

Figure 2:
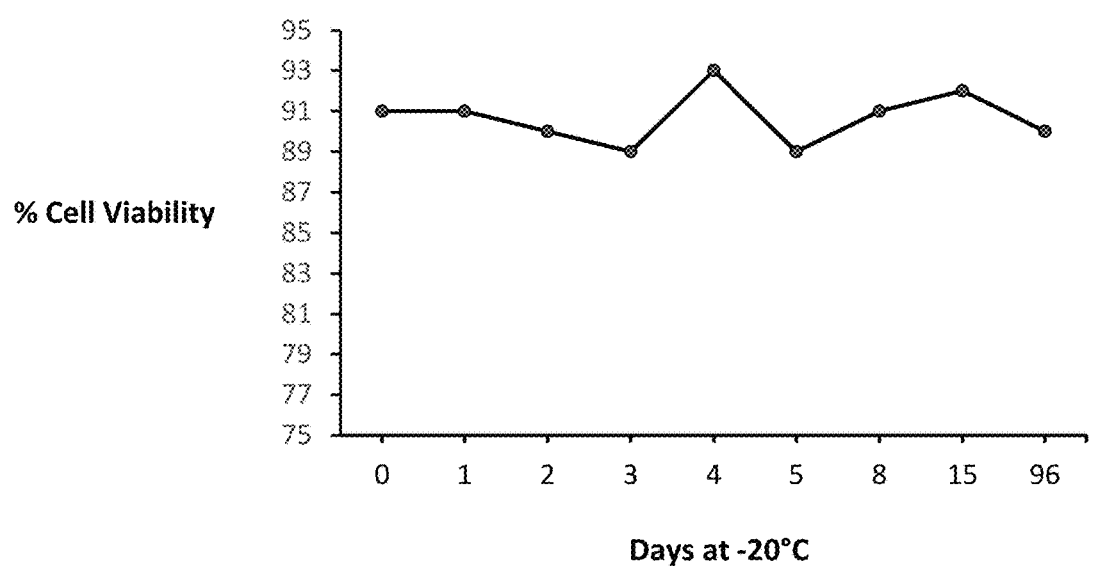
FIG. 2 is a graphical representation of the stability of cell viability in an exemplary embodiment of an amniotic composition stored at −18° C.

Referring to FIG. 2, the amniotic composition was surprisingly found to be stable when stored at −18° C. for at least six months without substantial loss of cell viability. Referring to FIG. 2, a degradation study to determine the viability of the cells in the amniotic composition stored at −18° C. was assessed over a period of 180 days. On each indicated day, a vial of amniotic composition was removed from −18° C. storage, thawed, and the cells therein were counted using a hemocytometer. Over the course of the study, the viability of the cells ranged from 89% to 93% viable cells. The percentage of viable cells remained substantially unchanged relative to their pre-storage viability of 91%. The amniotic composition may therefore be useful for shipping to physician offices, urgent care facilities, emergency rooms and other facilities where −18° C. freezers are common whereas −80° C. freezers are not readily available.

Various embodiments of methods for producing the amniotic composition may provide an improved concentration of live healthy cells that exceeds the concentration found in commercially available amniotic membrane preparations. Referring to Table I below and cell microscopy images shown in FIGS. 3 and 4, preparations of the amniotic composition and a commercially available amniotic membrane preparation were compared for total cell concentration, viable cell concentration, percent cell viability, and cell morphology.

As shown in Table I, the amniotic composition was compared to preparations of BioDRestore™ Elemental Tissue Matrix (referred to as BioDRestore). The BioDRestore product is a morselized, flowable tissue allograft derived from amniotic tissues. (BioDRestore™ Elemental Tissue Matrix is a product of BioD, LLC, Memphis, Tenn.). The amniotic composition contains a similar cell viability and larger cell size (indicator of cell health) as the BioDRestore product. However, the amniotic composition contains a significantly higher concentration of viable cells as compared to the BioDRestore product (2.7 million cells/mL vs. 660,000 cells/mL, respectively). Additionally, the amniotic composition was found to provide a substantially consistent concentration of viable cells that did not significantly vary between placenta preparations (data not shown).

TABLE I

| | BioDRestore | Amniotic Composition |
|---|---|---|
| Total Cell Concentration (cells/mL) | 900,000 | 4,300,000 |
| Viable Cell Concentration (cells/mL) | 660,000 | 2,700,000 |
| Dead Cell Concentration (cells/mL) | 240,000 | 1,600,000 |
| Cell Viability | 73% | 62% |
| Average Viable Cell Size (µm) | 12.7 | 13.3 |

Figure 3:
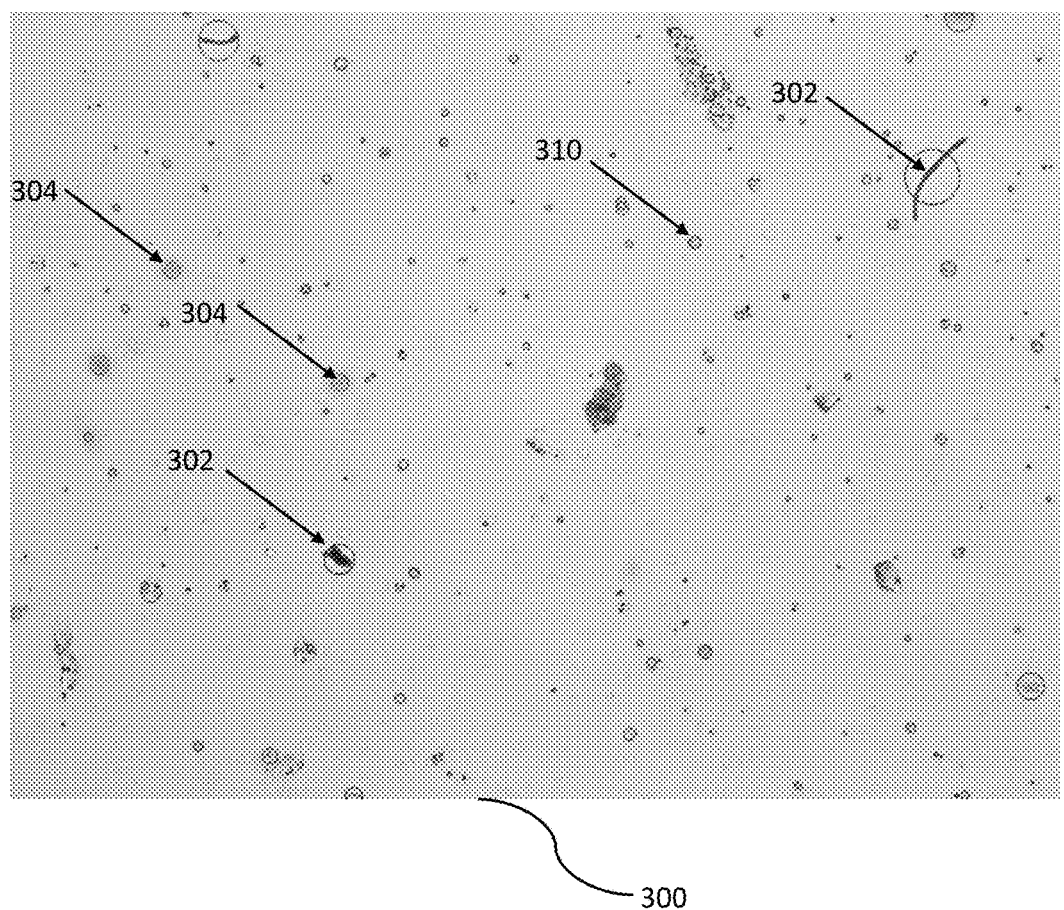
FIG. 3 is a microscopy image of a BioDRestore™ Elemental Tissue Matrix product.
Figure 4:
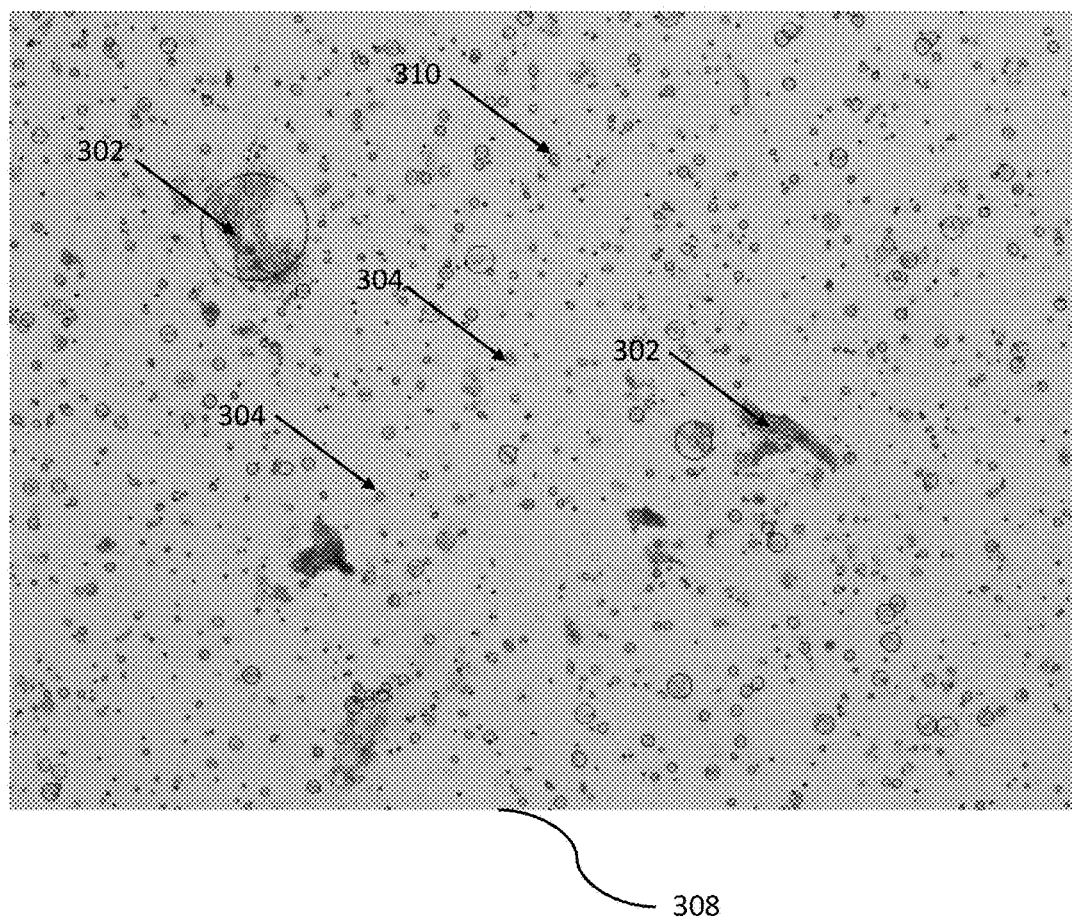
FIG. 4 is a microscopy image of exemplary embodiment of an amniotic composition.

Referring to FIGS. 3 and 4, light microscopy images of the BioDRestore® preparation and the amniotic composition is shown. The microscopy images are shown in 10× magnification. The BioDRestore® product 300 has an overall cell viability of 73% with very few viable cells 304 (circled in red) found in the sample (as reported in Table I). The BioDRestore® product 300 also shows a low amount of extracellular debris 302 and dead cells 310 (circled in blue). In contrast, 62% of the cells 304 of the amniotic composition 308 shown in FIG. 4 are viable, which is more than four times the concentration of viable cells 304 in the Bio-DRestore product 300.

The various embodiments of the amniotic composition may effectively treat some diseases, soft tissue damage, and/or may be used for cosmetic applications. In one embodiment, a therapeutically effective amount of the amniotic composition prepared according to the methods described above may be applied to a variety of tissues. In some embodiments, the tissues may be skin damage such as acne, abrasions, fistulas, excision sites on skin, persistent skin ulcers due to poor wound healing, and/or traumatic wounds. In some embodiments, the amniotic composition may be applied to damaged tissue internal to the body through surgical placement and/or injection. For example, the amniotic composition may be applied internally to damaged tendons and ligaments, bone injuries, damaged tissue after surgical tumor removal, muscle inflammation or tears, and the like.

In various embodiments, the amniotic composition may be administered or delivered to the target tissue using any suitable technique to effect contact between the amniotic composition and the target site including topical, mucosal, subcutaneous, intravenous, surgical placement to the target tissue (such as a body area open during surgery and/or arthroscopic placement), subcutaneous injection, and/or intramuscular. In various embodiments, treatment to the target tissue may be administered as many times and/or for as long as a duration as needed to effect healing, augmentation, and/or soft tissue repair and/or reconstruction.

In one embodiment, the amniotic composition may be applied to the target tissue comprising soft tissue damage to promote healing, repair, and/or reconstruction of the soft tissue. For example, the damaged soft tissue may be the surgical site after removal of a skin cancer, a diabetic ulcer of the foot, dental abscess, bone voids, a fistula, lesion, cyst, surgically created wound, and the like. In some embodiments, the amniotic composition may be directly applied to the damaged soft tissue, such as in a wound irrigation flush or incorporated into a carrier such as a time release capsule or a gel. In some embodiments, the amniotic composition may be absorbed into the surface of a bandage, wound dressing, and/or swab for application onto the target site.

In other embodiments, the amniotic composition may be applied to the skin in cosmetic applications. For example, the amniotic composition may be applied to the face as part of a facial for treatment of skin damage such as acne and/or sunburn. In some embodiments, a cosmetic injectable may comprise the amniotic composition for injection reduce or eliminate creases and wrinkles by facilitating tissue building in these areas.

In some embodiments, a kit comprising the amniotic composition may be provided to a medical professional or patient for an at least partially complete set of supplies for treatment of the target site. For example, the kit configured for treatment of a skin surface wound may comprise the amniotic composition, a bandage for receiving the amniotic composition and application onto the wound, wound surface cleaning agents, a carrier for the amniotic composition such as a gel, an outer bandage for wound protection for the duration of the treatment, and/or instructions for the user. In some embodiments, the kit may comprise a container configured to hold and store its contents and may be suitable for storage at −18° C. without cracking.

In the foregoing description, the invention has been described with reference to specific exemplary embodiments. Various modifications and changes may be made, however, without departing from the scope of the present invention as set forth. The description and figures are to be regarded in an illustrative manner, rather than a restrictive one and all such modifications are intended to be included within the scope of the present invention. Accordingly, the scope of the invention should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present invention and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises", "comprising", or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

The present invention has been described above with reference to an exemplary embodiment. However, changes and modifications may be made to the exemplary embodiment without departing from the scope of the present invention. These and other changes or modifications are intended to be included within the scope of the present invention.

APPENDIX A

| Accession | Description | 15232f-FTK | 15261c-FT | 15312c-FT | 15232f-FTK | 15261c-FTK |
|---|---|---|---|---|---|---|
| | | Unique peptides per protein | | | Protein Ion Area (sum of top 3 peptides) | |
| D1MGQ2 | Alpha-2 globin chain OS = Homo sapiens GN = HBA2 PE = 3 SV = 1 | 2 | 6 | 2 | 1.90E+09 | 1.00E+10 |
| V9H1D9 | Alpha globin OS = Homo sapiens PE = 3 SV = 1 | 1 | | 1 | 4.00E+06 | 1.70E+10 |
| V9HWE1 | Epididymis luminal protein 113 OS = Homo sapiens GN = HEL113 PE = 2 SV = 1 | 39 | 50 | 44 | 2.90E+09 | 4.80E+09 |
| P08727 | Keratin, type I cytoskeletal 19 OS = Homo sapiens GN = KRT19 PE = 1 SV = 4 | 21 | 21 | 23 | 3.40E+09 | 5.50E+09 |
| A0A024R462 | Fibronectin 1, isoform CRA_n OS = Homo sapiens GN = FN1 PE = 4 SV = 1 | 65 | 80 | 93 | 1.90E+09 | 1.30E+09 |
| Q09666 | Neuroblast differentiation associated protein AHNAK OS = Homo sapiens GN = AHNAK PE = 1 SV = 2 | 122 | 121 | 151 | 7.00E+08 | 6.60E+09 |
| P05787 | Keratin, type II cytoskeletal 8 OS = Homo sapiens GN = KRT8 PE = 1 SV = 7 | 23 | 22 | 28 | 6.20E+08 | 8.70E+08 |
| Q15149 | Plectin OS = Homo sapiens GN = PLEC PE = 1 SV = 3 | 138 | 145 | 168 | 3.10E+08 | 3.00E+09 |
| P35555 | Fibrillin-1 OS = Homo sapiens GN = FBN1 PE = 1 SV = 3 | 69 | 95 | 93 | 1.50E+08 | 6.30E+09 |
| A0A024R5Z7 | Annexin OS = Homo sapiens GN = ANXA2 PE = 3 SV = 1 | 26 | 27 | 28 | 5.10E+09 | 3.50E+10 |
| D9YZU5 | Hemoglobin, beta OS = Homo sapiens GN = HBB PE = 3 SV = 1 | 1 | 1 | 2 | 2.00E+10 | 8.80E+09 |
| V9HVY1 | Epididymis secretory sperm binding protein Li 78p OS = Homo sapiens GN = HEL-S-78p PE = 2 SV = 1 | 18 | 21 | 24 | 2.70E+08 | 2.90E+10 |
| B2RBS8 | cDNA, FLJ95666, highly similar to Homo sapiens albumin (ALB), mRNA OS = Homo sapiens PE = 2 SV = 1 | 30 | 36 | | 3.80E+09 | 4.60E+08 |
| A0A024R1N1 | Myosin, heavy polypeptide 9, non-muscle, isoform CRA_a OS = Homo sapiens GN = MYH9 PE = 4 SV = 1 | 59 | 53 | 56 | 2.40E+08 | 3.00E+09 |
| P08729 | Keratin, type II cytoskeletal 7 OS = Homo sapiens GN = KRT7 PE = 1 SV = 5 | 31 | 23 | 7 | 1.90E+08 | 6.20E+09 |
| Q4TZM4 | Hemoglobin beta chain (Fragment) OS = Homo sapiens GN = HBB PE = 3 SV = 1 | 1 | 2 | 2 | 9.90E+08 | |
| P02538 | Keratin, type II cytoskeletal 6A OS = Homo sapiens GN = KRT6A PE = 1 SV = 3 | 8 | | | 1.00E+09 | |
| Q8IUL9 | Hemoglobin beta chain variant Hb.Sinai-Bel Air (Fragment) OS = Homo sapiens GN = HBB PE = 3 SV = 1 | 1 | | | 1.40E+06 | 2.30E+09 |
| B2RA03 | cDNA, FLJ94640, highly similar to Homo sapiens keratin 18 (KRT18), mRNA OS = Homo sapiens PE = 2 SV = 1 | 22 | 23 | 26 | 1.70E+08 | 1.90E+09 |
| P02545 | Prelamin-A/C OS = Homo sapiens GN = LMNA PE = 1 SV = 1 | 37 | 36 | 39 | 5.20E+08 | 5.00E+09 |
| P02671 | Fibrinogen alpha chain OS = Homo sapiens GN = FGA PE = 1 SV = 2 | 26 | 24 | 29 | 1.70E+09 | 3.20E+08 |
| O75369 | Filamin-B OS = Homo sapiens GN = FLNB PE = 1 SV = 2 | 58 | 52 | 70 | 1.90E+08 | 6.10E+08 |
| V9HWB4 | Epididymis secretory sperm binding protein Li 89n OS = Homo sapiens GN = HEL-S-89n PE = 2 SV = 1 | 26 | 21 | 24 | 4.30E+08 | 1.00E+10 |
| P02679 | Fibrinogen gamma chain OS = Homo sapiens GN = FGG PE = 1 SV = 3 | 20 | 25 | 27 | 3.20E+09 | 4.50E+08 |
| P21333 | Filamin-A OS = Homo sapiens GN = FLNA PE = 1 SV = 4 | 50 | 58 | 38 | 2.00E+08 | 6.60E+08 |
| B4DKV4 | cDNA FLJ60647, highly similar to Keratin, type II cytoskeletal 6B OS = Homo sapiens PE = 2 SV = 1 | 1 | 1 | 1 | 2.80E+08 | 6.80E+08 |
| P02533 | Keratin, type I cytoskeletal 14 OS = Homo sapiens GN = KRT14 PE = 1 SV = 4 | 9 | 9 | 10 | 7.10E+08 | 8.30E+08 |
| A0A024R8S5 | Protein disulfide-isomerase OS = Homo sapiens GN = P4HB PE = 3 SV = 1 | 28 | 24 | 24 | 9.00E+08 | |
| Q9P2E9 | Ribosome-binding protein 1 OS = Homo sapiens GN = RRBP1 PE = 1 SV = 4 | 37 | | | 1.60E+08 | 5.10E+08 |
| V9HW88 | Calreticulin, isoform CRA_b OS = Homo sapiens GN = HEL-S-99n PE = 2 SV = 1 | 20 | 15 | 18 | 4.40E+08 | 6.70E+08 |
| B4E1B2 | cDNA FLJ53691, highly similar to Serotransferrin OS = Homo sapiens PE = 2 SV = 1 | 27 | | | 3.30E+08 | 1.40E+09 |
| P30101 | Protein disulfide-isomerase A3 OS = Homo sapiens GN = PDIA3 PE = 1 SV = 4 | 19 | 16 | 16 | 8.20E+08 | 2.40E+08 |
| D3GKD9 | G-gamma globin Paulinia variant OS = Homo sapiens GN = HBG2 PE = 3 SV = 1 | 4 | 1 | 1 | 1.60E+09 | 3.30E+09 |
| P15924 | Desmoplakin OS = Homo sapiens GN = DSP PE = 1 SV = 3 | 47 | 48 | 76 | 9.40E+07 | 6.10E+08 |
| P04083 | Annexin A1 OS = Homo sapiens GN = ANXA1 PE = 1 SV = 2 | 17 | 18 | 21 | 1.00E+08 | 2.50E+08 |
| P14625 | Endoplasmin OS = Homo sapiens GN = HSP90B1 PE = 1 SV = 1 | 25 | 20 | 27 | 5.70E+08 | 8.00E+08 |
| Q9Y490 | Talin-1 OS = Homo sapiens GN = TLN1 PE = 1 SV = 3 | 37 | 30 | 11 | 7.40E+07 | 3.10E+08 |
| P35556 | Fibrillin-2 OS = Homo sapiens GN = FBN2 PE = 1 SV = 3 | 32 | 53 | 30 | 2.90E+08 | 3.90E+09 |
| Q04695 | Keratin, type I cytoskeletal 17 OS = Homo sapiens GN = KRT17 PE = 1 SV = 2 | 7 | 4 | 7 | 2.10E+08 | 5.90E+09 |
| V9HWG3 | Epididymis secretory protein Li 45 OS = Homo sapiens GN = HEL-S-45 PE = 2 SV = 1 | 17 | 26 | 22 | 1.50E+09 | |
| P63261 | Actin, cytoplasmic 2 OS = Homo sapiens GN = ACTG1 PE = 1 SV = 1 | 5 | 7 | 7 | 2.30E+09 | 2.90E+08 |
| D9YZU8 | Hemoglobin, gamma A OS = Homo sapiens GN = HBG1 PE = 3 SV = 1 | 3 | | | 4.80E+08 | |
| A0N071 | Delta globin OS = Homo sapiens GN = HBD PE = 3 SV = 1 | 3 | 2 | 3 | 3.40E+08 | 3.80E+08 |
| O95678 | Keratin, type II cytoskeletal 75 OS = Homo sapiens GN = KRT75 PE = 1 SV = 2 | 1 | | | 6.30E+07 | |
| P13647 | Keratin, type II cytoskeletal 5 OS = Homo sapiens GN = KRT5 PE = 1 SV = 3 | 12 | 12 | 17 | 2.80E+08 | 3.20E+08 |
| P62736 | Actin, aortic smooth muscle OS = Homo sapiens GN = ACTA2 PE = 1 SV = 1 | 2 | | | 1.20E+08 | |
| P11047 | Laminin subunit gamma-1 OS = Homo sapiens GN = LAMC1 PE = 1 SV = 3 | 19 | 26 | 15 | 1.10E+08 | |

APPENDIX A-continued

| ID | Description | C1 | C2 | C3 | C4 | C5 |
|---|---|---|---|---|---|---|
| P12814 | Alpha-actinin-1 OS = Homo sapiens GN = ACTN1 PE = 1 SV = 2 | 14 | 13 | 8 | 1.10E+08 | 2.50E+08 |
| O43707 | Alpha-actinin-4 OS = Homo sapiens GN = ACTN4 PE = 1 SV = 2 | 13 | 13 | 20 | 1.30E+08 | 3.90E+08 |
| V9HW22 | Epididymis luminal protein 33 OS = Homo sapiens GN = HEL-S-72p PE = 2 SV = 1 | 7 | 8 | 9 | 1.40E+08 | 3.30E+08 |
| B2R4R0 | Histone H4 OS = Homo sapiens GN = HIST1H4H PE = 2 SV = 1 | 8 | 7 | 8 | 1.40E+09 | 5.80E+09 |
| P13667 | Protein disulfide-isomerase A4 OS = Homo sapiens GN = PDIA4 PE = 1 SV = 2 | 17 | 14 | 14 | 2.80E+08 | 1.90E+08 |
| P80723 | Brain acid soluble protein 1 OS = Homo sapiens GN = BASP1 PE = 1 SV = 2 | 13 | 7 | 7 | 2.90E+08 | 3.00E+08 |
| A0A087WZW | Protein IGKV3-11 OS = Homo sapiens GN = IGKV3-11 PE = 4 SV = 1 | 6 | | | 6.70E+08 | |
| P38646 | Stress-70 protein, mitochondrial OS = Homo sapiens GN = HSPA9 PE = 1 SV = 2 | 19 | 12 | 13 | 1.60E+08 | 2.60E+08 |
| P98160 | Basement membrane-specific heparan sulfate proteoglycan core protein OS = Homo sapiens GN = HSPG2 | 24 | 26 | 46 | 1.50E+08 | 3.50E+08 |
| P00558 | Phosphoglycerate kinase 1 OS = Homo sapiens GN = PGK1 PE = 1 SV = 3 | 13 | 19 | 17 | 2.50E+08 | 7.90E+08 |
| P35580 | Myosin-10 OS = Homo sapiens GN = MYH10 PE = 1 SV = 3 | 7 | 9 | 11 | 1.80E+07 | 4.90E+07 |
| P00915 | Carbonic anhydrase 1 OS = Homo sapiens GN = CA1 PE = 1 SV = 2 | 7 | 5 | 6 | 7.10E+08 | 2.80E+08 |
| P40926 | Malate dehydrogenase, mitochondrial OS = Homo sapiens GN = MDH2 PE = 1 SV = 3 | 13 | 12 | 13 | 3.90E+08 | 4.40E+08 |
| P06733 | Alpha-enolase OS = Homo sapiens GN = ENO1 PE = 1 SV = 2 | 13 | 16 | 16 | 2.40E+08 | 1.10E+09 |
| Q6LES2 | Annexin (Fragment) OS = Homo sapiens GN = ANXA4 PE = 1 SV = 1 | 14 | 8 | 13 | 3.40E+08 | 3.20E+08 |
| P54652 | Heat shock-related 70 kDa protein 2 OS = Homo sapiens GN = HSPA2 PE = 1 SV = 1 | 6 | 6 | 4 | 6.90E+07 | 1.70E+08 |
| V9HW26 | ATP synthase subunit alpha OS = Homo sapiens GN = HEL-S-123m PE = 1 SV = 1 | 12 | 17 | 16 | 2.30E+08 | 4.90E+08 |
| P13646 | Keratin, type I cytoskeletal 13 OS = Homo sapiens GN = KRT13 PE = 1 SV = 4 | 2 | | 4 | 2.10E+07 | |
| P35908 | Keratin, type II cytoskeletal 2 epidermal OS = Homo sapiens GN = KRT2 PE = 1 SV = 2 | 3 | | | 1.40E+07 | |
| P04075 | Fructose-bisphosphate aldolase A OS = Homo sapiens GN = ALDOA PE = 1 SV = 2 | 12 | 10 | 12 | 3.90E+08 | 5.60E+08 |
| P68363 | Tubulin alpha-1B chain OS = Homo sapiens GN = TUBA1B PE = 1 SV = 1 | 13 | 4 | | 2.70E+08 | 6.90E+08 |
| P23142 | Fibulin-1 OS = Homo sapiens GN = FBLN1 PE = 1 SV = 4 | 10 | 2 | 11 | 2.00E+08 | 8.90E+07 |
| A0A087WUZ | Spectrin beta chain, non-erythrocytic 1 OS = Homo sapiens GN = SPTBN1 PE = 1 SV = 1 | 17 | 27 | | 4.90E+07 | 2.20E+08 |
| A0A0G2JIW1 | Heat shock 70 kDa protein 1B OS = Homo sapiens PE = 1 SV = 1 | 11 | | | 1.10E+08 | |
| P06396 | Gelsolin OS = Homo sapiens GN = GSN PE = 1 SV = 1 | 10 | 16 | 12 | 2.00E+08 | 3.10E+08 |
| P10809 | 60 kDa heat shock protein, mitochondrial OS = Homo sapiens GN = HSPD1 PE = 1 SV = 2 | 11 | 11 | 14 | 2.00E+08 | 1.60E+08 |
| A0A087WYC | Alpha-1-antitrypsin OS = Homo sapiens GN = SERPINA1 PE = 1 SV = 1 | 8 | 12 | 8 | 2.50E+08 | 5.50E+08 |
| B3VMW0 | Ig gamma-1 chain C region OS = Homo sapiens GN = IGHG1 PE = 1 SV = 1 | 7 | | | 6.00E+08 | |
| A0A0D9SGF6 | Lactoferrin OS = Homo sapiens PE = 2 SV = 1 | 2 | 4 | 6 | 3.10E+07 | 7.60E+07 |
| Q06830 | Spectrin alpha chain, non-erythrocytic 1 OS = Homo sapiens GN = SPTAN1 PE = 1 SV = 1 | 20 | 30 | 19 | 5.20E+07 | 2.30E+08 |
| V9HWE0 | Peroxiredoxin-1 OS = Homo sapiens GN = PRDX1 PE = 1 SV = 1 | 8 | 8 | 10 | 3.00E+08 | 5.40E+08 |
| W8QEY1 | Annexin OS = Homo sapiens GN = HEL-S-7 PE = 2 SV = 1 | 11 | 16 | 14 | 3.50E+08 | 1.20E+09 |
| V9HWB8 | Lactoferrin OS = Homo sapiens GN = HEL-S-30 PE = 1 SV = 1 | 2 | | | 1.40E+07 | |
| V9HW31 | Pyruvate kinase OS = Homo sapiens GN = HEL-S-271 PE = 1 SV = 1 | 13 | 15 | 15 | 1.60E+08 | 5.50E+08 |
| V9HW80 | ATP synthase subunit beta OS = Homo sapiens GN = HEL-S-271 PE = 1 SV = 1 | 11 | 13 | 13 | 1.50E+08 | 9.70E+08 |
| P02647 | Epididymis luminal protein 220 OS = Homo sapiens GN = HEL-S-70 PE = 1 SV = 1 | 15 | 16 | 15 | 1.20E+08 | 2.30E+08 |
| A4QPB0 | Apolipoprotein A-I OS = Homo sapiens GN = APOA1 PE = 1 SV = 1 | 10 | 17 | 13 | 2.80E+08 | 8.80E+08 |
| A0A087WYC | IQ motif containing GTPase activating protein 1 OS = Homo sapiens GN = IQGAP1 PE = 1 SV = 1 | 14 | 15 | 19 | 5.00E+07 | 1.50E+08 |
| A0A024RBH2 | Clathrin heavy chain OS = Homo sapiens GN = CLTC PE = 1 SV = 1 | 13 | 35 | 30 | 1.40E+08 | 4.70E+08 |
| A0A024RBH2 | Cytoskeleton-associated protein 4, isoform CRA_c OS = Homo sapiens GN = CKAP4 PE = 4 SV = 1 | 13 | 14 | 16 | 2.20E+08 | 2.80E+08 |
| A23284 | Spectrin alpha chain, erythrocytic 1 OS = Homo sapiens GN = SPTA1 PE = 1 SV = 1 | 16 | | | 3.90E+07 | |
| P23284 | Peptidyl-prolyl cis-trans isomerase B OS = Homo sapiens GN = PPIB PE = 1 SV = 2 | 12 | 9 | 12 | 5.30E+08 | 6.80E+08 |
| P35527 | Keratin, type I cytoskeletal 9 OS = Homo sapiens GN = KRT9 PE = 1 SV = 3 | 12 | 6 | 4 | 8.60E+07 | 9.90E+07 |
| P04406 | Glyceraldehyde-3-phosphate dehydrogenase OS = Homo sapiens GN = GAPDH PE = 1 SV = 3 | 8 | 14 | 16 | 9.10E+08 | 2.60E+09 |
| A2A274 | Aconitate hydratase, mitochondrial OS = Homo sapiens GN = ACO2 PE = 1 SV = 1 | 8 | 9 | | 1.40E+08 | 2.10E+08 |
| P07996 | Thrombospondin-1 OS = Homo sapiens GN = THBS1 PE = 1 SV = 2 | 11 | | | 4.70E+07 | |
| Q5SU16 | Beta 5-tubulin OS = Homo sapiens GN = TUBB PE = 2 SV = 1 | 2 | 2 | 4 | 1.20E+08 | 4.70E+08 |
| A0A024R1X8 | Junction plakoglobin, isoform CRA_a OS = Homo sapiens GN = JUP PE = 4 SV = 1 | 11 | 14 | 16 | 6.10E+07 | 2.40E+08 |
| P08238 | Heat shock protein HSP 90-beta OS = Homo sapiens GN = HSP90AB1 PE = 1 SV = 4 | 4 | 3 | 4 | 2.50E+07 | 4.10E+07 |
| P60174 | Triosephosphate isomerase OS = Homo sapiens GN = TPI1 PE = 1 SV = 3 | 11 | 12 | 10 | 2.40E+08 | 5.50E+08 |
| B2RSB3 | Histone H2A OS = Homo sapiens PE = 2 SV = 1 | 5 | 3 | 3 | 1.30E+09 | 1.00E+09 |
| A8K259 | cDNA FLJ78501, highly similar to Homo sapiens serpin peptidase inhibitor, clade H (heat shock protein 47) | 8 | 9 | | 1.40E+08 | 2.80E+08 |
| H7BZJ3 | Protein disulfide-isomerase A3 (Fragment) OS = Homo sapiens GN = PDIA3 PE = 1 SV = 1 | 1 | 1 | 1 | 6.30E+08 | 5.30E+08 |

APPENDIX A-continued

| | | | | | |
|---|---|---|---|---|---|
| P13645 | Keratin, type I cytoskeletal 10 OS = Homo sapiens GN = KRT10 PE = 1 SV = 6 | 4 | | 5 | 5.40E+07 |
| V9HWA9 | Epididymis secretory sperm binding protein Li 62p OS = Homo sapiens GN = HEL-S-62p PE = 2 SV = 1 | 12 | 11 | 10 | 3.40E+07 | 1.00E+08 |
| B4DJ30 | cDNA FLJ61290, highly similar to Neutral alpha-glucosidase AB OS = Homo sapiens PE = 2 SV = 1 | 7 | 4 | 9 | 1.00E+08 | 1.30E+08 |
| V9HW43 | Epididymis secretory protein Li 102 OS = Homo sapiens GN = HEL-S-102 PE = 2 SV = 1 | 6 | 9 | 8 | 2.10E+08 | 1.60E+09 |
| P68371 | Tubulin beta-4B chain OS = Homo sapiens GN = TUBB4B PE = 1 SV = 1 | 3 | 3 | | 5.80E+07 | 2.40E+08 |
| Q9BXX0 | EMILIN-2 OS = Homo sapiens GN = EMILIN2 PE = 1 SV = 3 | 13 | 14 | 8 | 7.10E+07 | 3.00E+08 |
| Q15084 | Protein disulfide-isomerase A6 OS = Homo sapiens GN = PDIA6 PE = 1 SV = 1 | 7 | 6 | 7 | 2.00E+08 | 3.50E+08 |
| Q6GMX3 | IGL@ protein OS = Homo sapiens GN = IGL@ PE = 2 SV = 1 | 3 | 4 | 2 | 1.20E+08 | 5.80E+08 |
| P01023 | Alpha-2-macroglobulin OS = Homo sapiens GN = A2M PE = 1 SV = 3 | 8 | 8 | 7 | 1.10E+08 | 1.40E+08 |
| B4DJQ5 | cDNA FLJ59211, highly similar to Glucosidase 2 subunit beta OS = Homo sapiens PE = 2 SV = 1 | 10 | 5 | 6 | 1.70E+08 | 2.30E+08 |
| P48735 | Isocitrate dehydrogenase [NADP], mitochondrial OS = Homo sapiens GN = IDH2 PE = 1 SV = 2 | 9 | 7 | 13 | 9.70E+07 | 1.10E+08 |
| O15230 | Laminin subunit alpha-5 OS = Homo sapiens GN = LAMA5 PE = 1 SV = 8 | 13 | 15 | 1 | 3.60E+07 | 1.40E+08 |
| P22626 | Heterogeneous nuclear ribonucleoproteins A2/B1 OS = Homo sapiens GN = HNRNPA2B1 PE = 1 SV = 2 | 9 | 9 | 9 | 2.40E+08 | 5.30E+08 |
| H6VRG1 | Keratin 1 OS = Homo sapiens GN = KRT1 PE = 3 SV = 1 | 10 | | | 1.10E+08 | |
| Q0IN1 | Keratin 77 OS = Homo sapiens GN = KRT77 PE = 1 SV = 1 | 2 | | | 5.60E+08 | |
| P00738 | Haptoglobin OS = Homo sapiens GN = HP PE = 1 SV = 1 | 7 | 8 | | 5.90E+08 | 1.20E+09 |
| P27824 | Calnexin OS = Homo sapiens GN = CANX PE = 1 SV = 2 | 10 | 17 | 14 | 1.70E+08 | 3.50E+08 |
| A5Z217 | Mutant desmin OS = Homo sapiens PE = 2 SV = 1 | 2 | 4 | 1 | 2.30E+07 | 3.50E+07 |
| P67809 | Nuclease-sensitive element-binding protein 1 OS = Homo sapiens GN = YBX1 PE = 1 SV = 3 | 7 | 2 | | 4.40E+07 | 3.70E+07 |
| Q5XTR9 | Hemoglobin delta-beta fusion protein (Fragment) OS = Homo sapiens GN = HBD/HBB PE = 3 SV = 1 | 1 | 1 | 1 | 3.20E+07 | 3.40E+07 |
| P16157 | Ankyrin-1 OS = Homo sapiens GN = ANK1 PE = 1 SV = 3 | 14 | 3 | 2 | 5.90E+07 | 3.80E+07 |
| B4DRS2 | Histone H2B OS = Homo sapiens PE = 2 SV = 1 | 7 | 2 | 8 | 1.70E+09 | 1.90E+09 |
| P63104 | 14-3-3 protein zeta/delta OS = Homo sapiens GN = YWHAZ PE = 1 SV = 1 | 7 | 6 | 7 | 1.60E+08 | 4.70E+08 |
| P04843 | Dolichyl-diphospho oligosaccharide--protein glycosyltransferase subunit 1 OS = Homo sapiens GN = RPN1 | 9 | 10 | 11 | 6.10E+07 | 1.70E+08 |
| Q00839 | Heterogeneous nuclear ribonucleoprotein U OS = Homo sapiens GN = HNRNPU PE = 1 SV = 6 | 8 | 8 | 9 | 5.00E+07 | 1.80E+08 |
| P00747 | Plasminogen OS = Homo sapiens GN = PLG PE = 1 SV = 2 | 11 | 18 | 20 | 1.20E+08 | 5.80E+08 |
| B2RDY9 | Epididymis tissue sperm binding protein Li 18mP OS = Homo sapiens GN = HEL-S-18mP PE = 2 SV = 1 | 8 | 4 | 5 | 6.20E+07 | 1.00E+08 |
| E9KL48 | Integrin beta-1 OS = Homo sapiens GN = ITGB1 PE = 1 SV = 1 | 10 | 12 | 11 | 1.40E+07 | 2.00E+08 |
| P05556 | Adenylyl cyclase-associated protein OS = Homo sapiens PE = 2 SV = 1 | 11 | 11 | 5 | 8.00E+07 | 3.70E+08 |
| P07900 | Heat shock protein HSP 90-alpha OS = Homo sapiens GN = HSP90AA1 PE = 1 SV = 5 | 3 | 3 | 4 | 3.50E+07 | 5.50E+07 |
| Q59FP5 | Spectrin, beta, erythrocytic (Includes spherocytosis, clinical type I) variant (Fragment) OS = Homo sapiens | 10 | 2 | 1 | 3.20E+07 | 1.70E+07 |
| Q6UY14 | ADAMTS-like protein 4 OS = Homo sapiens GN = ADAMTSL4 PE = 1 SV = 2 | 9 | 14 | 11 | 7.70E+07 | 2.50E+08 |
| B2RDE1 | cDNA, FLJ96568, highly similar to Homo sapiens tropomyosin 3 (TPM3), mRNA OS = Homo sapiens | 5 | 2 | 3 | 8.50E+07 | 1.40E+08 |
| P67936 | Tropomyosin alpha-4 chain OS = Homo sapiens GN = TPM4 PE = 1 SV = 3 | 4 | 3 | | 1.50E+08 | 2.30E+08 |
| V9HWK2 | Epididymis luminal protein 114 OS = Homo sapiens GN = HEL114 PE = 2 SV = 1 | 12 | 13 | 4 | 8.60E+07 | 1.50E+08 |
| P09382 | Galectin-1 OS = Homo sapiens GN = LGALS1 PE = 1 SV = 2 | 4 | 7 | 7 | 2.00E+08 | 1.40E+09 |
| P29966 | Myristoylated alanine-rich C-kinase substrate OS = Homo sapiens GN = MARCKS PE = 1 SV = 4 | 7 | 4 | 1 | 3.10E+08 | 6.20E+08 |
| A0A024R319 | Laminin, beta 2 (Laminin S), isoform CRA_a OS = Homo sapiens GN = LAMB2 PE = 4 SV = 1 | 11 | 29 | 2 | 3.10E+07 | 2.50E+08 |
| Q13885 | Tubulin beta-2A chain OS = Homo sapiens GN = TUBB2A PE = 1 SV = 1 | 1 | | 5 | 6.60E+06 | 2.50E+08 |
| P27348 | 14-3-3 protein theta OS = Homo sapiens GN = YWHAQ PE = 1 SV = 1 | 4 | 5 | 7 | 9.80E+07 | 7.90E+09 |
| D3DTX7 | Collagen, type I, alpha 1, isoform CRA_a OS = Homo sapiens GN = COL1A1 PE = 4 SV = 1 | 2 | 1 | 2 | 7.20E+08 | 1.40E+08 |
| Q49A63 | Amine oxidase [flavin-containing] OS = Homo sapiens GN = MAOA PE = 2 SV = 1 | 8 | 8 | 9 | 1.40E+08 | 4.20E+08 |
| P27338 | Amine oxidase [flavin-containing] B OS = Homo sapiens GN = MAOB PE = 1 SV = 3 | 8 | 10 | 6 | 1.40E+08 | 6.20E+08 |
| P30040 | Endoplasmic reticulum resident protein 29 OS = Homo sapiens GN = ERP29 PE = 1 SV = 4 | 6 | 3 | 4 | 1.00E+08 | 1.00E+08 |
| E9KL44 | Epididymis tissue sperm binding protein Li 14m OS = Homo sapiens GN = HEL114 PE = 2 SV = 1 | 7 | 12 | 6 | 4.00E+07 | 1.90E+08 |
| A0A0G2JPR0 | Complement C4-A OS = Homo sapiens GN = C4A PE = 1 SV = 1 | 9 | 3 | 7 | 4.80E+07 | 8.00E+07 |
| P61247 | 40S ribosomal protein S3a OS = Homo sapiens GN = RPS3A PE = 1 SV = 2 | 7 | 7 | 10 | 8.40E+07 | 1.70E+08 |
| B3KQF5 | cDNA FLJ90381 fis, clone NT2RP2005035, highly similar to Calumenin OS = Homo sapiens PE = 2 SV = 1 | 1 | 8 | 10 | 4.40E+07 | 2.60E+08 |
| A0A024R755 | Calumenin, isoform CRA_a OS = Homo sapiens GN = CALU PE = 4 SV = 1 | 1 | | | 2.70E+07 | |
| Q96HE7 | ERO1-like protein alpha OS = Homo sapiens GN = ERO1L PE = 1 SV = 2 | 4 | 4 | 9 | 1.20E+08 | 1.50E+08 |
| V9HW12 | Epididymis secretory sperm binding protein Li 2a OS = Homo sapiens GN = HEL-S-2a PE = 2 SV = 1 | 8 | 2 | 4 | 3.80E+08 | 1.60E+08 |
| Q59GB4 | Dihydropyrimidinase-like 2 variant (Fragment) OS = Homo sapiens PE = 2 SV = 1 | 1 | 12 | 3 | 6.60E+07 | 2.80E+08 |
| B2R7W4 | cDNA, FLJ93632, highly similar to Homo sapiens heterogeneous nuclear ribonucleoprotein R (HNRPR) | 7 | 3 | 1 | 2.00E+07 | 4.10E+07 |

APPENDIX A-continued

| ID | Description | | | | |
|---|---|---|---|---|---|
| A8K9A4 | cDNA FLJ75154, highly similar to Homo sapiens heterogeneous nuclear ribonucleoprotein C (C1/C2) | 8 | 6 | 4 | 1.10E+08 | 2.50E+08 |
| A0A0G2JPD4 | Uncharacterized protein OS = Homo sapiens PE = 4 SV = 1 | 2 | | | 1.70E+08 | 1.70E+08 |
| P30043 | Flavin reductase (NADPH) OS = Homo sapiens GN = BLVRB PE = 1 SV = 3 | 5 | 5 | | 5.10E+07 | 1.70E+08 |
| B4DEA8 | cDNA FLJ56425, highly similar to Very-long-chain specific acyl-CoAdehydrogenase, mitochondrial (EC 1.3.99.—) OS = Ho | 9 | 8 | 9 | 3.40E+07 | 7.70E+07 |
| B3KNB4 | cDNA FLJ14168 fis, clone NT2RP2001440, highly similar to 14-3-3 protein gamma OS = Homo sapiens PE = 2 SV = 1 | 5 | 2 | | 6.90E+07 | 1.80E+08 |
| A0A024RDW | Collagen, type IV, alpha 2, isoform CRA_a OS = Homo sapiens GN = COL4A2 PE = 4 SV = 1 | 6 | 6 | 5 | 1.90E+08 | 3.40E+08 |
| Q4W4Y1 | Dopamine receptor interacting protein 4 OS = Homo sapiens GN = DRIP4 PE = 2 SV = 1 | 2 | 2 | 3 | 3.60E+07 | 5.40E+07 |
| P23396 | 40S ribosomal protein S3 OS = Homo sapiens GN = RPS3 PE = 1 SV = 1 | 10 | 6 | 6 | 9.90E+07 | 2.40E+08 |
| P00338 | L-lactate dehydrogenase A chain OS = Homo sapiens GN = LDHA PE = 1 SV = 2 | 8 | 12 | 8 | 1.20E+08 | 5.70E+08 |
| O00469 | Procollagen-lysine, 2-oxoglutarate 5-dioxygenase 2 OS = Homo sapiens GN = PLOD2 PE = 1 SV = 2 | 6 | 4 | 6 | 8.20E+07 | 8.70E+07 |
| P10909 | Clusterin OS = Homo sapiens GN = CLU PE = 1 SV = 1 | 6 | 12 | 7 | 1.60E+08 | 1.50E+09 |
| Q86U75 | Dihydropyrimidinase-like 2 OS = Homo sapiens PE = 2 SV = 1 | 1 | 7 | 1 | 1.90E+07 | |
| Q6NZI2 | Polymerase 1 and transcript release factor OS = Homo sapiens GN = PTRF PE = 1 SV = 1 | 5 | 7 | 5 | 1.30E+08 | 6.80E+08 |
| P04040 | Catalase OS = Homo sapiens GN = CAT PE = 1 SV = 3 | 7 | 1 | | 2.10E+08 | 7.20E+07 |
| Q14103 | Heterogeneous nuclear ribonucleoprotein D0 OS = Homo sapiens GN = HNRNPD PE = 1 SV = 1 | 3 | 5 | 4 | 1.00E+08 | 2.20E+08 |
| G3XAI2 | Laminin subunit beta-1 OS = Homo sapiens GN = LAMB1 PE = 1 SV = 1 | 7 | 9 | 1 | 3.50E+07 | 7.70E+07 |
| Q6N030 | Putative uncharacterized protein DKFZp686I15212 OS = Homo sapiens GN = DKFZp686I15212 PE = 1 SV = 1 | 2 | 4 | 3 | 1.60E+07 | 1.30E+08 |
| A0A024R1A3 | Ubiquitin-activating enzyme E1 (A1S9T and BN75 temperature sensitivity complementing), isoform CRA_a OS = Homo | 5 | 7 | 5 | 3.00E+07 | 7.40E+07 |
| P02749 | Beta-2-glycoprotein 1 OS = Homo sapiens GN = APOH PE = 1 SV = 3 | 4 | 1 | 2 | 1.00E+08 | 1.00E+08 |
| B0YJ32 | Laminin alpha-3 chain variant 1 OS = Homo sapiens GN = LAMA3 PE = 4 SV = 1 | 9 | | 12 | 2.70E+07 | |
| H7BYY1 | Tropomyosin 1 (Alpha), isoform CRA_m OS = Homo sapiens GN = TPM1 PE = 1 SV = 1 | 1 | | | 3.20E+07 | |
| AQA024QZ30 | Succinate dehydrogenase [ubiquinone] flavoprotein subunit, mitochondrial OS = Homo sapiens GN = SDHA PE = 3 SV = 1 | 6 | 4 | | 5.30E+07 | 9.50E+07 |
| Q99959 | Plakophilin-2 OS = Homo sapiens GN = PKP2 PE = 1 SV = 2 | 9 | 5 | 7 | 7.60E+07 | 1.10E+08 |
| Q05682 | Caldesmon OS = Homo sapiens GN = CALD1 PE = 1 SV = 3 | 9 | 4 | | 3.60E+07 | 4.20E+07 |
| Q86UP2 | Kinectin OS = Homo sapiens GN = KTN1 PE = 1 SV = 1 | 10 | 6 | 4 | 2.70E+07 | 5.80E+07 |
| P08123 | Collagen alpha-2(I) chain OS = Homo sapiens GN = COL1A2 PE = 1 SV = 7 | 5 | 7 | 7 | 1.00E+08 | 1.40E+09 |
| B2RGI2 | cDNA, FLJ92973, highly similar to Homo sapiens villin 2 (ezrin) (VIL2), mRNA OS = Homo sapiens PE = 2 SV = 1 | | | | 5.40E+07 | |
| Q6FIC5 | Chloride intracellular channel protein OS = Homo sapiens GN = CLIC4 PE = 2 SV = 1 | 4 | 2 | 2 | 2.30E+07 | 3.40E+07 |
| P62258 | 14-3-3 protein epsilon OS = Homo sapiens GN = YWHAE PE = 1 SV = 1 | 5 | 8 | 7 | 1.00E+08 | 3.00E+08 |
| P02452 | Collagen alpha-1(I) chain OS = Homo sapiens GN = COL1A1 PE = 1 SV = 5 | 4 | 6 | 6 | 1.30E+08 | 7.80E+08 |
| P13489 | Ribonuclease inhibitor OS = Homo sapiens GN = RNH1 PE = 1 SV = 2 | 6 | 6 | 3 | 5.40E+07 | 1.30E+08 |
| Q9Y4L1 | Hypoxia up-regulated protein 1 OS = Homo sapiens GN = HYOU1 PE = 1 SV = 1 | 7 | | 3 | 3.10E+08 | |
| P37802 | Transgelin-2 OS = Homo sapiens GN = TAGLN2 PE = 1 SV = 3 | 6 | 9 | 10 | 1.00E+08 | 2.20E+08 |
| P21796 | Voltage-dependent anion-selective channel protein 1 OS = Homo sapiens GN = VDAC1 PE = 1 SV = 2 | 4 | 4 | 5 | 1.20E+08 | 6.00E+08 |
| P13797 | Plastin-3 OS = Homo sapiens GN = PLS3 PE = 1 SV = 4 | 5 | | 2 | 2.50E+07 | |
| P04003 | C4b-binding protein alpha chain OS = Homo sapiens GN = C4BPA PE = 1 SV = 2 | 9 | 3 | 4 | 4.00E+07 | 4.20E+07 |
| P12429 | Annexin A3 OS = Homo sapiens GN = ANXA3 PE = 1 SV = 3 | 7 | 5 | 4 | 3.30E+07 | 4.60E+07 |
| P13804 | Electron transfer flavoprotein subunit alpha, mitochondrial OS = Homo sapiens GN = ETFA PE = 1 SV = 1 | 4 | 4 | 6 | 3.50E+07 | 7.50E+07 |
| D3DX01 | Amine oxidase OS = Homo sapiens GN = ABP1 PE = 3 SV = 1 | 4 | 4 | 13 | 1.10E+08 | 1.80E+08 |
| P07585 | Decorin OS = Homo sapiens GN = DCN PE = 1 SV = 1 | 4 | 6 | 4 | 1.00E+08 | 6.50E+08 |
| A0A024R6C9 | Dihydrolipoamide S-succinyltransferase (E2 component of 2-oxo-glutarate complex), isoform CRA_a OS = Homo sapie | 6 | 5 | 4 | 5.20E+07 | 1.50E+08 |
| A0A024R962 | HCG40889, isoform CRA_b OS = Homo sapiens GN = hCG_40889 PE = 4 SV = 1 | 8 | 3 | 8 | 4.60E+07 | 4.40E+07 |
| B5BU24 | 14-3-3 protein beta/alpha OS = Homo sapiens GN = YWHAB PE = 2 SV = 1 | 2 | 1 | 1 | 5.60E+07 | |
| A0A024QZN9 | Voltage-dependent anion channel 2, isoform CRA_a OS = Homo sapiens GN = VDAC2 PE = 4 SV = 1 | 6 | 7 | 7 | 1.10E+08 | 3.60E+08 |
| Q99714 | 3-hydroxyacyl-CoA dehydrogenase type-2 OS = Homo sapiens GN = HSD17B10 PE = 1 SV = 3 | 4 | 2 | 6 | 3.90E+07 | 3.60E+07 |
| Q9BS26 | Endoplasmic reticulum resident protein 44 OS = Homo sapiens GN = ERP44 PE = 1 SV = 1 | 3 | 4 | 4 | 6.20E+07 | 1.80E+08 |
| D9YZV5 | Tropomyosin 1 (Alpha) isoform 4 OS = Homo sapiens GN = TPM1 PE = 3 SV = 1 | 1 | | | 3.90E+07 | |
| D9ZGG2 | Vitronectin OS = Homo sapiens GN = VTN PE = 4 SV = 1 | 4 | 8 | 7 | 1.10E+08 | 2.00E+09 |
| B4DS66 | cDNA FLJ54290, highly similar to Mitochondrial inner membrane protein OS = Homo sapiens PE = 2 SV = 1 | 6 | | | 3.60E+07 | |
| P15428 | 15-hydroxyprostaglandin dehydrogenase [NAD(+)] OS = Homo sapiens GN = HPGD PE = 1 SV = 1 | 5 | 1 | 1 | 8.30E+07 | 3.20E+07 |
| P30044 | Peroxiredoxin-5, mitochondrial OS = Homo sapiens GN = PRDX5 PE = 1 SV = 4 | 3 | 6 | 6 | 6.20E+07 | 2.20E+08 |
| P06748 | Nucleophosmin OS = Homo sapiens GN = NPM1 PE = 1 SV = 2 | 4 | 3 | 4 | 1.20E+08 | 3.70E+08 |
| B7Z6Z4 | Myosin light polypeptide 6 OS = Homo sapiens GN = MYL6 PE = 1 SV = 1 | 6 | 6 | 6 | 1.50E+08 | 4.80E+08 |

APPENDIX A-continued

| Accession | Description | C1 | C2 | C3 | C4 |
|---|---|---|---|---|---|
| Q15293 | Reticulocalbin-1 OS = Homo sapiens GN = RCN1 PE = 1 SV = 1 | 5 | 4 | 6 | 1.30E+08 | 2.10E+08 |
| P07305 | Histone H1.0 OS = Homo sapiens GN = H1F0 PE = 1 SV = 1 | 3 | 2 | 3 | 3.10E+08 | 3.20E+08 |
| P06753 | Tropomyosin alpha-3 chain OS = Homo sapiens GN = TPM3 PE = 1 SV = 2 | 1 | | | | |
| P30048 | Thioredoxin-dependent peroxide reductase, mitochondrial OS = Homo sapiens GN = PRDX3 PE = 1 SV = 3 | 6 | 4 | 6 | 1.30E+08 | 2.70E+08 |
| D3DQ69 | SERPINE1 mRNA binding protein 1, isoform CRA_c OS = Homo sapiens GN = SERBP1 PE = 4 SV = 1 | 5 | | | 3.80E+07 | 8.70E+07 |
| A0A024R6W | Aspartate aminotransferase OS = Homo sapiens GN = GOT2 PE = 3 SV = 1 | 6 | 1 | | 5.10E+07 | 1.30E+08 |
| Q9NZM1 | Myoferlin OS = Homo sapiens GN = MYOF PE = 1 SV = 1 | 5 | 20 | 5 | 4.00E+07 | |
| P09622 | Dihydrolipoyl dehydrogenase, mitochondrial OS = Homo sapiens GN = DLD PE = 1 SV = 2 | 5 | 1 | 1 | 4.60E+07 | |
| Q14112 | Nidogen-2 OS = Homo sapiens GN = NID2 PE = 1 SV = 3 | 7 | 2 | | 4.30E+07 | 1.50E+08 |
| P02462 | Collagen alpha-1(IV) chain OS = Homo sapiens GN = COL4A1 PE = 1 SV = 1 | 3 | 4 | 4 | 1.30E+08 | 3.00E+08 |
| D9YZU7 | Hemoglobin, epsilon 1 OS = Homo sapiens GN = HBE1 PE = 3 SV = 1 | 1 | | | 8.30E+07 | |
| A8K5A4 | cDNA FLJ76826, highly similar to Homo sapiens ceruloplasmin (ferroxidase) (CP), mRNA OS = Homo sapiens PE = 2 SV = | 6 | 3 | 3 | 2.60E+07 | 8.40E+07 |
| Q02218 | 2-oxoglutarate dehydrogenase, mitochondrial OS = Homo sapiens GN = OGDH PE = 1 SV = 3 | 5 | | | 3.20E+07 | |
| P19338 | Nucleolin OS = Homo sapiens GN = NCL PE = 1 SV = 3 | 7 | 4 | 3 | 4.40E+07 | 6.80E+07 |
| V9HWC7 | Epididymis secretory sperm binding protein Li 128m OS = Homo sapiens GN = HEL-S-128m PE = 2 SV = 1 | 5 | 6 | 3 | 2.30E+07 | 1.40E+08 |
| Q8NBS9 | Thioredoxin domain-containing protein 5 OS = Homo sapiens GN = TXNDC5 PE = 1 SV = 2 | 5 | 5 | 4 | 1.20E+08 | 1.10E+08 |
| Q99497 | Protein deglycase DJ-1 OS = Homo sapiens GN = PARK7 PE = 1 SV = 2 | 4 | 4 | 2 | 8.20E+07 | 1.60E+08 |
| Q9UHQ9 | NADH-cytochrome b5 reductase 1 OS = Homo sapiens GN = CYB5R1 PE = 1 SV = 1 | 8 | 7 | 12 | 8.30E+07 | 1.70E+08 |
| B2R659 | cDNA, FLJ92803, highly similar to Homo sapiens hydroxysteroid (17-beta) dehydrogenase 4 (HSD17B4), mRNA OS = H | 5 | 3 | 5 | 3.20E+07 | 5.00E+07 |
| Q5EC54 | Heterogeneous nuclear ribonucleoprotein K transcript variant OS = Homo sapiens GN = HNRPK PE = 2 SV = 1 | 5 | 10 | 7 | 4.20E+07 | 1.50E+08 |
| E2RYJ0 | Anion exchange protein OS = Homo sapiens GN = SLC4A1 PE = 2 SV = 1 | 6 | 2 | 1 | 3.90E+07 | 1.30E+08 |
| O95831 | Apoptosis-inducing factor 1, mitochondrial OS = Homo sapiens GN = AIFM1 PE = 1 SV = 1 | 6 | 3 | 3 | 3.10E+07 | 5.20E+07 |
| Q53F64 | 3-hydroxyisobutyrate dehydrogenase OS = Homo sapiens GN = HIBADH PE = 3 SV = 1 | 2 | 1 | | 5.90E+07 | 1.50E+08 |
| B4DRS6 | Sideroflexin OS = Homo sapiens PE = 2 SV = 1 | 3 | 6 | 4 | 2.90E+07 | 1.20E+08 |
| P55084 | Trifunctional enzyme subunit beta, mitochondrial OS = Homo sapiens GN = HADHB PE = 1 SV = 3 | 5 | 7 | 6 | 5.00E+07 | 1.20E+08 |
| Q5JR94 | 40S ribosomal protein S8 OS = Homo sapiens GN = RPS8 PE = 2 SV = 1 | 5 | 3 | 7 | 7.60E+07 | 9.30E+07 |
| A0A024RA75 | Collagen alpha-3(VI) chain OS = Homo sapiens GN = COL6A3 PE = 1 SV = 5 | 6 | 27 | 12 | 2.40E+07 | 2.40E+08 |
| P12111 | | | | | | |
| O60664 | Perilipin-3 OS = Homo sapiens GN = PLIN3 PE = 1 SV = 3 | 5 | 2 | 4 | 3.20E+07 | 6.10E+07 |
| P31947 | 14-3-3 protein sigma OS = Homo sapiens GN = SFN PE = 1 SV = 1 | 5 | 3 | 6 | 7.40E+07 | 3.60E+07 |
| O43242 | 26S proteasome non-ATPase regulatory subunit 3 OS = Homo sapiens GN = PSMD3 PE = 1 SV = 2 | 3 | 4 | | 8.80E+06 | |
| Q8TC04 | Keratin 23 (Histone deacetylase inducible) OS = Homo sapiens GN = KRT23 PE = 2 SV = 1 | 2 | 1 | | 2.40E+07 | 2.80E+07 |
| P58107 | Epiplakin OS = Homo sapiens GN = EPPK1 PE = 1 SV = 2 | 2 | | 1 | 7.10E+06 | |
| Q13751 | Laminin subunit beta-3 OS = Homo sapiens GN = LAMB3 PE = 1 SV = 1 | 5 | 4 | 1 | 1.20E+07 | |
| G8JLB6 | Heterogeneous nuclear ribonucleoprotein H OS = Homo sapiens GN = HNRNPH1 PE = 1 SV = 1 | 3 | | 4 | 3.90E+07 | 8.50E+07 |
| P43121 | Cell surface glycoprotein MUC18 OS = Homo sapiens GN = MCAM PE = 1 SV = 2 | 6 | 3 | 2 | 4.70E+07 | |
| E7EPK1 | Septin-7 OS = Homo sapiens GN = SEPT7 PE = 1 SV = 2 | 3 | 1 | 1 | 2.40E+07 | 1.40E+08 |
| B4DQE1 | Annexin OS = Homo sapiens PE = 2 SV = 1 | 4 | 2 | 3 | 4.50E+07 | 8.40E+07 |
| A0A087WSV | Nucleobindin 2, isoform CRA_b OS = Homo sapiens GN = NUCB2 PE = 1 SV = 1 | 5 | | 1 | 2.00E+07 | |
| Q13228 | Selenium-binding protein 1 OS = Homo sapiens GN = SELENBP1 PE = 1 SV = 2 | | | | 1.70E+07 | |
| F8W031 | Uncharacterized protein (Fragment) OS = Homo sapiens PE = 1 SV = 1 | 3 | 1 | 3 | 5.40E+07 | 8.90E+07 |
| P20700 | Lamin-B1 OS = Homo sapiens GN = LMNB1 PE = 1 SV = 2 | 2 | 3 | 2 | 1.60E+07 | 5.30E+07 |
| Q15582 | Transforming growth factor-beta-induced protein ig-h3 OS = Homo sapiens GN = TGFBI PE = 1 SV = 1 | 6 | 5 | 9 | 3.90E+07 | 2.10E+08 |
| P05204 | Non-histone chromosomal protein HMG-17 OS = Homo sapiens GN = HMGN2 PE = 1 SV = 3 | 2 | 2 | 2 | 9.40E+07 | 2.20E+08 |
| O76015 | Keratin, type I cuticular Ha8 OS = Homo sapiens GN = KRT38 PE = 1 SV = 3 | 1 | | | 1.50E+08 | |
| P07686 | Beta-hexosaminidase subunit beta OS = Homo sapiens GN = HEXB PE = 1 SV = 3 | 6 | 2 | 1 | 9.10E+07 | 4.90E+07 |
| P00352 | Retinal dehydrogenase 1 OS = Homo sapiens GN = ALDH1A1 PE = 1 SV = 2 | 2 | 4 | | 4.50E+07 | 2.60E+07 |
| B2RR28 | cDNA, FLJ94136, highly similar to Homo sapiens synaptotagmin binding, cytoplasmic RNA interacting protein (SYNCR | 1 | 3 | 2 | 2.80E+07 | 2.80E+07 |
| Q9NYU2 | UDP-glucose:glycoprotein glucosyltransferase 1 OS = Homo sapiens GN = UGGT1 PE = 1 SV = 3 | 5 | 3 | 4 | 2.70E+07 | 2.60E+07 |
| B2RAN1 | cDNA, FLJ95012, highly similar to Homo sapiens UDP-glucose pyrophosphorylase 2 (UGP2), mRNA OS = Homo sapien | 5 | | | 7.10E+07 | |
| Q13011 | Delta(3,5)-Delta(2,4)-dienoyl-CoA isomerase, mitochondrial OS = Homo sapiens GN = ECH1 PE = 1 SV = 1 | 4 | 1 | 2 | 1.50E+07 | |
| P62269 | 40S ribosomal protein S18 OS = Homo sapiens GN = RPS18 PE = 1 SV = 3 | 5 | 4 | 5 | 4.60E+07 | 1.50E+08 |
| P48047 | ATP synthase subunit O, mitochondrial OS = Homo sapiens GN = ATP5O PE = 1 SV = 1 | 6 | 5 | 6 | 6.50E+07 | 2.30E+08 |

APPENDIX A-continued

| | | | | | |
|---|---|---|---|---|---|
| A0A024R814 | Ribosomal protein L7, isoform CRA_a OS = Homo sapiens GN = RPL7 PE = 3 SV = 1 | 5 | 6 | 4 | 9.70E+07 | 2.00E+08 |
| P35625 | Metalloproteinase inhibitor 3 OS = Homo sapiens GN = TIMP3 PE = 1 SV = 2 | 3 | 8 | 7 | 3.20E+07 | 1.40E+09 |
| B2R950 | cDNA, FLJ94213, highly similar to Homo sapiens pregnancy-zone protein (PZP), mRNA OS = Homo sapiens PE = 2 SV = 1 | 3 | 4 | 3 | 1.90E+07 | |
| P16402 | Histone H1.3 OS = Homo sapiens GN = HIST1H1D PE = 1 SV = 2 | 4 | 4 | 3 | 9.40E+08 | 1.70E+09 |
| Q4LE64 | NUMA1 variant protein (Fragment) OS = Homo sapiens GN = NUMA1 variant protein PE = 2 SV = 1 | 3 | 1 | 2 | 8.90E+06 | 3.90E+06 |
| Q59GY2 | Ribosomal protein L4 variant (Fragment) OS = Homo sapiens PE = 2 SV = 1 | 5 | 5 | 6 | 4.10E+07 | 1.50E+08 |
| E9KL35 | Epididymis tissue sperm binding protein Li 3a OS = Homo sapiens PE = 1 SV = 1 | | | 3 | 5.20E+07 | |
| P13639 | Elongation factor 2 OS = Homo sapiens GN = EEF2 PE = 1 SV = 4 | 4 | 7 | 6 | 3.60E+07 | 1.30E+08 |
| A0A024R2A7 | Lectin, mannose-binding, 1, isoform CRA_b OS = Homo sapiens GN = LMAN1 PE = 4 SV = 1 | 5 | 7 | 9 | 1.30E+08 | 3.40E+08 |
| A0A0C4DGB | Calpastatin OS = Homo sapiens GN = CAST PE = 1 SV = 1 | 4 | 8 | 5 | 3.20E+08 | |
| P62424 | 60S ribosomal protein L7a OS = Homo sapiens GN = RPL7A PE = 1 SV = 1 | 4 | 4 | 3 | 7.90E+08 | 4.10E+08 |
| V9HWE9 | Epididymis secretory protein Li 22 OS = Homo sapiens GN = HEL-S-22 PE = 2 SV = 1 | 3 | 7 | 6 | 1.20E+07 | 2.00E+08 |
| P46781 | 40S ribosomal protein S9 OS = Homo sapiens GN = RPS9 PE = 1 SV = 3 | 5 | 6 | 6 | 4.60E+08 | 1.30E+08 |
| Q99536 | Synaptic vesicle membrane protein VAT-1 homolog OS = Homo sapiens GN = VAT1 PE = 1 SV = 2 | 4 | 3 | 3 | 4.10E+08 | 1.70E+08 |
| B3KQQ3 | cDNA PSEC0016 fis, clone NT2RM1001076, highly similar to Procollagen-lysine,2-oxoglutarate 5-dioxygenase 3 (EC 1. | 3 | | | 6.50E+07 | 5.50E+07 |
| Q7Z406 | Myosin-14 OS = Homo sapiens GN = MYH14 PE = 1 SV = 2 | 2 | 24 | 24 | 1.80E+07 | |
| B4DH02 | cDNA FLJ50510, highly similar to Heat shock 70 kDa protein 4 OS = Homo sapiens PE = 2 SV = 1 | 4 | | | 2.00E+07 | |
| Q6NS36 | Ferritin (Fragment) OS = Homo sapiens GN = FTH1 PE = 2 SV = 1 | 3 | 5 | 3 | 2.10E+08 | 2.70E+08 |
| P62249 | 40S ribosomal protein S16 OS = Homo sapiens GN = RPS16 PE = 1 SV = 2 | 5 | 4 | | 6.30E+07 | 2.20E+08 |
| Q59FR8 | Galectin (Fragment) OS = Homo sapiens PE = 2 SV = 1 | 3 | 4 | 4 | 6.80E+08 | 7.50E+08 |
| Q9Y277 | Voltage-dependent anion-selective channel protein 3 OS = Homo sapiens GN = VDAC3 PE = 1 SV = 1 | 2 | 2 | 1 | 4.90E+08 | 2.10E+08 |
| Q14126 | Desmoglein-2 OS = Homo sapiens GN = DSG2 PE = 1 SV = 2 | 5 | 9 | 12 | 3.70E+07 | 9.10E+07 |
| D9IAI1 | Epididymis secretory protein Li 34 OS = Homo sapiens GN = HEL-S-34 PE = 2 SV = 2 | 4 | 1 | | 2.50E+07 | 1.10E+08 |
| B4DWA6 | cDNA FLJ60094, highly similar to F-actin capping protein subunit beta OS = Homo sapiens PE = 2 SV = 1 | 4 | 2 | 3 | 3.90E+07 | 6.60E+07 |
| E9PK25 | Cofilin-1 OS = Homo sapiens GN = CFL1 PE = 1 SV = 1 | 3 | 5 | 3 | 3.90E+08 | 2.80E+08 |
| F4ZW66 | NF110b OS = Homo sapiens PE = 2 SV = 1 | 4 | 2 | | 3.40E+07 | 7.50E+07 |
| Q53SS8 | Epididymis secretory protein Li 85 OS = Homo sapiens GN = PCBP1 PE = 2 SV = 1 | 4 | 5 | 3 | 8.20E+07 | 2.00E+08 |
| A0A0C4DFU2 | Superoxide dismutase OS = Homo sapiens GN = SOD2 PE = 1 SV = 1 | 4 | 5 | 5 | 2.00E+08 | 4.10E+08 |
| P07737 | Profilin-1 OS = Homo sapiens GN = PFN1 PE = 1 SV = 2 | 4 | 7 | 6 | 5.90E+08 | 4.00E+08 |
| P23229 | Integrin alpha-6 OS = Homo sapiens GN = ITGA6 PE = 1 SV = 5 | 4 | 4 | 8 | 2.50E+07 | 2.70E+07 |
| B2R657 | Annexin OS = Homo sapiens PE = 2 SV = 1 | 3 | 3 | 2 | 1.50E+07 | 5.60E+07 |
| A0A024RDG1 | Vesicle clocking protein p115, isoform CRA_a OS = Homo sapiens GN = VDP PE = 4 SV = 1 | 2 | | | 1.60E+07 | |
| V9HW63 | Epididymis secretory sperm binding protein Li 97n OS = Homo sapiens GN = HEL-S-97n PE = 2 SV = 1 | 2 | 3 | 3 | 1.30E+08 | 1.30E+08 |
| F8WAR4 | MICOS complex subunit MIC19 OS = Homo sapiens GN = CHCH D3 PE = 1 SV = 1 | 4 | 1 | 2 | 3.90E+07 | 1.50E+08 |
| A0A024R325 | Succinyl-CoA ligase subunit beta OS = Homo sapiens GN = SUCLG2 PE = 3 SV = 1 | 3 | 2 | 2 | 1.60E+07 | 3.10E+08 |
| I6TRR8 | SND1-BRAF fusion OS = Homo sapiens PE = 2 SV = 1 | 5 | 3 | 1 | 3.60E+07 | 4.20E+07 |
| Q8NBJ5 | Procollagen galactosyltransferase 1 OS = Homo sapiens GN = COLGALT1 PE = 1 SV = 1 | 4 | 1 | | 4.70E+08 | 2.60E+07 |
| Q14204 | Cytoplasmic dynein 1 heavy chain 1 OS = Homo sapiens GN = DYNC1H1 PE = 1 SV = 5 | 4 | 5 | 6 | 1.50E+07 | 3.60E+07 |
| O94905 | Erlin-2 OS = Homo sapiens GN = ERLIN2 PE = 1 SV = 1 | 2 | 2 | | 6.10E+06 | 8.70E+07 |
| P28331 | NADH-ubiquinone oxidoreductase 75 kDa subunit, mitochondrial OS = Homo sapiens GN = NDUFS1 PE = 1 SV = 3 | 3 | 5 | 3 | 1.40E+07 | 6.10E+07 |
| Q5RJ85 | HLA class I histocompatibility antigen, alpha chain G OS = Homo sapiens GN = HLA-G PE = 1 SV = 1 | 1 | 2 | 2 | 1.30E+07 | |
| P13727 | Bone marrow proteoglycan OS = Homo sapiens GN = PRG2 PE = 1 SV = 2 | 4 | 2 | 5 | 2.20E+08 | 1.50E+08 |
| P14136 | Glial fibrillary acidic protein OS = Homo sapiens GN = GFAP PE = 1 SV = 1 | 1 | 1 | | 6.70E+07 | 1.60E+08 |
| Q6N092 | Putative uncharacterized protein DKFZp686K18196 (Fragment) OS = Homo sapiens GN = DKFZp686K18196 PE = 2 SV = 1 | 3 | 6 | 2 | 1.20E+08 | 2.20E+08 |
| P53621 | Coatomer subunit alpha OS = Homo sapiens GN = COPA PE = 1 SV = 2 | 5 | 2 | 4 | 1.40E+07 | 5.80E+07 |
| P16401 | Histone H1.5 OS = Homo sapiens GN = HIST1H1B PE = 1 SV = 3 | 4 | 4 | 4 | 2.70E+08 | 5.90E+08 |
| Q8IVF2 | Protein AHNAK2 OS = Homo sapiens GN = AHNAK2 PE = 1 SV = 2 | 4 | 5 | 25 | 3.40E+07 | 1.90E+08 |
| D6RER5 | Septin-11 OS = Homo sapiens GN = SEPT11 PE = 1 SV = 1 | 2 | 2 | | 7.90E+06 | 7.40E+07 |
| Q92499 | ATP-dependent RNA helicase DDX1 OS = Homo sapiens GN = DDX1 PE = 1 SV = 2 | 3 | 1 | 1 | 7.80E+06 | 6.20E+07 |
| Q9Y310 | tRNA-splicing ligase RtcB homolog OS = Homo sapiens GN = RTCB PE = 1 SV = 1 | 4 | | | 3.00E+07 | |
| P51572 | B-cell receptor-associated protein 31 OS = Homo sapiens GN = BCAP31 PE = 1 SV = 3 | 4 | 7 | 6 | 5.50E+07 | 2.50E+08 |
| O00299 | Chloride intracellular channel protein 1 OS = Homo sapiens GN = CLIC1 PE = 1 SV = 4 | 4 | 6 | 4 | 2.40E+07 | 1.70E+08 |
| P24752 | Acetyl-CoA acetyltransferase, mitochondrial OS = Homo sapiens GN = ACAT1 PE = 1 SV = 1 | 4 | 3 | | 2.70E+07 | 1.30E+08 |

APPENDIX A-continued

| ID | Description | | | | |
|---|---|---|---|---|---|
| P00918 | Carbonic anhydrase 2 OS=Homo sapiens GN=CA2 PE=1 SV=2 | 3 | 1 | 1 | 1.00E+08 | 7.00E+07 |
| O00468 | Agrin OS=Homo sapiens GN=AGRN PE=1 SV=5 | 5 | 6 | 2 | 2.00E+07 | 7.70E+07 |
| P51991 | Heterogeneous nuclear ribonucleoprotein A3 OS=Homo sapiens GN=HNRNPA3 PE=1 SV=2 | 3 | 5 | 3 | 5.70E+07 | 1.90E+08 |
| D6RF35 | Vitamin D-binding protein OS=Homo sapiens GN=GC PE=1 SV=1 | 4 | 4 | 3 | 4.00E+07 | 7.60E+07 |
| L7RSL3 | Receptor protein-tyrosine kinase OS=Homo sapiens GN=FLT1 PE=3 SV=1 | 2 | 2 | 7 | 3.30E+07 | 4.80E+07 |
| A8K690 | cDNA FLJ76863, highly similar to Homo sapiens stress-induced-phosphoprotein 1 (Hsp70/Hsp90-organizing protein) | 3 | 2 | 1 | 2.20E+07 | 8.10E+07 |
| O701 | UDP-glucose 6-dehydrogenase OS=Homo sapiens GN=UGDH PE=1 SV=1 | 4 | 4 | 4 | 3.90E+07 | 7.90E+07 |
| J3QQ67 | 60S ribosomal protein L18 (Fragment) OS=Homo sapiens GN=RPL18 PE=1 SV=1 | 2 | 3 | 2 | 4.60E+07 | 2.00E+08 |
| P40925 | Malate dehydrogenase, cytoplasmic OS=Homo sapiens GN=MDH1 PE=1 SV=4 | 4 | 2 | | 3.70E+07 | 7.70E+07 |
| Q9GZM7 | Tubulointerstitial nephritis antigen like OS=Homo sapiens GN=TINAGL1 PE=1 SV=1 | 3 | 4 | 6 | 1.10E+08 | 2.20E+08 |
| Q079S4 | Prolow-density lipoprotein receptor related protein 1 OS=Homo sapiens GN=LRP1 PE=1 SV=2 | 4 | 6 | 1 | 1.60E+07 | 6.20E+07 |
| A0A0C4DG17 | 40S ribosomal protein SA OS=Homo sapiens GN=RPSA PE=1 SV=1 | 3 | 4 | 5 | 5.60E+07 | 1.60E+08 |
| D3DV26 | S100 calcium binding protein A10 (Annexin II ligand, calpactin I, light polypeptide (P11)), isoform CRA_b (Fragment) | 1 | 2 | 2 | 2.00E+08 | 1.30E+09 |
| A8K486 | Peptidyl-prolyl cis-trans isomerase OS=Homo sapiens PE=2 SV=1 | 4 | 7 | 6 | 1.40E+08 | 5.80E+08 |
| P13010 | X-ray repair cross complementing protein 5 OS=Homo sapiens GN=XRCC5 PE=1 SV=3 | 3 | 2 | 1 | 1.70E+07 | 8.20E+07 |
| B3KT93 | Polyadenylate-binding protein OS=Homo sapiens PE=2 SV=1 | 4 | 5 | 3 | 1.80E+07 | 7.90E+07 |
| B2R954 | cDNA, FLJ94534, highly similar to Homo sapiens capping protein (actin filament), gelsolin-like(CAPG), mRNA OS=Hom | 4 | 5 | 6 | 4.10E+07 | 7.50E+07 |
| A0A024R3W | Eukaryotic translation elongation factor 1 beta 2, isoform CRA_a OS=Homo sapiens GN=EEF1B2 PH=3 SV=1 | 3 | 2 | 2 | 2.60E+07 | 6.70E+07 |
| Q96AG4 | Leucine-rich repeat containing protein 59 OS=Homo sapiens GN=LRRC59 PE=1 SV=1 | 3 | 4 | 2 | 2.80E+07 | 9.20E+07 |
| P14060 | 3 beta-hydroxysteroid dehydrogenase/Delta 5-->4 isomerase type 1 OS=Homo sapiens GN=HSD3B1 PE=1 SV=2 | 3 | 5 | 7 | 5.60E+07 | 1.60E+08 |
| Q05D08 | PA2G4 protein (Fragment) OS=Homo sapiens GN=PA2G4 PE=2 SV=1 | 4 | 3 | 2 | 5.70E+07 | 8.80E+07 |
| Q15366 | Poly(rC)-binding protein 2 OS=Homo sapiens GN=PCBP2 PH=1 SV=1 | 3 | 2 | | 3.90E+07 | 8.70E+07 |
| C3VMY8 | Alpha B crystallin OS=Homo sapiens GN=CRYAB PE=2 SV=1 | 3 | 2 | 1 | 2.00E+07 | |
| A0A024R497 | Acyl-CoA synthetase long-chain family member 3, isoform CRA_a OS=Homo sapiens GN=ACSL3 PE=4 SV=1 | 3 | 2 | 9 | 2.80E+07 | 8.50E+07 |
| E7EVA0 | Microtubule-associated protein OS=Homo sapiens GN=MAP4 PE=1 SV=1 | 4 | 4 | 1 | 2.20E+07 | 3.40E+07 |
| P49411 | Elongation factor Tu, mitochondrial OS=Homo sapiens GN=TUFM PE=1 SV=2 | 4 | 2 | | 2.80E+07 | 8.10E+07 |
| Q6DHW4 | Uncharacterized protein OS=Homo sapiens PE=2 SV=1 | 1 | | | 1.30E+07 | |
| Q6ZR64 | HBV PreS1-transactivated protein 1 OS=Homo sapiens GN=MXRA7 PE=1 SV=1 | 3 | 1 | 2 | 2.40E+07 | 9.30E+07 |
| A8KAJ3 | cDNA FLJ77823, highly similar to Homo sapiens EGF-containing fibulin-like extracellular matrix protein 1, transcript v | 3 | 8 | 3 | 2.80E+07 | 4.50E+08 |
| P29401 | Transketolase OS=Homo sapiens GN=TKT PE=1 SV=3 | 3 | 3 | | 2.40E+07 | 4.40E+07 |
| O95833 | Chloride intracellular channel protein 3 OS=Homo sapiens GN=CLIC3 PE=1 SV=2 | 4 | 1 | | 1.30E+07 | 1.70E+07 |
| A8K4Z4 | cDNA FLJ75549, highly similar to Homo sapiens ribosomal protein, large, P0 (RPLP0), transcript variant 1, mRNA OS= | 3 | 5 | 5 | 4.50E+07 | 1.90E+08 |
| Q59EA2 | Coronin (Fragment) OS=Homo sapiens PE=2 SV=1 | 4 | 2 | 2 | 3.00E+07 | 5.90E+07 |
| J9II7 | Lamin B2, isoform CRA_a OS=Homo sapiens GN=LMNB2 PE=1 SV=1 | 2 | 3 | 2 | 3.10E+07 | 8.70E+07 |
| P13674 | Prolyl 4-hydroxylase subunit alpha-1 OS=Homo sapiens GN=P4HA1 PE=1 SV=2 | 3 | 3 | 4 | 5.90E+07 | 6.00E+07 |
| P14866 | Heterogeneous nuclear ribonucleoprotein L OS=Homo sapiens GN=HNRNPL PE=1 SV=2 | 4 | 4 | 3 | 4.10E+07 | 6.50E+07 |
| P21291 | Cysteine and glycine-rich protein 1 OS=Homo sapiens GN=CSRP1 PE=1 SV=3 | 4 | 3 | 4 | 4.80E+07 | 7.90E+07 |
| E9PRY8 | Elongation factor 1-delta OS=Homo sapiens GN=EEF1D PE=1 SV=1 | 3 | 2 | 1 | 3.40E+07 | 8.20E+07 |
| A8K8U1 | cDNA FLJ77762, highly similar to Homo sapiens cullin-associated and neddylation-dissociated 1 (CAND1), mRNA= | 3 | 2 | | 9.20E+06 | 3.30E+07 |
| Q9NP72 | Ras-related protein Rab-18 OS=Homo sapiens GN=RAB18 PE=1 SV=1 | 2 | 2 | 2 | 5.70E+06 | 3.50E+07 |
| B4DRM3 | cDNA FLJ54492, highly similar to Homo sapiens Eukaryotic translation initiation factor 4B OS=Homo sapiens PE=2 SV=4 | 3 | 1 | 2 | 1.20E+06 | 2.40E+06 |
| O15347 | High mobility group protein B3 OS=Homo sapiens GN=HMGB3 PE=1 SV=4 | 2 | 3 | | 3.00E+07 | 1.60E+08 |
| P14543 | Nidogen-1 OS=Homo sapiens GN=NID1 PE=1 SV=3 | 4 | 13 | 1 | 1.50E+08 | 3.10E+08 |
| Q99623 | Prohibitin-2 OS=Homo sapiens GN=PHB2 PE=1 SV=2 | 3 | 3 | 3 | 3.80E+07 | 1.40E+08 |
| P11171 | Protein 4.1 OS=Homo sapiens GN=EPB41 PE=1 SV=4 | 3 | | | 4.70E+07 | |
| Q14766 | Latent-transforming growth factor beta-binding protein 1 OS=Homo sapiens GN=LTBP1 PE=1 SV=4 | 3 | 8 | 2 | 8.60E+06 | |
| Q59GX9 | Ribosomal protein L5 variant (Fragment) OS=Homo sapiens PE=2 SV=1 | 3 | | | 3.10E+07 | 1.70E+08 |
| Q6FGS1 | TPD52L2 protein OS=Homo sapiens GN=TPD52L2 PE=1 SV=1 | 4 | | | 8.40E+07 | |
| B7Z525 | cDNA FLJ55039, moderately similar to Hepatoma-derived growth factor OS=Homo sapiens PE=2 SV=1 | 2 | | | 2.40E+07 | |
| Q00577 | Transcriptional activator protein Pur-alpha OS=Homo sapiens GN=PURA PE=1 SV=1 | 3 | 1 | | 1.50E+07 | 2.00E+07 |
| P83731 | 60S ribosomal protein L24 OS=Homo sapiens GN=RPL24 PE=1 SV=1 | 3 | 3 | | 4.10E+07 | 1.70E+08 |
| P62879 | Guanine nucleotide-binding protein G(I)/G(S)/G(T) subunit beta-2 OS=Homo sapiens GN=GNB2 PE=1 SV=3 | 2 | | | 1.40E+07 | |
| B4DPQ0 | Complement C1r subcomponent OS=Homo sapiens GN=C1R PE=1 SV=1 | 1 | | | 2.20E+07 | |

APPENDIX A-continued

| | | | | | |
|---|---|---|---|---|---|
| A0A024R1N4 | X-ray repair complementing defective repair in Chinese hamster cells 6 (Ku autoantigen, 70 kDa), isoform CRA_a OS= | 3 | 4 | 3.00E+07 | 1.00E+08 |
| A0A024R7B7 | CDC37 cell division cycle 37 homolog (S. cerevisiae), isoform CRA_a OS = Homo sapiens GN = CDC37 PE = 4 SV = 1 | 2 | 4 | 1.90E+07 | 5.90E+07 |
| D3DR65 | SPFH domain family, member 1, isoform CRA_a OS = Homo sapiens GN = SPFH1 PE = 4 SV = 1 | 1 | 2 | 1.30E+07 | 9.10E+07 |
| P38117 | Electron transfer flavoprotein subunit beta OS = Homo sapiens GN = ETFB PE = 1 SV = 3 | 4 | 2 | 6.70E+07 | 4.20E+07 |
| Q15075 | Early endosome antigen 1 OS = Homo sapiens GN = EEA1 PE = 1 SV = 2 | 4 | 3 | 1.20E+07 | 6.70E+08 |
| P02461 | Collagen alpha-1(III) chain OS = Homo sapiens GN = COL3A1 PE = 1 SV = 4 | 2 | 2 | 1.30E+08 | 6.70E+08 |
| Q01813 | ATP-dependent 6-phosphofructokinase, platelet type OS = Homo sapiens GN = PFKP PE = 1 SV = 2 | 2 | 3 | 3.00E+07 | 3.40E+07 |
| Q9H2U2 | Inorganic pyrophosphatase 2, mitochondrial OS = Homo sapiens GN = PPA2 PE = 1 SV = 2 | 2 | 4 | 3.10E+07 | 2.30E+07 |
| Q12797 | Aspartyl/asparaginyl beta-hydroxylase OS = Homo sapiens GN = ASPH PE = 1 SV = 3 | 3 | 1 | 5.30E+06 | |
| V9HWC9 | Superoxide dismutase [Cu—Zn] OS = Homo sapiens GN = HEL-S-44 PE = 2 SV = 1 | 1 | 3 | 9.70E+07 | 1.70E+08 |
| P16989 | Y-box-binding protein 3 OS = Homo sapiens GN = YBX3 PE = 1 SV = 4 | 1 | 2 | 2.50E+07 | |
| Q5S3G3 | MHC class I antigen OS = Homo sapiens GN = HLA-A PE = 2 SV = 1 | 1 | | | |
| D9HTE9 | Plasma membrane citrate carrier OS = Homo sapiens GN = SLC25A1 PE = 2 SV = 1 | 3 | 3 | 4.60E+07 | 9.40E+07 |
| P17858 | ATP-dependent 6-phosphofructokinase, liver type OS = Homo sapiens GN = PFKL PE = 1 SV = 6 | 2 | 2 | 3.30E+07 | 4.10E+07 |
| P62701 | 40S ribosomal protein S4, X isoform OS = Homo sapiens GN = RPS4X PE = 1 SV = 2 | 5 | 6 | 4.80E+07 | 1.30E+08 |
| B7Z4C3 | cDNA FLJ50805, highly similar to Erythrocyte membrane protein band 4.2 OS = Homo sapiens PE = 2 SV = 1 | 3 | | 3.10E+07 | |
| Q59F66 | Target of Nesh-SH3 OS = Homo sapiens GN = ABI3BP PE = 1 SV = 1 | 3 | 1 | 3.10E+07 | 6.40E+07 |
| Q53FE8 | cDNA FLJ36526 fis, clone TRACH2003347, highly similar to NSFL1 cofactor p47 (Fragment) OS = Homo sapiens PE = 2 SV | 4 | 1 | 1.10E+08 | 3.70E+07 |
| B5BU28 | Catenin beta-1 OS = Homo sapiens GN = CTNNB1 PE = 2 SV = 1 | 2 | | 2.30E+07 | |
| Q59FG9 | Chondroitin sulfate proteoglycan 2 (Versican) variant (Fragment) OS = Homo sapiens PE = 2 SV = 2 | 3 | 8 | 1.80E+07 | 2.70E+08 |
| P15880 | 40S ribosomal protein S2 OS = Homo sapiens GN = RPS2 PE = 1 SV = 1 | 3 | 4 | 4.00E+07 | 1.70E+08 |
| Q13753 | Laminin subunit gamma-2 OS = Homo sapiens GN = LAMC2 PE = 1 SV = 2 | 3 | 6 | 1.10E+07 | |
| Q5SSJ5 | Heterochromatin protein 1-binding protein 3 OS = Homo sapiens GN = HP1BP3 PE = 1 SV = 1 | 3 | 1 | 3.90E+07 | 4.70E+08 |
| D7UNW5 | Polypeptide N-acetylgalactosaminyltransferase OS = Homo sapiens GN = GALNT6 PE = 2 SV = 1 | 1 | | 4.40E+06 | |
| D3YTG3 | Citrate synthase, mitochondrial OS = Homo sapiens GN = CS PE = 1 SV = 1 | 3 | 3 | 5.30E+07 | 4.70E+08 |
| O75390 | Succinyl-CoA ligase [ADP/GDP-forming] subunit alpha, mitochondrial OS = Homo sapiens GN = SUCLG1 PE = 1 SV = 4 | 2 | 1 | 2.60E+07 | 7.10E+07 |
| P53597 | 40S ribosomal protein S6 OS = Homo sapiens GN = RPS6 PE = 2 SV = 1 | 1 | 1 | 3.20E+07 | 1.00E+08 |
| A2A3R6 | Thiosulfate sulfurtransferase OS = Homo sapiens GN = TST PE = 1 SV = 4 | 3 | 3 | 4.80E+07 | 1.40E+08 |
| Q16762 | Receptor protein-tyrosine kinase (Fragment) OS = Homo sapiens PE = 2 SV = 1 | 2 | 4 | 3.80E+07 | 1.70E+08 |
| A8K21T7 | T-complex protein 1 subunit gamma (Fragment) OS = Homo sapiens PE = 2 SV = 1 | 3 | 6 | 1.60E+07 | 4.50E+08 |
| Q59H77 | RAB8A, member RAS oncogene family, isoform CRA_a OS = Homo sapiens GN = RAB8A PE = 3 SV = 1 | 1 | | 2.30E+07 | |
| A0A024R7I3 | GTP-binding nuclear protein Ran (Fragment) OS = Homo sapiens GN = RAN PE = 1 SV = 1 | 3 | | 2.90E+06 | |
| J3KQF5 | Insulin-like growth factor-binding protein 1 OS = Homo sapiens GN = IGFBP1 PE = 1 SV = 1 | 3 | 2 | 4.80E+07 | 1.60E+08 |
| P08833 | Membrane-associated progesterone receptor component 1 OS = Homo sapiens GN = PGRMC1 PE = 1 SV = 3 | 5 | 4 | 6.50E+07 | 4.70E+08 |
| O00264 | 26S proteasome non-ATPase regulatory subunit 4 OS = Homo sapiens GN = PSMD4 PE = 1 SV = 1 | 4 | 3 | 3.60E+07 | 1.20E+08 |
| A8K6Q8 | cDNA FLJ75881, highly similar to Homo sapiens transferrin receptor (p90, CD71) (TFRC), mRNA OS = Homo sapiens PE | 5 | | 1.70E+07 | 6.60E+07 |
| Q6ZN17 | Protein lin-28 homolog B OS = Homo sapiens GN = LIN28B PE = 1 SV = 1 | 1 | | 4.70E+07 | |
| B7ZKY6 | Ig mu chain C region OS = Homo sapiens GN = IGHM PE = 1 SV = 1 | 2 | 5 | 4.90E+07 | 1.10E+08 |
| P62979 | Ubiquitin-40S ribosomal protein S27a OS = Homo sapiens GN = RPS27A PE = 1 SV = 2 | 2 | 4 | 1.20E+08 | 3.80E+08 |
| P05023 | Sodium/potassium-transporting ATPase subunit alpha-1 OS = Homo sapiens GN = ATP1A1 PE = 1 SV = 1 | 3 | | 9.30E+06 | |
| A0N5G5 | Rheumatoid factor D5 light chain (Fragment) OS = Homo sapiens GN = V<kappa>3 PE = 2 SV = 1 | 1 | | 1.40E+07 | 6.50E+07 |
| Q92930 | Ras-related protein Rab-8B OS = Homo sapiens GN = RAB8B PE = 1 SV = 1 | | | 1.70E+06 | |
| A0A024R4E5 | High density lipoprotein binding protein (Vigilin), isoform CRA_a OS = Homo sapiens GN = HDLBP PE = 1 SV = 1 | 3 | 1 | 1.60E+07 | 3.60E+07 |
| Q5VWC4 | | | | 9.50E+07 | |
| P62917 | 60S ribosomal protein L8 OS = Homo sapiens GN = RPL8 PE = 1 SV = 2 | 2 | 4 | 8.00E+07 | 2.30E+08 |
| A0A087WYJ9 | Lymphocyte cytosolic protein 1 (L-plastin), isoform CRA_a OS = Homo sapiens GN = LCP1 PE = 4 SV = 1 | 3 | 3 | 3.80E+07 | 8.60E+07 |
| A0A024RDT4 | Enoyl-CoA hydratase, mitochondrial OS = Homo sapiens GN = ECHS1 PE = 1 SV = 4 | 2 | 3 | 6.00E+06 | 7.20E+07 |
| P30084 | Heterogeneous nuclear ribonucleoprotein U-like protein 2 OS = Homo sapiens GN = HNRNPUL2 PE = 1 SV = 1 | 3 | 4 | 2.20E+07 | 5.40E+07 |
| Q14240 | L-lactate dehydrogenase B chain OS = Homo sapiens GN = LDHB PE = 1 SV = 2 | 2 | 3 | 2.50E+07 | 8.90E+07 |
| Q1KMD3 | Protein kinase C delta-binding protein OS = Homo sapiens GN = PRKCDBP PE = 1 SV = 3 | 3 | 2 | 7.20E+06 | 1.80E+07 |
| P07195 | Prolyl 4-hydroxylase subunit alpha-2 OS = Homo sapiens GN = P4HA2 PE = 1 SV = 1 | 3 | 5 | 3.00E+07 | 1.90E+08 |
| Q969G5 | | 4 | 1 | 3.10E+07 | |
| O15460 | | | | 2.40E+07 | |

APPENDIX A-continued

| ID | Description | | | | |
|---|---|---|---|---|---|
| Q6IPH7 | RPL14 protein OS = Homo sapiens GN = RPL14 PE = 1 SV = 1 | 3 | 3 | 5.80E+07 | 1.70E+08 |
| P37837 | Transaldolase OS = Homo sapiens GN = TALDO1 PE = 1 SV = 1 | 3 | 2 | 4.80E+07 | 7.60E+07 |
| B2RAH5 | Protein phosphatase 1 regulatory subunit OS = Homo sapiens PE = 2 SV = 1 | 2 | 1 | 1.50E+06 |  |
| O43493 | Trans-Golgi network integral membrane protein 2 OS = Homo sapiens GN = TGOLN2 PE = 1 SV = 2 | 2 |  | 1.60E+07 | 5.70E+07 |
| P34897 | Serine hydroxymethyltransferase, mitochondrial OS = Homo sapiens GN = SHMT2 PE = 1 SV = 3 | 3 |  | 2.10E+07 |  |
| A1L0S7 | TNS1 protein (Fragment) OS = Homo sapiens GN = TNS1 PE = 2 SV = 1 | 2 | 3 | 3.00E+07 | 1.20E+08 |
| A8MXP9 | Matrin-3 OS = Homo sapiens GN = MATR3 PE = 1 SV = 1 | 3 | 3 | 1.10E+07 | 3.40E+07 |
| P23246 | Splicing factor, proline- and glutamine-rich OS = Homo sapiens GN = SFPQ PE = 1 SV = 2 | 2 | 9 | 2.50E+07 | 1.20E+08 |
| P12109 | Collagen alpha-1(V) chain OS = Homo sapiens GN = COL6A1 PE = 1 SV = 3 | 2 | 6 | 3.70E+07 | 2.40E+08 |
| Q6FII1 | Glutathione S-transferase kappa 1 OS = Homo sapiens GN = LOC51064 PE = 2 SV = 1 | 2 | 2 | 2.20E+07 | 8.90E+07 |
| Q96KP4 | Cytosolic non-specific dipeptidase OS = Homo sapiens GN = CNDP2 PE = 1 SV = 2 | 3 | 1 | 1.80E+07 | 6.80E+07 |
| P60866 | 40S ribosomal protein S20 OS = Homo sapiens GN = RPS20 PE = 1 SV = 1 | 3 | 2 | 3.50E+07 | 1.40E+08 |
| Q9Y678 | Coatomer subunit gamma-1 OS = Homo sapiens GN = COPG1 PE = 1 SV = 1 | 4 | 3 | 2.90E+07 | 5.40E+07 |
| P27635 | 60S ribosomal protein L10 OS = Homo sapiens GN = RPL10 PE = 1 SV = 1 | 3 | 1 | 1.70E+07 | 8.90E+07 |
| B4DLV7 | cDNA FLJ60299, highly similar to Rab GDP dissociation inhibitor beta OS = Homo sapiens PE = 2 SV = 1 | 3 | 2 | 2.60E+07 | 4.40E+07 |
| P02792 | Ferritin light chain OS = Homo sapiens GN = FTL PE = 1 SV = 2 | 1 | 1 | 2.70E+07 | 3.20E+08 |
| Q9UHD8 | Septin-9 OS = Homo sapiens GN = SEPT9 PE = 1 SV = 2 | 3 |  | 2.30E+07 | 4.60E+07 |
| Q53GG0 | LETM1 and EF = hand domain-containing protein 1, mitochondrial OS = Homo sapiens GN = LETM1 PE = 1 SV = 1 | 2 |  | 1.90E+07 | 6.50E+07 |
| O95202 | | 1 |  | 2.20E+07 |  |
| A0A024R4H0 | Procollagen-lysine 1, 2-oxoglutarate 5-dioxygenase 1, isoform CRA_a OS = Homo sapiens GN = PLOD1 PE = 4 SV = 1 | 3 | 3 | 2.10E+07 | 8.00E+07 |
| A8K3Q7 | Annexin OS = Homo sapiens PE = 2 SV = 1 | 3 |  | 9.80E+06 | 2.60E+07 |
| I0B0K7 | Truncated profilaggrin OS = Homo sapiens GN = FLG PE = 4 SV = 1 | 2 | 2 | 1.40E+06 |  |
| H3BQK9 | Microtubule-actin cross-linking factor 1, isoforms 1/2/3/5 OS = Homo sapiens GN = MACF1 PE = 1 SV = 1 | 2 |  | 1.60E+07 | 1.40E+07 |
| P84098 | 60S ribosomal protein L19 OS = Homo sapiens GN = RPL19 PE = 1 SV = 1 | 2 | 2 | 2.60E+07 | 2.20E+08 |
| B2R9K8 | cDNA, FLJ94440, highly similar to Homo sapiens chaperonin containing TCP1, subunit 6A (zeta 1)(CCT6A), mRNA OS = | 3 | 2 | 1.40E+07 | 4.60E+07 |
| P50990 | T-complex protein 1 subunit theta OS = Homo sapiens GN = CCT8 PE = 1 SV = 4 | 2 | 2 | 1.80E+07 | 6.80E+07 |
| Q59F19 | Ribosomal protein L12 variant (Fragment) OS = Homo sapiens PE = 2 SV = 1 | 3 | 3 | 1.90E+07 | 5.60E+07 |
| Q59EP2 | Angiotensinogen variant (Fragment) OS = Homo sapiens PE = 2 SV = 1 | 2 | 1 | 3.80E+07 | 7.30E+07 |
| Q15643 | Thyroid receptor interacting protein 11 OS = Homo sapiens GN = TRIP11 PE = 1 SV = 3 | 1 |  | 7.10E+06 |  |
| R4GMU1 | Mitotic checkpoint protein BUB3 OS = Homo sapiens GN = BUB3 PE = 1 SV = 1 | 3 | 2 | 1.60E+07 | 2.20E+07 |
| O43684 | Mitotic checkpoint protein BUB3 OS = Homo sapiens GN = BUB3 PE = 1 SV = 1 | 3 |  | 9.60E+06 | 2.10E+07 |
| J3QQX2 | Rho GDP-dissociation inhibitor 1 OS = Homo sapiens GN = ARHGDIA PE = 1 SV = 1 | 1 | 2 | 4.10E+07 | 1.60E+08 |
| O00159 | Unconventional myosin-Ic OS = Homo sapiens GN = MYO1C PE = 1 SV = 4 | 4 | 3 | 1.40E+07 | 7.70E+07 |
| Q53207 | 60S ribosomal protein L9 OS = Homo sapiens GN = RPL9 PE = 2 SV = 1 | 2 | 2 | 2.90E+07 | 8.20E+07 |
| Q59GX2 | BAG family molecular chaperone regulator 3 OS = Homo sapiens GN = BAG3 PE = 1 SV = 3 | 3 | 5 | 1.00E+08 | 3.10E+08 |
| I2G9F9 | Solute carrier family 2 (Facilitated glucose transporter), member 1 variant (Fragment) OS = Homo sapiens PE = 2 SV = 1 | 2 | 2 | 5.20E+07 | 2.30E+08 |
| Q9HBB3 | MHC class I antigen OS = Homo sapiens GN = HLA-C PE = 2 SV = 1 | 4 | 4 | 7.80E+07 | 2.60E+08 |
| P38159 | RNA-binding motif protein, X chromosome OS = Homo sapiens GN = RBMX PE = 1 SV = 3 | 3 | 2 | 3.40E+07 | 1.30E+08 |
| Q597H1 | Transformation related protein 14 OS = Homo sapiens GN = TRG14 PE = 2 SV = 1 | 3 | 1 | 2.10E+07 | 1.70E+08 |
| M0QXB5 | Persulfide dioxygenase ETHE1, mitochondrial OS = Homo sapiens GN = ETHE1 PE = 1 SV = 1 | 3 | 2 | 9.10E+07 | 1.30E+08 |
| Q05639 | Elongation factor 1-alpha 2 OS = Homo sapiens GN = EEF1A2 PE = 1 SV = 1 | 2 |  | 7.40E+07 | 4.10E+07 |
| O95817 | BAG family molecular chaperone regulator 3 OS = Homo sapiens GN = BAG3 PE = 1 SV = 3 | 2 |  | 2.80E+08 |  |
| O94919 | Endonuclease domain-containing 1 protein OS = Homo sapiens GN = ENDOD1 PE = 1 SV = 2 |  | 1 | 1.40E+07 |  |
| P42126 | Enoyl-CoA delta isomerase 1, mitochondrial OS = Homo sapiens GN = ECI1 PE = 1 SV = 1 | 2 | 1 | 8.30E+06 |  |
| B2RB23 | cDNA, FLJ75700, highly similar to Homo sapiens complement component 1, q subcomponent binding protein (C1QBP | 1 | 1 | 1.90E+07 | 4.60E+07 |
| D6RCF4 | cDNA FLJ95265, highly similar to Homo sapiens acetyl-Coenzyme A acyltransferase 2 (mitochondrial 3-oxoacyl-Coen | 2 | 2 | 2.10E+07 | 7.10E+07 |
| B2RSH0 | CDGSH iron-sulfur domain containing protein 2 OS = Homo sapiens GN = CISD2 PE = 1 SV = 1 | 1 | 2 | 1.30E+07 | 5.50E+07 |
| P04181 | Ornithine aminotransferase, mitochondrial OS = Homo sapiens GN = OAT PE = 1 SV = 1 | 2 |  | 4.00E+08 |  |
| A8K651 | cDNA FLJ75700, highly similar to Homo sapiens complement component 1 | 1 |  | 2.00E+06 |  |
| P51884 | Lumican OS = Homo sapiens GN = LUM PE = 1 SV = 2 | 2 | 3 | 1.60E+07 | 6.70E+07 |
| Q05707 | Collagen alpha-1(XIV) chain OS = Homo sapiens GN = COL14A1 PE = 1 SV = 3 | 3 | 9 | 2.40E+07 | 5.70E+08 |
| P25815 | Protein S100-P OS = Homo sapiens GN = S100P PE = 1 SV = 2 | 3 | 22 | 3.00E+07 | 5.10E+08 |
| A0A024R374 | Cathepsin B, isoform CRA_a OS = Homo sapiens GN = CTSB PE = 3 SV = 1 | 3 | 4 | 1.30E+08 | 3.00E+08 |
| | | 3 | 3 | 1.30E+08 | 3.20E+08 |

APPENDIX A-continued

| ID | Description | | | |
|---|---|---|---|---|
| P62888 | 60S ribosomal protein L30 OS = Homo sapiens GN = RPL30 PE = 1 SV = 2 | 1 | 4 | 2.80E+07 | 1.60E+08 |
| P49419 | Alpha-aminoadipic semialdehyde dehydrogenase OS = Homo sapiens GN = ALDH7A1 PE = 1 SV = 5 | 2 | 3 | 1.90E+07 | |
| P15104 | Glutamine synthetase OS = Homo sapiens GN = GLUL PE = 1 SV = 4 | 2 | 3 | 2.60E+07 | |
| P62263 | 40S ribosomal protein S14 OS = Homo sapiens GN = RPS14 PE = 1 SV = 3 | 2 | 4 | 3.70E+07 | 1.40E+08 |
| P53618 | Coatomer subunit beta OS = Homo sapiens GN = COB1 PE = 1 SV = 1 | 2 | 4 | 1.10E+07 | 2.50E+07 |
| A8K3C3 | T-complex protein 1 subunit delta OS = Homo sapiens PE = 2 SV = 1 | 2 | 3 | 3.30E+07 | 1.70E+07 |
| B2RBR9 | cDNA, FLJ95650, highly similar to Homo sapiens karyopherin (importin) beta 1 (KPNB1), mRNA OS = Homo sapiens PE = 2 | 2 | 5 | 1.90E+07 | 4.60E+07 |
| Q6N091 | Putative uncharacterized protein DKFZp686C02220 (Fragment) OS = Homo sapiens GN = DKFZp686C02220 PE = 2 SV = 1 | 1 | 1 | 1.80E+07 | |
| A0A0A1HAW | H. sapiens ras-related Hrab2 protein OS = Homo sapiens PE = 2 SV = 1 | 2 | 2 | 1.80E+07 | 4.30E+07 |
| A0A024R1Q8 | Ribosomal protein L23, isoform CRA_b OS = Homo sapiens GN = RPL23 PE = 3 SV = 1 | 2 | 1 | 1.80E+07 | 1.70E+08 |
| Q9U1U6 | Drebrin-like protein OS = Homo sapiens GN = DBNL PE = 1 SV = 1 | 2 | 1 | 1.50E+07 | 3.00E+07 |
| Q14789 | Golgin subfamily B member 1 OS = Homo sapiens GN = GOLGB1 PE = 1 SV = 2 | 3 | 1 | 3.00E+06 | 5.60E+07 |
| A0A024R451 | Serpin peptidase inhibitor, clade E (Nexin, plasminogen activator inhibitor type 1), member 2, isoform CRA_a OS = Ho | 2 | | 5.60E+07 | |
| P17987 | T-complex protein 1 subunit alpha OS = Homo sapiens GN = TCP1 PE = 1 SV = 1 | 2 | 1 | 1.90E+07 | |
| B2RE46 | cDNA, FLJ96923, highly similar to Homo sapiens ribophorin II (RPN2), mRNA OS = Homo sapiens PE = 2 SV = 1 | 2 | 3 | 2.80E+07 | 1.00E+08 |
| Q06323 | Proteasome activator complex subunit 1 OS = Homo sapiens GN = PSME1 PE = 1 SV = 1 | 2 | 1 | 2.90E+07 | |
| O75396 | Vesicle-trafficking protein SEC22b OS = Homo sapiens GN = SEC22B PE = 1 SV = 4 | 2 | 1 | 2.20E+07 | 4.10E+08 |
| P46977 | Dolichyl-diphosphooligosaccharide-protein glycosyltransferase subunit STT3A OS = Homo sapiens GN = STT3A PE = 1 S | 2 | 2 | 1.20E+07 | 2.50E+07 |
| A0A024R5X2 | HCG2001986, isoform CRA_a OS = Homo sapiens GN = hCG_2001986 PE = 4 SV = 1 | 4 | 4 | 2.40E+07 | 1.20E+08 |
| D3DR6 | Inter-alpha (Globulin) inhibitor H2, isoform CRA_a OS = Homo sapiens GN = ITIH2 PE = 4 SV = 1 | 2 | 5 | 4.10E+07 | 1.40E+08 |
| A0A087X0X3 | Heterogeneous nuclear ribonucleoprotein M OS = Homo sapiens GN = HNRNPM PE = 1 SV = 1 | 2 | 4 | 1.20E+07 | 1.10E+08 |
| A0A075MGT | HLA class 1 antigen OS = Homo sapiens GN = HLA-B PE = 3 SV = 1 | 1 | 3 | 1.60E+07 | 1.70E+08 |
| B4E1C2 | Kininogen 1, isoform CRA_b OS = Homo sapiens GN = KNG1 PE = 2 SV = 1 | 2 | 2 | 2.00E+07 | 4.60E+07 |
| P03973 | Antileukoproteinase OS = Homo sapiens GN = SLPI PE = 1 SV = 1 | 1 | 1 | 1.70E+07 | 1.80E+07 |
| V9HW55 | Epididymis secretory protein Li 275 OS = Homo sapiens GN = HEL-S-275 PE = 2 SV = 1 | 2 | | 3.50E+07 | |
| Q8NC56 | LEM domain-containing protein 2 OS = Homo sapiens GN = LEMD2 PE = 1 SV = 1 | 2 | 1 | 1.10E+07 | 1.50E+07 |
| V9HW90 | Epididymis luminal protein 75 OS = Homo sapiens GN = HEL-75 PE = 2 SV = 1 | 2 | 1 | 2.10E+07 | |
| P78371 | T-complex protein 1 subunit beta OS = Homo sapiens GN = CCT2 PE = 1 SV = 4 | 2 | 2 | 8.00E+06 | |
| A0A024R687 | Pleckstrin homology domain containing, family C (With FERM domain) member 1, isoform CRAb OS = Homo sapiens | 2 | 3 | 2.30E+07 | 4.20E+07 |
| A0A024R0E5 | Capping protein (Actin filament) muscle Z-line, alpha 1, isoform CRA_a OS = Homo sapiens GN = CAPZA1 PE = 4 SV = 1 | 2 | 5 | 6.20E+07 | 1.30E+08 |
| A0A024R1S8 | LIM and SH3 protein 1, isoform CRA_b OS = Homo sapiens GN = LASP1 PE = 4 SV = 1 | 3 | | 4.50E+07 | |
| B2R6V9 | cDNA, FLJ93141, highly similar to Homo sapiens coagulation factor XIII, A1 polypeptide (F13A1), mRNA OS = Homo sa | 3 | 1 | 8.80E+06 | 8.60E+07 |
| Q06210 | Glutamine-fructose-6-phosphate aminotransferase [isomerizing] 1 OS = Homo sapiens GN = GFPT1 PE = 1 SV = 3 | 2 | | 9.30E+06 | |
| O76021 | Ribosomal L1 domain-containing protein 1 OS = Homo sapiens GN = RSL1D1 PE = 1 SV = 1 | 2 | | 6.10E+06 | |
| B2R4C0 | 60S ribosomal protein L18a OS = Homo sapiens PE = 2 SV = 1 | 2 | 3 | 4.90E+07 | 1.10E+08 |
| P62316 | Small nuclear ribonucleoprotein Sm D2 OS = Homo sapiens GN = SNRPD2 PE = 1 SV = 1 | 2 | 2 | 4.40E+07 | 1.10E+08 |
| P25398 | 40S ribosomal protein S12 OS = Homo sapiens GN = RPS12 PE = 1 SV = 3 | 3 | 4 | 6.50E+07 | 2.10E+08 |
| Q96N66 | Lysophospholipid acyltransferase 7 OS = Homo sapiens GN = MBOAT7 PE = 1 SV = 2 | 2 | 1 | 2.10E+07 | |
| O60437 | Periplakin OS = Homo sapiens GN = PPL PE = 1 SV = 4 | 2 | 19 | 2.20E+07 | |
| P99999 | Cytochrome c OS = Homo sapiens GN = CYCS PE = 1 SV = 2 | 2 | 2 | 7.10E+07 | 8.90E+07 |
| P35611 | Alpha-adducin OS = Homo sapiens GN = ADD1 PE = 1 SV = 2 | 2 | 1 | 6.50E+06 | |
| Q08257 | Quinone oxidoreductase OS = Homo sapiens GN = CRYZ PE = 1 SV = 1 | 2 | 1 | 1.60E+07 | 4.70E+07 |
| V9HWA6 | Epididymis luminal protein 32 OS = Homo sapiens GN = HEL32 PE = 2 SV = 1 | 2 | | 1.20E+07 | 5.30E+07 |
| B2R4R9 | HCG26477 OS = Homo sapiens GN = RPS28 PE = 2 SV = 1 | 2 | 3 | 1.40E+07 | 7.80E+07 |
| Q53GW1 | Vesicle transport-related protein isoform a variant (Fragment) OS = Homo sapiens PE = 2 SV = 1 | 2 | 1 | 6.50E+06 | |
| K7E500 | Histone H3.3 (Fragment) OS = Homo sapiens GN = H3F3B PE = 1 SV = 1 | 2 | | 1.20E+09 | |
| Q15717 | ELAV-like protein 1 OS = Homo sapiens GN = ELAVL1 PE = 1 SV = 2 | 2 | 4 | 2.50E+07 | 3.50E+07 |
| Q4LE36 | ACLY variant protein (Fragment) OS = Homo sapiens GN = ACLY variant protein PE = 2 SV = 1 | 2 | 2 | 7.30E+06 | 2.10E+07 |
| Q14554 | Protein disulfide-isomerase A5 OS = Homo sapiens GN = PDIA5 PE = 1 SV = 1 | 2 | 2 | 4.00E+07 | |
| Q93084 | Sarcoplasmic/endoplasmic reticulum calcium ATPase 3 OS = Homo sapiens GN = ATP2A3 PE = 1 SV = 2 | 2 | | 3.70E+07 | |
| B4E290 | cDNA FLJ50039, highly similar to Homo sapiens solute carrier family 25, member 24, transcript variant 1, mRNA OS= | 2 | 2 | 2.00E+07 | 3.50E+07 |
| P17302 | Gap junction alpha-1 protein OS = Homo sapiens GN = GJA1 PE = 1 SV = 2 | 1 | 3 | 5.30E+07 | 1.80E+08 |
| A0A0A0MSG | Four and a half LIM domains protein 2 OS = Homo sapiens GN = FHL2 PE = 1 SV = 1 | 2 | 2 | 1.60E+07 | |

APPENDIX A-continued

| | | | | | |
|---|---|---|---|---|---|
| Q96GT9 | X antigen family member 2 OS = Homo sapiens GN = XAGE2 PE = 1 SV = 1 | 2 | 1 | 5.30E+06 | |
| M0R0R2 | 40S ribosomal protein S5 OS = Homo sapiens GN = RPS5 PE = 1 SV = 1 | 2 | 1 | 5.90E+07 | 1.20E+08 |
| P02747 | Complement C1q subcomponent subunit C OS = Homo sapiens GN = C1QC PE = 1 SV = 3 | 2 | 3 | 3.30E+07 | 1.10E+08 |
| Q00765 | Receptor expression-enhancing protein 5 OS = Homo sapiens GN = REEP5 PE = 1 SV = 3 | 2 | 2 | 3.00E+07 | 1.50E+08 |
| P39023 | 60S ribosomal protein L3 OS = Homo sapiens GN = RPL3 PE = 1 SV = 2 | 2 | 3 | 6.60E+07 | 1.70E+08 |
| O15143 | Actin-related protein 2/3 complex subunit 1B OS = Homo sapiens GN = ARPC1B PE = 1 SV = 3 | 1 | 8 | 2.40E+07 | 1.90E+07 |
| A0A024R944 | Serpin peptidase inhibitor, clade C (Antithrombin), member 1, isoform CRA_a OS = Homo sapiens GN = SERPINC1 PE = 3 | 2 | 6 | 2.40E+07 | 5.40E+07 |
| A0A024R8N2 | Integrin beta OS = Homo sapiens GN = ITGB4 PE = 3 SV = 1 | 2 | 1 | 1.60E+06 | 2.90E+07 |
| P04899 | Guanine nucleotide-binding protein G(i) subunit alpha-2 OS = Homo sapiens GN = GNAI2 PE = 1 SV = 3 | 2 | 9 | | 8.00E+07 |
| P06703 | Protein S100-A6 Os = Homo sapiens GN = S100A6 PE = 1 SV = 1 | 2 | 3 | 2.50E+07 | 7.30E+08 |
| Q9Y4K0 | Lysyl oxidase homolog 2 OS = Homo sapiens GN = LOXL2 PE = 1 SV = 1 | 2 | 3 | 2.50E+08 | 6.60E+07 |
| B7Z6Q5 | Beta-galactosidase OS = Homo sapiens PE = 2 SV = 1 | 2 | 7 | 1.60E+07 | |
| Q9NZN4 | EH domain containing protein 2 OS = Homo sapiens GN = EHD2 PE = 1 SV = 2 | 2 | 1 | 3.10E+07 | 8.90E+07 |
| Q9BRP8 | Partner of Y14 and mago OS = Homo sapiens GN = WIBG PE = 1 SV = 1 | 2 | | 9.50E+06 | |
| B3RFR9 | Hydroxysteroid (17-beta) dehydrogenase 1 isoform OS = Homo sapiens PH = 2 SV = 1 | 2 | | 1.70E+06 | |
| O95881 | Thioredoxin domain-containing protein 12 OS = Homo sapiens GN = TXNDC12 PE = 1 SV = 1 | 1 | | 7.70E+06 | |
| P26373 | 60S ribosomal protein L13 OS = Homo sapiens GN = RPL13 PE = 1 SV = 4 | 2 | 2 | 2.90E+07 | 1.80E+08 |
| Q16270 | Insulin-like growth factor-binding protein 7 OS = Homo sapiens GN = IGFBP7 PE = 1 SV = 1 | 2 | 4 | 5.00E+06 | 1.60E+07 |
| P05198 | Eukaryotic translation initiation factor 2 subunit 1 OS = Homo sapiens GN = EIF2S1 PE = 1 SV = 3 | 2 | 1 | 3.40E+07 | |
| A0A024R3D8 | Acetyltransferase component of pyruvate dehydrogenase complex OS = Homo sapiens GN = DLAT PE = 3 SV = 1 | 2 | | 1.80E+07 | |
| Q5U000 | Cathepsin Z OS = Homo sapiens PE = 2 SV = 1 | 2 | | 2.30E+07 | |
| O14818 | Proteasome subunit alpha type-7 OS = Homo sapiens GN = PSMA7 PE = 1 SV = 1 | 2 | | 1.70E+07 | |
| A0A024R8L7 | Acyl coenzyme A oxidase OS = Homo sapiens GN = ACOX1 PE = 3 SV = 1 | 1 | 3 | 2.40E+07 | 1.00E+07 |
| P26447 | Protein S100-A4 OS = Homo sapiens GN = S100A4 PE = 1 SV = 1 | 2 | 3 | 2.90E+08 | 8.40E+08 |
| P0DME0 | Protein SETSIP OS = Homo sapiens GN = SETSIP PE = 1 SV = 1 | 1 | | 3.80E+07 | |
| P05164 | Myeloperoxidase OS = Homo sapiens GN = MPO PE = 1 SV = 1 | 3 | | 2.50E+07 | |
| P36551 | Oxygen-dependent coproporphyrinogen-III oxidase, mitochondrial OS = Homo sapiens GN = CPOX PE = 1 SV = 3 | 2 | 1 | 1.00E+07 | 1.50E+07 |
| A0A024R2M | Oxidative-stress responsive 1, isoform CRA_a OS = Homo sapiens GN = OXSR1 PE = 4 SV = 1 | 2 | | 4.50E+06 | |
| Q27J81 | Inverted formin-2 OS = Homo sapiens GN = INF2 PE = 1 SV = 2 | 1 | | 6.60E+06 | |
| P27144 | Adenylate kinase 4, mitochondrial OS = Homo sapiens GN = AK4 PE = 1 SV = 1 | 2 | 2 | 3.00E+07 | 4.30E+07 |
| E9PI68 | Signal peptidase complex subunit 2 OS = Homo sapiens GN = SPCS2 PE = 1 SV = 1 | 1 | | 3.20E+06 | |
| A8K2N0 | cDNA FLJ77835, highly similar to Homo sapiens complement component 1, s subcomponent (C1S), transcript variant | 2 | | 6.80E+06 | |
| Q13596 | Sorting nexin-1 OS = Homo sapiens GN = SNX1 PE = 1 SV = 3 | 2 | | 3.10E+07 | |
| L7N2F9 | Uncharacterized protein (Fragment) OS = Homo sapiens PE = 4 SV = 1 | | | | |
| P50502 | Hsc70-interacting protein (Fragment) OS = Homo sapiens GN = ST13 PE = 1 SV = 2 | 3 | 1 | 3.00E+07 | 6.40E+07 |
| P39060 | Collagen alpha-1(XVIII) chain OS = Homo sapiens GN = COL18A1 PE = 1 SV = 5 | 2 | 3 | 1.60E+07 | 4.90E+07 |
| E9LUH4 | Mutant methyl CpG binding protein 2 variant 1 OS = Homo sapiens GN = MECP2 PE = 2 SV = 1 | 1 | | 6.80E+06 | |
| V9HW37 | Epididymis secretory protein Li 69 OS = Homo sapiens GN = HEL-S-69 PE = 1 SV = 1 | 3 | 1 | 2.40E+07 | |
| B2R4F3 | cDNA, FLJ92068, highly similar to Homo sapiens Rho GDP dissociation inhibitor (GDI) beta (ARHGDIB), mRNA OS = Ho | 3 | 1 | 2.00E+07 | |
| A0A024R6Z0 | Dynein, cytoplasmic 1, light intermediate chain 2, isoform CRA_a OS = Homo sapiens GN = DYNC1L12 PE = 4 SV = 1 | 2 | 5 | 5.30E+06 | |
| Q59E85 | Caveolin (Fragment) OS = Homo sapiens PE = 2 SV = 1 | 1 | 2 | 9.20E+07 | 4.90E+08 |
| E5KJ15 | Dynamin-like 120 kDa protein, mitochondrial OS = Homo sapiens GN = OPA1 PE = 1 SV = 1 | 2 | 1 | 2.10E+06 | 3.80E+07 |
| Q59EF6 | Calpain 2, large [catalytic] subunit variant (Fragment) OS = Homo sapiens PE = 2 SV = 1 | 1 | 3 | 4.30E+07 | 6.20E+07 |
| P05109 | Protein S100-A8 OS = Homo sapiens GN = S100A8 PE = 1 SV = 1 | 2 | 2 | 5.60E+07 | 2.70E+08 |
| O15173 | Membrane-associated progesterone receptor component 2 OS = Homo sapiens GN = PGRMC2 PE = 1 SV = 1 | 1 | 5 | 4.90E+07 | 2.00E+08 |
| Q59EP1 | Annexin (Fragment) OS = Homo sapiens PE = 2 SV = 1 | 1 | 2 | 8.00E+06 | |
| Q8211 | ATP-dependent RNA helicase A OS = Homo sapiens GN = DHX9 PE = 1 SV = 4 | 2 | 2 | 2.10E+06 | 4.10E+07 |
| B4DZF2 | cDNA FLJ59571, highly similar to Eukaryotic translation initiation factor 4gamma 2 OS = Homo sapiens PE = 2 SV = 1 | 1 | | 8.60E+05 | 2.30E+06 |
| B2RD79 | Ubiquitin carboxyl-terminal hydrolase OS = Homo sapiens PE = 2 SV = 1 | 2 | 1 | 2.00E+07 | 1.10E+07 |
| P08754 | Guanine nucleotide-binding protein G(k) subunit alpha OS = Homo sapiens GN = GNAI3 PE = 1 SV = 3 | 1 | | | |
| Q9Y5M8 | Signal recognition particle receptor subunit beta OS = Homo sapiens GN = SRPRB PE = 1 SV = 3 | 1 | 1 | 1.60E+07 | |
| P02649 | Apolipoprotein E OS = Homo sapiens GN = APOE PE = 1 SV = 1 | 1 | | 1.80E+07 | |
| P63096 | Guanine nucleotide-binding protein G(i) subunit alpha-1 OS = Homo sapiens GN = GNAI1 PE = 1 SV = 2 | 1 | 4 | 1.40E+07 | 8.20E+07 |

APPENDIX A-continued

| ID | Description | | | | |
|---|---|---|---|---|---|
| Q00325 | Phosphate carrier protein, mitochondrial OS = Homo sapiens GN = SLC25A3 PE = 1 SV = 2 | 2 | 2 | 1.70E+08 | 3.60E+08 |
| P52209 | 6-phosphogluconate dehydrogenase, decarboxylating OS = Homo sapiens GN = PGD PE = 1 SV = 3 | 2 | 3 | 3.60E+07 | 1.60E+08 |
| A8K8F6 | cDNA FLJ78417, highly similar to Homo sapiens low density lipoprotein receptor-related protein associated protein 1 | 3 | 1 | 2.70E+07 | 7.10E+07 |
| P35268 | 60S ribosomal protein L22 OS = Homo sapiens GN = RPL22 PE = 1 SV = 2 | 2 | 2 | 7.30E+07 | 1.70E+08 |
| P62906 | 60S ribosomal protein L10a OS = Homo sapiens GN = RPL10A PE = 1 SV = 2 | 4 | 3 | 6.80E+07 | 1.60E+08 |
| B7Z8Q2 | cDNA FLJ55606, highly similar to Alpha-2-HS-glycoprotein OS = Homo sapiens PE = 2 SV = 1 | 2 | 1 | 5.20E+07 | 1.20E+08 |
| B4DPZ4 | cDNA FLJ60782, highly similar to Rho-GTPase-activating protein 1 OS = Homo sapiens PE = 2 SV = 1 | 1 | | 1.90E+07 | |
| H0YMV8 | 40S ribosomal protein S27 OS = Homo sapiens GN = RPS27L PE = 1 SV = 1 | 1 | | 2.00E+07 | |
| A2KBB9 | Anti-(ED-B) scFV (Fragment) OS = Homo sapiens PE = 2 SV = 1 | | | 7.10E+06 | 3.70E+07 |
| Q14520 | Hyaluronan-binding protein 2 OS = Homo sapiens GN = HABP2 PE = 1 SV = 1 | 2 | | 2.10E+07 | |
| B7Z268 | Single-stranded DNA binding protein 1, isoform CRA_c OS = Homo sapiens GN = SSBP1 PE = 2 SV = 1 | 1 | 1 | 2.00E+07 | 4.70E+07 |
| P12110 | Collagen alpha-2(VI) chain OS = Homo sapiens GN = COL6A2 PE = 1 SV = 4 | 2 | 6 | 5 | 1.50E+07 | 1.70E+08 |
| A0A024R233 | Tight junction protein 2 (Zona occludens 2), isoform CRA_a OS = Homo sapiens GN = TJP2 PE = 4 SV = 1 | | | 2.40E+06 | |
| P62851 | 40S ribosomal protein S25 OS = Homo sapiens GN = RPS25 PE = 1 SV = 1 | 2 | 2 | 3.40E+07 | 1.80E+08 |
| Q02978 | Mitochondrial 2-oxoglutarate/malate carrier protein OS = Homo sapiens GN = SLC25A11 PE = 1 SV = 3 | 2 | 1 | 1.20E+07 | 6.30E+07 |
| Q5TDH0 | Protein DDI1 homolog 2 OS = Homo sapiens GN = DDI2 PE = 1 SV = 1 | | | 5.10E+06 | |
| P22059 | Oxysterol-binding protein 1 OS = Homo sapiens GN = OSBP PE = 1 SV = 1 | | | 5.50E+06 | |
| P22830 | Ferrochelatase, mitochondrial OS = Homo sapiens GN = FECH PE = 1 SV = 1 | | | 4.70E+06 | |
| A0A024RAZ7 | Heterogeneous nuclear ribonucleoprotein A1, isoform CRA_b OS = Homo sapiens GN = HNRPA1 PE = 4 SV = 1 | | 3 | 3 | 1.20E+08 | 1.90E+08 |
| Q9BXP8 | Pappalysin-2 OS = Homo sapiens GN = PAPPA2 PE = 1 SV = 1 | | 3 | 1.30E+07 | |
| O00232 | 26S proteasome non-ATPase regulatory subunit 12 OS = Homo sapiens GN = PSMD12 PE = 1 SV = 3 | | | 1.40E+07 | |
| Q08431 | Lactadherin OS = Homo sapiens GN = MFGE8 PE = 1 SV = 2 | 2 | 3 | 1 | 1.40E+07 | 1.20E+08 |
| B4DLJ5 | cDNA FLJ55716, highly similar to Desmocollin-2 OS = Homo sapiens PE = 2 SV = 1 | 3 | 1 | 5 | 1.90E+07 | 9.80E+07 |
| Q53GF9 | Full-length cDNA 5-PRIME end of clone CS0DF013YM24 of Fetal brain of Homo sapiens (Human) variant (Fragment) | 2 | 3 | 3 | 7.30E+07 | 1.60E+08 |
| B3KXY9 | Hexokinase OS = Homo sapiens PE = 2 SV = 1 | 2 | 4 | 3 | 3.60E+07 | 6.10E+07 |
| P28838 | Cytosol aminopeptidase OS = Homo sapiens GN = LAP3 PE = 1 SV = 3 | 2 | 1 | | 2.40E+07 | 1.30E+08 |
| Q9NZU5 | LIM and cysteine-rich domains protein 1 OS = Homo sapiens GN = LMCD1 PE = 1 SV = 1 | 1 | | 1.10E+07 | |
| U3KQ56 | Glyoxylate reductase/hydroxypyruvate reductase OS = Homo sapiens GN = GRHPR PE = 1 SV = 1 | | | 5.20E+06 | |
| A0A0A6YYJ8 | Putative RNA-binding protein Luc7-like 2 OS = Homo sapiens GN = LUC7L2 PE = 4 SV = 1 | | | 4.00E+06 | |
| P50479 | PDZ and LIM domain protein 4 OS = Homo sapiens GN = PDLIM4 PE = 1 SV = 2 | 2 | | 1.40E+07 | |
| B4DKQ5 | MHC class I antigen (Fragment) OS = Homo sapiens GN = HLA-A PE = 3 SV = 1 | 1 | | 7.40E+06 | |
| Q6FGH9 | ZYX protein (Fragment) OS = Homo sapiens GN = ZYX PE = 2 SV = 2 | | 2 | | 2.20E+07 | 1.30E+08 |
| Q8NCA5 | Myotrophin OS = Homo sapiens GN = MTPN PE = 1 SV = 1 | 1 | | 9.20E+06 | |
| P43034 | Protein FAM98A OS = Homo sapiens GN = FAM98A PE = 1 SV = 1 | 1 | | 3.00E+07 | |
| A0A0A0MSV | Platelet-activating factor acetylhydrolase IB subunit alpha OS = Homo sapiens GN = PAFAH1B1 PE = 1 SV = 1 | 2 | | 2.00E+07 | |
| B5BUB5 | Tapasin OS = Homo sapiens GN = TAPBP PE = 1 SV = 1 | 1 | 1 | 4.50E+07 | 6.60E+07 |
| B3KS98 | Autoantigen La (Fragment) OS = Homo sapiens GN = SSB PE = 2 SV = 1 | | | 6.90E+06 | |
| D0W033 | Eukaryotic translation initiation factor 3 subunit H OS = Homo sapiens GN = EIF3H PE = 1 SV = 1 | 2 | | 5.30E+07 | |
| Q9BUS0 | MHC class I antigen (Fragment) OS = Homo sapiens GN = HLA-A PE = 3 SV = 1 | 1 | | 1.00E+07 | 3.50E+07 |
| P58546 | Myotrophin OS = Homo sapiens GN = MTPN PE = 1 SV = 1 | | | 1.20E+07 | |
| B2R829 | cDNA, FLJ93711, highly similar to Homo sapiens myeloid cell nuclear differentiation antigen (MNDA), mRNA OS = Hom | 1 | | 6.60E+06 | 2.10E+07 |
| Q9UBS4 | DnaJ homolog subfamily B member 11 OS = Homo sapiens GN = DNAJB11 PE = 1 SV = 1 | 2 | | 1.10E+07 | 5.10E+07 |
| A0A024R3I1 | Tripartite motif-containing 29, isoform CRA_a OS = Homo sapiens GN = TRIM29 PE = 4 SV = 1 | 4 | | 1.80E+07 | |
| H0YAC1 | Plasma kallikrein (Fragment) OS = Homo sapiens GN = KLKB1 PE = 1 SV = 1 | | | 1.40E+07 | |
| J3KNQ4 | Alpha-parvin OS = Homo sapiens GN = PARVA PE = 1 SV = 1 | 3 | 1 | 3.10E+07 | 6.90E+07 |
| Q13219 | Pappalysin-1 OS = Homo sapiens GN = PAPPA PE = 1 SV = 3 | | | 2.90E+06 | |
| Q59ER5 | Polypeptide N-acetylgalactosaminyltransferase 2 OS = Homo sapiens GN = GALNT2 PE = 1 SV = 1 | 1 | | 1.10E+07 | |
| A8K401 | WD repeat-containing protein 1 isoform 1 variant (Fragment) OS = Homo sapiens PE = 2 SV = 1 | 2 | | 2.10E+07 | 1.10E+08 |
| A0A024RDE8 | Prohibitin, isoform CRA_a OS = Homo sapiens GN = PHB PE = 2 SV = 1 | 2 | 3 | | 1.40E+07 | |
| P23634 | PDZ and LIM domain 5, isoform CRA_c OS = Homo sapiens GN = PDLIM5 PE = 4 SV = 1 | 4 | 1 | 2.00E+07 | 1.00E+08 |
| A8K7Q1 | Plasma membrane calcium-transporting ATPase 4 OS = Homo sapiens GN = ATP2B4 PE = 1 SV = 2 | 2 | 2 | 2.10E+07 | 4.50E+07 |
| P62195 | 26S protease regulatory subunit 8 OS = Homo sapiens GN = PSMC5 PE = 1 SV = 1 | | | 1.10E+07 | |

APPENDIX A-continued

| ID | Description | | | |
|---|---|---|---|---|
| B2R7C7 | Alkaline phosphatase OS = Homo sapiens PE = 2 SV = 1 | 1 | 3 | 2.90E+06 | 5.00E+07 |
| A0A087X117 | Nodal modulator 1 OS = Homo sapiens GN = NOMO1 PE = 1 SV = 1 | 2 | 1 | 7.70E+06 | 3.00E+07 |
| B2RDG0 | Proteasome subunit alpha type OS = Homo sapiens PE = 2 SV = 1 | 2 | | 2.40E+07 | |
| L7RXH5 | Mitogen-activated protein kinase OS = Homo sapiens GN = MAPK3 PE = 2 SV = 1 | 1 | | 1.50E+07 | |
| Q5ST28 | Splicing factor 3B subunit 1 OS = Homo sapiens GN = SF3B1 PE = 1 SV = 3 | 1 | | 2.20E+06 | |
| Q13185 | ATP-binding cassette sub-family F member 1 (Fragment) OS = Homo sapiens GN = ABCF1 PE = 1 SV = 6 | 1 | | 9.80E+04 | |
| O15400 | Chromobox protein homolog 3 OS = Homo sapiens GN = CBX3 PE = 1 SV = 4 | 1 | | 4.00E+07 | |
| Q53H88 | Syntaxin-7 OS = Homo sapiens GN = STX7 PE = 1 SV = 4 | 2 | 2 | 1.10E+07 | 5.70E+07 |
| B4E1Z4 | Dynactin 2 variant (Fragment) OS = Homo sapiens PE = 2 SV = 1 | 1 | 1 | 1.60E+07 | 5.00E+07 |
| P24043 | Laminin subunit alpha-2 OS = Homo sapiens GN = LAMA2 PE = 1 SV = 1 | 2 | | 9.90E+06 | |
| P49821 | NADH dehydrogenase [ubiquinone] flavoprotein 1, mitochondrial OS = Homo sapiens GN = NDUFV1 PE = 1 SV = 4 | 1 | | 3.20E+06 | |
| P08559 | Pyruvate dehydrogenase E1 component subunit alpha, somatic form, mitochondrial OS = Homo sapiens GN = PDHA1P | 2 | 1 | 1.80E+06 | 3.70E+07 |
| Q9H444 | Charged multivesicular body protein 4b OS = Homo sapiens GN = CHMP4B PE = 1 SV = 1 | 1 | | 5.60E+06 | |
| P26038 | Moesin OS = Homo sapiens GN = MSN PE = 1 SV = 3 | 1 | | 1.00E+07 | |
| G3V3D1 | Epididymal secretory protein E1 (Fragment) OS = Homo sapiens GN = NPC2 PE = 1 SV = 1 | 1 | 1 | 1.30E+07 | 4.50E+07 |
| P05108 | Cholesterol side chain cleavage enzyme, mitochondrial OS = Homo sapiens GN = CYP11A1 PE = 1 SV = 2 | 1 | | 6.10E+06 | |
| Q96KG9 | N-terminal kinase-like protein OS = Homo sapiens GN = SCYL1 PE = 1 SV = 1 | 1 | | 8.00E+06 | |
| P51888 | Prolargin OS = Homo sapiens GN = PRELP PE = 1 SV = 1 | 3 | 1 | 2.20E+07 | 7.60E+07 |
| Q8TD35 | Tyrosine-protein kinase receptor OS = Homo sapiens GN = TFG/ALK fusion PE = 2 SV = 1 | 1 | 2 | 3.40E+07 | 1.50E+08 |
| A8K4W2 | cDNA FLJ78635, highly similar to Homo sapiens ATP synthase, H+ transporting, mitochondrial F0 complex, subunit b, | 4 | 5 | 2.90E+07 | 1.10E+08 |
| Q92621 | Nuclear pore complex protein Nup205 OS = Homo sapiens GN = NUP205 PE = 1 SV = 3 | 1 | | 3.20E+06 | |
| A0A024R994 | Copine III, isoform CRA_a OS = Homo sapiens GN = CPNE3 PE = 4 SV = 1 | 1 | 1 | 2.80E+07 | 5.40E+07 |
| Q5U043 | 5-(hydroxymethyl)glutathione dehydrogenase OS = Homo sapiens PE = 2 SV = 1 | 1 | 2 | 8.30E+06 | 9.40E+07 |
| Q01844 | RNA binding protein EWS OS = Homo sapiens GN = EWSR1 PE = 1 SV = 1 | 3 | | 3.00E+07 | |
| A0A024R9N6 | EH-domain containing 4, isoform CRA_a OS = Homo sapiens GN = EHD4 PE = 4 SV = 1 | 1 | 1 | 9.90E+06 | |
| A0A024R9D7 | 2,4-dienoyl CoA reductase 1, mitochondrial, isoform CRA_b OS = Homo sapiens GN = DECR1 PE = 4 SV = 2 | 1 | 1 | 1.70E+07 | 2.00E+07 |
| P17936 | Insulin-like growth factor binding protein 3 OS = Homo sapiens GN = IGFBP3 PE = 1 SV = 2 | 6 | 2 | | 4.30E+08 |
| Q7L5L3 | Glycerophosphodiester phosphodiesterase domain-containing protein 3 OS = Homo sapiens GN = GDPD3 PE = 2 SV = 3 | 1 | 2 | 6.20E+06 | |
| Q8TF42 | Ubiquitin associated and SH3 domain-containing protein 3 OS = Homo sapiens GN = UBASH3B PH1 SV = 2 | | | 1.20E+07 | |
| P52943 | Cysteine-rich protein 2 OS = Homo sapiens GN = CRIP2 PE = 1 SV = 1 | 2 | | 4.50E+07 | |
| A0A024R7M | Transmembrane emp24 protein transport domain containing 9, isoform CRA_a OS = Homo sapiens GN = TMED9 PE = 3 | 2 | 2 | 2.80E+07 | 1.10E+08 |
| P62277 | 40S ribosomal protein S13 OS = Homo sapiens GN = RPS13 PE = 1 SV = 2 | 1 | 1 | 2.30E+07 | 2.10E+08 |
| O75367 | Core histone macro-H2A1 OS = Homo sapiens GN = H2AFY PE = 1 SV = 4 | 4 | 6 | 1.10E+08 | |
| Q9H9B4 | Sideroflexin-1 OS = Homo sapiens GN = SFXN1 PE = 1 SV = 4 | 6 | 7 | 2.70E+07 | |
| P22695 | Cytochrome b-c1 complex subunit 2, mitochondrial OS = Homo sapiens GN = UQCRC2 PE = 1 SV = 3 | 2 | 2 | 1.40E+07 | 4.20E+07 |
| A2NB46 | Cold agglutinin FS-2 L-chain (Fragment) OS = Homo sapiens GN = FH PE = 1 SV = 1 | 1 | 1 | 3.30E+07 | 1.40E+08 |
| P09497 | Clathrin light chain B OS = Homo sapiens GN = CLTB PE = 1 SV = 1 | 4 | 2 | 1.00E+08 | 1.90E+08 |
| P10620 | Microsomal glutathione S-transferase 1 OS = Homo sapiens GN = MGST1 PE = 1 SV = 1 | 1 | 1 | 1.10E+08 | 6.80E+08 |
| P42166 | Lamina-associated polypeptide 2, isoform alpha OS = Homo sapiens GN = TMPO PE = 1 SV = 2 | 1 | | 2.20E+07 | |
| P19827 | Inter-alpha-trypsin inhibitor heavy chain H1 OS = Homo sapiens GN = ITIH1 PE = 1 SV = 3 | 1 | 1 | 2.00E+07 | 3.90E+07 |
| B2R673 | cDNA, FLJ92818, highly similar to Homo sapiens pyruvate dehydrogenase complex, component X (PDHX), mRNA OS= | 1 | | | |
| Q96QR8 | Transcriptional activator protein Pur-beta OS = Homo sapiens GN = PURB PE = 1 SV = 3 | 1 | | 4.10E+07 | |
| Q15363 | Transmembrane emp24 domain-containing protein 2 OS = Homo sapiens GN = TMED2 PE = 1 SV = 1 | 1 | 1 | 2.70E+06 | 2.30E+08 |
| P07954 | Fumarate hydratase, mitochondrial OS = Homo sapiens GN = FH PE = 1 SV = 3 | 1 | 1 | 1.90E+07 | 1.00E+07 |
| Q8TC12 | Retinol dehydrogenase 11 OS = Homo sapiens GN = RDH11 PE = 1 SV = 2 | 4 | | 3.50E+06 | |
| Q32P28 | Prolyl 3-hydroxylase 1 OS = Homo sapiens GN = P3H1 PE = 1 SV = 2 | 1 | | 9.20E+06 | |
| Q9U70 | N-acetyl-D-glucosamine kinase OS = Homo sapiens GN = NAGK PE = 1 SV = 1 | 1 | | | |
| A0A024R883 | ATPase, H+ transporting, lysosomal 13 kDa, V1 subunit G1, isoform CRA_a OS = Homo sapiens GN = ATP6V1G1 PE = 4 SV | 1 | | 1.00E+07 | |
| Q6P988 | Palmitoleoyl-protein carboxylesterase NOTUM OS = Homo sapiens GN = NOTUM PE = 1 SV = 2 | 1 | | 5.00E+06 | |
| P07814 | Bifunctional glutamate/proline-tRNA ligase OS = Homo sapiens GN = EPRS PE = 1 SV = 5 | 4 | | 5.30E+06 | |
| Q9NVI7 | ATPase family AAA domain-containing protein 3A OS = Homo sapiens GN = ATAD3A PE = 1 SV = 2 | 1 | 1 | 1.00E+06 | |
| B4E1U9 | cDNA FLJ54776, highly similar to Cell division control protein 42 homolog OS = Homo sapiens PE = 2 SV = 1 | 2 | 1 | 1.30E+07 | 1.80E+08 |

APPENDIX A-continued

| ID | Description | C1 | C2 | C3 | C4 |
|---|---|---|---|---|---|
| Q9H4A6 | Golgi phosphoprotein 3 OS = Homo sapiens GN = GOLPH3 PE = 1 SV = 1 | 1 | | 1.20E+07 | |
| Q9NRN7 | L-aminoadipate-semialdehyde dehydrogenase-phosphopantetheinyl transferase OS = Homo sapiens GN = AASDHPPT | 1 | | 2.50E+06 | |
| A6NFX8 | ADP-sugar pyrophosphatase OS = Homo sapiens GN = NUDT5 PE = 1 SV = 1 | 1 | | 1.20E+07 | 2.40E+07 |
| Q59E89 | DnaJ (Hsp40) homolog, subfamily B, member 4 variant (Fragment) OS = Homo sapiens PE = 2 SV = 1 | 1 | | 9.90E+06 | |
| A8K132 | cDNA FLJ75476, highly similar to Homo sapiens glutaminase (GLS), mRNA OS = Homo sapiens PE = 2 SV = 1 | 1 | | 1.00E+07 | |
| P12268 | Inosine-5'-monophosphate dehydrogenase 2 OS = Homo sapiens GN = IMPDH2 PE = 1 SV = 2 | 1 | | 8.60E+06 | |
| P62854 | 40S ribosomal protein S26 OS = Homo sapiens GN = RPS26 PE = 1 SV = 3 | 2 | | 7.50E+06 | 8.00E+07 |
| Q9UBI6 | Guanine nucleotide-binding protein G(I)/G(S)/G(O) subunit gamma-12 OS = Homo sapiens GN = GNG12 PE = 1 SV = 3 | 2 | | 6.20E+06 | |
| P62913 | 60S ribosomal protein L11 OS = Homo sapiens GN = RPL11 PE = 1 SV = 2 | 2 | | 1.10E+08 | 2.20E+08 |
| Q12846 | Syntaxin-4 OS = Homo sapiens GN = STX4 PE = 1 SV = 2 | 1 | | 2.50E+06 | |
| A0A024RDS2 | Periostin, osteoblast specific factor, isoform CRA_c OS = Homo sapiens GN = POSTN PE = 4 SV = 1 | 1 | | 7.70E+06 | 5.10E+07 |
| B7Z5P5 | cDNA FLJ56478, highly similar to Homo sapiens COBL-like 1 (COBLL1), mRNA OS = Homo sapiens PE = 2 SV = 1 | 1 | | 3.80E+06 | |
| A0A024R571 | EH domain-containing protein 1 OS = Homo sapiens GN = EHD1 PE = 1 SV = 1 | 2 | | 2.20E+07 | |
| Q5JXB2 | Putative ubiquitin-conjugating enzyme E2 N-like OS = Homo sapiens GN = UBE2NL PE = 1 SV = 1 | 1 | | 4.90E+06 | 2.50E+07 |
| Q5U0D2 | Transgelin OS = Homo sapiens GN = TAGLN PE = 2 SV = 1 | 2 | | 1.50E+06 | |
| Q8NFV4 | Alpha/beta hydrolase domain-containing protein 11 OS = Homo sapiens GN = ABHD11 PE = 2 SV = 1 | 1 | | 3.70E+07 | 2.00E+08 |
| A0A087WT5 | Transthyretin OS = Homo sapiens GN = TTR PE = 1 SV = 1 | 2 | | 1.60E+07 | |
| Q99961 | Endophilin-A2 OS = Homo sapiens GN = SH3GL1 PE = 1 SV = 1 | 1 | | 3.60E+06 | |
| B7Z5J8 | cDNA FLJ56136, highly similar to Solute carrier family 2, facilitated glucose transporter member 14 OS = Homo sapiens | 1 | | 1.20E+07 | |
| P63151 | Serine/threonine-protein phosphatase 2A 55 kDa regulatory subunit B alpha isoform OS = Homo sapiens GN = PPP2R2 | | | 2.10E+06 | |
| Q13344 | Fus-like protein (Fragment) OS = Homo sapiens PE = 2 SV = 1 | | | 2.30E+07 | |
| Q53HB7 | Diablo isoform 1 variant (Fragment) OS = Homo sapiens PE = 2 SV = 1 | 3 | | 4.10E+06 | 1.00E+08 |
| Q9BU40 | Chordin-like protein 1 OS = Homo sapiens GN = CHRDL1 PE = 1 SV = 1 | 2 | | 1.70E+07 | 2.20E+07 |
| P53992 | Protein transport protein Sec24C OS = Homo sapiens GN = SEC24C PE = 1 SV = 3 | | | 6.50E+07 | |
| Q8N1B4 | Vacuolar protein sorting-associated protein 52 homolog OS = Homo sapiens GN = VPS52 PE = 1 SV = 1 | | | 1.00E+06 | |
| Q6P5V6 | SNX5 protein (Fragment) OS = Homo sapiens GN = SNX5 PE = 2 SV = 1 | | | 4.10E+07 | 7.40E+07 |
| Q8WVX7 | Ribosomal protein S19 (Fragment) OS = Homo sapiens PE = 2 SV = 1 | 3 | 4 | 1.70E+06 | |
| P55382 | Methionine aminopeptidase 1 OS = Homo sapiens GN = METAP1 PE = 1 SV = 1 | | | 9.80E+06 | 1.60E+07 |
| P17980 | 26S protease regulatory subunit 6A OS = Homo sapiens GN = PSMC3 PE = 1 SV = 3 | 1 | 1 | 1.40E+06 | |
| Q15459 | Splicing factor 3A subunit 1 OS = Homo sapiens GN = SF3A1 PE = 1 SV = 1 | 1 | 1 | 3.50E+06 | 7.80E+07 |
| A0A024RDJ1 | DC2 protein, isoform CRA_a OS = Homo sapiens GN = DC2 PE = 4 SV = 1 | | | 1.10E+07 | |
| P55060 | Exportin-2 OS = Homo sapiens GN = CSE1L PE = 1 SV = 3 | | | 4.60E+06 | |
| B5BTZ8 | Small nuclear ribonucleoprotein polypeptide B" OS = Homo sapiens GN = SNRPB2 PE = 2 SV = 1 | 3 | | 1.10E+07 | 2.00E+07 |
| A0A024QZT4 | Serpin peptidase inhibitor, clade B (Ovalbumin), member 9, isoform CRA_a OS = Homo sapiens GN = SERPINB9 PE = 3 SV | 1 | | 9.60E+06 | 6.10E+07 |
| Q32MZ4 | Leucine-rich repeat flightless-interacting protein 1 OS = Homo sapiens GN = LRRFIP1 PE = 1 SV = 1 | | | 1.10E+07 | |
| P12270 | Nucleoprotein TPR OS = Homo sapiens GN = TPR PE = 1 SV = 3 | 3 | | 5.50E+06 | |
| A0A024RAI1 | ARP3 actin-related protein 3 homolog (Yeast), isoform CRA_a OS = Homo sapiens GN = ACTR3 PE = 3 SV = 1 | 1 | | 1.50E+06 | |
| P55884 | Eukaryotic translation initiation factor 3 subunit B OS = Homo sapiens GN = EIF3B PE = 1 SV = 3 | | | 4.40E+07 | |
| Q99426 | Tubulin-folding cofactor B OS = Homo sapiens GN = TBCB PE = 1 SV = 2 | | | 3.70E+05 | |
| A0A068LKQ0 | Ig heavy chain variable region (Fragment) OS = Homo sapiens PE = 4 SV = 1 | 2 | | 3.00E+07 | 8.20E+07 |
| Q9GZU2 | Paternally-expressed gene 3 protein OS = Homo sapiens GN = PEG3 PE = 4 SV = 1 | | | 1.90E+06 | |
| A0A0B4J2D5 | Protein LOC102724023 OS = Homo sapiens GN = LOC102724023 PE = 4 SV = 1 | | | 4.10E+07 | 1.10E+08 |
| Q59EC0 | Adenosine deaminase, RNA-specific isoform ADAR-a variant (Fragment) OS = Homo sapiens PE = 2 SV = 1 | 3 | 4 | 9.70E+06 | |
| Q9UHG3 | Prenylcysteine oxidase 1 OS = Homo sapiens GN = PCYOX1 PE = 1 SV = 3 | | | | |
| Q9NZJ3 | Charged multivesicular body protein 5 OS = Homo sapiens GN = CHMP5 PE = 3 SV = 1 | | | | 7.00E+07 |
| A0A024QZS4 | Peptidyl-prolyl cis-trans isomerase OS = Homo sapiens GN = PPIF PE = 3 SV = 1 | 1 | | 2.30E+06 | |
| B3KY04 | cDNA FLJ46506 fis, clone THYMU3030752, highly similar to BTB/POZ domain-containing protein KCTD12 OS = Homo s | 1 | | 6.10E+06 | 2.90E+07 |
| Q4LE33 | TNC variant protein (Fragment) OS = Homo sapiens GN = TNC variant protein PE = 2 SV = 1 | 1 | | | 5.60E+06 |
| Q4LE58 | EIF4G1 variant protein (Fragment) OS = Homo sapiens GN = EIF4G1 variant protein PE = 2 SV = 1 | 1 | | | |
| P02743 | Serum amyloid P-component (Fragment) OS = Homo sapiens GN = APCS PE = 1 SV = 2 | 1 | | 2.00E+07 | |
| Q14444 | Caprin-1 OS = Homo sapiens GN = CAPRIN1 PE = 1 SV = 2 | | | 2.10E+07 | |
| P27695 | DNA-(apurinic or apyrimidinic site) lyase OS = Homo sapiens GN = APEX1 PE = 1 SV = 2 | | | 1.20E+07 | |
| Q14IF0 | Glutamate-cysteine ligase OS = Homo sapiens GN = GCLC PE = 2 SV = 1 | | | 3.60E+06 | |

APPENDIX A-continued

| ID | Description | | | |
|---|---|---|---|---|
| A8K2Y2 | cDNA FLJ78120, highly similar to Homo sapiens eukaryotic translation initiation factor 2, subunit 3 gamma, 52 kDa (EI | 1 | | 3.30E+07 | 3.60E+07 |
| Q9UBC2 | Epidermal growth factor receptor substrate 15-like 1 OS = Homo sapiens GN = EPS15L1 PE = 1 SV = 1 | | | 3.40E+06 | |
| A0A087WY3 | YTH domain-containing family protein 3 OS = Homo sapiens GN = YTHDF3 PE = 1 SV = 1 | | | 4.30E+05 | |
| P21281 | V-type proton ATPase subunit B, brain isoform OS = Homo sapiens GN = ATP6V1B2 PE = 1 SV = 3 | | | 1.50E+07 | |
| P18065 | Insulin-like growth factor-binding protein 2 OS = Homo sapiens GN = IGFBP2 PE = 1 SV = 2 | 1 | | 5.70E+06 | 5.30E+07 |
| J3KPF3 | 4F2 cell-surface antigen heavy chain OS = Homo sapiens GN = SLC3A2 PE = 1 SV = 1 | 1 | | 1.90E+07 | |
| C1PHA2 | Kinesin-like protein OS = Homo sapiens GN = KIF5B-ALK PE = 2 SV = 1 | 1 | | 6.90E+06 | |
| Q96TA1 | Niban-like protein 1 OS = Homo sapiens GN = FAM129B PE = 1 SV = 1 | | | 3.80E+07 | |
| B2R5W3 | cDNA, FLJ92658, highly similar to Homo sapiens poly (ADP-ribose) polymerase family, member 1 (PARP1), mRNA OS | | | 3.70E+06 | |
| B7Z4C8 | 60S ribosomal protein L31 OS = Homo sapiens GN = RPL31 PE = 1 SV = 1 | 2 | | 9.70E+04 | 1.40E+08 |
| B2R8I2 | cDNA, FLJ93914, highly similar to Homo sapiens histidine-rich glycoprotein (HRG), mRNA OS = Homo sapiens PE = 2 SV | | | | |
| P51149 | Ras-related protein Rab-7a OS = Homo sapiens GN = RAB7A PE = 1 SV = 1 | 2 | | 1.10E+07 | 1.10E+08 |
| B3KUY2 | Prostaglandin E synthase 3 (Cytosolic), isoform CRA_c OS = Homo sapiens GN = PTGES3 PE = 2 SV = 1 | | | 1.20E+07 | |
| A0A087X2I1 | 26S protease regulatory subunit 10B OS = Homo sapiens GN = PSMC6 PE = 1 SV = 1 | | | 1.70E+07 | |
| O76003 | Glutaredoxin-3 OS = Homo sapiens GN = GLRX3 PE = 1 SV = 2 | | | 1.70E+07 | |
| P12273 | Prolactin-inducible protein OS = Homo sapiens GN = PIP PE = 1 SV = 1 | 3 | | 2.80E+06 | |
| K7ELC2 | 40S ribosomal protein S15 OS = Homo sapiens GN = RPS15 PE = 1 SV = 1 | 1 | | 4.00E+07 | 8.00E+07 |
| P50579 | Methionine aminopeptidase 2 OS = Homo sapiens GN = METAP2 PE = 1 SV = 1 | | | 3.00E+06 | |
| Q9Y3A6 | Transmembrane emp24 domain-containing protein 5 OS = Homo sapiens GN = TMED5 PE = 1 SV = 1 | 1 | | 4.60E+06 | 4.80E+07 |
| Q03591 | Complement factor H-related protein 1 OS = Homo sapiens GN = CFHR1 PE = 1 SV = 1 | | | 8.40E+06 | |
| B4DWB5 | cDNA FLJ53931, highly similar to Bifunctional 3'-phosphoadenosine5'-phosphosulfate synthetase 2 OS = Homo sapien | | | 9.80E+06 | |
| P22413 | Ectonucleotide pyrophosphatase/phosphodiesterase family member 1 OS = Homo sapiens GN = ENPP1 PE = 1 SV = 2 | | | 5.80E+06 | 5.00E+07 |
| Q9BXP5 | Serrate RNA effector molecule homolog OS = Homo sapiens GN = SRRT PE = 4 SV = 1 | 3 | | 1.90E+07 | |
| A0A024R2A3 | HCG1979072, isoform CRA_b OS = Homo sapiens GN = hCG_1979072 PE = 4 SV = 1 | | | 2.20E+07 | |
| A0A024RBF6 | HCG26523, isoform CRA_a OS = Homo sapiens GN = hCG_26523 PE = 4 SV = 1 | | | 5.10E+07 | |
| Q9UGM3 | Deleted in malignant brain tumors 1 protein OS = Homo sapiens GN = DMBT1 PE = 1 SV = 1 | | | 3.70E+07 | |
| B2R6S5 | UMP-CMP kinase OS = Homo sapiens GN = CMPK PE = 2 SV = 1 | | | 1.30E+07 | |
| Q5T1J5 | Putative coiled-coil-helix-coiled-coil-helix domain-containing protein CHCHD2P9, mitochondrial OS = Homo sapiens G | 1 | | 1.80E+07 | 7.90E+07 |
| A8K761 | NADH dehydrogenase (Ubiquinone) 1 beta subcomplex, 10, 22 kDa, isoform CRA_b OS = Homo sapiens GN = NDUFB10 | 2 | | 5.70E+06 | 4.60E+07 |
| Q13409 | Cytoplasmic dynein 1 intermediate chain 2 OS = Homo sapiens GN = DYNC1I2 PE = 1 SV = 3 | | | 2.60E+07 | |
| A8K0G3 | AP complex subunit beta OS = Homo sapiens PE = 2 SV = 1 | 2 | | 1.20E+07 | 5.00E+07 |
| B3KXB8 | cDNA FLJ45106 fis, clone BRAWH3033293, highly similar to Synaptopodin OS = Homo sapiens PE = 2 SV = 1 | 1 | | 7.20E+06 | 2.80E+07 |
| P14868 | Aspartate-tRNA ligase, cytoplasmic OS = Homo sapiens GN = DARS PE = 1 SV = 2 | | | 1.70E+07 | |
| Q9UNA0 | A disintegrin and metalloproteinase with thrombospondin motifs 5 OS = Homo sapiens GN = ADAMTS5 PE = 1 SV = 2 | 2 | | 1.80E+06 | 1.10E+08 |
| P61956 | Small ubiquitin-related modifier 2, isoform CRA_b OS = Homo sapiens GN = SUMO2 PE = 1 SV = 3 | | | 1.10E+07 | |
| A0A024RAM | Microtubule-associated protein 1B, isoform CRA_b OS = Homo sapiens GN = MAP1B PE = 4 SV = 1 | 2 | | 7.80E+06 | 3.10E+07 |
| P35221 | Catenin alpha-1 OS = Homo sapiens GN = CTNNA1 PE = 1 SV = 1 | 1 | | 1.10E+07 | 4.20E+07 |
| P00492 | Hypoxanthine-guanine phosphoribosyltransferase OS = Homo sapiens GN = HPRT1 PE = 1 SV = 2 | | | 1.80E+07 | |
| P43652 | Afamin OS = Homo sapiens GN = AFM PE = 1 SV = 1 | | | 3.80E+06 | |
| A0A024RBB7 | Nucleosome assembly protein 1-like 1, isoform CRA_a OS = Homo sapiens GN = NAP1L1 PE = 3 SV = 1 | 1 | | 3.40E+07 | 2.50E+07 |
| B4DNE1 | cDNA FLJ52708, highly similar to Basigin OS = Homo sapiens PE = 2 SV = 1 | 3 | | 3.30E+07 | 6.80E+07 |
| P31930 | Cytochrome b-c1 complex subunit 1, mitochondrial OS = Homo sapiens GN = UQCRC1 PE = 1 SV = 3 | 1 | | | 5.00E+07 |
| B3KXW5 | cDNA FLJ46199 fis, clone TEST14007965, highly similar to AP-1 complex subunit gamma-1 OS = Homo sapiens PE = 2 SV | | | 1.10E+07 | |
| Q32Q14 | NDUFA7 protein (Fragment) OS = Homo sapiens GN = NDUFA7 PE = 2 SV = 1 | 1 | | 7.30E+06 | |
| Q5TBU5 | HCG1773630 OS = Homo sapiens GN = hCG_1773630 PE = 4 SV = 1 | | | 1.60E+07 | |
| P05387 | 60S acidic ribosomal protein P2 OS = Homo sapiens GN = RPLP2 PE = 1 SV = 1 | 3 | | | 8.30E+07 |
| O43491 | Band 4.1-like protein 2 OS = Homo sapiens GN = EPB41L2 PE = 1 SV = 1 | 1 | | 2.20E+07 | 5.00E+07 |
| Q9NPJ3 | Acyl-coenzyme A thioesterase 13 OS = Homo sapiens GN = ACOT13 PE = 1 SV = 1 | | | 1.80E+07 | |
| E5KMI6 | Lon protease homolog, mitochondrial OS = Homo sapiens GN = LONP1 PE = 3 SV = 1 | 1 | | 2.00E+06 | |
| Q9P253 | Vacuolar protein sorting-associated protein 18 homolog OS = Homo sapiens GN = VPS18 PE = 1 SV = 2 | 2 | | 2.00E+07 | 3.00E+07 |
| A0A0A0MSE | Hydroxyacyl-coenzyme A dehydrogenase, mitochondrial OS = Homo sapiens GN = HADH PE = 1 SV = 1 | | | 9.00E+06 | |
| P02760 | Protein AMBP OS = Homo sapiens GM = AMBP PE = 1 SV = 1 | | | 3.60E+05 | |
| O43818 | U3 small nucleolar RNA-interacting protein 2 OS = Homo sapiens GN = RRP9 PE = 1 SV = 1 | | | | |

APPENDIX A-continued

| ID | Description | Col1 | Col2 | Col3 |
|---|---|---|---|---|
| Q92530 | Proteasome inhibitor PI31 subunit OS = Homo sapiens GN = PSMF1 PE = 1 SV = 2 | 1 | 1 | 1.40E+07 |
| A0A024R2Q4 | Ribosomal protein L15 OS = Homo sapiens GN = RPL15 PE = 3 SV = 1 | 1 | 3 | 7.90E+07 | 1.20E+08 |
| G3V1L9 | Tight junction protein 1 (Zona occludens 1), isoform CRA_a OS = Homo sapiens GN = TJP1 PE = 1 SV = 1 | 2 | 3 | 8.20E+06 |
| A0A024R8D5 | HCG30600, isoform CRA_a OS = Homo sapiens GN = hCG_30600 PE = 4 SV = 1 | 1 | 2 | 3.10E+08 | 5.00E+08 |
| P54819 | Adenylate kinase 2, mitochondrial OS = Homo sapiens GN = AK2 PE = 1 SV = 2 | 2 | 4 | 2.30E+07 | 1.00E+08 |
| P33316 | Deoxyuridine 5′-triphosphate nucleotidohydrolase, mitochondrial OS = Homo sapiens GN = DUT PE = 1 SV = 4 | 2 | 2 | 1.70E+07 |
| O00231 | 26S proteasome non-ATPase regulatory subunit 11 OS = Homo sapiens GN = PSMD11 PE = 1 SV = 3 | 1 | 1 | 4.20E+06 | 2.20E+07 |
| Q16706 | Alpha-mannosidase 2 OS = Homo sapiens GN = MAN2A1 PE = 1 SV = 2 | 1 | 1 | 1.20E+06 |
| P14174 | Macrophage migration inhibitory factor OS = Homo sapiens GN = MIF PE = 1 SV = 4 | 1 | 1 | 4.10E+07 | 3.10E+08 |
| A8MUS3 | 60S ribosomal protein L23a OS = Homo sapiens GN = RPL23A PE = 1 SV = 1 | 1 | 3 | 7.00E+07 | 1.60E+08 |
| Q9Y2W1 | Thyroid hormone receptor-associated protein 3 OS = Homo sapiens GN = THRAP3 PE = 1 SV = 2 | 1 | 1 | 2.20E+06 |
| B5BU01 | Eukaryotic translation initiation factor 2 beta OS = Homo sapiens GN = EIF2S2 PE = 2 SV = 1 | 2 | | 6.40E+06 |
| A4D1B5 | Gamma-secretase-activating protein OS = Homo sapiens GN = GSAP PE = 1 SV = 2 | 1 | | 1.50E+07 |
| B7Z6C2 | cDNA FLJ50663, highly similar to Phosphoglucomutase-1 (EC 5.4.2.2) OS = Homo sapiens PE = 2 SV = 1 | 1 | 1 | 1.20E+07 | 2.80E+07 |
| P46939 | Utrophin OS = Homo sapiens GN = UTRN PE = 1 SV = 2 | 1 | 1 | 1.10E+06 | 9.40E+06 |
| D3DPK5 | SH3 domain binding glutamic acid-rich protein like 3, isoform CRA_a (Fragment) OS = Homo sapiens GN = SH3BGRL3 P | 1 | | 1.00E+07 |
| B2R9F3 | cDNA, FLJ94363, highly similar to Homo sapiens transporter 1, ATP-binding cassette, sub-family B(MDR/TAP) (TAP1) | 1 | | 1.10E+07 |
| P07738 | Bisphosphoglycerate mutase OS = Homo sapiens GN = BPGM PE = 1 SV = 2 | 1 | | 2.80E+07 |
| Q16822 | Phosphoenolpyruvate carboxykinase [GTP], mitochondrial OS = Homo sapiens GN = PCK2 PE = 1 SV = 3 | 1 | | 5.50E+06 |
| Q8N9N5 | Protein BANP OS = Homo sapiens GN = BANP PE = 1 SV = 1 | 1 | | 1.40E+08 |
| A8K517 | Ribosomal protein S23, isoform CRA_a OS = Homo sapiens GN = RPS23 PE = 2 SV = 1 | 1 | 1 | 1.60E+07 | 1.30E+08 |
| P62318 | Small nuclear ribonucleoprotein Sm D3 OS = Homo sapiens GN = SNRPD3 PE = 1 SV = 1 | 1 | 1 | 3.80E+07 | 1.10E+08 |
| P49458 | Signal recognition particle 9 kDa protein OS = Homo sapiens GN = SRP9 PE = 1 SV = 2 | 1 | | 5.30E+06 |
| Q8TCS8 | Polyribonucleotide nucleotidyltransferase 1, mitochondrial OS = Homo sapiens GN = PNPT1 PE = 1 SV = 2 | 1 | | 6.80E+06 |
| P35998 | 26S protease regulatory subunit 7 OS = Homo sapiens GN = PSMC2 PE = 1 SV = 3 | 1 | 1 | 1.70E+07 | 2.10E+07 |
| O00151 | PDZ and LIM domain protein 1 OS = Homo sapiens GN = PDLIM1 PE = 1 SV = 4 | 4 | 1 | 5.70E+07 | 9.20E+07 |
| B7Z7F0 | cDNA FLJ56420, highly similar to Aspartyl aminopeptidase (EC 3.4.11.21) OS = Homo sapiens PE = 2 SV = 1 | 2 | 1 | 3.90E+07 | 1.20E+08 |
| B5BUB1 | RuvB-like 1 (Fragment) OS = Homo sapiens GN = RUVBL1 PE = 2 SV = 1 | 1 | | 1.30E+07 |
| P31153 | S-adenosylmethionine synthase isoform type-2 OS = Homo sapiens GN = MAT2A PE = 1 SV = 1 | 1 | | 7.20E+06 |
| B2R983 | cDNA, FLJ94267, highly similar to Homo sapiens glutathione S-transferase omega 1 (GSTO1), mRNA OS = Homo sapie | 2 | 1 | 1.40E+07 | 9.00E+07 |
| M0QXF9 | Branched-chain-amino-acid aminotransferase (Fragment) OS = Homo sapiens GN = BCAT2 PE = 1 SV = 1 | 1 | | 6.50E+06 |
| A0A024R718 | Pre-B-cell colony enhancing factor 1, isoform CRA_a OS = Homo sapiens GN = PBEF1 PE = 4 SV = 1 | 1 | 1 | 1.80E+07 | 4.00E+07 |
| Q4LE40 | C14orf159 variant protein (Fragment) OS = Homo sapiens GN = C14orf159 variant protein PE = 2 SV = 1 | 1 | | 2.00E+07 |
| A8K646 | cDNA FLJ75699, highly similar to Homo sapiens osteoclast stimulating factor 1 (OSTF1), mRNA OS = Homo sapiens PE | 1 | | 3.50E+06 |
| A4D2P0 | Ras-related C3 botulinum toxin substrate 1 (Rho family, small GTP binding protein Rac1) OS = Homo sapiens GN = RAC | 1 | 1 | 1.30E+07 | 1.60E+08 |
| P09110 | 3-ketoacyl-CoA thiolase, peroxisomal OS = Homo sapiens GN = ACAA1 PE = 1 SV = 2 | 3 | | | 3.40E+07 |
| E7EPT4 | NADH dehydrogenase [ubiquinone] flavoprotein 2, mitochondrial OS = Homo sapiens GN = NDUFV2 PE = 1 SV = 1 | 1 | | 1.50E+07 | 5.50E+07 |
| P00734 | Prothrombin OS = Homo sapiens GN = F2 PE = 1 SV = 2 | 3 | 1 | 3.30E+06 | 9.50E+07 |
| A8K455 | S-adenosylmethionine synthase OS = Homo sapiens PE = 2 SV = 1 | 1 | | 7.20E+06 |
| B3KM95 | Phosphatidate cytidylyltransferase OS = Homo sapiens PE = 2 SV = 1 | 1 | | 1.70E+06 |
| B4DI63 | cDNA FLJ59205, highly similar to Mimecan OS = Homo sapiens PE = 2 SV = 1 | 5 | 5 | 3.60E+07 | 2.60E+08 |
| A8K525 | cDNA FLJ76817, highly similar to Homo sapiens non-POU domain containing, octamer-binding (NONO), mRNA OS = H | 2 | 2 | 1.30E+07 | 4.40E+07 |
| P18085 | ADP-ribosylation factor 4 OS = Homo sapiens GN = ARF4 PE = 1 SV = 3 | 2 | 1 | 3.90E+07 | 1.10E+08 |
| U3KQV3 | Uncharactenzed protein (Fragment) OS = Homo sapiens PE = 4 SV = 5 | 1 | | 4.70E+07 |
| P60468 | Protein transport protein Sec61 subunit beta OS = Homo sapiens GN = SEC61B PE = 1 SV = 1 | 3 | | 7.50E+06 |
| A8K2W3 | cDNA FLJ78516 OS = Homo sapiens PE = 2 SV = 1 | 1 | | 7.90E+06 |
| A0A024RB01 | Integrin, alpha 5 (Fibronectin receptor, alpha polypeptide), isoform CRA_b OS = Homo sapiens GN = ITGA5 PE = 3 SV = 1 | 2 | 1 | 1.50E+07 | 4.80E+07 |
| P35606 | Coatomer subunit beta′ OS = Homo sapiens GN = COPB2 PE = 1 SV = 2 | 4 | | 2.10E+07 | 3.30E+07 |
| O43143 | Pre-mRNA-splicing factor ATP-dependent RNA helicase DHX15 OS = Homo sapiens GN = DHX15 PE = 1 SV = 2 | 1 | | 5.30E+06 |
| Q16881 | Thioredoxin reductase 1, cytoplasmic OS = Homo sapiens GN = TXNRD1 PE = 1 SV = 3 | 1 | | 5.60E+06 |
| A0A024RSC5 | Pyruvate carboxylase (Fragment) OS = Homo sapiens GN = PC PE = 4 SV = 1 | 6 | 1 | 9.80E+06 | 7.10E+07 |
| B2R5M8 | Isocitrate dehydrogenase [NADP] OS = Homo sapiens PE = 2 SV = 1 | 1 | | 2.60E+06 |
| B2R7S3 | cDNA, FLJ93580, highly similar to Homo sapiens TRAF family member-associated NFKB activator (TANK), transcript v | 1 | | 1.10E+06 |

APPENDIX A-continued

| ID | Description | | | |
|---|---|---|---|---|
| P02790 | Hemopexin OS = Homo sapiens GN = HPX PE = 1 SV = 2 | 1 | 1 | 3.80E+07 | 1.40E+08 |
| K7ER00 | Phenylalanine-tRNA ligase alpha subunit OS = Homo sapiens GN = FARSA PE = 1 SV = 1 | 1 | | 9.00E+06 | |
| P15121 | Aldose reductase OS = Homo sapiens GN = AKR1B1 PE = 1 SV = 3 | 1 | | 2.00E+07 | |
| B2RBH2 | cDNA, FLJ95508, highly similar to Homo sapiens 5'-nucleotidase, ecto (CD73) (NT5E), mRNA OS = Homo sapiens PE = 2 | 2 | 1 | 2.20E+06 | 3.20E+07 |
| A0A0AOMQS | Laminin subunit alpha-4 OS = Homo sapiens GN = LAMA4 PE = 1 SV = 1 | 10 | 1 | 1.20E+07 | 9.30E+07 |
| B3KUL5 | Oxysterol-binding protein OS = Homo sapiens PE = 2 SV = 1 | 1 | | | |
| P53539 | Protein fosB OS = Homo sapiens GN = FOSB PE = 2 SV = 1 | 1 | | | |
| A8K878 | Mesencephalic astrocyte-derived neurotrophic factor OS = Homo sapiens GN = MANF PE = 1 SV = 1 | 1 | 1 | 1.50E+07 | 3.80E+07 |
| B7ZKJ8 | ITIH4 protein OS = Homo sapiens GN = ITIH4 PE = 1 SV = 1 | 2 | | 3.60E+07 | 2.90E+07 |
| P18077 | 60S ribosomal protein L35a OS = Homo sapiens GN = RPL35A PE = 1 SV = 2 | 2 | 2 | 1.50E+07 | 1.00E+08 |
| V9HWD3 | Epididymis luminal protein 117 OS = Homo sapiens GN = HEL117 PE = 2 SV = 1 | 2 | | 9.60E+06 | |
| V9HW44 | Epididymis secretory protein Li 303 OS = Homo sapiens GN = HEL-S-303 PE = 2 SV = 1 | 1 | | 5.90E+06 | 4.00E+07 |
| H3BN98 | Uncharacterized protein (Fragment) OS = Homo sapiens PE = 4 SV = 2 | 1 | 2 | 3.70E+07 | |
| Q6ZTQ4 | Cadherin-related family member 3 OS = Homo sapiens GN = CDHR3 PE = 1 SV = 1 | 1 | | | |
| Q7Z4W1 | L-xylulose reductase OS = Homo sapiens GN = DCXR PE = 1 SV = 2 | 2 | 1 | 1.40E+07 | 6.20E+07 |
| P50402 | Emerin OS = Homo sapiens GN = EMD PE = 1 SV = 1 | 1 | | 1.10E+07 | 1.10E+08 |
| P08697 | Alpha-2-antiplasmin OS = Homo sapiens GN = SERPINF2 PE = 1 SV = 3 | 2 | | 4.60E+07 | 4.80E+07 |
| J3KN66 | Torsin-1A-interacting protein 1 OS = Homo sapiens GN = TOR1AIP1 PE = 1 SV = 1 | 2 | 1 | 2.10E+07 | |
| A0A087WZE | High mobility group nucleosome-binding domain containing protein 3 OS = Homo sapiens GN = HMGN3 PE = 1 SV = 1 | 2 | | 3.10E+07 | |
| Q14203 | Dynactin subunit 1 OS = Homo sapiens GN = DCTN1 PE = 1 SV = 3 | 1 | | 4.70E+06 | |
| O95758 | Polypyrimidine tract-binding protein 3 OS = Homo sapiens GN = PTBP3 PE = 1 SV = 2 | 1 | | 3.60E+07 | |
| Q16610 | Extracellular matrix protein 1 OS = Homo sapiens GN = ECM1 PPE = 1 SVPE = 2 | 1 | 1 | 2.40E+07 | 2.20E+08 |
| B7Z9B8 | cDNA FLJ56912, highly similar to Fibulin-2 OS = Homo sapiens PE = 2 SV = 1 | 4 | 2 | 1.40E+06 | 1.30E+08 |
| Q9UEY8 | Gamma-adducin OS = Homo sapiens GN = ADD3 PE = 1 SV = 1 | 1 | | | |
| Q6ZU43 | cDNA FLJ4007 fis, clone TEST1402376 2 OS = Homo sapiens PE = 2 SV = 1 | 1 | | 5.70E+06 | |
| Q5HYL6 | Putative uncharacterized protein DKFZp686E1899 OS = Homo sapiens GN = DKFZp686E1899 PE = 2 SV = 1 | 1 | 3 | | 3.50E+07 |
| Q53GF0 | Cytidine 5'-monophosphate N-acetylneuraminic acid synthetase variant (Fragment) OS = Homo sapiens PE = 2 SV = 1 | 1 | | 1.10E+07 | |
| O75947 | ATP synthase subunit d, mitochondrial OS = Homo sapiens GN = ATP5H PE = 1 SV = 3 | 2 | 4 | 3.00E+07 | 1.30E+08 |
| Q9Y230 | RuvB-like 2 OS = Homo sapiens GN = RUVBL2 PE = 1 SV = 3 | 1 | | 1.80E+06 | |
| Q6YN16 | Hydroxysteroid dehydrogenase-like protein 2 OS = Homo sapiens GN = HSDL2 PE = 1 SV = 1 | 1 | | 5.50E+06 | |
| B7ZLH8 | EVPL protein OS = Homo sapiens GN = EVPL PE = 2 SV = 1 | 2 | 23 | 7.10E+06 | |
| Q70UQ0 | Inhibitor of nuclear factor kappa-B kinase-interacting protein OS = Homo sapiens GN = IKBIP PE = 1 SV = 1 | 2 | | 3.20E+07 | |
| B4DUT8 | Calponin OS = Homo sapiens GN = CNN2 PE = 1 SV = 1 | 5 | | 7.30E+06 | 5.70E+08 |
| Q6ZMU0 | N-acylsphingosine amidohydrolase (Acid ceramidase) 1, isoform CRA_c OS = Homo sapiens GN = ASAH1 PE = 4 SV = 1 | 1 | | 1.80E+07 | |
| D3DSQ1 | Elongation factor 1-gamma OS = Homo sapiens GN = EEF1G PE = 1 SV = 3 | 1 | | 2.40E+07 | |
| P26641 | Protein ARPC4-TTLL3 OS = Homo sapiens GN = ARPC4-TTLL3 PE = 4 SV = 1 | 1 | 2 | 3.30E+07 | 7.90E+07 |
| P21912 | Succinate dehydrogenase [ubiquinone] iron-sulfur subunit, mitochondrial OS = Homo sapiens GN = SDHB PE = 1 SV = 3 | 4 | 1 | 2.40E+07 | 5.70E+07 |
| O43175 | D-3-phosphoglycerate dehydrogenase OS = Homo sapiens GN = PHGDH PE = 1 SV = 4 | 2 | | 6.50E+06 | |
| Q59ED7 | Putative uncharacterized protein (Fragment) OS = Homo sapiens PE = 2 SV = 1 | 1 | | 1.10E+07 | |
| B4DNC2 | cDNA FLJ51906, highly similar to Heat-shock protein beta-6 OS = Homo sapiens PE = 2 SV = 1 | 5 | 1 | 5.70E+07 | 5.70E+08 |
| O15511 | Actin-related protein 2/3 complex subunit 5 OS = Homo sapiens GN = ARPC5 PE = 1 SV = 3 | 1 | | 1.80E+07 | |
| P50213 | Isocitrate dehydrogenase [NAD] subunit alpha, mitochondrial OS = Homo sapiens GN = IDH3A PE = 1 SV = 1 | 1 | | 2.60E+07 | |
| A0A0A6YYG9 | Protein ARPC4-TTLL3 OS = Homo sapiens GN = ARPC4-TTLL3 PE = 4 SV = 1 | 1 | | 3.10E+07 | |
| O00629 | Importin subunit alpha-3 OS = Homo sapiens GN = KPNA4 PE = 1 SV = 1 | 1 | | | |
| H7BY55 | Complement decay-accelerating factor OS = Homo sapiens GN = CD55 PE = 1 SV = 2 | 1 | | 2.20E+07 | |
| A0A024R046 | High mobility group nucleosomal binding domain 4, isoform CRA_a OS = Homo sapiens GN = HMGN4 PE = 4 SV = 1 | 1 | | 3.40E+06 | |
| P40763 | Signal transducer and activator of transcription 3 OS = Homo sapiens GN = STAT3 PE = 1 SV = 2 | 1 | | | |
| B2R7B5 | cDNA FLJ93365, highly similar to Homo sapiens KH domain containing, RNA binding, signal transduction associated SHINC3 OS = Homo sapiens GN = SHINC3 PE = 2 SV = 1 | 1 | 1 | 5.50E+07 | 6.30E+07 |
| A6QKW0 | Myeloid-derived growth factor OS = Homo sapiens GN = MYDGF PE = 1 SV = 1 | 1 | 1 | 3.60E+06 | |
| M0QYN0 | cDNA FLJ77680, highly similar to Homo sapiens protein phosphatase 2 (formerly 2A), regulatory subunit A (PR 65), al | 2 | | 6.20E+07 | 3.40E+07 |
| A8K3H8 | 26S proteasome non-ATPase regulatory subunit 10 OS = Homo sapiens GN = PSMD10 PE = 1 SV = 1 | 1 | | 2.40E+07 | 7.00E+07 |
| O75832 | | | | 3.10E+07 | |
| Q9Y3U8 | 60S ribosomal protein L36 OS = Homo sapiens GN = RPL36 PE = 1 SV = 3 | 2 | 1 | 3.30E+07 | 1.20E+08 |

APPENDIX A-continued

| Accession | Description | Count 1 | Count 2 | Value 1 | Value 2 |
|---|---|---|---|---|---|
| Q15435 | Protein phosphatase 1 regulatory subunit 7 OS = Homo sapiens GN = PPP1R7 PE = 1 SV = 1 | 1 | | 6.20E+06 | |
| Q32MA0 | Dual specificity phosphatase 16 OS = Homo sapiens GN = DUSP16 PE = 2 SV = 1 | 1 | | 6.50E+07 | |
| D3DVC4 | Nestin, isoform CRA_c OS = Homo sapiens GN = NES PE = 3 SV = 1 | 1 | | 9.70E+07 | |
| A5PLM9 | Cathepsin L1 OS = Homo sapiens GN = CTSL1 PE = 2 SV = 1 | 1 | | 3.90E+07 | |
| Q6NUK7 | Non-specific protein-tyrosine kinase (Fragment) OS = Homo sapiens GN = LYN PE = 2 SV = 1 | 1 | 1 | 6.70E+06 | 1.30E+07 |
| P08246 | Neutrophil elastase OS = Homo sapiens GN = ELANE PE = 1 SV = 1 | 1 | 1 | 2.90E+07 | 1.10E+08 |
| Q9NWH2 | Transmembrane protein 242 OS = Homo sapiens GN = TMEM242 PE = 1 SV = 1 | 1 | | 2.00E+07 | |
| P11717 | Cation-independent mannose-6-phosphate receptor OS = Homo sapiens GN = IGF2R PE = 1 SV = 3 | 1 | | 1.00E+07 | |
| A8K6K7 | cDNA FLJ76881, highly similar to Homo sapiens glycogen synthase 1 (muscle) (GYS1), mRNA OS = Homo sapiens PE = 2 | 1 | | 7.30E+06 | |
| P42677 | 40S ribosomal protein S27 OS = Homo sapiens GN = RPS27 PE = 1 SV = 3 | 1 | | 1.90E+07 | |
| Q9H0B8 | Cysteine-rich secretory protein LCCL domain-containing protein 2 OS = Homo sapiens GN = CRISPLD2 PE = 2 SV = 1 | 2 | | | 4.80E+07 |
| P61163 | Alpha-centractin OS = Homo sapiens GN = ACTR1A PE = 1 SV = 1 | 1 | | 1.90E+07 | 1.00E+08 |
| Q7Z4I7 | LIM and senescent cell antigen-like-containing domain protein 2 OS = Homo sapiens GN = LIMS2 PE = 1 SV = 1 | 1 | | 9.60E+06 | |
| E7EMB3 | Calmodulin OS = Homo sapiens GN = CALM2 PE = 1 SV = 1 | 2 | 2 | 1.20E+07 | 2.90E+08 |
| Q15437 | Protein transport protein Sec23B OS = Homo sapiens GN = SEC23B PE = 1 SV = 1 | 1 | | 4.40E+07 | |
| E7D7X9 | Pyrroline-5-carboxylate reductase OS = Homo sapiens GN = PYCR2 PE = 2 SV = 2 | | | | |
| A0A024RB87 | RAP1B, member of RAS oncogene family, isoform CRA_a OS = Homo sapiens GN = RAP1B PE = 4 SV = 1 | 2 | | 6.60E+07 | 9.90E+07 |
| E9PIR9 | Absent in melanoma 1-like protein OS = Homo sapiens GN = AIM1L PE = 1 SV = 1 | 1 | | 1.80E+08 | |
| Q68DE3 | Basic helix-loop-helix domain-containing protein KIAA2018 OS = Homo sapiens GN = KIAA2018 PE = 1 SV = 3 | 1 | | 6.80E+07 | |
| A0A024RD93 | Phosphoribosylaminoimidazole carboxylase, phosphoribosylaminoimidazole succinocarboxamide synthetase, isofor | | | | |
| P36542 | ATP synthase subunit gamma, mitochondrial OS = Homo sapiens GN = ATP5C1 PE = 1 SV = 1 | 2 | 1 | 2.40E+07 | 1.10E+08 |
| Q5M9N0 | Coiled-coil domain-containing protein 158 OS = Homo sapiens GN = CCDC158 PE = 1 SV = 2 | 1 | | 4.60E+07 | |
| P54920 | Alpha-soluble NSF attachment protein OS = Homo sapiens GN = NAPA PE = 1 SV = 3 | 2 | | 9.60E+06 | 3.10E+07 |
| Q9H1B7 | Interferon regulatory factor 2-binding protein-like OS = Homo sapiens GN = IRF2BPL PE = 1 SV = 1 | 1 | | 2.10E+06 | |
| Q14247 | Src substrate cortactin OS = Homo sapiens GN = CTTN PE = 1 SV = 2 | 1 | | 1.00E+07 | 3.30E+07 |
| F4ZW62 | NF45 OS = Homo sapiens PE = 1 SV = 1 | 1 | | 3.30E+07 | 1.70E+07 |
| Q9Y3E8 | CGI-150 protein OS = Homo sapiens PE = 2 SV = 1 | 1 | | 1.50E+07 | |
| Q92896 | Golgi apparatus protein 1 OS = Homo sapiens GN = GLG1 PE = 1 SV = 2 | 1 | | 8.60E+06 | 2.30E+07 |
| A0A024RB16 | Family with sequence similarity 62 (C2 domain containing), member A, isoform CRA_a OS = Homo sapiens GN = FAM62 | 3 | | 1.50E+07 | 2.50E+07 |
| A8K2L6 | Annexin OS = Homo sapiens PE = 2 SV = 1 | 1 | | 3.20E+08 | 4.00E+08 |
| Q96D15 | Reticulocalbin-3 OS = Homo sapiens GN = RCN3 PE = 1 SV = 1 | 1 | | 1.10E+07 | 1.60E+07 |
| P54886 | Delta-1-pyrroline-5-carboxylate synthase OS = Homo sapiens GN = ALDH18A1 PE = 1 SV = 1 | 1 | | 1.20E+07 | |
| Q9UFN0 | Protein NipSnap homolog 3A OS = Homo sapiens GN = NIPSNAP3A PE = 2 SV = 2 | 1 | | 1.00E+07 | |
| B2RB70 | Neurocalcin delta, isoform CRA_a OS = Homo sapiens GN = NCALD PE = 2 SV = 1 | 1 | | 7.20E+06 | |
| Q59FB9 | Toll interacting protein variant (Fragment) OS = Homo sapiens PE = 2 SV = 1 | 1 | | 3.30E+06 | 3.00E+07 |
| P25508 | Colorectal mutant cancer protein OS = Homo sapiens GN = MCC PE = 1 SV = 1 | 1 | | 2.70E+06 | |
| Q9Y446 | Plakophilin-3 OS = Homo sapiens GN = PKP3 PE = 1 SV = 1 | 1 | | 1.80E+07 | |
| A8K566 | cDNA FLJ78246, highly similar to Homo sapiens splicing factor 3a, subunit 3, 60 kDa (SF3A3), mRNA OS = Homo sapien | 1 | 8 | 5.70E+06 | |
| B4E2A6 | cDNA FLJ55508, highly similar to Sad1/unc-84-like protein 2 OS = Homo sapiens PE = 2 SV = 1 | | | | |
| A0A0A0MTJ9 | Neutral cholesterol ester hydrolase 1 OS = Homo sapiens GN = NCEH1 PE = 1 SV = 1 | 1 | | 5.80E+06 | |
| B3KQC9 | cDNA FLJ90240 fis, clone NT2RM2001126, highly similar to Multiple PDZ domain protein OS = Homo sapiens PE = 2 SV = | 1 | | 6.00E+07 | |
| L7UZ7 | Integrin beta OS = Homo sapiens GN = ITGB3 PE = 2 SV = 1 | 1 | | 8.20E+05 | |
| Q9GV75 | Isoleucyl-tRNA synthetase, cytoplasmic variant (Fragment) OS = Homo sapiens PE = 2 SV = 2 | | | | |
| Q13242 | Serine/arginine-rich splicing factor 9 OS = Homo sapiens GN = SRSF9 PE = 1 SV = 1 | 1 | | 2.90E+07 | |
| F8VW96 | Cysteine and glycine-rich protein 2 OS = Homo sapiens GN = CSRP2 PE = 2 SV = 1 | 1 | | 2.00E+07 | |
| A0A087WW6 | 26S proteasome non-ATPase regulatory subunit 1 OS = Homo sapiens GN = PSMD1 PE = 1 SV = 1 | 1 | | 1.70E+07 | |
| V9HW62 | Lactoylglutathione lyase OS = Homo sapiens GN = HEL-S-74 PE = 2 SV = 1 | 1 | | 8.30E+06 | 4.60E+07 |
| K7ELC7 | 60S ribosomal protein L27 (Fragment) OS = Homo sapiens GN = RPL27 PE = 1 SV = 1 | 1 | 1 | 3.30E+07 | 1.00E+08 |
| P62280 | 40S ribosomal protein S11 OS = Homo sapiens GN = RPS11 PE = 1 SV = 3 | 1 | 3 | | 9.10E+07 |
| P26885 | Peptidyl-prolyl cis-trans isomerase FKBP2 OS = Homo sapiens GN = FKBP2 PE = 1 SV = 2 | 1 | 2 | 6.10E+07 | |
| Q6UVK1 | Chondroitin sulfate proteoglycan 4 OS = Homo sapiens GN = CSPG4 PE = 1 SV = 2 | 1 | | 3.10E+07 | |
| B5ME19 | Eukaryotic translation initiation factor 3 subunit C-like protein OS = Homo sapiens GN = EIF3CL PE = 3 SV = 1 | 1 | | 4.10E+06 | |
| Q13151 | Heterogeneous nuclear ribonucleoprotein A0 OS = Homo sapiens GN = HNRNPA0 PE = 1 SV = 1 | 1 | | 1.30E+07 | |

APPENDIX A-continued

| ID | Description | | | |
|---|---|---|---|---|
| M0QYS1 | 60S ribosomal protein L13a (Fragment) OS = Homo sapiens GN = RPL13A PE = 1 SV = 2 | 1 | 1.20E+07 | 1.10E+08 |
| Q96K75 | Zinc finger protein 514 OS = Homo sapiens GN = ZNF514 PE = 2 SV = 1 | 1 | 1.60E+07 | |
| B4DMN1 | cDNA FLJ61136, highly similar to Ras-related protein Rab-11A OS = Homo sapiens | 1 | 2.40E+07 | |
| A0A024RAD5 | Dolichyl-diphosphooligosaccharide-protein glycosyltransferase 48 kDa subunit OS = Homo sapiens GN = DDOST PE = 3 | 2 | 2.70E+07 | 1.80E+08 |
| A0A024QYR8 | Dinucleotide oxidase disulfide thiol exchanger 3 superfamily member 2 OS = Homo sapiens GN = TM9SF2 PE = 2 SV = 1 | 3 | 3.60E+07 | 2.20E+07 |
| O00154 | Cytosolic acyl coenzyme A thioester hydrolase OS = Homo sapiens GN = ACOT7 PE = 1 SV = 3 | 1 | 4.90E+07 | |
| A0A0A0MTH | Integrin-linked protein kinase OS = Homo sapiens GN = ILK PE = 1 SV = 1 | 3 | 8.60E+06 | 7.30E+07 |
| A8K644 | Splicing factor, arginine/serine-rich 4, isoform CRA_b OS = Homo sapiens GN = SFRS4 PE = 2 SV = 1 | 2 | 3.50E+07 | 2.70E+07 |
| Q59EI9 | ADP,ATP carrier protein, liver isoform T2 variant (Fragment) OS = Homo sapiens PE = 2 SV = 1 | 4 | 3.70E+07 | 1.30E+08 |
| Q53HV2 | Chaperonin containing TCP1, subunit 7 (Eta) variant (Fragment) OS = Homo sapiens | 1 | 2.60E+07 | 2.70E+07 |
| A0A024RAR8 | Type 1 tumor necrosis factor receptor shedding aminopeptidase regulator, isoform CRA_a OS = Homo sapiens GN = AR | | 8.40E+06 | |
| V9HWD8 | Epididymis secretory sperm binding protein Li 163pA OS = Homo sapiens GN = HEL-S-163pA PE = 2 SV = 1 | 1 | 1.20E+07 | |
| P13073 | Cytochrome c oxidase subunit 4 isoform 1, mitochondrial OS = Homo sapiens GN = COX4I1 PE = 1 SV = 1 | 1 | 5.00E+07 | 2.30E+08 |
| E9PR17 | CD59 glycoprotein OS = Homo sapiens GN = CD59 PE = 1 SV = 1 | 3 | 2.90E+07 | 1.70E+08 |
| A0A0C4DFR6 | Protein SEC13 homolog OS = Homo sapiens GN = SEC13 PE = 1 SV = 1 | | 1.30E+07 | |
| Q92522 | Histone H1x OS = Homo sapiens GN = H1FX PE = 1 SV = 1 | | 3.40E+07 | |
| Q8NBX0 | Saccharopine dehydrogenase-like oxidoreductase OS = Homo sapiens GN = SCCPDH PE = 1 SV = 1 | 3 | 9.20E+06 | 5.80E+07 |
| P62330 | ADP-ribosylation factor 6 OS = Homo sapiens GN = ARF6 PE = 1 SV = 1 | | 1.70E+07 | 2.70E+07 |
| Q9Y305 | Acyl-coenzyme A thioesterase 9, mitochondrial OS = Homo sapiens GN = ACOT9 PE = 1 SV = 1 | 1 | 1.50E+07 | 7.90E+07 |
| Q16658 | Fascin OS = Homo sapiens GN = FSCN1 PE = 1 SV = 3 | | | 3.60E+07 |
| P04275 | von Willebrand factor OS = Homo sapiens GN = VWF PE = 1 SV = 4 | | 3.00E+07 | |
| L0R5A1 | Alternative protein CSF2RB OS = Homo sapiens GN = CSF2RB PE = 4 SV = 1 | | 1.40E+05 | |
| P50570 | Dynamin-2 OS = Homo sapiens GN = DNM2 PE = 1 SV = 2 | | 3.20E+07 | |
| A6NMB1 | Sialic acid-binding Ig-like lectin 16 OS = Homo sapiens GN = SIGLEC16 PE = 2 SV = 3 | | 1.20E+09 | |
| P06727 | Apolipoprotein A-IV OS = Homo sapiens GN = APOA4 PE = 1 SV = 1 | 2 | 2.60E+07 | 6.30E+07 |
| Q5T9B7 | Adenylate kinase isoenzyme 1 OS = Homo sapiens GN = AK1 PE = 1 SV = 1 | | 2.60E+07 | |
| A8K3H0 | cDNA FLJ75548, highly similar to Homo sapiens microfibrillar associated protein 5 (MFAP5), mRNA OS = Homo sapien | 2 | 2.90E+07 | 1.60E+08 |
| Q9UGM5 | Fetuin-B OS = Homo sapiens GN = FETUB PE = 1 SV = 1 | | 3.00E+06 | |
| Q0D2Q6 | Phosphoglycerate mutase 1 (Brain) OS = Homo sapiens GN = PGAM1 PE = 2 SV = 1 | 2 | 2.00E+07 | |
| P55001 | Microfibrillar-associated protein 2 OS = Homo sapiens GN = MFAP2 PE = 2 SV = 1 | 2 | 8.70E+06 | |
| Q86V15 | Zinc finger protein castor homolog 1 OS = Homo sapiens GN = CASZ1 PE = 1 SV = 4 | | 7.40E+06 | |
| Q92743 | Serine protease HTRA1 OS = Homo sapiens GN = HTRA1 PE = 1 SV = 1 | 3 | | 1.40E+08 |
| A8K5K0 | cDNA FLJ78309, highly similar to Homo sapiens heterogeneous nuclear ribonucleoprotein U-like 1 (HNRPUL1), trans 1 | | 1.70E+07 | |
| Q15008 | 26S proteasome non-ATPase regulatory subunit 6 OS = Homo sapiens GN = PSMD6 PE = 1 SV = 1 | | 2.40E+07 | |
| P00387 | NADH-cytochrome b5 reductase 3 OS = Homo sapiens GN = CYB5R3 PE = 1 SV = 3 | 8 | 2.60E+07 | 2.70E+08 |
| Q14165 | Malectin OS = Homo sapiens GN = MLEC PE = 1 SV = 1 | 1 | 1.20E+07 | 2.40E+07 |
| O75822 | Eukaryotic translation initiation factor 3 subunit J OS = Homo sapiens GN = EIF3J PE = 1 SV = 2 | 2 | 7.80E+06 | |
| A8K586 | Protein TRAJ56 (Fragment) OS = Homo sapiens GN = TRAJ56 PE = 4 SV = 1 | | | |
| B2R7P8 | AP-3 complex subunit beta OS = Homo sapiens PE = 2 SV = 1 | 1 | 7.20E+06 | |
| E9PGN7 | cDNA, FLJ93545, highly similar to Homo sapiens 5-aminoimidazole-4-carboxamide ribonucleotide formyltransferase/ | | 4.20E+06 | |
| O60493 | Plasma protease C1 inhibitor OS = Homo sapiens GN = SERPING1 PE = 1 SV = 1 | 1 | | 6.60E+07 |
| A0A024R758 | Sorting nexin-3 OS = Homo sapiens GN = SNX3 PE = 1 SV = 3 | | 1.20E+07 | |
| A0A0A6YYL6 | Uncharacterized protein OS = Homo sapiens GN = NAG6 PE = 4 SV = 1 | | | |
| Q12841 | Follistatin-related protein 1 OS = Homo sapiens GN = FSTL1 PE = 1 SV = 1 | 2 | 9.80E+07 | 6.50E+07 |
| A8K8Z4 | Protein RPL17-C18orf32 OS = Homo sapiens GN = RPL17-C18orf32 PE = 3 SV = 1 | | 1.60E+07 | |
| O94973 | cDNA FLJ78071, highly similar to Human MHC class III complement component C6 mRNA OS = Homo sapiens PE = 2 SV | | | |
| Q9Y2V2 | AP-2 complex subunit alpha-2 OS = Homo sapiens GN = AP2A2 PE = 1 SV = 2 | 1 | 5.00E+06 | 7.90E+07 |
| U6A3P2 | Calcium-regulated heat stable protein 1 OS = Homo sapiens GN = CARHSP1 PE = 1 SV = 2 | 1 | 5.00E+06 | 1.10E+09 |
| P68032 | Mutant hemoglobin alpha 2 globin chain (Fragment) OS = Homo sapiens GN = HBA2 PE = 3 SV = 1 | 2 | | 2.60E+09 |
| B4DUV1 | Actin, alpha cardiac muscle 1 OS = Homo sapiens GN = ACTC1 PE = 1 SV = 1 | 8 | | 1.30E+09 |
| Q53H26 | cDNA FLJ78504, highly similar to Homo sapiens keratin 6A (KRT6A), mRNA OS = Homo sapiens PE = 2 SV = 1 | 3 | | 5.00E+08 |
| | Fibulin-1 OS = Homo sapiens PE = 2 SV = 1 | 25 | | 6.10E+08 |
| | Transferrin variant (Fragment) OS = Homo sapiens PE = 2 SV = 1 | 23 | | |

APPENDIX A-continued

| | | | |
|---|---|---|---|
| Q6MZV7 | Putative uncharacterized protein DKFZp686C11235 OS = Homo sapiens GN = DKFZp686C11235 PE = 2 SV = 1 | 5 | 1.20E+09 |
| Q8IV28 | NID2 protein OS = Homo sapiens GN = NID2 PE = 2 SV = 1 | 2 9 | 8.60E+07 |
| Q6PSS8 | IGK@ protein OS = Homo sapiens GN = IGK@ PE = 1 SV = 1 | 5 | 1.30E+09 |
| P68366 | Tubulin alpha-4A chain OS = Homo sapiens GN = TUBA4A PE = 1 SV = 1 | 1 4 | 1.00E+07 |
| A7BI36 | p180/ribosome receptor OS = Homo sapiens GN = RRBP1 PE = 2 SV = 2 | 19 16 | 1.60E+08 |
| D3GKD8 | A-gamma globin Osilo variant OS = Homo sapiens GN = HBG1 PE = 3 SV = 1 | 1 1 | 6.10E+08 |
| Q59EJ3 | Heat shock 70 kDa protein 1A variant (Fragment) OS = Homo sapiens PE = 2 SV = 1 | 11 14 | 2.60E+08 |
| Q6N093 | Putative uncharacterized protein DKFZp686I04196 (Fragment) OS = Homo sapiens GN = DKFZp686I04196 PE = 2 SV = 1 | 4 3 | 4.70E+08 |
| P68104 | Elongation factor 1-alpha 1 OS = Homo sapiens GN = EEF1A1 PE = 1 SV = 1 | 5 8 | 5.80E+08 |
| B2R6L0 | cDNA, FLJ93005, highly similar to Homo sapiens tubulin, beta polypeptide (TUBB), mRNA OS = Homo sapiens PE = 2 SV = 1 | 1 | 4.50E+08 |
| P06899 | Histone H2B type 1-J OS = Homo sapiens GN = HIST1H2BJ PE = 1 SV = 3 | 1 | 7.10E+07 |
| Q5XKE5 | Keratin, type II cytoskeletal 79 OS = Homo sapiens GN = KRT79 PE = 1 SV = 2 | 1 1 | 6.90E+09 |
| A8K3B0 | cDNA FLJ77877, highly similar to Human ENO2 neuron specific (gamma) enolase OS = Homo sapiens PE = 1 SV = 1 | 1 | 2.40E+07 |
| Q2M2I5 | Keratin, type I cytoskeletal 24 OS = Homo sapiens GN = KRT24 PE = 1 SV = 1 | 8 22 | 3.00E+08 |
| P02511 | Alpha-crystallin B chain OS = Homo sapiens GN = CRYAB PE = 1 SV = 2 | 7 2 | 5.40E+08 |
| V9HWH9 | Protein S100 OS = Homo sapiens GN = HEL-S-43 PE = 1 SV = 1 | 5 3 | 9.80E+08 |
| A6NMH8 | Tetraspanin OS = Homo sapiens GN = CD81 PE = 1 SV = 1 | 3 | 1.40E+08 |
| E7EQR4 | Ezrin OS = Homo sapiens GN = EZR PE = 1 SV = 3 | 3 8 | 7.20E+07 |
| P0COS5 | Histone H2A.Z OS = Homo sapiens GN = H2AFZ PE = 1 SV = 2 | 1 | 2.40E+08 |
| B8XPJ8 | Membrane bound catechol-O-methyltransferase OS = Homo sapiens GN = COMT PE = 2 SV = 1 | 2 1 | 1.50E+08 |
| X5D2L1 | Hydroxysteroid 11-beta dehydrogenase 1 isoform A (Fragment) OS = Homo sapiens GN = HSD11B1 PE = 2 SV = 1 | 6 2 | 2.50E+08 |
| P05120 | Plasminogen activator inhibitor 2 OS = Homo sapiens GN = SERPINB2 PE = 1 SV = 2 | 4 6 | 2.60E+08 |
| Q9Y4G6 | Talin-2 OS = Homo sapiens GN = TLN2 PE = 1 SV = 4 | 2 | 3.30E+07 |
| H6VRG2 | Keratin 1 OS = Homo sapiens GN = KRT1 PE = 3 SV = 1 | 3 | 2.80E+07 |
| B7Z6L0 | Annexin OS = Homo sapiens PE = 2 SV = 1 | 5 4 | 1.30E+08 |
| D6REE5 | Guanine nucleotide-binding protein subunit beta-2-like 1 (Fragment) OS = Homo sapiens GN = GNB2L1 PE = 1 SV = 1 | 6 | 7.90E+07 |
| A0A087X1U6 | Epiplakin OS = Homo sapiens GN = EPPK1 PE = 1 SV = 1 | 2 3 | 1.20E+08 |
| Q53G35 | Phosphoglycerate mutase (Fragment) OS = Homo sapiens PE = 2 SV = 1 | 5 | 2.90E+07 |
| Q16891 | MICOS complex subunit MIC60 OS = Homo sapiens GN = IMMT PE = 1 SV = 1 | 6 3 | 2.20E+08 |
| B2R4M6 | Protein S100 OS = Homo sapiens PE = 2 SV = 1 | 4 2 | 1.10E+08 |
| D9ZV4 | Tropomyosin 1 (Alpha) isoform 1 OS = Homo sapiens GN = TPM1 PE = 3 SV = 1 | 1 | 2.10E+08 |
| Q7Z4Y4 | GTP:AMP phosphotransferase AK3, mitochondrial OS = Homo sapiens GN = AK3 PE = 2 SV = 1 | 3 | 6.10E+07 |
| P49368 | T-complex protein 1 subunit gamma OS = Homo sapiens GN = CCT3 PE = 1 SV = 4 | 5 4 | 4.40E+07 |
| H9ZY12 | Thioredoxin OS = Homo sapiens GN = TXN PE = 2 SV = 1 | 4 2 | 1.70E+08 |
| M0QXB4 | Coatomer protein complex, subunit epsilon, isoform CRA_g OS = Homo sapiens GN = COPE PE = 1 SV = 1 | 2 1 | 4.50E+07 |
| Q8IUE6 | Histone H2A type 2-B OS = Homo sapiens GN = HIST2H2AB PE = 1 SV = 3 | 1 | 1.50E+08 |
| A0A024R056 | Guanine nucleotide binding protein (G protein), beta polypeptide 1, isoform CRA_a OS = Homo sapiens GN = GNB1 PE = 4 SV = 1 | 3 1 | 8.90E+07 |
| A0A0D9SF53 | ATP-dependent RNA helicase DDX3X OS = Homo sapiens GN = DDX3X PE = 1 SV = 1 | 3 2 | 9.20E+07 |
| P62244 | 40S ribosomal protein S15a OS = Homo sapiens GN = RPS15A PE = 1 SV = 2 | 4 | 1.20E+08 |
| Q07960 | Rho GTPase-activating protein 1 OS = Homo sapiens GN = ARHGAP1 PE = 1 SV = 1 | 4 4 | 3.40E+07 |
| P27169 | Serum paraoxonase/arylesterase 1 OS = Homo sapiens GN = PON1 PE = 1 SV = 3 | 2 | 5.30E+07 |
| H7BY58 | Protein-L-isoaspartate O-methyltransferase OS = Homo sapiens GN = PCMT1 PE = 1 SV = 1 | 2 | 3.00E+07 |
| Q6DD88 | Atlastin-3 OS = Homo sapiens GN = ATL3 PE = 1 SV = 1 | 3 2 | 5.60E+07 |
| A0A024R1K7 | Tyrosine 3-monooxygenase/tryptophan 5-monooxygenase activation protein, eta polypeptide, isoform CRA_b OS = Homo sapiens | 1 | 5.80E+07 |
| A0A024R9Q1 | Thrombospondin 1, isoform CRA_a OS = Homo sapiens GN = THBS1 PE = 4 SV = 1 | 3 13 | 8.30E+07 |
| V9HW13 | Cathepsin D (Lysosomal aspartyl peptidase), isoform CRA_a OS = Homo sapiens GN = HEL-S-130P PE = 2 SV = 1 | 2 2 | 7.90E+07 |
| A0A024R498 | Serpin peptidase inhibitor, clade E (Nexin, plasminogen activator inhibitor type 1), member 2, isoform CRA_b OS = Homo sapiens | 3 5 | 1.40E+08 |
| P48059 | LIM and senescent cell antigen-like-containing domain protein 1 OS = Homo sapiens GN = LIMS1 PE = 1 SV = 4 | 3 | 7.40E+07 |
| Q7Z2K6 | Endoplasmic reticulum metallopeptidase 1 OS = Homo sapiens GN = ERMP1 PE = 1 SV = 2 | 3 | 2.20E+07 |
| A0A087X1N8 | Serpin B6 OS = Homo sapiens GN = SERPINB6 PE = 1 SV = 1 | 3 2 | 6.60E+07 |
| O95782 | AP-2 complex subunit alpha-1 OS = Homo sapiens GN = AP2A1 PE = 1 SV = 3 | 3 1 | 3.90E+07 |
| A8KT4 | cDNA FLJ75774, highly similar to Homo sapiens lectin, mannose-binding 2 (LMAN2), mRNA OS = Homo sapiens PE = 2 SV = 1 | 3 | 1.20E+08 |
| Q13425 | Beta-2-syntrophin OS = Homo sapiens GN = SNTB2 PE = 1 SV = 1 | 3 3 | 6.50E+07 |

APPENDIX A-continued

| Accession | Description | | | Value |
|---|---|---|---|---|
| C7DJS2 | Glutathione S-transferase pi (Fragment) OS = Homo sapiens GN = GSTP1 PE = 2 SV = 1 | 1 | 1 | 5.20E+07 |
| E9PCR7 | 2-oxoglutarate dehydrogenase, mitochondrial OS = Homo sapiens GN = OGDH PE = 1 SV = 1 | 3 | | 3.40E+07 |
| Q13724 | Mannosyl-oligosaccharide glucosidase OS = Homo sapiens GN = MOGS PE = 1 SV = 1 | 3 | 3 | 8.10E+07 |
| P61626 | Lysozyme C OS = Homo sapiens GN = LYZ PE = 1 SV = 1 | 2 | 1 | 9.00E+07 |
| B2RDE8 | cDNA, FLJ96580, highly similar to Homo sapiens hepatoma-derived growth factor (high-mobility group protein 1-like) (HDGF), m | 2 | 1 | 4.10E+07 |
| A8K6A6 | cDNA FLJ78619, highly similar to Homo sapiens melanoma cell adhesion molecule (MCAM), mRNA OS = Homo sapiens PE = 2 SV = 1 | 2 | 1 | 3.70E+07 |
| Q86UE4 | Protein LYRIC OS = Homo sapiens GN = MTDH PE = 1 SV = 1 | 2 | | 5.00E+07 |
| B2RSR5 | cDNA, FLJ94025, highly similar to Homo sapiens tripartite motif-containing 28 (TRIM28), mRNA OS = Homo sapiens PE = 2 SV = 1 | 3 | 1 | 2.40E+07 |
| P08311 | Cathepsin G OS = Homo sapiens GN = CTSG PE = 1 SV = 2 | 2 | | 2.50E+07 |
| Q08380 | Galectin-3-binding protein OS = Homo sapiens GN = LGALS3BP PE = 1 SV = 1 | 3 | | 4.30E+07 |
| P15153 | Ras-related C3 botulinum toxin substrate 2 OS = Homo sapiens GN = RAC2 PE = 1 SV = 1 | 1 | 2 | 9.10E+07 |
| Q86YZ3 | Hornerin OS = Homo sapiens GN = HRNR PE = 1 SV = 2 | 2 | | 2.30E+06 |
| A0A087WY0 | Thrombospondin type-1 domain-containing protein 7A OS = Homo sapiens GN = THSD7A PE = 1 SV = 1 | 2 | | 3.90E+07 |
| A0A024QZN7 | Chromosome 10 open reading frame 70, isoform CRA_b OS = Homo sapiens GN = C10orf70 PE = 4 SV = 1 | 2 | | 1.10E+08 |
| Q9NQC3 | Reticulon-4 OS = Homo sapiens GN = RTN4 PE = 1 SV = 2 | 3 | 1 | 1.60E+08 |
| P68431 | Histone H3.1 OS = Homo sapiens GN = HIST1H3A PE = 1 SV = 2 | 3 | | 4.50E+09 |
| Q5U0I6 | H. sapiens ras-related Hrab1A protein OS = Homo sapiens GN = RAB1A PE = 2 SV = 1 | 2 | 4 | 2.90E+08 |
| Q5JR05 | Rho-related GTP-binding protein RhoC OS = Homo sapiens GN = RHOC PE = 3 SV = 1 | 2 | | 1.30E+08 |
| Q2F838 | Eukaryotic translation elongation factor 1 gamma (Fragment) OS = Homo sapiens PE = 2 SV = 1 | 1 | | |
| Q9P0L0 | Vesicle-associated membrane protein-associated protein A OS = Homo sapiens GN = VAPA PE = 1 SV = 3 | 2 | 4 | 9.10E+07 |
| E9PNQ8 | Thy-1 membrane glycoprotein (Fragment) OS = Homo sapiens GN = THY1 PE = 1 SV = 1 | 2 | | 1.70E+08 |
| A0A024R518 | Leucine rich repeat containing 54, isoform CRA_a OS = Homo sapiens GN = LRRC54 PE = 4 SV = 1 | 2 | | 9.30E+07 |
| P78372 | DNA-dependent protein kinase catalytic subunit OS = Homo sapiens GN = PRKDC PE = 1 SV = 3 | 3 | 1 | 2.10E+07 |
| B4DUP2 | cDNA FLJ56155, highly similar to UTP–glucose-1-phosphate uridylyltransferase 2 (EC 2.7.7.9) OS = Homo sapiens PE = 2 SV = 1 | 3 | 3 | 8.40E+07 |
| Q96QK1 | Vacuolar protein sorting-associated protein 35 OS = Homo sapiens GN = VPS35 PE = 1 SV = 2 | 2 | | 2.50E+07 |
| J9R021 | Eukaryotic translation initiation factor 3 subunit A OS = Homo sapiens GN = eIF3a PE = 2 SV = 1 | 4 | | 2.40E+07 |
| O94788 | Retinal dehydrogenase 2 OS = Homo sapiens GN = ALDH1A2 PE = 1 SV = 3 | 2 | | 5.50E+07 |
| B3KNX0 | cDNA FLJ30621 fis, clone CTONG2001681, highly similar to Complement C1s subcomponent (EC 3.4.21.42) OS = Homo sapiens PE | 2 | | 1.60E+07 |
| P16615 | Sarcoplasmic/endoplasmic reticulum calcium ATPase 2 OS = Homo sapiens GN = ATP2A2 PE = 1 SV = 1 | 2 | 2 | 1.10E+08 |
| A0A0C4DGV | Semaphorin-3B OS = Homo sapiens GN = SEMA3B PE = 1 SV = 1 | 2 | | 9.20E+07 |
| B4DNB9 | cDNA FLJ53069, highly similar to AP-2 complex subunit mu-1 OS = Homo sapiens PE = 2 SV = 1 | 2 | | 1.10E+09 |
| P61604 | 10 kDa heat shock protein, mitochondrial OS = Homo sapiens GN = HSPE1 PE = 1 SV = 2 | 3 | | 1.10E+08 |
| P20618 | Proteasome subunit beta type-1 OS = Homo sapiens GN = PSMB1 PE = 1 SV = 1 | 1 | | 2.00E+07 |
| O76024 | Wolframin OS = Homo sapiens GN = WFS1 PE = 1 SV = 2 | 2 | | 6.10E+07 |
| H0YKD8 | 60S ribosomal protein L28 OS = Homo sapiens GN = RPL28 PE = 1 SV = 1 | 3 | 2 | 1.10E+08 |
| J3QRS3 | Myosin regulatory light chain 12A OS = Homo sapiens GN = MYL12A PE = 1 SV = 1 | 2 | 5 | 9.50E+07 |
| Q09028 | Histone-binding protein RBBP4 OS = Homo sapiens GN = RBBP4 PE = 1 SV = 3 | 2 | | 4.70E+07 |
| I3L504 | Eukaryotic translation initiation factor 5A-1 OS = Homo sapiens GN = EIF5A PE = 1 SV = 1 | 2 | 1 | 1.30E+08 |
| A0A024R845 | RAB14, member RAS oncogene family, isoform CRA_a OS = Homo sapiens GN = RAB14 PE = 3 SV = 1 | 2 | 1 | 8.80E+07 |
| A0A0A0MQT | Retinol binding protein 1, cellular OS = Homo sapiens GN = RBP1 PE = 1 SV = 1 | 2 | | 6.70E+07 |
| H0Y166 | Dehydrogenase/reductase SDR family member 7 (Fragment) OS = Homo sapiens GN = DHRS7 PE = 1 SV = 1 | 1 | | 9.20E+07 |
| B1AP13 | Complement decay-accelerating factor OS = Homo sapiens GN = CD55 PE = 1 SV = 1 | 2 | | 9.00E+07 |
| Q6ZMJ2 | Scavenger receptor class A member 5 OS = Homo sapiens GN = SCARA5 PE = 2 SV = 1 | 2 | | 4.30E+07 |
| I1W660 | Dickkopf-like protein 1 OS = Homo sapiens GN = DKK1 PE = 2 SV = 1 | 2 | | 1.60E+08 |
| P26599 | Polypyrimidine tract-binding protein 1 OS = Homo sapiens GN = PTBP1 PE = 1 SV = 1 | 2 | 1 | 1.00E+08 |
| A0A024R035 | Complement component 9, isoform CRA_a OS = Homo sapiens GN = C9 PE = 4 SV = 1 | 2 | 2 | 8.40E+07 |
| P22352 | Glutathione peroxidase 3 OS = Homo sapiens GN = GPX3 PE = 1 SV = 2 | 2 | | 5.50E+07 |
| A0A0A0MTS | Glucose-6-phosphate isomerase (Fragment) OS = Homo sapiens GN = GPI PE = 1 SV = 1 | 2 | 1 | 5.50E+07 |
| A5PLK9 | Metalloendopeptidase OS = Homo sapiens GN = BMP1 PE = 2 SV = 1 | 2 | | 1.70E+07 |
| P11177 | Pyruvate dehydrogenase E1 component subunit beta, mitochondrial OS = Homo sapiens GN = PDHB PE = 1 SV = 3 | 1 | 1 | 3.30E+07 |
| A2RUM7 | Ribosomal protein L5 OS = Homo sapiens GN = RPL5 PE = 2 SV = 1 | 3 | 3 | 7.80E+07 |
| B4EIJ8 | cDNA FLJ56285, highly similar to ADP-ribosylation factor-like protein 8B OS = Homo sapiens PE = 2 SV = 1 | 2 | | 8.30E+07 |
| P22692 | Insulin-like growth factor-binding protein 4 OS = Homo sapiens GN = IGFBP4 PE = 1 SV = 2 | 1 | | 9.40E+07 |

APPENDIX A-continued

| | | | |
|---|---|---|---|
| D3DP46 | Signal peptidase complex subunit 3 homolog (S. cerevisiae), isoform CRA_a OS = Homo sapiens GN = SPCS3 PE = 4 SV = 1 | 2 | 5.40E+07 |
| B4DKM6 | cDNA FLJ54305, highly similar to Serum paraoxonase/arylesterase 2 (EC 3.1.1.2) OS = Homo sapiens PE = 2 SV = 1 | 2 | 6.10E+07 |
| P36405 | ADP-ribosylation factor-like protein 3 OS = Homo sapiens GN = ARL3 PE = 1 SV = 1 | | 1.50E+07 |
| B2RGF3 | Splicing factor arginine/serine-rich 3 OS = Homo sapiens GN = SFRS3 PE = 2 SV = 1 | 2 | 1.70E+08 |
| Q9UMS4 | Pre-mRNA-processing factor 19 OS = Homo sapiens GN = PRPF19 PE = 1 SV = 1 | 2 | 3.50E+07 |
| P26368 | Splicing factor U2AF 65 kDa subunit OS = Homo sapiens GN = U2AF2 PE = 1 SV = 4 | 2 | 1.80E+07 |
| B4E0X1 | Beta-2-microglobulin OS = Homo sapiens PE = 2 SV = 1 | | 1.10E+08 |
| Q6DK41 | Protein Wnt (Fragment) OS = Homo sapiens GN = WNT5A PE = 2 SV = 2 | 1 | 5.00E+07 |
| Q5JWF2 | Guanine nucleotide-binding protein G(s) subunit alpha isoforms XLas OS = Homo sapiens GN = GNAS PE = 1 SV = 2 | | 3.50E+07 |
| O00764 | Pyridoxal kinase OS = Homo sapiens GN = PDXK PE = 1 SV = 1 | 1 | 1.20E+07 |
| P32320 | Cytidine deaminase OS = Homo sapiens GN = CDA PE = 1 SV = 2 | 4 | 2.10E+07 |
| Q53GL6 | RNA binding protein (Autoantigenic, hnRNP-associated with lethal yellow) long isoform variant (Fragment) OS = Homo sapiens G | 2 | 5.10E+07 |
| B3KS79 | cDNA FLJ35730 fis, clone TESTI2003131, highly similar to ALPHA-1-ANTICHYMOTRYPSIN OS = Homo sapiens PE = 2 SV = 1 | 2 | 2.60E+07 |
| Q96CS3 | FAS-associated factor 2 OS = Homo sapiens GN = FAF2 PE = 1 SV = 2 | | 1.30E+07 |
| A1L0T0 | Acetolactate synthase-like protein OS = Homo sapiens GN = IILVBL PE = 1 SV = 2 | 1 | 4.70E+07 |
| Q6IPI1 | Ribosomal protein L29 OS = Homo sapiens GN = RPL29 PE = 2 SV = 1 | 1 | 2.60E+08 |
| A5YM53 | ITGAV protein OS = Homo sapiens GN = ITGAV PE = 2 SV = 1 | 2 | 1.40E+07 |
| A8K6C9 | cDNA FLJ78037, highly similar to Homo sapiens insulin-like growth factor 2 (somatomedin A), mRNA OS = Homo sapiens PE = 2 SV | | 2.80E+07 |
| A8K3I0 | cDNA FLJ78437, highly similar to Homo sapiens cartilage oligomeric matrix protein (COMP), mRNA OS = Homo sapiens PE = 2 SV = 1 | | 1.80E+07 |
| C7EXL7 | MHC class I antigen OS = Homo sapiens GN = HLA-Cw PE = 3 SV = 1 | | 2.10E+08 |
| A0A024RAF7 | Endothelin converting enzyme 1, isoform CRA_b OS = Homo sapiens GN = ECE1 PE = 4 SV = 1 | 1 | 1.80E+07 |
| H3BS72 | Very-long-chain (3R)-3-hydroxyacyl-CoA dehydratase 3 OS = Homo sapiens GN = HACD3 PE = 1 SV = 1 | | 1.40E+07 |
| Q9NYL4 | Peptidyl-prolyl cis-trans isomerase FKBP11 OS = Homo sapiens GN = FKBP11 PE = 1 SV = 1 | | 6.80E+07 |
| A8K769 | cDNA FLJ77721, highly similar to Homo sapiens secretory carrier membrane protein 2 (SCAMP2), mRNA OS = Homo sapiens PE = 2 | | 5.20E+06 |
| A0A024QZJ7 | Coiled-coil domain containing 6, isoform CRA_a OS = Homo sapiens GN = CCDC6 PE = 4 SV = 1 | | 1.80E+07 |
| Q63ZY3 | KN motif and ankyrin repeat domain-containing protein 2 OS = Homo sapiens GN = KANK2 PE = 1 SV = 1 | 2 | 3.80E+07 |
| P42224 | Signal transducer and activator of transcription 1-alpha/beta OS = Homo sapiens GN = STAT1 PE = 1 SV = 2 | | 1.80E+07 |
| O75462 | Cytokine receptor-like factor 1 OS = Homo sapiens GN = CRLF1 PE = 1 SV = 1 | 1 | 4.80E+07 |
| A4D2Q0 | Unc-84 homolog A (C. elegans) OS = Homo sapiens GN = UNC84A PE = 4 SV = 1 | 2 | 1.20E+07 |
| Q9UHX1 | Poly(U)-binding-splicing factor PUF60 OS = Homo sapiens GN = PUF60 PE = 1 SV = 1 | 1 | 3.80E+07 |
| Q13666 | 40S ribosomal protein S21 OS = Homo sapiens GN = RPS21 PE = 2 SV = 2 | | 2.90E+07 |
| P09466 | Glycodelin OS = Homo sapiens GN = PAEP PE = 1 SV = 1 | | 7.30E+07 |
| A0A024RAN2 | Calpastatin, isoform CRA_a OS = Homo sapiens GN = CAST PE = 4 SV = 1 | 3 | 7.80E+07 |
| P27105 | Erythrocyte band 7 integral membrane protein OS = Homo sapiens GN = STOM PE = 1 SV = 3 | | 2.50E+07 |
| C9JF17 | Apolipoprotein D (Fragment) OS = Homo sapiens GN = APOD PE = 1 SV = 1 | | 4.60E+07 |
| Q9HDC9 | Adipocyte plasma membrane-associated protein OS = Homo sapiens GN = APMAP PE = 1 SV = 2 | 1 | 3.20E+08 |
| Q96RG5 | Insulin receptor substrate 2 insertion mutant (Fragment) OS = Homo sapiens GN = IRS2 PE = 4 SV = 1 | | |
| P62847 | 40S ribosomal protein S24 OS = Homo sapiens GN = RPS24 PE = 1 SV = 1 | 1 | 8.90E+07 |
| P62081 | 40S ribosomal protein S7 OS = Homo sapiens GN = RPS7 PE = 1 SV = 1 | 2 | 1.90E+08 |
| Q9HAV7 | GrpE protein homolog 1, mitochondrial OS = Homo sapiens GN = GRPEL1 PE = 1 SV = 2 | 1 | 3.20E+07 |
| Q96PD5 | N-acetylmuramoyl-L-alanine amidase OS = Homo sapiens GN = PGLYRP2 PE = 1 SV = 1 | | |
| H3BNX8 | Cytochrome c oxidase subunit 5A, mitochondrial OS = Homo sapiens GN = COX5A PE = 1 SV = 1 | 1 | 6.10E+07 |
| P24310 | Cytochrome c oxidase subunit 7A1, mitochondrial OS = Homo sapiens GN = COX7A1 PE = 1 SV = 2 | | 1.70E+07 |
| Q7L4Q3 | Glutathione peroxidase OS = Homo sapiens GN = GPX1 PE = 2 SV = 1 | 1 | 3.20E+07 |
| A8K4A5 | cDNA FLJ77482, highly similar to Human atrial natriuretic peptide clearance receptor (ANP C-receptor) mRNA OS = Homo sapiens | | 3.50E+07 |
| A0A024R0V4 | Vasodilator-stimulated phosphoprotein, isoform CRA_a OS = Homo sapiens GN = VASP PE = 4 SV = 1 | 1 | 3.40E+07 |
| P35610 | Sterol O-acyltransferase 1 OS = Homo sapiens GN = SOAT1 PE = 1 SV = 3 | | 4.90E+07 |
| Q96SM3 | Probable carboxypeptidase X1 OS = Homo sapiens GN = CPXM1 PE = 2 SV = 2 | | 9.10E+06 |
| B2RDI5 | cDNA, FLJ96627, highly similar to Homo sapiens calpain 1, (mu/l) large subunit (CAPN1), mRNA | 3 | 2.80E+07 |
| Q13201 | Multimerin-1 OS = Homo sapiens GN = MMRN1 PE = 1 SV = 3 | | |
| O14907 | Tax1-binding protein 3 OS = Homo sapiens GN = TAX1BP3 PE = 1 SV = 2 | | 3.50E+07 |
| Q65ZC8 | Single-chain Fv (Fragment) OS = Homo sapiens GN = scFv PE = 2 SV = 1 | | 6.70E+07 |
| Q59GG8 | Coronin (Fragment) OS = Homo sapiens PE = 3 SV = 1 | | 4.40E+07 |

APPENDIX A-continued

| ID | Description | Count | Value |
|---|---|---|---|
| Q14696 | LDLR chaperone MESD OS = Homo sapiens GN = MESDC2 PE = 1 SV = 2 | 1 | 3.70E+07 |
| Q8TAA3 | Proteasome subunit alpha type-7-like OS = Homo sapiens GN = PSMA8 PE = 2 SV = 3 | 1 | 2.60E+07 |
| Q9H2P1 | DC16 OS = Homo sapiens PE = 2 SV = 1 | 1 | 1.80E+07 |
| A0A0B4J1S4 | 15 kDa selenoprotein OS = Homo sapiens GN = SEP15 PE = 1 SV = 1 | 1 | 1.40E+07 |
| F8W727 | 60S ribosomal protein L32 OS = Homo sapiens GN = RPL32 PE = 1 SV = 1 | 2 | 1.40E+08 |
| P11279 | Lysosome-associated membrane glycoprotein 1 OS = Homo sapiens GN = LAMP1 PE = 1 SV = 3 | 1 | 1.20E+08 |
| O43488 | Aflatoxin B1 aldehyde reductase member 2 OS = Homo sapiens GN = AKR7A2 PE = 1 SV = 3 | 1 | 2.30E+07 |
| A0A024R118 | Methyltransferase like 7A, isoform CRA_a OS = Homo sapiens GN = METTL7A PE = 4 SV = 1 | 1 | 7.50E+07 |
| A0A024QZK8 | Heterogeneous nuclear ribonucleoprotein H3 (2H9), isoform CRA_a OS = Homo sapiens GN = HNRPH3 | 1 | 4.00E+07 |
| B3KM21 | Family with sequence similarity 36, member A, isoform CRA_a OS = Homo sapiens GN = FAM36A PE = 2 SV = 1 | | 1.90E+07 |
| Q53HQ0 | Flotillin 1 variant (Fragment) OS = Homo sapiens PE = 2 SV = 1 | | 1.70E+07 |
| A0A087WYF | MICOS complex subunit MIC27 OS = Homo sapiens GN = APOOL PE = 1 SV = 1 | 1 | 2.70E+07 |
| Q9BRX8 | Redox-regulatory protein FAM213A OS = Homo sapiens GN = FAM213A PE = 1 SV = 3 | | 8.10E+07 |
| B7Z8W8 | Reticulon OS = Homo sapiens PE = 2 SV = 1 | 1 | 1.20E+08 |
| Q6IAX6 | 3'-phosphoadenosine 5'-phosphosulfate synthase 1 OS = Homo sapiens GN = PAPSS1 PE = 2 SV = 1 | | 3.20E+07 |
| Q76LA1 | CSTB protein OS = Homo sapiens GN = CSTB PE = 2 SV = 1 | 1 | 7.10E+07 |
| F8VVA7 | Coatomer subunit zeta-1 OS = Homo sapiens GN = CPPZ1 PE = 1 SV = 1 | | 2.50E+07 |
| B3KN29 | cDNA FLJ13371 fis, clone PLACE1000656, highly similar to PRA1 family protein 2 OS = Homo sapiens | | 3.90E+07 |
| B4DW13 | HCG23341, isoform CRA_d OS = Homo sapiens GN = hCG_23341 PE = 2 SV = 1 | | 2.60E+07 |
| F8WA42 | Sulfatase-modifying factor 2 OS = Homo sapiens GN = SUMF2 PE = 1 SV = 1 | 1 | 2.90E+07 |
| A4D2D2 | Procollagen C-endopeptidase enhancer OS = Homo sapiens GN = PCOLCE PE = 4 SV = 1 | 1 | 7.10E+07 |
| Q13283 | Ras GTPase-activating protein-binding protein 1 OS = Homo sapiens GN = G3BP1 PE = 1 SV = 1 | | 1.50E+07 |
| Q9NX40 | OCIA domain-containing protein 1 OS = Homo sapiens GN = OCIAD1 PE = 1 SV = 1 | | 8.20E+07 |
| P59665 | Neutrophil defensin 1 OS = Homo sapiens GN = DEFA1 PE = 1 SV = 1 | | 1.50E+08 |
| A8K4K9 | cDNA FLJ76169 OS = Homo sapiens PE = 2 SV = 1 | | 1.40E+07 |
| J3KQ48 | Peptidyl-tRNA hydrolase 2, mitochondrial OS = Homo sapiens GN = PTRH2 PE = 1 SV = 1 | 1 | 1.90E+07 |
| D3DR22 | Hydroxysteroid (17-beta) dehydrogenase 12, isoform CRA_a OS = Homo sapiens GN = HSD17B12 PE = 3 SV = 1 | | 1.10E+08 |
| P35914 | Hydroxymethylglutaryl-CoA lyase, mitochondrial OS = Homo sapiens GN = HMGCL PE = 1 SV = 2 | | 2.30E+07 |
| B2RDT8 | cDNA, FLJ96764, highly similar to Homo sapiens sorting nexin 8 (SNX8), mRNA OS = Homo sapiens | | |
| P26006 | Integrin alpha-3 OS = Homo sapiens GN = ITGA3 PE = 1 SV = 5 | | 1.30E+08 |
| A8MU27 | Small ubiquitin-related modifier 3 OS = Homo sapiens GN = SUMO3 PE = 1 SV = 1 | 1 | |
| Q969X5 | Endoplasmic reticulum-Golgi intermediate compartment protein 1 OS = Homo sapiens GN = ERGIC1 | 1 | 2.80E+07 |
| E7EMK3 | Flotillin-2 OS = Homo sapiens GN = FLOT2 PE = 1 SV = 1 | | 4.80E+07 |
| P61160 | Actin-related protein 2 OS = Homo sapiens GN = ACTR2 PE = 1 SV = 1 | | |
| B1AHD1 | NHP2-like protein 1 OS = Homo sapiens GN = NHP2L1 PE = 1 SV = 1 | 1 | 1.80E+07 |
| F8VV71 | Ubiquitin-conjugating enzyme E2 N OS = Homo sapiens GN = UBE2N PE = 1 SV = 1 | 1 | 7.20E+07 |
| Q9BY32 | Inosine triphosphate pyrophosphatase OS = Homo sapiens GN = ITPA PE = 1 SV = 2 | | 8.30E+07 |
| Q16629 | Serine/arginine-rich splicing factor 7 OS = Homo sapiens GN = SRSF7 PE = 1 SV = 1 | 2 | 1.40E+07 |
| Q9BW30 | Tubulin polymerization-promoting protein family member 3 OS = Homo sapiens GN = TPPP3 PE = 1 SV = 1 | 1 | 2.30E+08 |
| Q59E93 | Membrane alanine aminopeptidase variant (Fragment) OS = Homo sapiens PE = 2 SV = 1 | | 1.20E+07 |
| Q5VV89 | Microsomal glutathione S-transferase 3 OS = Homo sapiens GN = MGST3 PE = 1 SV = 1 | 1 | 7.10E+07 |
| Q9Y3Y2 | Chromatin target of PRMT1 protein OS = Homo sapiens GN = CHTOP PE = 1 SV = 2 | | 1.60E+07 |
| B2R4D5 | Actin-related protein 2/3 complex subunit 3 OS = Homo sapiens PE = 2 SV = 1 | | 6.10E+07 |
| H7BXI1 | Extended synaptotagmin-2 (Fragment) OS = Homo sapiens GN = ESYT2 PE = 1 SV = 1 | | |
| Q32Q10 | RSU1 protein (Fragment) OS = Homo sapiens GN = RSU1 PE = 2 SV = 1 | | |
| J3KTL2 | Serine/arginine-rich splicing factor 1 OS = Homo sapiens GN = SRSF1 PE = 1 SV = 1 | 2 | 4.30E+07 |
| G3V5Z7 | Proteasome subunit alpha type OS = Homo sapiens GN = PSMA6 PE = 1 SV = 1 | | 2.40E+07 |
| P84157 | Matrix-remodeling-associated protein 7 OS = Homo sapiens GN = MXRA7 PE = 1 SV = 1 | | 2.10E+07 |
| A0A024QZF2 | Related RAS viral (R-ras) oncogene homolog, isoform CRA_a OS = Homo sapiens GN = RRAS PE = 4 SV = 1 | | 1.90E+08 |
| A0A024R866 | Ribosomal protein L35, isoform CRA_a OS = Homo sapiens GN = RPL35 PE = 3 SV = 1 | 1 | |
| B3KQQ9 | cDNA PSEC0048 fis, clone NT2RP2000028, highly similar to Serine protease 23 OS = Homo sapiens | | |
| Q8WUY3 | Protein prune homolog 2 OS = Homo sapiens GN = PRUNE2 PE = 1 SV = 3 | | |
| Q9UNL2 | Translocon-associated protein subunit gamma OS = Homo sapiens GN = SSR3 PE = 1 SV = 1 | 1 | 2.60E+07 |

APPENDIX A-continued

| ID | Description | Count | Value |
|---|---|---|---|
| A0A087WX7 | Chorionic somatomammotropin hormone 2 OS = Homo sapiens GN = CSH2 PE = 3 SV = 1 | 1 | 1.30E+07 |
| Q96IY4 | Carboxypeptidase B2 OS = Homo sapiens GN = CPB2 PE = 1 SV = 2 | 1 | 3.90E+07 |
| X6R8A1 | Carboxypeptidase OS = Homo sapiens GN = CTSA PE = 1 SV = 1 | 1 | 1.70E+07 |
| P23497 | Nuclear autoantigen Sp-100 OS = Homo sapiens GN = SP100 PE = 1 SV = 1 | 1 | 3.10E+07 |
| Q96IJ7 | Protein disulfide-isomerase TMX3 OS = Homo sapiens GN = TMX3 PE = 1 SV = 3 | 1 | 2.40E+07 |
| P25789 | Proteasome subunit alpha type-4 OS = Homo sapiens GN = PSMA4 PE = 1 SV = 1 | 1 | 4.70E+07 |
| A0A024RDR0 | High-mobility group box 1, isoform CRA_a OS = Homo sapiens GN = HMGB1 PE = 4 SV = 1 | 1 | 1.40E+08 |
| V9GYM3 | Apolipoprotein A-II OS = Homo sapiens GN = APDA2 PE = 1 SV = 1 | 1 | 1.00E+08 |
| P49207 | 60S ribosomal protein L34 OS = Homo sapiens GN = RPL34 PE = 1 SV = 3 | 1 | 1.20E+08 |
| P46063 | ATP-dependent DNA helicase Q1 OS = Homo sapiens GN = RECQL PE = 1 SV = 3 | 1 | 3.30E+05 |
| Q92520 | Protein FAM3C OS = Homo sapiens GN = FAM3C PE = 1 SV = 1 | 1 | 1.80E+07 |
| A4D1W8 | Ependymin related protein 1 (Zebrafish), isoform CRA_b OS = Homo sapiens GN = UCC1 PE = 4 SV = 1 | | 5.70E+07 |
| D3DQ70 | SERPINE1 mRNA binding protein 1, isoform CRA_d OS = Homo sapiens GN = SERBP1 PE = 4 SV = 1 | | 5.80E+07 |
| B4DNR4 | cDNA FLJ52338, highly similar to Calpain-9 (EC 3.4.22.—) OS = Homo sapiens PE = 2 SV = 1 | | 2.70E+07 |
| P26583 | High mobility group protein B2 OS = Homo sapiens GN = HMGB2 PE = 1 SV = 2 | | 6.20E+07 |
| P28066 | Proteasome subunit alpha type-5 OS = Homo sapiens GN = PSMA5 PE = 1 SV = 3 | | 1.70E+07 |
| B2RDQ3 | cDNA, FLJ96718, highly similar to Homo sapiens splicing factor, arginine/serine-rich 10 interleukin-27 subunit beta OS = Homo sapiens GN = EBI3 PE = 1 SV = 1 | 1 | 4.40E+07 |
| Q14213 | | | 1.10E+08 |
| P24158 | Myeloblastin OS = Homo sapiens GN = PRTN3 PE = 1 SV = 3 | | 4.70E+07 |
| Q99715 | Collagen alpha-1(XII) chain OS = Homo sapiens GN = COL12A1 PE = 1 SV = 2 | 2 | 2.60E+07 |
| P27487 | Dipeptidyl peptidase 4 OS = Homo sapiens GN = DPP4 PE = 1 SV = 2 | 5 | 1.60E+07 |
| O14498 | Immunoglobulin superfamily containing leucine-rich repeat protein OS = Homo sapiens GN = ISLR | 1 | 7.90E+07 |
| Q8IW90 | MTCH1 protein (Fragment) OS = Homo sapiens GN = MTCH1 PE = 2 SV = 2 | 2 | 4.70E+07 |
| F8WCF6 | Protein ARPC4-TTLL3 OS = Homo sapiens GN = ARPC4-TTLL3 PE = 4 SV = 1 | 3 | 8.20E+07 |
| A0A0C4DGQ | Calpain small subunit 1 OS = Homo sapiens GN = CAPNS1 PE = 1 SV = 1 | 1 | |
| P11233 | Ras-related protein Ral-A OS = Homo sapiens GN = RALA PE = 1 SV = 1 | | 2.60E+07 |
| O43181 | NADH dehydrogenase [ubiquinone] iron-sulfur protein 4, mitochondrial OS = Homo sapiens GN = NDUFS4 | | 4.00E+07 |
| A0A087X1L7 | Left-right determination factor 2 OS = Homo sapiens GN = LEFTY2 PE = 1 SV = 1 | 1 | 1.40E+08 |
| P0CP74 | Putative cytochrome b-c1 complex subunit Rieske-like protein 1 OS = Homo sapiens GN = UQCRFS1P1 | | 1.40E+07 |
| P54727 | UV excision repair protein RAD23 homolog B OS = Homo sapiens GN = RAD23B PE = 1 SV = 1 | | 5.70E+07 |
| Q5I0G2 | Prolactin OS = Homo sapiens GN = PRL PE = 1 SV = 1 | | 8.40E+07 |
| E5KNY5 | Leucine-rich PPR-motif containing OS = Homo sapiens GN = LRPPRC PE = 4 SV = 1 | | 1.70E+07 |
| A4PBF7 | TATA box binding protein (TBP)-associated factor 4B OS = Homo sapiens GN = taf4b PE = 2 SV = 1 | | 4.80E+08 |
| P10768 | S-formylglutathione hydrolase OS = Homo sapiens GN = ESD PE = 1 SV = 2 | | 2.50E+07 |
| Q59FZ8 | Nebulette isoform variant (Fragment) OS = Homo sapiens PE = 2 SV = 1 | | 1.00E+08 |
| A8MYS5 | Post-GPI attachment to proteins factor 2 OS = Homo sapiens GN = PGAP2 PE = 4 SV = 2 | 2 | 2.80E+08 |
| Q7Z7H5 | Transmembrane emp24 domain-containing protein 4 OS = Homo sapiens GN = TMED4 PE = 1 SV = 1 | 2 | 4.20E+07 |
| P02458 | Collagen alpha-1(II) chain OS = Homo sapiens GN = COL2A1 PE = 1 SV = 3 | 1 | 1.80E+09 |
| Q14258 | E3 ubiquitin/ISG15 ligase TRIM25 OS = Homo sapiens GN = TRIM25 PE = 1 SV = 2 | | 1.40E+08 |
| J3KQN4 | 60S ribosomal protein L36a OS = Homo sapiens GN = RPL36A PE = 3 SV = 1 | | 1.30E+08 |
| Q92626 | Peroxidasin homolog OS = Homo sapiens GN = PXDN PE = 1 SV = 2 | 2 | 2.70E+07 |
| Q14019 | Coactosin-like protein OS = Homo sapiens GN = COTL1 PE = 1 SV = 3 | 1 | 3.40E+07 |
| B2R761 | cDNA, FLJ93299, highly similar to Homo sapiens sterol carrier protein 2 (SCP2), mRNA | | 3.30E+07 |
| P05161 | Ubiquitin-like protein ISG15 OS = Homo sapiens GN = ISG15 PE = 1 SV = 5 | | 2.30E+07 |
| A8K103 | cDNA FLJ75454, highly similar to Homo sapiens arrestin, beta 1 (ARRB1), transcript variant 1 | 1 | 2.60E+07 |
| Q13421 | Mesothelin OS = Homo sapiens GN = MSLN PE = 1 SV = 2 | 4 | 9.30E+06 |
| Q96FQ6 | Protein S100-A16 OS = Homo sapiens GN = S100A16 PE = 1 SV = 1 | 1 | 2.90E+07 |
| P10155 | 60 kDa SS-A/Ro ribonucleoprotein OS = Homo sapiens GN = TROVE2 PE = 1 SV = 2 | 1 | 4.50E+07 |
| P56199 | Integrin alpha-1 OS = Homo sapiens GN = ITGA1 PE = 1 SV = 2 | | 2.20E+07 |
| A0A024R8U5 | Splicing factor, arginine/serine-rich 2, isoform CRA_a OS = Homo sapiens GN = SFRS2 PE = 4 SV = 1 | | 8.40E+07 |
| A6XNE2 | Complement factor D preproprotein OS = Homo sapiens PE = 2 SV = 1 | | |
| Q9BUD6 | Spondin-2 OS = Homo sapiens GN = SPON2 PE = 1 SV = 3 | 1 | |

APPENDIX A-continued

| ID | Description | Count | Value |
|---|---|---|---|
| K7ERQ8 | Uncharacterized protein (Fragment) OS = Homo sapiens PE = 3 SV = 1 | 1 | 7.60E+07 |
| Q14151 | Scaffold attachment factor B2 OS = Homo sapiens GN = SAFB2 PE = 1 SV = 1 | 1 | 1.40E+07 |
| A4D1G5 | 40S ribosomal protein S27 OS = Homo sapiens GN = LOC392748 PE = 3 SV = 1 | 1 | 1.20E+08 |
| B2R679 | cDNA, FLJ92825, highly similar to Homo sapiens SARIa gene homolog 1 (S. cerevisiae) (SARA1) | 1 | 5.30E+07 |
| Q8IUX7 | Adipocyte enhancer-binding protein 1 OS = Homo sapiens GN = AEBP1 PE = 1 SV = 1 | | 2.40E+07 |
| P46776 | 60S ribosomal protein L27a OS = Homo sapiens GN = RPL27A PE = 1 SV = 2 | 2 | 2.60E+08 |
| P23526 | Adenosylhomocysteinase OS = Homo sapiens GN = AHCY PE = 1 SV = 4 | | 6.50E+07 |
| A8K7E0 | cDNA FLJ76911, highly similar to Homo sapiens biglycan (BGN), mRNA OS = Homo sapiens PE = 2 SV = 1 | 1 | 3.10E+07 |
| A0A024QYT5 | Serpin peptidase inhibitor, clade E (Nexin, plasminogen activator inhibitor type 1), member 1 | 1 | 2.50E+07 |
| A6NEL0 | Non-histone chromosomal protein HMG-14 OS = Homo sapiens GN = HMGN1 PE = 1 SV = 1 | | |
| Q9BTV4 | Transmembrane protein 43 OS = Homo sapiens GN = TMEM43 PE = 1 SV = 1 | 2 | 1.10E+08 |
| B1AJZ9 | Forkhead-associated domain-containing protein 1 OS = Homo sapiens GN = FHAD1 PE = 2 SV = 2 | 1 | 1.50E+09 |
| P61960 | Ubiquitin-fold modifier 1 OS = Homo sapiens GN = UFM1 PE = 1 SV = 1 | | 1.60E+07 |
| O43615 | Mitochondrial import inner membrane translocase subunit TIM44 OS = Homo sapiens GN = TIMM44 | | 1.30E+07 |
| Q14683 | Structural maintenance of chromosomes protein 1A OS = Homo sapiens GN = SMC1A PE = 1 SV = 2 | | |
| P30626 | Sorcin OS = Homo sapiens GN = SRI PE = 1 SV = 1 | 1 | 1.70E+08 |
| P61254 | 60S ribosomal protein L26 OS = Homo sapiens GN = RPL26 PE = 1 SV = 1 | 1 | 8.50E+07 |
| A0A024R6I9 | Serpin peptidase inhibitor, clade A (Alpha-1 antiproteinase, antitrypsin), member 4, isoform CRA | 3 | 1.50E+07 |
| D4QEZ8 | Short-chain acyl-CoA dehydrogenase OS = Homo sapiens GN = ACADS PE = 2 SV = 1 | | 7.70E+07 |
| H9STE0 | Cytochrome c oxidase subunit 2 OS = Homo sapiens GN = COX2 PE = 3 SV = 1 | 1 | 6.20E+07 |
| Q99442 | Translocation protein SEC62 OS = Homo sapiens GN = SEC62 PE = 1 SV = 1 | | 2.00E+07 |
| Q59EG8 | Proteasome 26S non-ATPase subunit 2 variant (Fragment) OS = Homo sapiens PE = 2 SV = 1 | | 2.30E+08 |
| P50238 | Cysteine-rich protein 1 OS = Homo sapiens GN = CRIP1 PE = 1 SV = 3 | | 1.00E+08 |
| P15531 | Nucleoside diphosphate kinase A OS = Homo sapiens GN = NME1 PE = 1 SV = 1 | 2 | |
| Q01638 | Interleukin-1 receptor-like 1 OS = Homo sapiens GN = IL1RL1 PE = 1 SV = 4 | 1 | 1.20E+08 |
| P14550 | Alcohol dehydrogenase [NADP(+)] OS = Homo sapiens GN = AKR1A1 PE = 1 SV = 3 | | 2.80E+07 |
| B7Z6S9 | Glucosylceramidase (Thioltransferase), isoform CRA_c OS = Homo sapiens PE = 2 SV = 1 | | 6.70E+06 |
| Q9HCU0 | cDNA FLJ61541, highly similar to Homo sapiens PDZ and LIM domain 5 (PDLIM5), transcript variant 2 | 3 | 4.10E+07 |
| Q96Y6 | Endosialin OS = Homo sapiens GN = CD248 PE = 1 SV = 1 | | 2.40E+07 |
| P51970 | PDZ and LIM domain protein 2 OS = Homo sapiens GN = PDLIM2 PE = 1 SV = 1 | | 3.60E+07 |
| P00167 | NADH dehydrogenase [ubiquinone] 1 alpha subcomplex subunit 8 OS = Homo sapiens GN = NDUFA8 | 2 | 2.90E+07 |
| O60330 | Cytochrome b5 OS = Homo sapiens GN = CYB5A PE = 1 SV = 2 | 1 | 2.30E+06 |
| B2RBF9 | Protocadherin gamma-A12 OS = Homo sapiens GN = PCDHGA12 PE = 2 SV = 1 | | |
| Q15019 | cDNA, FLJ95487, highly similar to Homo sapiens peptidyl arginine deiminase, type 1 (PADI1) | 1 | 9.20E+07 |
| A0A024RAM | Septin-2 OS = Homo sapiens GN = SEPT2 PE = 1 SV = 1 | 4 | 1.90E+08 |
| O43681 | ATPase ASNA1 OS = Homo sapiens GN = ASNA1 PE = 1 SV = 2 | | 2.20E+07 |
| P01591 | Immunoglobulin J chain OS = Homo sapiens GN = JCHAIN PE = 1 SV = 4 | | 1.60E+07 |
| A8K6K4 | cDNA FLJ77565, highly similar to Homo sapiens interleukin 1 receptor accessory protein (IL1RAP) | | 1.10E+08 |
| Q9BUT1 | 3-hydroxybutyrate dehydrogenase type 2 OS = Homo sapiens GN = BDH2 PE = 1 SV = 2 | | 2.30E+08 |
| A0A075B716 | 40S ribosomal protein S17 OS = Homo sapiens GN = RPS17 PE = 1 SV = 1 | | 5.70E+07 |
| Q59GK9 | Ribosomal protein L21 variant (Fragment) OS = Homo sapiens PE = 2 SV = 1 | 1 | 1.90E+08 |
| A8MT02 | Small nuclear ribonucleoprotein-associated proteins B and B' OS = Homo sapiens GN = SNRPB PE = 1 SV = 3 | | 5.20E+07 |
| P01031 | Complement C5 OS = Homo sapiens GN = C5 PE = 1 SV = 4 | | 1.30E+07 |
| X6R2S6 | Signal peptidase complex subunit 1 OS = Homo sapiens GN = SPCS1 PE = 1 SV = 1 | | 5.50E+07 |
| Q6SA08 | Testis-specific serine/threonine-protein kinase 4 OS = Homo sapiens GN = TSSK4 PE = 1 SV = 1 | 1 | 2.60E+07 |
| A6NFQ7 | Divergent paired-related homeobox OS = Homo sapiens GN = DPRX PE = 3 SV = 1 | | |
| H0YET1 | Liprin-beta-2 (Fragment) OS = Homo sapiens GN = PPFIBP2 PE = 1 SV = 1 | | 5.20E+07 |
| Q14498 | RNA-binding protein 39 OS = Homo sapiens GN = RBM39 PE = 1 SV = 2 | | |
| O95428 | Papilin OS = Homo sapiens GN = PAPLN PE = 2 SV = 4 | | |
| E9PB61 | THO complex subunit 4 OS = Homo sapiens GN = ALYREF PE = 1 SV = 1 | | 3.90E+07 |
| Q9BSL1 | Ubiquitin-associated domain-containing protein 1 OS = Homo sapiens GN = UBAC1 PE = 1 SV = 1 | | 2.60E+05 |
| Q9Y6C9 | Mitochondrial carrier homolog 2 OS = Homo sapiens GN = MTCH2 PE = 1 SV = 1 | | 6.40E+07 |

APPENDIX A-continued

| ID | Description | | Count |
|---|---|---|---|
| A0A024R8J2 | Protein tyrosine phosphatase type IVA, member 1, isoform CRA_a OS = Homo sapiens GN = PTP4A1 | 1 | |
| B4DPP6 | cDNA FLJ54371, highly similar to Serum albumin OS = Homo sapiens PE = 2 SV = 1 | | 34 |
| B3KY79 | cDNA FLJ46620 fis, clone TLUNG2000654, highly similar to Keratin, type II cytoskeletal 7 | | 2 |
| A8K3K1 | cDNA FLJ78096, highly similar to Homo sapiens actin, alpha, cardiac muscle (ACTC), mRNA | | 1 |
| Q6GMX6 | IGH@ protein OS = Homo sapiens GN = IGH@ PE = 1 SV = 1 | | 7 |
| F5H5D3 | Tubulin alpha-1C chain OS = Homo sapiens GN = TUBA1C PE = 1 SV = 1 | | 4 |
| Q8TCD0 | Uncharacterized protein OS = Homo sapiens PE = 1 SV = 1 | | 6 |
| Q9NSB2 | Keratin, type II cuticular Hb4 OS = Homo sapiens GN = KRT84 PE = 2 SV = 2 | | 1 |
| P19013 | Keratin, type II cytoskeletal 4 OS = Homo sapiens GN = KRT4 PE = 1 SV = 4 | | 2 |
| B2ZZ89 | Epididymis luminal protein 102 OS = Homo sapiens GN = SPTBN1 PE = 2 SV = 1 | | 15 |
| B3KML9 | cDNA FLJ11352 fis, clone HEMBA1000020, highly similar to Tubulin beta-2C chain OS = Homo sapiens | | 4 |
| P50454 | Serpin H1 OS = Homo sapiens GN = SERPINH1 PE = 1 SV = 2 | | 10 |
| Q71UF1 | Aconitase OS = Homo sapiens GN = ACO2 PE = 4 SV = 1 | | 10 |
| E7EPZ9 | Tenascin-X OS = Homo sapiens GN = TNXB PE = 1 SV = 1 | | 9 |
| P61981 | 14-3-3 protein gamma OS = Homo sapiens GN = YWHAG PE = 1 SV = 2 | | 4 |
| Q9BUF5 | Tubulin beta-6 chain OS = Homo sapiens GN = TUBB6 PE = 1 SV = 1 | | 1 |
| P05187 | Alkaline phosphatase, placental type OS = Homo sapiens GN = ALPP PE = 1 SV = 2 | | 8 |
| O95171 | Sciellin OS = Homo sapiens GN = SCEL PE = 1 SV = 2 | | 5 |
| T2F9S8 | DNA-directed RNA polymerase II subunit RPB11-b2 OS = Homo sapiens GN = POLR2J3 PE = 2 SV = 1 | | 5 |
| A8K7F6 | cDNA FLJ78244, highly similar to Homo sapiens eukaryotic translation initiation factor 4A, isoform 1 | | 5 |
| D3DRA2 | Collagen, type XVII, alpha 1, isoform CRA_b OS = Homo sapiens GN = COL17A1 PE = 2 SV = 1 | | 4 |
| P08134 | Rho-related GTP-binding protein RhoC OS = Homo sapiens GN = RHOC PE = 1 SV = 1 | | 2 |
| O75841 | Uroplakin-1b OS = Homo sapiens GN = UPK1B PE = 2 SV = 5 | | 3 |
| A0A024R8W | DEAD (Asp-Glu-Ala-Asp) box polypeptide 48, isoform CRA_a OS = Homo sapiens GN = DDX48 PE = 3 SV = 1 | | 1 |
| H0Y449 | Nuclease-sensitive element-binding protein 1 (Fragment) OS = Homo sapiens GN = YBX1 PE = 1 SV = 1 | | 2 |
| H0Y300 | Haptoglobin OS = Homo sapiens GN = HP PE = 1 SV = 1 | | 2 |
| A4D0U5 | Testis derived transcript (3 LIM domains) OS = Homo sapiens GN = TES PE = 4 SV = 1 | | 2 |
| B7Z2B0 | cDNA FLJ53470, highly similar to Calcium/calmodulin-dependent protein kinase type II delta chain | | 1 |
| Q92599 | Septin-8 OS = Homo sapiens GN = SEPT8 PE = 1 SV = 4 | | 2 |
| Q53GR7 | Solute carrier family 25, member 13 (Citrin) variant (Fragment) OS = Homo sapiens PE = 2 SV = 1 | | 2 |
| A0A024R4N0 | HCG1640809, isoform CRA_b OS = Homo sapiens GN = hCG_1640809 PE = 4 SV = 1 | | 1 |
| A4D219 | Calcium/calmodulin-dependent protein kinase (CaM kinase) II beta OS = Homo sapiens GN = CAMK2B | | 1 |
| P23434 | Glycine cleavage system H protein, mitochondrial OS = Homo sapiens GN = GCSH PE = 1 SV = 1 | | 2 |
| A8K2U0 | Alpha-2-macroglobulin-like protein 1 OS = Homo sapiens GN = A2ML1 PE = 1 SV = 3 | | 3 |
| P00739 | Haptoglobin-related protein OS = Homo sapiens GN = HPR PE = 2 SV = 2 | | 1 |
| F5H423 | Uncharacterized protein OS = Homo sapiens PE = 3 SV = 1 | | 1 |
| D6NKH9 | L-lactate dehydrogenase OS = Homo sapiens PE = 2 SV = 1 | | 1 |
| Q6DEN2 | DPYSL3 protein OS = Homo sapiens GN = DPYSL3 PE = 2 SV = 1 | | 2 |
| O15231 | Zinc finger protein 185 OS = Homo sapiens GN = ZNF185 PE = 1 SV = 3 | | 2 |
| Q8WXI7 | Mucin-16 OS = Homo sapiens GN = MUC16 PE = 1 SV = 2 | | 3 |
| S4R3N1 | Protein HSPE1-MOB4 OS = Homo sapiens GN = HSPE1-MOB4 PE = 3 SV = 1 | | 2 |
| A0A0A0MT2 | Sodium/potassium-transporting ATPase subunit alpha-3 OS = Homo sapiens GN = ATP1A3 PE = 1 SV = 1 | | 1 |
| P02763 | Alpha-1-acid glycoprotein 1 OS = Homo sapiens GN = ORM1 PE = 1 SV = 1 | | 1 |
| B0YIW2 | Apolipoprotein C-III OS = Homo sapiens GN = APOC3 PE = 1 SV = 1 | | 2 |
| B2R4A2 | Cytochrome b-c1 complex subunit 7 OS = Homo sapiens PE = 2 SV = 1 | | 1 |
| A8K2N5 | Integrin beta OS = Homo sapiens PE = 2 SV = 1 | | 2 |
| B4DYN5 | Succinate dehydrogenase [ubiquinone] flavoprotein subunit, mitochondrial OS = Homo sapiens | | 2 |
| P07357 | Complement component C8 alpha chain OS = Homo sapiens GN = C8A PE = 1 SV = 2 | | 2 |
| Q8TAV2 | Similar to AFG3 ATPase family gene 3-like 2 (Yeast) (Fragment) OS = Homo sapiens PE = 2 SV = 1 | | 1 |
| A0A024R8Q1 | Glucosidase, alpha acid (Pompe disease, glycogen storage disease type II), isoform CRA_a GN = GAA | | 1 |
| B4E2S3 | Apoptosis inhibitor 5 OS = Homo sapiens GN = API5 PE = 1 SV = 3 | | 1 |
| Q9BZZ5 | | | 1 |
| Q9H3N1 | Thioredoxin-related transmembrane protein 1 OS = Homo sapiens GN = TMX1 PE = 1 SV = 1 | | 1 |

APPENDIX A-continued

| ID | Description | Count |
|---|---|---|
| H3BNC9 | Uncharacterized protein (Fragment) OS = Homo sapiens PE = 4 SV = 1 | 1 |
| A8K2U2 | Hexokinase OS = Homo sapiens PE = 2 SV = 1 | 1 |
| O15144 | Actin-related protein 2/3 complex subunit 2 OS = Homo sapiens GN = ARPC2 PE = 1 SV = 1 | 1 |
| P54136 | Arginine-tRNA ligase, cytoplasmic OS = Homo sapiens GN = RARS PE = 1 SV = 2 | 1 |
| Q9BVG4 | Protein PBDC1 OS = Homo sapiens GN = PBDC1 PE = 1 SV = 1 | 1 |
| Q14108 | Lysosome membrane protein 2 OS = Homo sapiens GN = SCARB2 PE = 1 SV = 2 | 1 |
| P10606 | Cytochrome c oxidase subunit 5B, mitochondrial OS = Homo sapiens GN = COX5B PE = 1 SV = 2 | 1 |
| Q9NSE4 | Isoleucine-tRNA ligase, mitochondrial OS = Homo sapiens GN = IARS2 PE = 1 SV = 2 | 1 |
| A0A024R259 | KIAA0427, isoform CRA_a OS = Homo sapiens GN = KIAA0427 PE = 4 SV = 1 | 1 |
| Q71V07 | Signal recognition particle subunit SRP72 OS = Homo sapiens PE = 2 SV = 1 | 1 |
| Q8WWI1 | LIM domain only protein 7 OS = Homo sapiens GN = LMO7 PE = 1 SV = 3 | 1 |
| Q8WXV6 | Plectin isoform 1a (Fragment) OS = Homo sapiens GN = PLEC1 PE = 2 SV = 1 | 1 |
| Q6P587 | Acylpyruvase FAHD1, mitochondrial OS = Homo sapiens GN = FAHD1 PE = 1 SV = 2 | 1 |
| J3KNL6 | Protein transport protein Sec16A OS = Homo sapiens GN = SEC16A PE = 1 SV = 1 | 1 |
| O75694 | Nuclear pore complex protein Nup155 OS = Homo sapiens GN = NUP155 PE = 1 SV = 1 | 1 |
| Q53G34 | Mitochondrial carrier homolog 2 variant (Fragment) OS = Homo sapiens PE = 2 SV = 1 | 1 |
| P0CF67 | Putative uncharacterized protein C3orf79 OS = Homo sapiens GN = C3orf79 PE = 4 SV = 1 | 1 |
| G8JLH6 | Tetraspanin (Fragment) OS = Homo sapiens GN = CD9 PE = 1 SV = 1 | 1 |
| B4DS05 | cDNA FLJ59403, highly similar to Nucleosome assembly protein 1-like 4 OS = Homo sapiens PE = 2 SV = 1 | 1 |
| Q9NT15 | Phosphatidylinositide phosphatase SAC1 OS = Homo sapiens GN = SACM1L PE = 1 SV = 2 | 1 |
| Q96T51 | RUN and FYVE domain-containing protein 1 OS = Homo sapiens GN = RUFY1 PE = 1 SV = 2 | 1 |
| S4R347 | Formin-binding protein 1-like OS = Homo sapiens GN = FNBP1L PE = 1 SV = 1 | 1 |
| Q13085 | Acetyl-CoA carboxylase 1 OS = Homo sapiens GN = ACACA PE = 1 SV = 2 | 1 |
| A0A087WXI5 | Cadherin-1 OS = Homo sapiens GN = CDH1 PE = 1 SV = 1 | 1 |
| K4P275 | Ig superfamily receptor LNIR OS = Homo sapiens GN = LNIR PE = 2 SV = 1 | 1 |
| B3KTJ9 | cDNA FLJ38393 fis, clone FEBRA2007212 OS = Homo sapiens PE = 2 SV = 1 | 1 |
| B2R856 | Acyl-coenzyme A oxidase OS = Homo sapiens PE = 2 SV = 1 | 1 |
| Q6N0B1 | Succinyl-CoA ligase subunit beta (Fragment) OS = Homo sapiens GN = DKFZp686D0880 PE = 2 SV = 1 | 1 |
| E9PLN8 | Uncharacterized protein (Fragment) OS = Homo sapiens PE = 4 SV = 1 | 1 |
| Q6IPX4 | 40S ribosomal protein S16 OS = Homo sapiens GN = RPS16 PE = 1 SV = 1 | 1 |
| Q53FN7 | BZW1 protein variant (Fragment) OS = Homo sapiens PE = 2 SV = 1 | 1 |
| Q9H6S3 | Epidermal growth factor receptor kinase substrate 8-like protein 2 OS = Homo sapiens GN = EPS8L2 | 1 |
| D6REX3 | Protein transport protein Sec31A OS = Homo sapiens GN = SEC31A PE = 1 SV = 1 | 1 |
| P61513 | 60S ribosomal protein L37a OS = Homo sapiens GN = RPL37A PE = 1 SV = 2 | 1 |
| Q9UBC9 | Small proline-rich protein 3 OS = Homo sapiens GN = SPRR3 PE = 1 SV = 2 | 1 |
| Q53FR4 | Vacuolar protein sorting 35 variant (Fragment) OS = Homo sapiens PE = 2 SV = 1 | 2 |
| A8K2Q6 | Peptidyl-prolyl cis-trans isomerase OS = Homo sapiens GN = PMEL PE = 2 SV = 1 | 1 |
| Q96M27 | Protein PRRC1 OS = Homo sapiens GN = PRRC1 PE = 1 SV = 1 | 1 |
| Q13835 | Plakophilin-1 OS = Homo sapiens GN = PKP1 PE = 1 SV = 2 | 1 |
| P16152 | Carbonyl reductase [NADPH] 1 OS = Homo sapiens GN = CBR1 PE = 1 SV = 3 | 1 |
| C9IZQ1 | Translocon-associated protein subunit alpha OS = Homo sapiens GN = SSR1 PE = 1 SV = 1 | 1 |
| Q9BSJ2 | Gamma-tubulin complex component 2 OS = Homo sapiens GN = TUBGCP2 PE = 1 SV = 2 | 1 |
| S4R435 | Protein RPS10-NUDT3 (Fragment) OS = Homo sapiens GN = RPS10-NUDT3 PE = 3 SV = 1 | 1 |
| L8ECD6 | Alternative protein PMEL OS = Homo sapiens GN = PMEL PE = 4 SV = 1 | 1 |
| A8K5T7 | cDNA FLJ75365, highly similar to Human protein SUGT1B (SUGT1) mRNA OS = Homo sapiens PE = 2 SV = 1 | 1 |
| A0A024RDT1 | Mitochondrial translational release factor 1, isoform CRA_a OS = Homo sapiens GN = MTRF1 PE = 4 SV = 1 | 1 |
| H0Y368 | Dolichol-phosphate mannosyltransferase subunit 1 (Fragment) OS = Homo sapiens GN = DPM1 PE = 1 SV = 1 | 1 |
| Q6ZP37 | CDNA FLJ26554 fis, clone LNF01773, highly similar to Galactokinase OS = Homo sapiens PE = 2 SV = 1 | 1 |
| B4DT31 | cDNA FLJ53425, highly similar to Far upstream element-binding protein 1 OS = Homo sapiens PE = 2 SV = 1 | 1 |
| B3KXM2 | Serine/threonine-protein phosphatase OS = Homo sapiens PE = 2 SV = 1 | 1 |
| Q16651 | Prostasin OS = Homo sapiens GN = PRSS8 PE = 1 SV = 1 | 1 |
| Q12904 | Aminoacyl tRNA synthase complex-interacting multifunctional protein 1 OS = Homo sapiens GN = AIMP1 | 1 |
| P56381 | ATP synthase subunit epsilon, mitochondrial OS = Homo sapiens GN = ATP5E PE = 1 SV = 2 | 1 |

APPENDIX A-continued

| Accession | Description | |
|---|---|---|
| K7EQE8 | Derlin-2 (Fragment) OS = Homo sapiens GN = DERL2 PE = 1 SV = 1 | 1 |
| O00161 | Synaptosomal-associated protein 23 OS = Homo sapiens GN = SNAP23 PE = 1 SV = 1 | 1 |
| B0YIW6 | Archain 1, isoform CRA_a OS = Homo sapiens GN = ARCN1 PE = 1 SV = 1 | 1 |
| Q8IWZ3 | Ankyrin repeat and KH domain-containing protein 1 OS = Homo sapiens GN = ANKHD1 PE = 1 SV = 1 | 1 |
| B4DX78 | cDNA FLJ55484, highly similar to ATP-dependent RNA helicase DDX39 (EC 3.6.1.—) OS = Homo sapiens | 1 |
| P51571 | Translocon-associated protein subunit delta OS = Homo sapiens GN = SSR4 PE = 1 SV = 1 | 1 |
| Q5T655 | Cilia- and flagella-associated protein 58 OS = Homo sapiens GN = CFAP58 PE = 1 SV = 1 | 1 |
| Q8NHY2 | E3 ubiquitin-protein ligase RFWD2 OS = Homo sapiens GN = RFWD2 PE = 1 SV = 1 | 1 |
| Q15788 | Nuclear receptor coactivator 1 OS = Homo sapiens GN = NCOA1 PE = 1 SV = 3 | 1 |
| P67812 | Signal peptidase complex catalytic subunit SEC11A OS = Homo sapiens GN = SEC11A PE = 1 SV = 1 | 1 |
| P49792 | E3 SUMO-protein ligase RanBP2 OS = Homo sapiens GN = RANBP2 PE = 1 SV = 2 | 1 |
| A0A0G2JPZ2 | Taste receptor type 2 OS = Homo sapiens GN = TAS2R42 PE = 3 SV = 1 | 1 |
| P02746 | Complement C1q subcomponent subunit B OS = Homo sapiens GN = C1QB PE = 1 SV = 3 | 1 |
| Q9HBA9 | Putative N-acetylated-alpha-linked acidic dipeptidase OS = Homo sapiens GN = FOLH1B PE = 2 SV = 1 | 1 |
| P21817 | Ryanodine receptor 1 OS = Homo sapiens GN = RYR1 PE = 1 SV = 3 | 1 |
| Q9Y3S1 | Serine/threonine-protein kinase WNK2 OS = Homo sapiens GN = WNK2 PE = 1 SV = 4 | 1 |
| P46937 | Transcriptional coactivator YAP1 OS = Homo sapiens GN = YAP1 PE = 1 SV = 2 | 1 |
| A0A0C4DGX5 | Ras-related protein Rab-25 OS = Homo sapiens GN = RAB25 PE = 1 SV = 1 | 1 |
| Q0P5U8 | FLJ90650 protein OS = Homo sapiens GN = FLJ90650 PE = 1 SV = 1 | 1 |
| Q7RTY8 | Transmembrane protease serine 7 OS = Homo sapiens GN = TMPRSS7 PE = 2 SV = 3 | 1 |
| Q96DA0 | Zymogen granule protein 16 homolog B OS = Homo sapiens GN = ZG16B PE = 1 SV = 3 | 1 |
| A0A087WXU | Extended synaptotagmin-2 OS = Homo sapiens GN = ESYT2 PE = 1 SV = 1 | 1 |

| Accession | Description | 15312c-FTK Protein Ion Area (sum of top 3 peptides) | Log(15232f/ 15261) | Log(15312/ 15261) | Log(15232f/ 15312c) |
|---|---|---|---|---|---|
| D1MGQ2 | Alpha-2 globin chain OS = Homo sapiens GN = HBA2 PE = 3 SV = 1 | 2.90E+09 | −0.72 | −0.54 | −0.18 |
| V9H1D9 | Alpha globin chain OS = Homo sapiens PE = 3 SV = 1 | 7.30E+06 | #DIV/0! | #DIV/0! | −0.26 |
| V9HWE1 | Epididymis luminal protein 113 OS = Homo sapiens GN = HEL113 PE = 2 SV = 1 | 5.30E+09 | −0.77 | −0.51 | −0.26 |
| P08727 | Keratin, type I cytoskeletal 19 OS = Homo sapiens GN = KRT19 PE = 1 SV = 4 | 5.70E+09 | −0.15 | 0.07 | −0.22 |
| A0A024R462 | Fibronectin 1, isoform CRA_n OS = Homo sapiens GN = FN1 PE = 4 SV = 1 | 8.10E+09 | −0.46 | 0.17 | −0.63 |
| Q09666 | Neuroblast differentiation associated protein AHNAK OS = Homo sapiens GN = AHNAK PE = 1 SV = 2 | 1.60E+09 | −0.27 | 0.09 | −0.36 |
| P05787 | Keratin, type II cytoskeletal 8 OS = Homo sapiens GN = KRT8 PE = 1 SV = 7 | 9.20E+09 | −0.03 | 0.14 | −0.17 |
| Q15149 | Plectin OS = Homo sapiens GN = PLEC PE = 1 SV = 3 | 7.70E+08 | −0.45 | −0.05 | −0.4 |
| P35555 | Fibrillin-1 OS = Homo sapiens GN = FBN1 PE = 1 SV = 3 | 2.30E+09 | −0.3 | −0.12 | −0.19 |
| A0A024R5Z7 | Annexin OS = Homo sapiens GN = ANXA2 PE = 3 SV = 1 | 9.50E+09 | −0.09 | 0.18 | −0.27 |
| D9YZU5 | Hemoglobin, beta OS = Homo sapiens GN = HBB PE = 3 SV = 1 | 4.60E+09 | −0.24 | −0.88 | 0.64 |
| V9HVY1 | Epididymis secretory sperm binding protein Li 78p OS = Homo sapiens GN = HEL-S-78p PE = 2 SV = 1 | 8.20E+09 | −0.51 | −0.03 | −0.48 |
| B2RBS8 | cDNA, FLJ95666, highly similar to Homo sapiens albumin (ALB), mRNA OS = Homo sapiens PE = 2 SV = 1 | 3.50E+08 | −0.88 | #NUM! | −0.16 |
| A0A024R1N1 | Myosin, heavy polypeptide 9, non-muscle, isoform CRA_a OS = Homo sapiens GN = MYH9 PE = 4 SV = 1 | 1.90E+09 | −0.28 | −0.12 | −0.16 |
| P08729 | Keratin, type II cytoskeletal 7 OS = Homo sapiens GN = KRT7 PE = 1 SV = 5 | 2.50E+09 | −0.2 | −0.2 | 0 |
| Q4TZM4 | Hemoglobin beta chain (Fragment) OS = Homo sapiens GN = HBB PE = 3 SV = 1 | | −0.8 | −0.39 | −0.4 |
| P02538 | Keratin, type II cytoskeletal 6A OS = Homo sapiens GN = KRT6A PE = 1 SV = 3 | | #DIV/0! | #DIV/0! | #DIV/0! |
| Q8IUL9 | Hemoglobin beta chain variant Hb.Sinai-Bel Air (Fragment) OS = Homo sapiens GN = HBB PE = 3 SV = 1 | | #DIV/0! | #DIV/0! | #DIV/0! |
| B2RA03 | cDNA, FLJ94640, highly similar to Homo sapiens keratin 18 (KRT18), mRNA OS = Homo sapiens PE = 2 SV = 1 | 2.40E+09 | −0.13 | 0.02 | −0.15 |
| P02545 | Prelamin-A/C OS = Homo sapiens GN = LMNA PE = 1 SV = 1 | 1.40E+09 | −0.56 | −0.13 | −0.43 |
| P02671 | Fibrinogen alpha chain OS = Homo sapiens GN = FGA PE = 1 SV = 2 | 4.90E+09 | −0.47 | −0.01 | −0.46 |
| O75369 | Filamin-B OS = Homo sapiens GN = FLNB PE = 1 SV = 2 | 4.60E+08 | −0.23 | 0.16 | −0.38 |
| V9HWB4 | Epididymis secretory sperm binding protein Li 89n OS = Homo sapiens GN = HEL-S-89n PE = 2 SV = 1 | 5.80E+08 | −0.15 | −0.02 | −0.13 |
| P02679 | Fibrinogen gamma chain OS = Homo sapiens GN = FGG PE = 1 SV = 3 | 9.50E+09 | −0.49 | −0.02 | −0.47 |

APPENDIX A-continued

| | | | | |
|---|---|---|---|---|
| P21333 | Filamin-A OS = Homo sapiens GN = FLNA PE = 1 SV = 4 | 1.80E+08 | -0.35 | -0.4 | 0.05 |
| B4DKV4 | cDNA FLJ60647, highly similar to Keratin, type II cytoskeletal 6B OS = Homo sapiens PE = 2 SV = 1 | 1.80E+09 | -0.37 | 0.44 | -0.81 |
| P02533 | Keratin, type I cytoskeletal 14 OS = Homo sapiens GN = KRT14 PE = 1 SV = 4 | 1.70E+09 | 0.02 | 0.4 | -0.38 |
| A0A024R8S5 | Protein disulfide-isomerase OS = Homo sapiens GN = P4HB PE = 3 SV = 1 | 7.30E+08 | 0.04 | -0.06 | 0.09 |
| Q9P2E9 | Ribosome-binding protein 1 OS = Homo sapiens GN = RRBP1 PE = 1 SV = 4 | | #DIV/0! | #DIV/0! | #DIV/0! |
| V9HW88 | Calreticulin, isoform CRA_b OS = Homo sapiens GN = HEL-S-99n PE = 2 SV = 1 | 5.80E+08 | -0.06 | 0.06 | -0.12 |
| B4E1B2 | cDNA FLJ53691, highly similar to Serotransferrin OS = Homo sapiens PE = 2 SV = 1 | | #DIV/0! | #DIV/0! | #DIV/0! |
| P30101 | Protein disulfide-isomerase A3 OS = Homo sapiens GN = PDIA3 PE = 1 SV = 4 | 8.30E+08 | 0.09 | 0.09 | -0.01 |
| D3GKD9 | G-gamma globin Paulinia variant OS = Homo sapiens GN = HBG2 PE = 3 SV = 1 | 5.50E+08 | 0.06 | -0.41 | 0.46 |
| P15924 | Desmoplakin OS = Homo sapiens GN = DSP PE = 1 SV = 3 | 5.20E+08 | -0.41 | 0.34 | -0.74 |
| P04083 | Annexin A1 OS = Homo sapiens GN = ANXA1 PE = 1 SV = 2 | 3.40E+08 | -0.52 | 0.01 | -0.53 |
| P14625 | Endoplasmin OS = Homo sapiens GN = HSP90B1 PE = 1 SV = 1 | 5.10E+08 | -0.03 | -0.08 | 0.05 |
| Q9Y490 | Talin-1 OS = Homo sapiens GN = TLN1 PE = 1 SV = 3 | 6.40E+07 | -0.53 | -0.59 | 0.06 |
| P35556 | Fibrillin-2 OS = Homo sapiens GN = FBN2 PE = 1 SV = 1 | 6.90E+08 | -0.44 | -0.06 | -0.38 |
| Q04695 | Keratin, type I cytoskeletal 17 OS = Homo sapiens GN = KRT17 PE = 1 SV = 2 | 7.30E+08 | -0.17 | 0.37 | -0.54 |
| V9HWG3 | Epididymis secretory protein Li 45 OS = Homo sapiens GN = HEL-S-45 PE = 2 SV = 1 | 1.40E+09 | -0.41 | -0.44 | 0.03 |
| P63261 | Actin, cytoplasmic 2 OS = Homo sapiens GN = ACTG1 PE = 1 SV = 1 | 3.60E+09 | -0.41 | -0.21 | -0.19 |
| D9YZU8 | Hemoglobin, gamma A OS = Homo sapiens GN = HBG1 PE = 3 SV = 1 | | #DIV/0! | #DIV/0! | #DIV/0! |
| A0N071 | Delta globin OS = Homo sapiens GN = HBD PE = 3 SV = 1 | 1.30E+08 | 0.07 | -0.35 | 0.42 |
| O95678 | Keratin, type II cytoskeletal 75 OS = Homo sapiens GN = KRT75 PE = 1 SV = 2 | | #DIV/0! | #DIV/0! | #DIV/0! |
| P13647 | Keratin, type II cytoskeletal 5 OS = Homo sapiens GN = KRT5 PE = 1 SV = 3 | 9.20E+08 | -0.13 | 0.38 | -0.52 |
| P62736 | Actin, aortic smooth muscle OS = Homo sapiens GN = ACTA2 PE = 1 SV = 1 | | #DIV/0! | #DIV/0! | #DIV/0! |
| P11047 | Laminin subunit gamma-1 OS = Homo sapiens GN = LAMC1 PE = 1 SV = 3 | 6.00E+07 | -0.46 | -0.73 | 0.26 |
| P12814 | Alpha-actinin-1 OS = Homo sapiens GN = ACTN1 PE = 1 SV = 2 | 1.20E+08 | -0.36 | -0.32 | -0.04 |
| O43707 | Alpha-actinin-4 OS = Homo sapiens GN = ACTN4 PE = 1 SV = 2 | 3.10E+08 | -0.48 | -0.1 | -0.38 |
| V9HW22 | Epididymis luminal protein 33 OS = Homo sapiens GN = HEL-S-72p PE = 2 SV = 1 | 1.90E+08 | -0.37 | -0.24 | -0.13 |
| B2R4R0 | Histone H4 OS = Homo sapiens GN = HIST1H4H PE = 2 SV = 1 | 3.60E+09 | -0.62 | -0.21 | -0.41 |
| P13667 | Protein disulfide-isomerase A4 OS = Homo sapiens GN = PDIA4 PE = 1 SV = 2 | 2.20E+08 | 0.17 | 0.06 | 0.1 |
| P80723 | Brain acid soluble protein 1 OS = Homo sapiens GN = BASP1 PE = 1 SV = 2 | 1.70E+08 | -0.01 | -0.25 | 0.23 |
| A0A087WZW | Protein IGKV3-11 OS = Homo sapiens GN = IGKV3-11 PE = 4 SV = 1 | | #DIV/0! | #DIV/0! | #DIV/0! |
| P38646 | Stress-70 protein, mitochondrial OS = Homo sapiens GN = HSPA9 PE = 1 SV = 2 | 1.50E+08 | -0.21 | -0.24 | 0.03 |
| P98160 | Basement membrane-specific heparan sulfate proteoglycan core protein OS = Homo sapiens GN = HSPG2 | 4.50E+08 | -0.37 | 0.11 | -0.48 |
| P00558 | Phosphoglycerate kinase 1 OS = Homo sapiens GN = PGK1 PE = 1 SV = 3 | 5.00E+08 | -0.5 | -0.2 | -0.3 |
| P35580 | Myosin-10 OS = Homo sapiens GN = MYH10 PE = 1 SV = 3 | 4.00E+07 | -0.43 | -0.09 | -0.35 |
| P00915 | Carbonic anhydrase 1 OS = Homo sapiens GN = CA1 PE = 1 SV = 1 | 1.90E+08 | 0.4 | -0.17 | 0.57 |
| P40926 | Malate dehydrogenase, mitochondrial OS = Homo sapiens GN = MDH2 PE = 1 SV = 3 | 2.70E+08 | -0.05 | -0.21 | 0.16 |
| P06733 | Alpha-enolase OS = Homo sapiens GN = ENO1 PE = 1 SV = 2 | 3.70E+08 | -0.66 | -0.47 | -0.19 |
| Q6LES2 | Annexin (Fragment) OS = Homo sapiens GN = ANXA4 PE = 1 SV = 1 | 3.20E+08 | 0.03 | 0 | 0.03 |
| P54652 | Heat shock-related 70 kDa protein 2 OS = Homo sapiens GN = HSPA2 PE = 1 SV = 1 | 7.10E+07 | -0.39 | -0.38 | -0.01 |
| V9HW26 | ATP synthase subunit alpha OS = Homo sapiens GN = HEL-S-123m PE = 2 SV = 1 | 3.40E+08 | -0.33 | -0.16 | -0.17 |
| P13646 | Keratin, type I cytoskeletal 13 OS = Homo sapiens GN = KRT13 PE = 1 SV = 4 | 1.90E+09 | -0.12 | -0.47 | 0.42 |
| P35908 | Keratin, type II cytoskeletal 2 epidermal OS = Homo sapiens GN = KRT2 PE = 1 SV = 2 | | #DIV/0! | #DIV/0! | -1.96 |
| P04075 | Fructose-bisphosphate aldolase A OS = Homo sapiens GN = ALDOA PE = 1 SV = 2 | 3.60E+08 | -0.16 | -0.19 | 0.03 |
| P68363 | Tubulin alpha-1B chain OS = Homo sapiens GN = TUBA1B PE = 1 SV = 1 | | #DIV/0! | #NUM! | #DIV/0! |
| P23142 | Fibulin-1 OS = Homo sapiens GN = FBLN1 PE = 1 SV = 4 | 2.40E+08 | -0.41 | 0.43 | -0.08 |
| A0A087WUZ | Spectrin beta chain, non-erythrocytic 1 OS = Homo sapiens GN = SPTBN1 PE = 1 SV = 1 | | #DIV/0! | #NUM! | #DIV/0! |
| A0A0G2JIW1 | Heat shock 70 kDa protein 1B OS = Homo sapiens GN = HSPA1B PE = 1 SV = 1 | | #DIV/0! | -0.65 | #DIV/0! |
| P06396 | Gelsolin OS = Homo sapiens GN = GSN PE = 1 SV = 1 | 3.10E+08 | -0.19 | 0 | -0.19 |
| P10809 | 60 kDa heat shock protein, mitochondrial OS = Homo sapiens GN = HSPD1 PE = 1 SV = 2 | 2.20E+08 | 0.1 | 0.14 | -0.04 |
| A0A024R6I7 | Alpha-1-antitrypsin OS = Homo sapiens GN = SERPINA1 PE = 1 SV = 1 | 2.30E+08 | -0.34 | -0.38 | 0.04 |
| A0A087WYC | Ig gamma-1 chain C region OS = Homo sapiens GN = IGHG1 PE = 1 SV = 1 | | #DIV/0! | #DIV/0! | #DIV/0! |
| B3VMW0 | Lactoferrin OS = Homo sapiens PE = 2 SV = 1 | 4.90E+07 | -0.39 | -0.19 | -0.2 |
| A0A0D9SGF6 | Spectrin alpha chain, non-erythrocytic 1 OS = Homo sapiens GN = SPTAN1 PE = 1 SV = 1 | 1.10E+08 | -0.65 | -0.32 | -0.33 |

APPENDIX A-continued

| ID | Description | | | |
|---|---|---|---|---|
| Q06830 | Peroxiredoxin-1 OS = Homo sapiens GN = PRDX1 PE = 1 SV = 1 | 6.00E+08 | -0.26 | 0.05 | -0.3 |
| V9HWE0 | Annexin OS = Homo sapiens GN = HEL-S-7 PE = 2 SV = 1 | 1.30E+09 | -0.54 | 0.03 | -0.57 |
| W8QEY1 | Lactoferrin OS = Homo sapiens PE = 2 SV = 1 | | #DIV/0! | #DIV/0! | #DIV/0! |
| V9HWB8 | Pyruvate kinase OS = Homo sapiens GN = HEL-S-30 PE = 1 SV = 1 | 4.50E+08 | -0.54 | -0.09 | -0.45 |
| V9HW31 | ATP synthase subunit beta OS = Homo sapiens GN = HEL-S-271 PE = 1 SV = 1 | 6.40E+08 | -0.81 | -0.18 | -0.63 |
| V9HW80 | Epididymis luminal protein 220 OS = Homo sapiens GN = HEL-S-70 PE = 1 SV = 1 | 1.50E+08 | -0.28 | -0.19 | -0.1 |
| P02647 | Apolipoprotein A-I OS = Homo sapiens GN = APOA1 PE = 1 SV = 1 | 4.50E+08 | -0.5 | -0.29 | -0.21 |
| A4QPB0 | IQ motif containing GTPase activating protein 1 OS = Homo sapiens GN = IQGAP1 PE = 1 SV = 1 | 1.30E+08 | -0.48 | -0.06 | -0.41 |
| A0A087VWQ | Clathrin heavy chain OS = Homo sapiens GN = CLTC PE = 1 SV = 1 | 3.10E+08 | -0.53 | -0.18 | -0.35 |
| A0A024RBH2 | Cytoskeleton-associated protein 4, isoform CRA_c OS = Homo sapiens GN = CKAP4 PE = 4 SV = 1 | 2.30E+08 | -0.1 | -0.09 | -0.02 |
| A0A087WZE | Spectrin alpha chain, erythrocytic 1 OS = Homo sapiens GN = SPTA1 PE = 1 SV = 1 | | #DIV/0! | #DIV/0! | #DIV/0! |
| P23284 | Peptidyl-prolyl cis-trans isomerase B OS = Homo sapiens GN = PPIB PE = 1 SV = 1 | 8.10E+08 | -0.11 | 0.08 | -0.18 |
| P35527 | Keratin, type I cytoskeletal 9 OS = Homo sapiens GN = KRT9 PE = 1 SV = 3 | 7.90E+07 | -0.06 | -0.1 | 0.04 |
| P04406 | Glyceraldehyde-3-phosphate dehydrogenase OS = Homo sapiens GN = GAPDH PE = 1 SV = 3 | 1.30E+09 | -0.46 | -0.3 | -0.15 |
| A2A274 | Aconitate hydratase, mitochondrial OS = Homo sapiens GN = ACO2 PE = 1 SV = 1 | | -0.18 | #NUM! | #DIV/0! |
| P07996 | Thrombospondin-1 OS = Homo sapiens GN = THBS1 PE = 1 SV = 2 | 1.60E+09 | 0.11 | 0.2 | -0.09 |
| Q5SU16 | Beta 5-tubulin OS = Homo sapiens GN = TUBB PE = 1 SV = 1 | 2.90E+08 | -0.59 | -0.21 | -0.38 |
| A0A024R1X8 | Junction plakoglobin, isoform CRA_a OS = Homo sapiens GN = JUP PE = 4 SV = 1 | 4.10E+08 | -0.59 | 0.23 | -0.83 |
| P08238 | Heat shock protein HSP 90-beta OS = Homo sapiens GN = HSP90AB1 PE = 1 SV = 4 | 3.10E+07 | -0.21 | -0.12 | -0.09 |
| P60174 | Triosephosphate isomerase OS = Homo sapiens GN = TPI1 PE = 1 SV = 3 | 2.40E+07 | -0.36 | -0.36 | 0 |
| B2R5B3 | Histone H2A OS = Homo sapiens PE = 2 SV = 1 | 1.60E+09 | 0.11 | 0.2 | -0.09 |
| A8K259 | cDNA FLJ78501, highly similar to Homo sapiens serpin peptidase inhibitor, clade H (heat shock protein 47) | | -0.3 | #NUM! | #DIV/0! |
| H7BZJ3 | Protein disulfide-isomerase A3 (Fragment) OS = Homo sapiens GN = PDIA3 PE = 1 SV = 1 | 6.00E+08 | 0.08 | 0.05 | 0.02 |
| P13645 | Keratin, type I cytoskeletal 10 OS = Homo sapiens GN = KRT10 PE = 1 SV = 6 | 1.30E+08 | -0.59 | -0.21 | -0.38 |
| V9HWA9 | Epididymis secretory sperm binding protein Li 62p OS = Homo sapiens GN = HEL-S-62p PE = 2 SV = 1 | 9.30E+07 | -0.47 | -0.03 | -0.44 |
| B4D130 | cDNA FLJ61290, highly similar to Neutral alpha-glucosidase AB OS = Homo sapiens GN = IDH2 PE = 1 SV = 2 | 1.40E+08 | -0.11 | 0.03 | -0.15 |
| V9HW43 | Epididymis secretory protein Li 102 OS = Homo sapiens GN = HEL-S-102 PE = 2 SV = 1 | 5.30E+08 | -0.88 | -0.48 | -0.4 |
| P68371 | Tubulin beta-4B chain OS = Homo sapiens GN = TUBB4B PE = 1 SV = 1 | | -0.62 | -0.28 | -0.07 |
| Q9BXX0 | EMILIN-2 OS = Homo sapiens GN = EMILIN2 PE = 1 SV = 3 | 1.00E+08 | -0.63 | #NUM! | -0.15 |
| Q15084 | Protein disulfide-isomerase A6 OS = Homo sapiens GN = PDIA6 PE = 1 SV = 1 | 3.30E+08 | -0.24 | -0.48 | -0.22 |
| Q6GMX3 | IGL@ protein OS = Homo sapiens GN = IGL@ PE = 2 SV = 1 | 2.60E+08 | -0.68 | -0.03 | -0.34 |
| P01023 | Alpha-2-macroglobulin OS = Homo sapiens GN = A2M PE = 1 SV = 3 | 6.90E+07 | -0.1 | -0.35 | 0.2 |
| B4DJQ5 | cDNA FLJ59211, highly similar to Glucosidase 2 subunit beta OS = Homo sapiens PE = 2 SV = 1 | 1.90E+08 | -0.13 | -0.31 | -0.05 |
| P48735 | Isocitrate dehydrogenase [NADP], mitochondrial OS = Homo sapiens GN = IDH2 PE = 1 SV = 2 | 2.40E+08 | -0.05 | -0.08 | -0.39 |
| O15230 | Laminin subunit alpha-5 OS = Homo sapiens GN = LAMA5 PE = 1 SV = 8 | 2.90E+07 | -0.59 | 0.34 | 0.09 |
| P22626 | Heterogeneous nuclear ribonucleoproteins A2/B1 OS = Homo sapiens GN = HNRNPA2B1 PE = 1 SV = 2 | 2.80E+08 | -0.34 | -0.28 | -0.07 |
| H6VRG1 | Keratin 1 OS = Homo sapiens GN = KRT1 PE = 3 SV = 1 | | #DIV/0! | #NUM! | #DIV/0! |
| Q0IIN1 | Keratin 77 OS = Homo sapiens GN = KRT77 PE = 1 SV = 1 | 1.00E+08 | -0.63 | -0.48 | -0.15 |
| P00738 | Haptoglobin OS = Homo sapiens GN = HP PE = 1 SV = 1 | 3.30E+08 | -0.24 | -0.03 | -0.22 |
| P27824 | Calnexin OS = Homo sapiens GN = CANX PE = 1 SV = 2 | 2.60E+08 | -0.68 | -0.35 | -0.34 |
| A5Z217 | Mutant desmin OS = Homo sapiens PE = 2 SV = 1 | | -0.31 | -0.1 | -0.22 |
| P67809 | Nuclease-sensitive element-binding protein 1 OS = Homo sapiens GN = YBX1 PE = 1 SV = 3 | 2.80E+08 | -0.18 | #NUM! | #DIV/0! |
| Q5XTR9 | Hemoglobin delta-beta fusion protein (Fragment) OS = Homo sapiens GN = HBD/HBB PE = 3 SV = 1 | 1.50E+08 | 0.08 | #NUM! | -0.67 |
| P16157 | Ankyrin-1 OS = Homo sapiens GN = ANK1 PE = 1 SV = 3 | 3.70E+07 | -1.03 | -0.36 | 0.2 |
| B4DR52 | Histone H2B OS = Homo sapiens PE = 2 SV = 2 | 2.90E+09 | 0.19 | -0.01 | -0.23 |
| P63104 | 14-3-3 protein zeta/delta OS = Homo sapiens GN = YWHAZ PE = 1 SV = 1 | 3.60E+08 | -0.05 | 0.18 | -0.35 |
| P04843 | Dolichyl-diphospho oligosaccharide--protein glycosyltransferase subunit 1 OS = Homo sapiens GN = RPN1 | 1.10E+08 | -0.47 | -0.12 | -0.26 |
| Q00839 | Heterogeneous nuclear ribonucleoprotein U OS = Homo sapiens GN = HNRNPU PE = 1 SV = 6 | 1.10E+08 | -0.45 | -0.19 | -0.34 |
| P00747 | Plasminogen OS = Homo sapiens GN = PLG PE = 1 SV = 2 | 3.70E+08 | -0.56 | -0.21 | -0.49 |
| B2RDY9 | Adenylyl cyclase-associated protein OS = Homo sapiens PE = 2 SV = 1 | 5.20E+07 | -0.68 | -0.2 | 0.08 |
| E9KL48 | Epididymis tissue sperm binding protein Li 18mP OS = Homo sapiens GN = GLUD1 PE = 2 SV = 1 | 2.50E+08 | -0.21 | -0.28 | -0.25 |
| P05556 | Integrin beta-1 OS = Homo sapiens GN = ITGB1 PE = 1 SV = 2 | 1.20E+08 | -0.15 | 0.1 | -0.18 |
| P07900 | Heat shock protein HSP 90-alpha OS = Homo sapiens GN = HSP90AA1 PE = 1 SV = 5 | 7.20E+07 | -0.67 | -0.49 | -0.31 |

APPENDIX A-continued

| ID | Description | Col1 | Col2 | Col3 |
|---|---|---|---|---|
| Q59FP5 | Spectrin, beta, erythrocytic (Includes spherocytosis, clinical type I) variant (Fragment) OS = Homo sapiens | 1.10E+07 | 0.27 | -0.19 | 0.46 |
| Q6UY14 | ADAMTS-like protein 4 OS = Homo sapiens GN = ADAMTSL4 PE = 1 SV = 2 | 9.90E+07 | -0.51 | -0.4 | -0.11 |
| B2RDE1 | cDNA, FLJ96568, highly similar to Homo sapiens tropomyosin 3 (TPM3), mRNA OS = Homo sapiens | 1.10E+08 | -0.22 | -0.1 | -0.11 |
| P67936 | Tropomyosin alpha-4 chain OS = Homo sapiens GN = TPM4 PE = 1 SV = 3 | 1.30E+08 | -0.19 | -0.25 | 0.06 |
| V9HWK2 | Epididymis luminal protein 114 OS = Homo sapiens GN = HEL114 PE = 2 SV = 1 | 3.60E+07 | -0.24 | -0.62 | 0.38 |
| P09382 | Galectin-1 OS = Homo sapiens GN = LGALS1 PE = 1 SV = 2 | 4.10E+08 | -0.85 | -0.53 | -0.31 |
| P29966 | Myristoylated alanine-rich C-kinase substrate OS = Homo sapiens GN = MARCKS PE = 1 SV = 4 | 3.10E+07 | -0.3 | -0.3 | 0 |
| A0A024R319 | Laminin, beta 2 (Laminin S), isoform CRA_a OS = Homo sapiens GN = LAMB2 PE = 4 SV = 1 | 3.00E+07 | -0.91 | -0.92 | 0.01 |
| Q13885 | Tubulin beta-2A chain OS = Homo sapiens GN = TUBB2A PE = 1 SV = 1 | 3.70E+07 | #DIV/0! | #DIV/0! | -0.75 |
| P27348 | 14-3-3 protein theta OS = Homo sapiens GN = YWHAQ PE = 1 SV = 1 | 1.80E+08 | -0.41 | -0.14 | -0.26 |
| D3DTX7 | Collagen, type I, alpha 1, isoform CRA_a OS = Homo sapiens GN = COL1A1 PE = 4 SV = 1 | 3.00E+09 | -1.04 | -0.42 | -0.62 |
| Q49A63 | Amine oxidase [flavin-containing] OS = Homo sapiens GN = MAOA PE = 2 SV = 1 | 2.00E+08 | -0.48 | -0.32 | -0.15 |
| P27338 | Amine oxidase [flavin-containing] B OS = Homo sapiens GN = MAOB PE = 1 SV = 3 | 1.80E+08 | -0.65 | -0.54 | -0.11 |
| P30040 | Endoplasmic reticulum resident protein 29 OS = Homo sapiens GN = ERP29 PE = 1 SV = 4 | 1.60E+08 | 0 | 0.2 | -0.2 |
| E9KL44 | Epididymis tissue sperm binding protein Li 14m OS = Homo sapiens PE = 2 SV = 1 | 1.20E+08 | -0.68 | -0.2 | -0.48 |
| A0A0G2JPR0 | Complement C4-A OS = Homo sapiens GN = C4A PE = 1 SV = 1 | 4.90E+07 | -0.22 | -0.21 | -0.01 |
| P61247 | 40S ribosomal protein S3a OS = Homo sapiens GN = RPS3A PE = 1 SV = 2 | 1.40E+08 | -0.31 | -0.08 | -0.22 |
| B3KQF5 | cDNA FLJ90381 fis, clone NT2RP2005035, highly similar to Calumenin OS = Homo sapiens PE = 2 SV = 1 | 3.00E+08 | -0.77 | 0.03 | -0.8 |
| A0A024R755 | Calumenin, isoform CRA_a OS = Homo sapiens GN = CALU PE = 4 SV = 1 | 2.80E+08 | #DIV/0! | #DIV/0! | #DIV/0! |
| Q96HE7 | ERO1-like protein alpha OS = Homo sapiens GN = ERO1L PE = 1 SV = 2 | 1.40E+08 | -0.1 | -0.03 | -0.07 |
| V9HW12 | Epididymis secretory sperm binding protein Li 2a OS = Homo sapiens GN = HEL-S-2a PE = 2 SV = 1 | 8.60E+07 | 0.38 | -0.27 | 0.65 |
| Q59GB4 | Dihydropyrimidinase-like 2 variant (Fragment) OS = Homo sapiens PE = 2 SV = 1 | 6.80E+07 | -0.63 | -0.61 | -0.01 |
| B2R7W4 | cDNA FLJ93632, highly similar to Homo sapiens heterogeneous nuclear ribonucleoprotein R (HNRPR) | 5.10E+07 | -0.31 | 0.09 | -0.41 |
| A8K9A4 | cDNA FLJ75154, highly similar to Homo sapiens heterogeneous nuclear ribonucleoprotein C (C1/C2) | 1.50E+08 | -0.36 | -0.22 | -0.13 |
| A0A0G2JPD4 | Uncharacterized protein OS = Homo sapiens PE = 4 SV = 1 |  | #DIV/0! | #DIV/0! | #DIV/0! |
| P30043 | Flavin reductase (NADPH) OS = Homo sapiens GN = BLVRB PE = 1 SV = 3 | 4.40E+08 | -0.52 | -0.13 | -0.22 |
| B4DEA8 | cDNA FLJ56425, highly similar to Very-long-chain specific acyl-CoA dehydrogenase, mitochondrial (EC 1.3.99.—) OS = Ho | 3.80E+06 | -0.36 | -0.13 | -0.22 |
| B3KNB4 | cDNA FLJ14168 fis, clone NT2RP2001440, highly similar to 14-3-3 protein gamma OS = Homo sapiens PE = 2 SV = 1 | 2.60E+08 | -0.42 | #NUM! | #DIV/0! |
| P04040 | Catalase OS = Homo sapiens GN = CAT PE = 1 SV = 3 | 2.70E+08 | 0.46 | -0.1 | -0.15 |
| Q14103 | Heterogeneous nuclear ribonucleoprotein D0 OS = Homo sapiens GN = HNRNPD PE = 1 SV = 1 | 3.50E+07 | -0.18 | -0.19 | 0.01 |
| G3XAI2 | Laminin subunit beta-1 OS = Homo sapiens GN = LAMB1 PE = 1 SV = 1 | 2.00E+07 | -0.38 | -0.18 | -0.21 |
| Q6N030 | Putative uncharacterized protein DKFZp686I15212 OS = Homo sapiens GN = DKFZp686I15212 PE = 1 SV = 1 | 1.20E+08 | -0.91 | -0.03 | -0.88 |
| A0A024R1A3 | Ubiquitin-activating enzyme E1 (A1S9T and BN75 temperature sensitivity complementing), isoform CRA_a OS = Homo | 4.60E+07 | -0.39 | -0.21 | -0.19 |
| P02749 | Beta-2-glycoprotein 1 OS = Homo sapiens GN = APOH PE = 1 SV = 3 | 1.20E+08 | 0 | 0.08 | -0.08 |
| B0YJ32 | Laminin alpha-3 chain variant 1 OS = Homo sapiens GN = LAMA3 PE = 4 SV = 1 | 6.00E+07 | -0.97 | -0.53 | -0.44 |
| H7BYY1 | Tropomyosin 1 (Alpha), isoform CRA_m OS = Homo sapiens GN = TPM1 PE = 1 SV = 1 |  | #DIV/0! | #DIV/0! | 0.7 |
| A0A024QZ30 | Succinate dehydrogenase [ubiquinone] flavoprotein subunit, mitochondrial OS = Homo sapiens GN = SDHA PE = 1 SV = 1 | 1.30E+08 | -0.72 | -0.42 | -0.3 |
| Q99959 | Plakophilin-2 OS = Homo sapiens GN = PKP2 PE = 1 SV = 2 |  | -0.25 | 0.07 | #DIV/0! |
| Q05682 | Caldesmon OS = Homo sapiens GN = CALD1 PE = 1 SV = 3 | 2.90E+07 | -0.16 | #NUM! | -0.08 |
| Q86GUP2 | Kinectin OS = Homo sapiens GN = KTN1 PE = 1 SV = 1 | 1.10E+09 | -0.07 | 0.07 | 0.24 |
| P08123 | Collagen alpha-2(I) chain OS = Homo sapiens GN = COL1A2 PE = 1 SV = 7 |  | -0.33 | -0.3 | -0.03 |
| B2R6I2 | cDNA, FLJ92973, highly similar to Homo sapiens villin 2 (ezrin) (VIL2), mRNA OS = Homo sapiens PE = 2 SV = 1 | 2.90E+07 | -1.15 | -0.1 | -1.04 |
| Q6FIC5 | Chloride intracellular channel protein OS = Homo sapiens GN = CLIC4 PE = 2 SV = 1 | 4.30E+07 | #DIV/0! | #DIV/0! | #DIV/0! |
| P62258 | 14-3-3 protein epsilon OS = Homo sapiens GN = YWHAE PE = 1 SV = 1 | 1.60E+08 | -0.17 | 0.1 | -0.27 |
| P02452 | Collagen alpha-1(I) chain OS = Homo sapiens GN = COL1A1 PE = 1 SV = 5 | 2.80E+08 | -0.78 | -0.44 | -0.33 |

APPENDIX A-continued

| ID | Description | Col1 | Col2 | Col3 | Col4 |
|---|---|---|---|---|---|
| P13489 | Ribonuclease inhibitor OS = Homo sapiens GN = RNH1 PE = 1 SV = 2 | 4.70E+07 | −0.38 | −0.44 | 0.06 |
| Q9Y4L1 | Hypoxia up-regulated protein 1 OS = Homo sapiens GN = HYOU1 PE = 1 SV = 1 | 2.80E+07 | | 0.02 | 0.04 |
| P37802 | Transgelin-2 OS = Homo sapiens GN = TAGLN2 PE = 1 SV = 3 | 2.30E+08 | −0.34 | −0.18 | −0.36 |
| P21796 | Voltage-dependent anion-selective channel protein 1 OS = Homo sapiens GN = VDAC1 PE = 1 SV = 2 | 4.00E+08 | −0.7 | 0.22 | −0.52 |
| P13797 | Plastin-3 OS = Homo sapiens GN = PLS3 PE = 1 SV = 4 | 1.50E+07 | | | 0.22 |
| P04003 | C4b-binding protein alpha chain OS = Homo sapiens GN = C4BPA PE = 1 SV = 2 | 1.00E+08 | −0.02 | 0.38 | −0.4 |
| P12429 | Annexin A3 OS = Homo sapiens GN = ANXA3 PE = 1 SV = 3 | 4.50E+07 | −0.14 | −0.01 | −0.13 |
| P13804 | Electron transfer flavoprotein subunit alpha, mitochondrial OS = Homo sapiens GN = ETFA PE = 1 SV = 1 | 6.60E+07 | −0.33 | −0.06 | −0.28 |
| D3DX01 | Amine oxidase OS = Homo sapiens GN = ABP1 PE = 3 SV = 1 | 4.90E+08 | −0.21 | 0.43 | −0.65 |
| P07585 | Decorin OS = Homo sapiens GN = DCN PE = 1 SV = 1 | 1.90E+08 | −0.81 | −0.53 | −0.28 |
| A0A024R6C9 | Dihydrolipoamide S-succinyltransferase (E2 component of 2-oxo-glutarate complex), isoform CRA_a OS = Homo sapie | 7.40E+07 | −0.46 | −0.31 | −0.15 |
| A0A024R962 | HCG40889, isoform CRA_b OS = Homo sapiens GN = hCG_40889 PE = 4 SV = 1 | 5.90E+07 | 0.02 | 0.13 | −0.11 |
| B5BU24 | 14-3-3 protein beta/alpha OS = Homo sapiens GN = YWHAB PE = 2 SV = 1 | | #DIV/0! | #DIV/0! | #DIV/0! |
| A0A024QZN9 | Voltage-dependent anion channel 2, isoform CRA_a OS = Homo sapiens GN = VDAC2 PE = 4 SV = 1 | 3.00E+08 | −0.51 | −0.08 | −0.44 |
| Q99714 | 3-hydroxyacyl-CoA dehydrogenase type-2 OS = Homo sapiens GN = HSD17B10 PE = 1 SV = 3 | 1.20E+08 | 0.03 | 0.52 | −0.49 |
| Q9BS26 | Endoplasmic reticulum resident protein 44 OS = Homo sapiens GN = ERP44 PE = 1 SV = 1 | 1.20E+08 | −0.46 | −0.18 | −0.29 |
| D9YZV5 | Tropomyosin 1 (Alpha) isoform 4 OS = Homo sapiens GN = TPM1 PE = 3 SV = 1 | | #DIV/0! | #DIV/0! | #DIV/0! |
| D9ZGG2 | Vitronectin OS = Homo sapiens GN = VTN PE = 4 SV = 1 | 1.00E+09 | −1.26 | −0.3 | −0.96 |
| B4DS66 | cDNA FLJ54290, highly similar to Mitochondrial inner membrane protein OS = Homo sapiens PE = 2 SV = 1 | | #DIV/0! | #DIV/0! | #DIV/0! |
| P15428 | 15-hydroxyprostaglandin dehydrogenase [NAD(+)] OS = Homo sapiens GN = HPGD PE = 1 SV = 1 | 3.90E+07 | 0.41 | 0.09 | 0.33 |
| P30044 | Peroxiredoxin-5, mitochondrial OS = Homo sapiens GN = PRDX5 PE = 1 SV = 4 | 2.40E+08 | −0.55 | 0.04 | −0.59 |
| P06748 | Nucleophosmin OS = Homo sapiens GN = NPM1 PE = 1 SV = 2 | 2.30E+08 | −0.49 | −0.21 | −0.28 |
| B7Z6Z4 | Myosin light polypeptide 6 OS = Homo sapiens GN = MYL6 PE = 1 SV = 1 | 2.60E+08 | −0.51 | −0.27 | −0.24 |
| Q15293 | Reticulocalbin-1 OS = Homo sapiens GN = RCN1 PE = 1 SV = 1 | 2.00E+08 | −0.21 | −0.02 | −0.19 |
| P07305 | Histone H1.0 OS = Homo sapiens GN = H1F0 PE = 1 SV = 3 | 4.10E+08 | −0.01 | 0.11 | −0.12 |
| P06753 | Tropomyosin alpha-3 chain OS = Homo sapiens GN = TPM3 PE = 1 SV = 2 | | #DIV/0! | #DIV/0! | #DIV/0! |
| P30048 | Thioredoxin-dependent peroxide reductase, mitochondrial OS = Homo sapiens GN = PRDX3 PE = 1 SV = 3 | 2.60E+08 | −0.32 | −0.02 | −0.3 |
| D3DQ69 | SERPINE1 mRNA binding protein 1, isoform CRA_c OS = Homo sapiens GN = SERBP1 PE = 4 SV = 1 | | #DIV/0! | #DIV/0! | #DIV/0! |
| A0A024R6W | Aspartate aminotransferase OS = Homo sapiens GN = GOT2 PE = 3 SV = 1 | | −0.23 | −0.18 | |
| Q9NZM1 | Myoferlin OS = Homo sapiens GN = MYOF PE = 1 SV = 1 | 5.00E+07 | −0.51 | −0.41 | −0.1 |
| P09622 | Dihydrolipoyl dehydrogenase, mitochondrial OS = Homo sapiens GN = DLD PE = 1 SV = 2 | 2.40E+07 | #DIV/0! | #DIV/0! | 0.28 |
| Q14112 | Nidogen-2 OS = Homo sapiens GN = NID2 PE = 1 SV = 3 | | −0.54 | #NUM! | #DIV/0! |
| P02462 | Collagen alpha-1(IV) chain OS = Homo sapiens GN = COL4A1 PE = 1 SV = 3 | 2.60E+08 | −0.36 | −0.06 | −0.3 |
| D9YZU7 | Hemoglobin, epsilon 1 OS = Homo sapiens GN = HBE1 PE = 3 SV = 1 | 4.60E+07 | −0.51 | −0.26 | −0.25 |
| A8K5A4 | cDNA FLJ76826, highly similar to Homo sapiens ceruloplasmin (ferroxidase) (CP), mRNA OS = Homo sapiens PE = 2 SV = | | #DIV/0! | #DIV/0! | #DIV/0! |
| Q02218 | 2-oxoglutarate dehydrogenase, mitochondrial OS = Homo sapiens GN = OGDH PE = 1 SV = 3 | | #DIV/0! | #DIV/0! | #DIV/0! |
| P19338 | Nucleolin OS = Homo sapiens GN = NCL PE = 1 SV = 3 | 6.60E+07 | −0.19 | −0.01 | −0.18 |
| V9HWC7 | Epididymis secretory sperm binding protein Li 128m OS = Homo sapiens GN = HEL-S-128m PE = 2 SV = 1 | 5.40E+07 | −0.78 | −0.41 | −0.37 |
| Q8NBS9 | Thioredoxin domain-containing protein 5 OS = Homo sapiens GN = TXNDC5 PE = 1 SV = 2 | 7.80E+07 | 0.04 | −0.15 | 0.19 |
| Q99497 | Protein deglycase DJ-1 OS = Homo sapiens GN = PARK7 PE = 1 SV = 2 | 5.90E+07 | −0.29 | −0.43 | 0.14 |
| Q9UHQ9 | NADH-cytochrome b5 reductase 1 OS = Homo sapiens GN = CYB5R1 PE = 1 SV = 1 | 3.80E+08 | −0.31 | 0.35 | −0.66 |
| B2R659 | cDNA, FLJ92803, highly similar to Homo sapiens hydroxysteroid (17-beta) dehydrogenase 4 (HSD17B4), mRNA OS = H | 2.10E+07 | −0.19 | −0.38 | 0.18 |
| Q5EC54 | Heterogeneous nuclear ribonucleoprotein K transcript variant OS = Homo sapiens GN = HNRPK PE = 2 SV = 1 | 9.20E+07 | −0.55 | −0.21 | −0.34 |
| E2RVJ0 | Anion exchange protein 3 OS = Homo sapiens GN = SLC4A1 PE = 2 SV = 1 | 5.50E+07 | −0.52 | −0.37 | −0.15 |
| O95831 | Apoptosis-inducing factor 1, mitochondrial OS = Homo sapiens GN = AIFM1 PE = 1 SV = 1 | 2.50E+07 | −0.22 | −0.32 | 0.09 |
| Q53F64 | Heterogeneous nuclear ribonucleoprotein AB isoform a variant (Fragment) OS = Homo sapiens PE = 2 SV = 1 | 7.20E+07 | −0.41 | −0.32 | −0.09 |
| B4DRS6 | Sideroflexin OS = Homo sapiens PE = 2 SV = 1 | 8.30E+07 | −0.62 | −0.16 | −0.46 |
| P55084 | Trifunctional enzyme subunit beta, mitochondrial OS = Homo sapiens GN = HADHB PE = 1 SV = 3 | | −0.38 | −0.12 | −0.26 |
| Q5JR94 | 40S ribosomal protein S8 OS = Homo sapiens GN = RPS8 PE = 2 SV = 1 | 9.10E+08 | −0.09 | 0.11 | −0.2 |
| A0A024RA75 | 3-hydroxyisobutyrate dehydrogenase OS = Homo sapiens GN = HIBADH PE = 3 SV = 1 | 1.20E+08 | −0.33 | −0.24 | −0.09 |
| P12111 | Collagen alpha-3(VI) chain OS = Homo sapiens GN = COL6A3 PE = 1 SV = 5 | 3.30E+07 | −1 | −0.4 | −0.6 |
| O60664 | Perilipin-3 OS = Homo sapiens GN = PLIN3 PE = 1 SV = 3 | 9.60E+07 | −0.28 | −0.29 | 0.01 |
| P31947 | 14-3-3 protein sigma OS = Homo sapiens GN = SFN PE = 1 SV = 1 | 3.10E+07 | 0.31 | 0.7 | −0.39 |
| | | 1.80E+08 | | | |

APPENDIX A-continued

| | | | | | |
|---|---|---|---|---|---|
| O43242 | 26S proteasome non-ATPase regulatory subunit 3 OS = Homo sapiens GN = PSMD3 PE = 1 SV = 2 | 1.80E+07 | -0.31 | #NUM! | #DIV/0! |
| Q8TC04 | Keratin 23 (Histone deacetylase inducible) OS = Homo sapiens GN = KRT23 PE = 2 SV = 1 | 4.80E+07 | -0.07 | #NUM! | #DIV/0! |
| P58107 | Epiplakin OS = Homo sapiens GN = EPPK1 PE = 1 SV = 2 | 4.90E+07 | #DIV/0! | #DIV/0! | -0.83 |
| Q13751 | Laminin subunit beta-3 OS = Homo sapiens GN = LAMB3 PE = 1 SV = 1 | 5.00E+07 | -0.34 | -0.23 | -0.61 |
| G8JLB6 | Heterogeneous nuclear ribonucleoprotein H OS = Homo sapiens GN = HNRNPH1 PE = 1 SV = 1 | | | | -0.11 |
| P43121 | Cell surface glycoprotein MUC18 OS = Homo sapiens GN = MCAM PE = 1 SV = 2 | 4.30E+07 | -0.77 | -0.51 | #DIV/0! |
| E7EPK1 | Septin-7 OS = Homo sapiens GN = SEPT7 PE = 1 SV = 2 | 6.70E+07 | -0.27 | -0.1 | -0.25 |
| B4DQE1 | Annexin OS = Homo sapiens PE = 2 SV = 1 | 2.30E+07 | #DIV/0! | #DIV/0! | -0.17 |
| A0A087WSV | Nucleobindin 2, isoform CRA_b OS = Homo sapiens GN = NUCB2 PE = 1 SV = 1 | | | | -0.06 |
| Q13228 | Selenium-binding protein 1 OS = Homo sapiens GN = SELENBP1 PE = 1 SV = 2 | 6.40E+07 | -0.22 | -0.14 | -0.07 |
| F8W031 | Uncharacterized protein (Fragment) OS = Homo sapiens PE = 1 SV = 1 | 3.20E+07 | -0.52 | -0.22 | -0.3 |
| P20700 | Lamin-B1 OS = Homo sapiens GN = LMNB1 PE = 1 SV = 2 | 2.20E+08 | -0.73 | 0.02 | -0.75 |
| Q15582 | Transforming growth factor-beta-induced protein ig-h3 OS = Homo sapiens GN = TGFBI PE = 1 SV = 1 | 1.80E+08 | -0.37 | -0.09 | -0.28 |
| P05204 | Non-histone chromosomal protein HMG-17 OS = Homo sapiens GN = HMGN2 PE = 1 SV = 3 | | | | #DIV/0! |
| O76015 | Keratin, type I cuticular Ha8 OS = Homo sapiens GN = KRT38 PE = 1 SV = 3 | 7.60E+07 | 0.27 | 0.19 | 0.08 |
| P07686 | Beta-hexosaminidase subunit beta OS = Homo sapiens GN = HEXB PE = 1 SV = 3 | | | | #DIV/0! |
| P00352 | Retinal dehydrogenase 1 OS = Homo sapiens GN = ALDH1A1 PE = 1 SV = 2 | 4.10E+07 | -0.34 | #NUM! | #DIV/0! |
| B2R8Z8 | cDNA, FLJ94136, highly similar to Homo sapiens synaptotagmin binding, cytoplasmic RNA interacting protein (SYNCR | 1.60E+07 | 0 | 0.17 | -0.17 |
| Q9NYU2 | UDP-glucose:glycoprotein glucosyltransferase 1 OS = Homo sapiens GN = UGGT1 PE = 1 SV = 3 | | 0.02 | -0.21 | 0.23 |
| B2RAN1 | cDNA, FLJ95012, highly similar to Homo sapiens UDP-glucose pyrophosphorylase 2 (UGP2), mRNA OS = Homo sapien | | #DIV/0! | #DIV/0! | #DIV/0! |
| Q13011 | Delta(3,5)-Delta(2,4)-dienoyl-CoA isomerase, mitochondrial OS = Homo sapiens GN = ECH1 PE = 1 SV = 2 | 7.60E+07 | -0.22 | #DIV/0! | -0.7 |
| P62269 | 40S ribosomal protein S18 OS = Homo sapiens GN = RPS18 PE = 1 SV = 3 | 9.80E+07 | -0.51 | -0.18 | -0.33 |
| P48047 | ATP synthase subunit O, mitochondrial OS = Homo sapiens GN = ATP5O PE = 1 SV = 1 | 1.70E+08 | -0.55 | -0.13 | -0.42 |
| A0A024R814 | Ribosomal protein L7, isoform CRA_a OS = Homo sapiens GN = RPL7 PE = 3 SV = 1 | 1.40E+08 | -0.31 | -0.15 | -0.16 |
| P35625 | Metalloproteinase inhibitor 3 OS = Homo sapiens GN = TIMP3 PE = 1 SV = 2 | 2.90E+08 | -1.64 | -0.68 | -0.96 |
| B2R950 | cDNA, FLJ94213, highly similar to Homo sapiens pregnancy-zone protein (PZP), mRNA OS = Homo sapiens PE = 2 SV = 1 | 4.10E+07 | #DIV/0! | #DIV/0! | -0.33 |
| P16402 | Histone H1.3 OS = Homo sapiens GN = HIST1H1D PE = 1 SV = 2 | 9.90E+08 | -0.26 | -0.23 | -0.02 |
| Q4LE64 | NUMA1 variant protein (Fragment) OS = Homo sapiens GN = NUMA1 variant protein PE = 2 SV = 1 | 1.20E+08 | 0.36 | 0.49 | -0.13 |
| Q59GY2 | Ribosomal protein L4 variant (Fragment) OS = Homo sapiens PE = 2 SV = 1 | 8.10E+07 | -0.56 | -0.27 | -0.3 |
| E9KL35 | Epididymis tissue sperm binding protein Li 3a OS = Homo sapiens GN = UGGT1 PE = 1 SV = 1 | 5.60E+07 | #DIV/0! | #DIV/0! | -0.03 |
| P13639 | Elongation factor 2 OS = Homo sapiens GN = EEF2 PE = 1 SV = 4 | 1.40E+08 | -0.56 | 0.03 | -0.59 |
| A0A024R2A7 | Lectin, mannose-binding, 1, isoform CRA_b OS = Homo sapiens GN = LMAN1 PE = 4 SV = 1 | 3.10E+08 | -0.42 | -0.04 | -0.38 |
| A0A0C4DGB | Calpastatin OS = Homo sapiens GN = CAST PE = 1 SV = 1 | | | | #DIV/0! |
| P62424 | 60S ribosomal protein L7a OS = Homo sapiens GN = RPL7A PE = 1 SV = 2 | 1.90E+08 | -0.72 | -0.33 | -0.38 |
| V9HWE9 | Epididymis secretory protein Li 22 OS = Homo sapiens GN = HEL-S-22 PE = 2 SV = 1 | 1.50E+08 | -1.22 | -0.12 | -1.1 |
| P46781 | 40S ribosomal protein S9 OS = Homo sapiens GN = RPS9 PE = 1 SV = 3 | 1.00E+08 | -0.45 | -0.11 | -0.34 |
| Q99536 | Synaptic vesicle membrane protein VAT-1 homolog OS = Homo sapiens GN = VAT1 PE = 1 SV = 2 | 1.20E+08 | -0.62 | -0.15 | -0.47 |
| B3KQQ3 | cDNA PSEC0016 fis, clone NT2RM1001076, highly similar to Procollagen-lysine,2-oxoglutarate 5-dioxygenase 3 (EC 1. | 9.80E+07 | 0.07 | 0.25 | -0.18 |
| Q7Z406 | Myosin-14 OS = Homo sapiens GN = MYH14 PE = 1 SV = 2 | 1.30E+08 | -0.86 | -0.41 | -0.86 |
| B4DH70 | cDNA FLJ50510, highly similar to Heat shock 70 kDa protein 4 OS = Homo sapiens PE = 2 SV = 1 | | | #DIV/0! | #DIV/0! |
| Q6NS36 | Ferritin (Fragment) OS = Homo sapiens GN = FTH1 PE = 2 SV = 1 | 8.30E+07 | -1.11 | -0.51 | -0.6 |
| P62249 | 40S ribosomal protein S16 OS = Homo sapiens GN = RPS16 PE = 1 SV = 2 | | -0.54 | #NUM! | -0.4 |
| Q59FR8 | Galectin (Fragment) OS = Homo sapiens PE = 2 SV = 1 | 1.70E+08 | -1.04 | -0.64 | -0.63 |
| Q9Y277 | Voltage-dependent anion-selective channel protein 3 OS = Homo sapiens GN = VDAC3 PE = 1 SV = 1 | 2.10E+08 | -0.63 | 0 | -0.73 |
| Q14126 | Desmoglein-2 OS = Homo sapiens GN = DSG2 PE = 1 SV = 2 | 2.00E+08 | -0.39 | 0.34 | #NUM! |
| D9IAI1 | Epididymis secretory protein Li 34 OS = Homo sapiens GN = HEL-S-34 PE = 2 SV = 1 | | -0.64 | #NUM! | -0.09 |
| B4DWA6 | cDNA FLJ60094, highly similar to F-actin capping protein subunit beta OS = Homo sapiens PE = 2 SV = 1 | 4.80E+07 | -0.23 | -0.14 | -0.45 |
| E9PK25 | Cofilin-1 OS = Homo sapiens GN = CFL1 PE = 1 SV = 1 | 1.10E+08 | -0.86 | -0.41 | #DIV/0! |
| F4ZW66 | NF110b OS = Homo sapiens PE = 2 SV = 1 | | -0.34 | #NUM! | -0.26 |
| Q53SS8 | Epididymis secretory protein Li 85 OS = Homo sapiens GN = PCBP1 PE = 2 SV = 1 | 1.50E+08 | -0.39 | -0.12 | 0 |
| A0A0C4DFU2 | Superoxide dismutase OS = Homo sapiens GN = SOD2 PE = 1 SV = 1 | 2.00E+08 | -0.31 | -0.31 | -0.71 |
| P07737 | Profilin-1 OS = Homo sapiens GN = PFN1 PE = 1 SV = 2 | 3.00E+08 | -0.83 | -0.12 | -0.39 |
| P23229 | Integrin alpha-6 OS = Homo sapiens GN = ITGA6 PE = 1 SV = 5 | 6.20E+07 | -0.03 | 0.36 | |

APPENDIX A-continued

| ID | Description | V1 | V2 | V3 | V4 |
|---|---|---|---|---|---|
| B2R657 | Annexin OS = Homo sapiens PE = 2 SV = 1 | 4.30E+07 | −0.57 | −0.11 | −0.46 |
| A0A024RDG1 | Vesicle clocking protein p115, isoform CRA_a OS = Homo sapiens GN = VDP PE = 4 SV = 1 | | | | #DIV/0! |
| V9HW63 | Epididymis secretory sperm binding protein Li 97n OS = Homo sapiens GN = HEL-S-97n PE = 2 SV = 1 | 1.20E+08 | 0 | −0.03 | 0.03 |
| F8WAR4 | MICOS complex subunit MIC19 OS = Homo sapiens GN = CHCHD3 PE = 1 SV = 1 | 3.80E+07 | −0.59 | −0.6 | 0.01 |
| A0A024R325 | Succinyl-CoA ligase subunit beta OS = Homo sapiens GN = SUCLG2 PE = 3 SV = 1 | 1.70E+07 | −0.29 | −0.26 | −0.03 |
| I6TRR8 | SND1-BRAF fusion OS = Homo sapiens PE = 2 SV = 1 | 4.50E+07 | −0.07 | 0.03 | −0.1 |
| Q8NBJ5 | Procollagen galactosyltransferase 1 OS = Homo sapiens GN = COLGALT1 PE = 1 SV = 1 | 6.40E+07 | 0.26 | 0.39 | −0.13 |
| Q14204 | Cytoplasmic dynein 1 heavy chain 1 OS = Homo sapiens GN = DYNC1H1 PE = 1 SV = 5 | 3.00E+07 | −0.38 | −0.08 | −0.3 |
| O94905 | Erlin-2 OS = Homo sapiens GN = ERLIN2 PE = 1 SV = 1 | 9.10E+07 | −1.15 | 0.02 | −1.17 |
| P28331 | NADH-ubiquinone oxidoreductase 75 kDa subunit, mitochondrial OS = Homo sapiens GN = NDUFS1 PE = 1 SV = 3 | 3.60E+07 | −0.64 | −0.23 | −0.41 |
| Q5RJ85 | HLA class I histocompatibility antigen, alpha chain G OS = Homo sapiens GN = HLA-G PE = 1 SV = 1 | 5.40E+07 | #DIV/0! | #DIV/0! | −0.62 |
| P13727 | Bone marrow proteoglycan OS = Homo sapiens GN = PRG2 PE = 1 SV = 2 | 7.00E+08 | 0.17 | 0.67 | −0.5 |
| P14136 | Glial fibrillary acidic protein OS = Homo sapiens GN = GFAP PE = 1 SV = 1 | | −0.38 | #NUM! | #DIV/0! |
| Q6N092 | Putative uncharacterized protein DKFZp686K18196 (Fragment) OS = Homo sapiens GN = DKFZp686K18196 PE = 2 SV = 1 | 9.80E+07 | −0.26 | −0.35 | 0.09 |
| P53621 | Coatomer subunit alpha OS = Homo sapiens GN = COPA PE = 1 SV = 2 | 4.80E+07 | −0.62 | −0.08 | −0.54 |
| P16401 | Histone H1.5 OS = Homo sapiens GN = HIST1H1B PE = 1 SV = 3 | 3.80E+08 | −0.34 | −0.19 | −0.15 |
| Q8IVF2 | Protein AHNAK2 OS = Homo sapiens GN = AHNAK2 PE = 1 SV = 2 | 3.80E+08 | −0.75 | 0.3 | −1.05 |
| D6REK5 | Septin-11 OS = Homo sapiens GN = SEPT11 PE = 1 SV = 1 | | −0.97 | #NUM! | #DIV/0! |
| Q2499 | ATP-dependent RNA helicase DDX1 OS = Homo sapiens GN = DDX1 PE = 1 SV = 5 | 1.80E+07 | −0.9 | −0.54 | −0.36 |
| Q9Y3I0 | tRNA-splicing ligase RtcB homolog OS = Homo sapiens GN = RTCB PE = 1 SV = 1 | | 0.15 | 0.67 | #DIV/0! |
| P51572 | B-cell receptor-associated protein 31 OS = Homo sapiens GN = BCAP31 PE = 1 SV = 3 | 1.40E+08 | −0.66 | −0.25 | −0.41 |
| O00299 | Chloride intracellular channel protein 1 OS = Homo sapiens GN = CLIC1 PE = 1 SV = 4 | 1.00E+08 | −0.85 | −0.23 | −0.62 |
| P24752 | Acetyl-CoA acetyltransferase, mitochondrial OS = Homo sapiens GN = ACAT1 PE = 1 SV = 1 | 3.80E+08 | −0.68 | −0.19 | −0.15 |
| P00918 | Carbonic anhydrase 2 OS = Homo sapiens GN = CA2 PE = 1 SV = 2 | 1.50E+07 | 0.15 | 0.3 | −1.05 |
| O00468 | Agrin OS = Homo sapiens GN = AGRN PE = 1 SV = 5 | 1.80E+07 | −0.59 | −0.67 | 0.82 |
| P51991 | Heterogeneous nuclear ribonucleoprotein A3 OS = Homo sapiens GN = HNRNPA3 PE = 1 SV = 2 | 1.20E+08 | −0.52 | −0.63 | 0.05 |
| D6RF35 | Vitamin D-binding protein OS = Homo sapiens GN = GC PE = 1 SV = 1 | 3.10E+07 | −0.28 | −0.2 | −0.32 |
| L7RSL3 | Receptor protein-tyrosine kinase OS = Homo sapiens GN = FLT1 PE = 3 SV = 1 | 8.00E+07 | −0.16 | −0.39 | 0.11 |
| A8K690 | cDNA FLJ76863, highly similar to Homo sapiens stress-induced-phosphoprotein 1 (Hsp70/Hsp90-organizing protein) | 4.30E+07 | −0.57 | 0.22 | −0.38 |
| O701 | UDP-glucose 6-dehydrogenase OS = Homo sapiens GN = UGDH PE = 1 SV = 1 | 1.00E+07 | −0.31 | −0.28 | −0.29 |
| J3QQ67 | 60S ribosomal protein L18 (Fragment) OS = Homo sapiens GN = RPL18 PE = 1 SV = 1 | 1.70E+08 | −0.64 | −0.9 | 0.59 |
| P40925 | Malate dehydrogenase, cytoplasmic OS = Homo sapiens GN = MDH1 PE = 1 SV = 4 | | −0.32 | −0.07 | −0.57 |
| Q9GZM7 | Tubulointerstitial nephritis antigen like OS = Homo sapiens GN = TINAGL1 PE = 1 SV = 1 | 4.10E+08 | −0.3 | 0.27 | −0.57 |
| Q079S4 | Prolow-density lipoprotein receptor related protein 1 OS = Homo sapiens GN = LRP1 PE = 1 SV = 1 | 1.60E+08 | −0.59 | −0.59 | 0 |
| A0A024C4DG17 | 40S ribosomal protein SA OS = Homo sapiens GN = RPSA PE = 1 SV = 1 | 1.60E+08 | −0.46 | 0 | −0.46 |
| D3DV26 | S100 calcium binding protein A10 (Annexin II ligand, calpactin I, light polypeptide (P11)), isoform CRA_b (Fragment) | 4.10E+09 | −0.81 | 0.5 | −1.31 |
| A8K486 | Peptidyl-prolyl cis-trans isomerase OS = Homo sapiens PE = 2 SV = 1 | 3.90E+08 | −0.62 | −0.17 | −0.44 |
| P13010 | X-ray repair cross complementing protein 5 OS = Homo sapiens GN = XRCC5 PH = 1 SV = 3 | 5.60E+07 | −0.68 | −0.17 | −0.52 |
| B3KT93 | Polyadenylate-binding protein OS = Homo sapiens PE = 2 SV = 1 | 3.90E+07 | −0.64 | −0.31 | −0.34 |
| B2R954 | cDNA, FLJ94534, highly similar to Homo sapiens capping protein (actin filament), gelsolin-like(CAPG), mRNA OS = Hom | 1.30E+08 | −0.26 | 0.24 | −0.5 |
| A0A024R3W | Eukaryotic translation elongation factor 1 beta 2, isoform CRA_a OS = Homo sapiens GN = EEF1B2 PH = 3 SV = 1 | 5.70E+07 | −0.41 | −0.07 | −0.34 |
| Q96AG4 | Leucine-rich repeat containing protein 59 OS = Homo sapiens GN = LRRC59 PE = 1 SV = 1 | 6.80E+07 | −0.52 | −0.13 | −0.39 |
| P14060 | 3 beta-hydroxysteroid dehydrogenase/Delta 5−>4 isomerase type 1 OS = Homo sapiens GN = HSD3B1 PE = 1 SV = 1 | 1.30E+08 | −0.46 | −0.09 | −0.37 |
| Q05D08 | PA2G4 protein (Fragment) OS = Homo sapiens GN = PA2G4 PE = 2 SV = 1 | 1.00E+08 | −0.19 | 0.06 | −0.24 |
| Q15366 | Poly(rC)-binding protein 2 OS = Homo sapiens GN = PCBP2 PH = 1 SV = 1 | | −0.35 | #NUM! | #DIV/0! |
| C3VMY8 | Alpha B crystallin OS = Homo sapiens GN = CRYAB PE = 2 SV = 1 | | #DIV/0! | #NUM! | #DIV/0! |
| A0A024R497 | Acyl-CoA synthetase long-chain family member 3, isoform CRA_a OS = Homo sapiens GN = ACSL3 PE = 4 SV = 1 | 1.30E+08 | −0.48 | 0.18 | −0.67 |
| E7EVA0 | Microtubule-associated protein OS = Homo sapiens GN = MAP4 PE = 1 SV = 1 | 2.60E+07 | −0.19 | −0.12 | −0.07 |
| P49411 | Elongation factor Tu, mitochondrial OS = Homo sapiens GN = TUFM PE = 1 SV = 2 | 4.70E+07 | −0.46 | −0.24 | −0.22 |
| Q6DHW4 | Uncharacterized protein (Fragment) OS = Homo sapiens PE = 2 SV = 1 | 1.90E+07 | #DIV/0! | #DIV/0! | −0.16 |
| Q6ZR64 | HBV PreS1-transactivated protein 1 OS = Homo sapiens GN = MXRA7 PE = 1 SV = 1 | 4.90E+07 | −0.59 | −0.28 | −0.31 |
| A8KAJ3 | cDNA FLJ77823, highly similar to Homo sapiens EGF-containing fibulin-like extracellular matrix protein 1, transcript v | | −1.21 | −0.72 | −0.48 |
| P29401 | Transketolase OS = Homo sapiens GN = TKT PE = 1 SV = 3 | 8.50E+07 | −0.26 | #NUM! | #DIV/0! |

APPENDIX A-continued

| | | | | |
|---|---|---|---|---|
| O95833 | Chloride intracellular channel protein 3 OS = Homo sapiens GN = CLIC3 PE = 1 SV = 2 | 1.10E+07 | -0.12 | -0.19 | 0.07 |
| A8K4Z4 | cDNA FLJ75549, highly similar to Homo sapiens ribosomal protein, large, P0 (RPLP0), transcript variant 1, mRNA OS= | 1.40E+08 | -0.63 | -0.13 | -0.49 |
| Q59EA2 | Coronin (Fragment) OS = Homo sapiens PE = 2 SV = 1 | 2.60E+07 | -0.29 | -0.36 | 0.06 |
| J9JID7 | Lamin B2, isoform CRA_a OS = Homo sapiens GN = LMNB2 PE = 1 SV = 1 | 6.30E+07 | -0.45 | -0.14 | -0.31 |
| P13674 | Prolyl 4-hydroxylase subunit alpha-1 OS = Homo sapiens GN = P4HA1 PE = 1 SV = 2 | 1.10E+08 | -0.01 | 0.26 | -0.27 |
| P14866 | Heterogeneous nuclear ribonucleoprotein L OS = Homo sapiens GN = HNRNPL PE = 1 SV = 2 | 3.70E+07 | -0.2 | -0.24 | 0.04 |
| P21291 | Cysteine and glycine-rich protein 1 OS = Homo sapiens GN = CSRP1 PE = 1 SV = 3 | 3.90E+07 | -0.22 | -0.31 | 0.09 |
| E9PRY8 | Elongation factor 1-delta OS = Homo sapiens GN = EEF1D PE = 1 SV = 1 | 5.90E+07 | -0.38 | -0.14 | -0.24 |
| A8K8U1 | cDNA FLJ77762, highly similar to Homo sapiens cullin-associated and neddylation-dissociated 1 (CAND1), mRNA OS= | 1.40E+07 | -0.55 | -0.37 | -0.18 |
| Q9NP72 | Ras-related protein Rab-18 OS = Homo sapiens GN = RAB18 PE = 1 SV = 1 | 3.50E+07 | -0.79 | 0 | -0.79 |
| B4DRM3 | cDNA FLJ54492, highly similar to Eukaryotic translation initiation factor 4B OS = Homo sapiens PE = 2 SV = 1 | 9.90E+05 | -0.3 | -0.38 | 0.08 |
| O15347 | High mobility group protein B3 OS = Homo sapiens GN = HMGB3 PE = 1 SV = 4 | 1.60E+08 | -0.03 | 0 | -0.03 |
| P14543 | Nidogen-1 OS = Homo sapiens GN = NID1 PE = 1 SV = 3 | 3.00E+07 | -0.91 | -1.01 | 0.1 |
| Q99623 | Prohibitin-2 OS = Homo sapiens GN = PHB2 PE = 1 SV = 2 | 9.70E+07 | -0.47 | -0.16 | -0.31 |
| P11171 | Protein 4.1 OS = Homo sapiens GN = EPB41 PE = 1 SV = 4 | | #DIV/0! | #DIV/0! | #DIV/0! |
| Q14766 | Latent-transforming growth factor beta-binding protein 1 OS = Homo sapiens GN = LTBP1 PE = 1 SV = 4 | 8.70E+06 | -0.74 | -1.29 | 0.55 |
| Q59GX9 | Ribosomal protein L5 variant (Fragment) OS = Homo sapiens PE = 2 SV = 1 | | #DIV/0! | #DIV/0! | #DIV/0! |
| Q6FGS1 | TPD52L2 protein OS = Homo sapiens GN = TPD52L2 PE = 1 SV = 1 | | #DIV/0! | #DIV/0! | #DIV/0! |
| B7Z525 | cDNA FLJ55039, moderately similar to Hepatoma-derived growth factor OS = Homo sapiens PE = 2 SV = 1 | | #DIV/0! | #DIV/0! | #DIV/0! |
| Q00577 | Transcriptional activator protein Pur-alpha OS = Homo sapiens GN = PURA PE = 1 SV = 2 | 3.70E+07 | -0.12 | 0.27 | -0.39 |
| P83731 | 60S ribosomal protein L24 OS = Homo sapiens GN = RPL24 PE = 1 SV = 1 | 1.00E+08 | -0.62 | -0.23 | -0.39 |
| P62879 | Guanine nucleotide-binding protein G(I)/G(S)/G(T) subunit beta-2 OS = Homo sapiens GN = GNB2 PE = 1 SV = 3 | 3.70E+07 | -0.55 | -0.14 | -0.42 |
| B4DPQ0 | Complement C1r subcomponent OS = Homo sapiens GN = C1R PE = 1 SV = 1 | | #DIV/0! | #DIV/0! | #DIV/0! |
| A0A024R1N4 | X-ray repair complementing defective repair in Chinese hamster cells 6 (Ku autoantigen, 70 kDa), isoform CRA_a OS= | 5.80E+07 | -0.52 | -0.24 | -0.29 |
| A0A024R7B7 | CDC37 cell division cycle 37 homolog (S. cerevisiae), isoform CRA_a OS = Homo sapiens GN = CDC37 PE = 4 SV = 1 | 2.90E+07 | #DIV/0! | #DIV/0! | -0.18 |
| D3DR65 | SPFH domain family, member 1, isoform CRA_a OS = Homo sapiens GN = SPFH1 PE = 4 SV = 1 | 5.60E+07 | -0.66 | -0.02 | -0.63 |
| P38117 | Electron transfer flavoprotein subunit beta OS = Homo sapiens GN = ETFB PE = 1 SV = 3 | 6.70E+07 | -0.13 | -0.13 | 0 |
| Q15075 | Early endosome antigen 1 OS = Homo sapiens GN = EEA1 PE = 1 SV = 2 | | -0.54 | -0.26 | #DIV/0! |
| P02461 | Collagen alpha-1(III) chain OS = Homo sapiens GN = COL3A1 PE = 1 SV = 4 | 7.20E+08 | -0.71 | 0.03 | -0.74 |
| Q01813 | ATP-dependent 6-phosphofructokinase, platelet type OS = Homo sapiens GN = PFKP PE = 1 SV = 2 | 3.60E+07 | -0.05 | 0.02 | -0.08 |
| Q9H2U2 | Inorganic pyrophosphatase 2, mitochondrial OS = Homo sapiens GN = PPA2 PE = 1 SV = 2 | | 0.13 | #NUM! | #DIV/0! |
| Q12797 | Aspartyl/asparaginyl beta-hydroxylase OS = Homo sapiens GN = ASPH PE = 1 SV = 3 | 3.90E+07 | #DIV/0! | -0.24 | -0.87 |
| V9HWC9 | Superoxide dismutase [Cu—Zn] OS = Homo sapiens GN = HEL-S-44 PE = 2 SV = 1 | 9.30E+07 | -0.24 | -0.26 | 0.02 |
| P16989 | Y-box-binding protein 3 OS = Homo sapiens GN = YBX3 PE = 1 SV = 4 | | #DIV/0! | #DIV/0! | #DIV/0! |
| Q5S3G3 | MHC class I antigen OS = Homo sapiens GN = HLA-A PE = 2 SV = 1 | 5.20E+07 | -0.31 | -0.26 | -0.05 |
| D9HTE9 | Plasma membrane calcium-transporting ATPase 1 OS = Homo sapiens GN = SLC25A1 PE = 2 SV = 1 | 4.40E+08 | -0.05 | 0.03 | -0.12 |
| P17858 | ATP-dependent 6-phosphofructokinase, liver type OS = Homo sapiens GN = PFKL PE = 1 SV = 6 | 9.60E+07 | -0.43 | -0.13 | -0.3 |
| P62701 | 40S ribosomal protein S4, X isoform OS = Homo sapiens GN = RPS4X PE = 1 SV = 2 | | #DIV/0! | #DIV/0! | #DIV/0! |
| B7Z4C3 | cDNA FLJ50805, highly similar to Erythrocyte membrane protein band 4.2 OS = Homo sapiens PE = 2 SV = 1 | 5.00E+07 | -0.31 | -0.11 | -0.21 |
| Q59F66 | DEAD box polypeptide 17 isoform p82 variant (Fragment) OS = Homo sapiens PE = 2 SV = 1 | | #DIV/0! | #DIV/0! | #DIV/0! |
| Q53FE8 | cDNA FLJ36526 fis, clone TRACH2003347, highly similar to NSFL1 cofactor p47 (Fragment) OS = Homo sapiens PE = 2 SV | | -0.53 | #DIV/0! | #DIV/0! |
| B5BU28 | Catenin beta-1 OS = Homo sapiens GN = CTNNB1 PE = 2 SV = 1 | | #DIV/0! | #NUM! | #DIV/0! |
| Q59FG9 | Chondroitin sulfate proteoglycan 2 (Versican) variant (Fragment) OS = Homo sapiens PE = 2 SV = 1 | | -1.18 | #NUM! | #DIV/0! |
| P15880 | 40S ribosomal protein S2 OS = Homo sapiens GN = RPS2 PE = 1 SV = 2 | 1.40E+08 | -0.63 | -0.08 | -0.54 |
| Q13753 | Laminin subunit gamma-2 OS = Homo sapiens GN = LAMC2 PE = 1 SV = 2 | 4.00E+07 | -0.63 | 0.03 | -0.56 |
| Q5SSJ5 | Heterochromatin protein 1-binding protein 3 OS = Homo sapiens GN = HP1BP3 PE = 1 SV = 1 | 3.80E+07 | -0.08 | -0.09 | 0.01 |
| D7UNW5 | Polypeptide N-acetylgalactosaminyltransferase OS = Homo sapiens GN = GALNT6 PE = 2 SV = 1 | | #DIV/0! | #DIV/0! | #DIV/0! |
| D3YTG3 | Target of Nesh-SH3 OS = Homo sapiens GN = ABI3BP PE = 1 SV = 1 | 7.50E+07 | -0.95 | -0.8 | -0.15 |
| O75390 | Citrate synthase, mitochondrial OS = Homo sapiens GN = CS PE = 1 SV = 2 | 6.60E+07 | -0.44 | -0.03 | -0.4 |
| P53597 | Succinyl-CoA ligase [ADP/GDP-forming] subunit alpha, mitochondrial OS = Homo sapiens GN = SUCLG1 PE = 1 SV = 4 | 8.70E+07 | -0.49 | -0.06 | -0.43 |
| A2A3R6 | 40S ribosomal protein S6 OS = Homo sapiens GN = RPS6 PE = 2 SV = 1 | 9.40E+07 | -0.46 | -0.17 | -0.29 |
| Q16762 | Thiosulfate sulfurtransferase OS = Homo sapiens GN = TST PE = 1 SV = 4 | 7.70E+07 | -0.65 | -0.34 | -0.31 |
| A8K2I7 | Receptor protein-tyrosine kinase OS = Homo sapiens PE = 2 SV = 1 | 4.50E+07 | -0.45 | 0 | -0.45 |

APPENDIX A-continued

| | | | | | |
|---|---|---|---|---|---|
| Q59H77 | T-complex protein 1 subunit gamma (Fragment) OS = Homo sapiens PE = 2 SV = 1 | | #DIV/0! | #DIV/0! | #DIV/0! |
| A0A024R7I3 | RAB8A, member RAS oncogene family, isoform CRA_a OS = Homo sapiens GN = RAB8A PE = 3 SV = 1 | | #DIV/0! | #DIV/0! | #DIV/0! |
| J3KQE5 | GTP-binding nuclear protein Ran (Fragment) OS = Homo sapiens GN = RAN PE = 1 SV = 1 | 9.70E+07 | −0.52 | −0.22 | −0.31 |
| P08833 | Insulin-like growth factor-binding protein 1 OS = Homo sapiens GN = IGFBP1 PE = 1 SV = 1 | 1.60E+08 | −0.86 | −0.47 | −0.39 |
| O00264 | Membrane-associated progesterone receptor component 1 OS = Homo sapiens GN = PGRMC1 PE = 1 SV = 3 | 1.20E+08 | −0.52 | 0 | −0.52 |
| A8K6Q8 | cDNA FLJ75881, highly similar to Homo sapiens transferrin receptor (p90, CD71) (TFRC), mRNA OS = Homo sapiens PE | | −0.59 | #NUM! | #DIV/0! |
| Q6ZN17 | Protein lin-28 homolog B OS = Homo sapiens GN = LIN28B PE = 1 SV = 1 | 9.50E+07 | −0.35 | −0.06 | −0.29 |
| B7ZKY6 | Membrane metallo-endopeptidase OS = Homo sapiens GN = MME PE = 2 SV = 1 | 1.50E+08 | −0.5 | −0.4 | −0.1 |
| P62979 | Ubiquitin-40S ribosomal protein S27a OS = Homo sapiens GN = RPS27A PE = 1 SV = 1 | | #DIV/0! | #NUM! | #DIV/0! |
| P05023 | Sodium/potassium-transporting ATPase subunit alpha-1 OS = Homo sapiens GN = ATP1A1 PE = 1 SV = 1 | | #DIV/0! | #NUM! | #DIV/0! |
| A0NSG5 | Rheumatoid factor D5 light chain (Fragment) OS = Homo sapiens GN = V<kappa>3 PE = 2 SV = 1 | | −0.67 | #NUM! | #DIV/0! |
| Q92930 | Ras-related protein Rab-8B OS = Homo sapiens GN = RAB8B PE = 1 SV = 1 | 4.40E+07 | −0.35 | #DIV/0! | −0.44 |
| A0A024R4E5 | High density lipoprotein binding protein (Vigilin), isoform CRA_a OS = Homo sapiens GN = HDLBP PE = 1 SV = 1 | | −0.35 | 0.09 | −0.44 |
| Q5VWC4 | 26S proteasome non-ATPase regulatory subunit 4 OS = Homo sapiens GN = PSMD4 PE = 1 SV = 1 | 1.30E+08 | −0.46 | −0.25 | −0.21 |
| P62917 | 60S ribosomal protein L8 OS = Homo sapiens GN = RPL8 PE = 1 SV = 2 | 5.40E+07 | −0.35 | −0.2 | −0.15 |
| A0A087WYJ9 | Ig mu chain C region OS = Homo sapiens GN = IGHM PE = 1 SV = 1 | | #DIV/0! | #NUM! | #DIV/0! |
| A0A024RDT4 | Lymphocyte cytosolic protein 1 (L-plastin), isoform CRA_a OS = Homo sapiens GN = LCP1 PE = 4 SV = 1 | | −1.08 | −0.27 | −0.12 |
| P30084 | Enoyl-CoA hydratase, mitochondrial OS = Homo sapiens GN = ECHS1 PE = 1 SV = 4 | 2.90E+07 | −0.39 | −0.55 | #DIV/0! |
| Q14240 | Eukaryotic initiation factor 4A-II OS = Homo sapiens GN = EIF4A2 PE = 1 SV = 2 | | −0.55 | −0.18 | −0.22 |
| Q1KMD3 | Heterogeneous nuclear ribonucleoprotein U-like protein 2 OS = Homo sapiens GN = HNRNPUL2 PE = 1 SV = 1 | 1.20E+07 | −0.4 | #DIV/0! | #DIV/0! |
| P07195 | L-lactate dehydrogenase B chain OS = Homo sapiens GN = LDHB PE = 1 SV = 2 | 8.50E+07 | −0.79 | −0.35 | −0.44 |
| Q969G5 | Protein kinase C delta-binding protein OS = Homo sapiens GN = PRKCDBP PE = 1 SV = 3 | 2.10E+08 | −0.42 | #DIV/0! | 0.06 |
| O15460 | Prolyl 4-hydroxylase subunit alpha-2 OS = Homo sapiens GN = P4HA2 PE = 1 SV = 1 | 1.20E+08 | −0.47 | −0.15 | −0.32 |
| Q6IPH7 | RPL14 protein OS = Homo sapiens GN = RPL14 PE = 1 SV = 1 | 3.70E+07 | −0.2 | −0.31 | 0.11 |
| P37837 | Transaldolase OS = Homo sapiens GN = TALDO1 PE = 1 SV = 2 | | #DIV/0! | #NUM! | #DIV/0! |
| B2RAH5 | Protein phosphatase 1 regulatory subunit OS = Homo sapiens PE = 1 SV = 1 | | −0.55 | #NUM! | #DIV/0! |
| O43493 | Trans-Golgi network integral membrane protein 2 OS = Homo sapiens GN = TGOLN2 PE = 1 SV = 2 | | −0.6 | −0.23 | −0.26 |
| P34897 | Serine hydroxymethyltransferase, mitochondrial OS = Homo sapiens GN = SHMT2 PE = 1 SV = 3 | | −0.49 | −0.31 | −0.37 |
| A1L0S7 | TNS1 protein (Fragment) OS = Homo sapiens GN = TNS1 PE = 2 SV = 1 | 2.00E+07 | −0.68 | −0.38 | −0.43 |
| A8MXP9 | Matrin-3 OS = Homo sapiens GN = MATR3 PE = 1 SV = 1 | 5.90E+07 | −0.81 | −0.29 | −0.32 |
| P23246 | Splicing factor, proline- and glutamine-rich OS = Homo sapiens GN = SFPQ PE = 2 SV = 2 | 1.00E+08 | −0.61 | −0.43 | −0.14 |
| P12109 | Collagen alpha-1(V) chain OS = Homo sapiens GN = COL6A1 PE = 1 SV = 3 | 4.60E+07 | −0.58 | −0.22 | −0.39 |
| Q6FI11 | Glutathione S-transferase kappa 1 OS = Homo sapiens GN = LOC51064 PE = 2 SV = 1 | 2.50E+07 | −0.6 | −0.27 | 0 |
| Q96KP4 | Cytosolic non-specific dipeptidase OS = Homo sapiens GN = CNDP2 PE = 1 SV = 1 | 8.50E+07 | −0.72 | −0.27 | −0.45 |
| P60866 | 40S ribosomal protein S20 OS = Homo sapiens GN = RPS20 PE = 1 SV = 1 | 2.90E+07 | −0.27 | −0.2 | −0.03 |
| Q9Y678 | Coatomer subunit gamma-1 OS = Homo sapiens GN = COPG1 PE = 1 SV = 1 | 4.80E+07 | −1.07 | −0.54 | −0.53 |
| P27635 | 60S ribosomal protein L10 OS = Homo sapiens GN = RPL10 PE = 1 SV = 4 | 2.80E+07 | −0.3 | −0.3 | 0 |
| B4DLV7 | cDNA FLJ60299, highly similar to Rab GDP dissociation inhibitor beta OS = Homo sapiens PE = 2 SV = 1 | 9.20E+07 | −0.53 | −0.14 | −0.44 |
| P02792 | Ferritin light chain OS = Homo sapiens GN = FTL PE = 1 SV = 2 | 2.30E+07 | −0.42 | #NUM! | #DIV/0! |
| Q9UHD8 | Septin-9 OS = Homo sapiens GN = SEPT9 PE = 1 SV = 2 | 5.80E+07 | −0.58 | #NUM! | −0.36 |
| Q53GG0 | Epithelial protein lost in neoplasm beta variant (Fragment) OS = Homo sapiens PE = 2 SV = 1 | | 0.06 | −0.3 | −0.63 |
| O95202 | LETM1 and EF−hand domain-containing protein 1, mitochondrial OS = Homo sapiens GN = LETM1 PE = 1 SV = 1 | 3.20E+06 | −0.93 | −0.14 | −0.37 |
| A0A024R4H0 | Procollagen-lysine, 2-oxoglutarate 5-dioxygenase 1, isoform CRA_a OS = Homo sapiens GN = PLOD1 PE = 4 SV = 1 | 1.10E+08 | −0.52 | −0.14 | −0.21 |
| A8K3Q7 | Annexin OS = Homo sapiens PE = 2 SV = 1 | 3.30E+07 | −0.58 | −0.37 | −0.38 |
| I0B0K7 | Truncated profilaggrin OS = Homo sapiens GN = FLG PE = 4 SV = 1 | 2.90E+07 | −0.47 | −0.09 | −0.13 |
| H3BQK9 | 60S ribosomal protein L19 OS = Homo sapiens GN = RPL19 PE = 1 SV = 1 | 4.60E+07 | −0.28 | −0.16 | #DIV/0! |
| P84098 | Microtubule-actin cross-linking factor 1, isoforms 1/2/3/5 OS = Homo sapiens GN = MACF1 PE = 4 SV = 1 | 5.10E+07 | −0.14 | 0.23 | −0.36 |
| B2R9K8 | cDNA, FLJ94440, highly similar to Homo sapiens chaperonin containing TCP1, subunit 6A (zeta 1)(CCT6A), mRNA OS= | | | | |
| P50990 | T-complex protein 1 subunit theta OS = Homo sapiens GN = CCT8 PE = 1 SV = 1 | | | | |
| Q59FI9 | Ribosomal protein L12 variant (Fragment) OS = Homo sapiens PE = 2 SV = 1 | | | | |
| Q59EP2 | Angiotensinogen variant (Fragment) OS = Homo sapiens PE = 2 SV = 1 | | | | |
| Q15643 | Thyroid receptor interacting protein 11 OS = Homo sapiens GN = TRIP11 PE = 1 SV = 3 | | | | |
| R4GMU1 | GDH/6PGL endoplasmic bifunctional protein OS = Homo sapiens GN = H6PD PE = 1 SV = 1 | 3.70E+07 | −0.14 | | |

APPENDIX A-continued

| ID | Description | Val1 | Val2 | Val3 | Val4 |
|---|---|---|---|---|---|
| O43684 | Mitotic checkpoint protein BUB3 OS = Homo sapiens GN = BUB3 PE = 1 SV = 1 | 7.70E+07 | −0.34 | −0.32 | −0.27 |
| J3QQX2 | Rho GDP-dissociation inhibitor 1 OS = Homo sapiens GN = ARHGDIA PE = 1 SV = 1 | 3.90E+07 | −0.59 | −0.3 | −0.44 |
| O00159 | Unconventional myosin-Ic OS = Homo sapiens GN = MYO1C PE = 1 SV = 4 | 5.80E+07 | −0.74 | −0.3 | −0.3 |
| Q53207 | 60S ribosomal protein L9 OS = Homo sapiens GN = RPL9 PE = 2 SV = 1 | 3.20E+08 | −0.45 | −0.15 | −0.51 |
| Q59GX2 | Solute carrier family 2 (Facilitated glucose transporter), member 1 variant (Fragment) OS = Homo sapiens PE = 2 SV = 1 | 5.80E+07 | −0.49 | 0.01 | −0.05 |
| I2G9F9 | MHC class I antigen OS = Homo sapiens GN = HLA-C PE = 2 SV = 1 | 2.00E+08 | −0.65 | −0.6 | −0.41 |
| Q9HBB3 | 60S ribosomal protein L6 OS = Homo sapiens PE = 2 SV = 1 | 6.40E+07 | −0.52 | −0.11 | −0.27 |
| P38159 | RNA-binding motif protein, X chromosome OS = Homo sapiens GN = RBMX PE = 1 SV = 3 | 1.40E+08 | −0.58 | −0.31 | −0.19 |
| Q597H1 | Transformation related protein 14 OS = Homo sapiens GN = TRG14 PE = 2 SV = 1 | 1.30E+08 | −0.27 | −0.08 | −0.24 |
| M0QXB5 | Persulfide dioxygenase ETHE1, mitochondrial OS = Homo sapiens GN = ETHE1 PE = 1 SV = 1 | | 0.26 | 0.5 | #DIV/0! |
| Q05639 | Elongation factor 1-alpha 2 OS = Homo sapiens GN = EEF1A2 PE = 1 SV = 1 | 2.60E+07 | #DIV/0! | #DIV/0! | −0.27 |
| O95817 | BAG family molecular chaperone regulator 3 OS = Homo sapiens GN = BAG3 PE = 1 SV = 3 | | #DIV/0! | #DIV/0! | #DIV/0! |
| O94919 | Endonuclease domain-containing 1 protein OS = Homo sapiens GN = ENDOD1 PE = 1 SV = 2 | 6.50E+07 | −0.38 | 0.15 | −0.53 |
| P42126 | Enoyl-CoA delta isomerase 1, mitochondrial OS = Homo sapiens GN = ECI1 PE = 1 SV = 1 | 1.60E+07 | −0.53 | −0.65 | 0.12 |
| B2RB23 | cDNA, FLJ95265, highly similar to Homo sapiens acetyl-Coenzyme A acyltransferase 2 (mitochondrial 3-oxoacyl-Coen | | −0.63 | #DIV/0! | #DIV/0! |
| D6RCF4 | CDGSH iron-sulfur domain containing protein 2 OS = Homo sapiens GN = CISD2 PE = 1 SV = 1 | | #DIV/0! | #DIV/0! | #DIV/0! |
| B2R5H0 | Protein S100 OS = Homo sapiens PE = 2 SV = 1 | | #DIV/0! | #DIV/0! | #DIV/0! |
| P04181 | Ornithine aminotransferase, mitochondrial OS = Homo sapiens GN = OAT PE = 1 SV = 1 | 8.60E+07 | −0.62 | 0.11 | −0.73 |
| A8K651 | cDNA FLJ75700, highly similar to Homo sapiens complement component 1, q subcomponent binding protein (C1QBP | 2.40E+08 | −1.38 | −0.38 | −1 |
| P51884 | Lumican OS = Homo sapiens GN = LUM PE = 1 SV = 2 | | −1.23 | #NUM! | #DIV/0! |
| Q05707 | Collagen alpha-1(XIV) chain OS = Homo sapiens GN = COL14A1 PE = 1 SV = 3 | 3.60E+08 | −0.36 | 0.08 | −0.44 |
| P25815 | Protein S100-P OS = Homo sapiens GN = S100P PE = 1 SV = 2 | 1.70E+08 | −0.39 | −0.27 | −0.12 |
| A0A024R374 | Cathepsin B, isoform CRA_a OS = Homo sapiens GN = CTSB PE = 3 SV = 1 | 1.10E+08 | −0.76 | −0.16 | −0.59 |
| P62888 | 60S ribosomal protein L30 OS = Homo sapiens GN = RPL30 PE = 1 SV = 2 | 2.00E+07 | −0.38 | #DIV/0! | −0.02 |
| P49419 | Alpha-aminoadipic semialdehyde dehydrogenase OS = Homo sapiens GN = ALDH7A1 PE = 1 SV = 5 | | #DIV/0! | #DIV/0! | −0.53 |
| P15104 | Glutamine synthetase OS = Homo sapiens GN = GLUL PE = 1 SV = 4 | 8.30E+07 | −0.58 | −0.23 | −0.35 |
| P62263 | 40S ribosomal protein S14 OS = Homo sapiens GN = RP514 PE = 1 SV = 3 | 1.80E+08 | −0.36 | −0.14 | −0.21 |
| P53618 | Coatomer subunit beta OS = Homo sapiens GN = COB1 PE = 1 SV = 3 | | 0.29 | #NUM! | #DIV/0! |
| A8K3C3 | T-complex protein 1 subunit delta OS = Homo sapiens PE = 2 SV = 1 | | −0.38 | #NUM! | #DIV/0! |
| B2RBR9 | Putative uncharacterized protein DKFZp686C02220 (Fragment) OS = Homo sapiens GN = DKFZp686C02220 PE = 2 SV = 1 | 6.20E+07 | −0.38 | 0.16 | −0.54 |
| Q6N091 | H. sapiens ras-related Hrab2 protein OS = Homo sapiens PE = 2 SV = 1 | 1.50E+08 | −0.98 | −0.05 | −0.92 |
| A0A0A1HAW | Ribosomal protein L23, isoform CRA_b OS = Homo sapiens GN = RPL23 PE = 3 SV = 1 | | −0.3 | #NUM! | #DIV/0! |
| A0A024R1Q8 | Drebrin-like protein OS = Homo sapiens GN = DBNL PE = 1 SV = 1 | 2.30E+07 | −1.27 | −0.39 | −0.88 |
| Q9U1U6 | Golgin subfamily B member 1 OS = Homo sapiens GN = GOLGB1 PE = 1 SV = 2 | | #DIV/0! | #DIV/0! | #DIV/0! |
| Q14789 | Serpin peptidase inhibitor, clade E (Nexin, plasminogen activator inhibitor type 1), member 2, isoform CRA_a OS = Ho | 2.40E+07 | −0.55 | −0.03 | −0.1 |
| A0A024R451 | T-complex protein 1 subunit alpha OS = Homo sapiens GN = TCP1 PE = 1 SV = 1 | 9.30E+07 | −1.27 | #DIV/0! | −0.52 |
| P17987 | cDNA, FLJ96923, highly similar to Homo sapiens ribophorin II (RPN2), mRNA OS = Homo sapiens PE = 1 SV = 1 | 1.30E+07 | −0.55 | −0.03 | 0.35 |
| B2RE46 | Proteasome activator complex subunit 1 OS = Homo sapiens GN = PSME1 PE = 1 SV = 1 | 5.00E+07 | −1.27 | −0.91 | −0.36 |
| Q06323 | Vesicle-trafficking protein SEC22b OS = Homo sapiens GN = SEC22B PE = 1 SV = 4 | 4.10E+07 | −0.32 | 0.21 | −0.53 |
| O75396 | Dolichyl-diphosphooligosaccharide-protein glycosyltransferase subunit STT3A OS = Homo sapiens GN = STT3A PE = 1 S | 3.40E+07 | −0.7 | −0.55 | −0.15 |
| P46977 | HCG2001986, isoform CRA_a OS = Homo sapiens GN = hCG_2001986 PE = 4 SV = 1 | 4.30E+07 | −0.53 | −0.51 | −0.02 |
| A0A024R5X2 | Inter-alpha (Globulin) inhibitor H2, isoform CRA_a OS = Homo sapiens GN = ITIH2 PE = 4 SV = 1 | 4.60E+07 | −0.96 | −0.38 | −0.58 |
| D3DRR6 | Heterogeneous nuclear ribonucleoprotein M OS = Homo sapiens GN = HNRNPM PE = 1 SV = 1 | | #DIV/0! | #DIV/0! | #DIV/0! |
| A0A075MGT | HLA class I antigen OS = Homo sapiens GN = HLA-B PE = 3 SV = 1 | | −1.03 | 0.16 | −0.54 |
| B4E1C2 | Kininogen 1, isoform CRA_b OS = Homo sapiens GN = KNG1 PE = 2 SV = 1 | 4.10E+07 | −0.36 | −0.05 | −0.92 |
| P03973 | Antileukoproteinase OS = Homo sapiens GN = SLPI PE = 1 SV = 1 | | −0.02 | #NUM! | #DIV/0! |
| V9HW55 | Epididymis secretory protein LI 275 OS = Homo sapiens GN = HEL-S-275 PE = 2 SV = 1 | 1.90E+07 | #DIV/0! | #DIV/0! | 0.27 |
| Q8NC56 | LEM domain-containing protein 2 OS = Homo sapiens GN = LEMD2 PE = 1 SV = 1 | 9.70E+06 | −0.13 | −0.19 | 0.05 |
| V9HW90 | Epididymis luminal protein 75 OS = Homo sapiens GN = HEL-75 PE = 2 SV = 1 | | #DIV/0! | #DIV/0! | #DIV/0! |
| P78371 | T-complex protein 1 subunit beta OS = Homo sapiens GN = CCT2 PE = 1 SV = 4 | 4.10E+07 | −0.36 | #DIV/0! | −0.71 |
| A0A024R687 | Pleckstrin homology domain containing, family C (With FERM domain) member 1, isoform CRAb OS = Homo sapiens | | −0.26 | −0.29 | #DIV/0! |
| A0A024R0E5 | Capping protein (Actin filament muscle Z-line, alpha 1, isoform CRA_a OS = Homo sapiens GN = CAPZA1 PE = 4 SV = 1 | 6.70E+07 | −0.32 | #DIV/0! | −0.03 |

APPENDIX A-continued

| ID | Description | Value | Col4 | Col5 | Col6 |
|---|---|---|---|---|---|
| A0A024R1S8 | LIM and SH3 protein 1, isoform CRA_b OS = Homo sapiens GN = LASP1 PE = 4 SV = 1 | | #DIV/0! | #DIV/0! | #DIV/0! |
| B2R6V9 | cDNA, FLJ93141, highly similar to Homo sapiens coagulation factor XIII, A1 polypeptide (F13A1), mRNA OS = Homo sa | 4.20E+07 | -0.99 | -0.31 | -0.68 |
| Q06210 | Glutamine-fructose-6-phosphate aminotransferase [isomerizing] 1 OS = Homo sapiens GN = GFPT1 PE = 1 SV = 3 | | #DIV/0! | #DIV/0! | #DIV/0! |
| O76021 | Ribosomal L1 domain-containing protein 1 OS = Homo sapiens GN = RSL1D1 PE = 1 SV = 3 | | #DIV/0! | #DIV/0! | -0.26 |
| B2R4C0 | 60S ribosomal protein L18a OS = Homo sapiens PE = 2 SV = 1 | 9.00E+07 | -0.35 | -0.09 | -0.09 |
| P62316 | Small nuclear ribonucleoprotein Sm D2 OS = Homo sapiens GN = SNRPD2 PE = 1 SV = 1 | 5.40E+07 | -0.4 | -0.31 | -0.27 |
| P25398 | 40S ribosomal protein S12 OS = Homo sapiens GN = RPS12 PE = 1 SV = 3 | 1.20E+08 | -0.51 | -0.24 | 0 |
| Q96N66 | Lysophospholipid acyltransferase 7 OS = Homo sapiens GN = MBOAT7 PE = 1 SV = 1 | 2.10E+08 | #DIV/0! | #DIV/0! | -0.98 |
| O60437 | Periplakin OS = Homo sapiens GN = PPL PE = 1 SV = 4 | 2.10E+08 | -0.1 | -0.23 | 0.13 |
| P99999 | Cytochrome c OS = Homo sapiens GN = CYCS PE = 1 SV = 2 | 5.30E+07 | #DIV/0! | #DIV/0! | #DIV/0! |
| P35611 | Alpha-adducin OS = Homo sapiens GN = ADD1 PE = 1 SV = 2 | | #DIV/0! | #NUM! | -0.48 |
| Q08257 | Quinone oxidoreductase OS = Homo sapiens GN = CRYZ PE = 1 SV = 1 | | -0.47 | -0.17 | -0.79 |
| V9HWA6 | Epididymis luminal protein 32 OS = Homo sapiens GN = HEL32 PE = 2 SV = 1 | 3.60E+07 | -0.65 | 0.04 | #DIV/0! |
| B2R4R9 | HCG26477 OS = Homo sapiens GN = RPS28 PE = 2 SV = 1 | 8.60E+07 | -0.75 | #DIV/0! | #DIV/0! |
| Q53GW1 | Vesicle transport-related protein isoform a variant (Fragment) OS = Homo sapiens PE = 2 SV = 1 | 2.90E+09 | #DIV/0! | #DIV/0! | -0.38 |
| K7E500 | Histone H3.3 (Fragment) OS = Homo sapiens GN = H3F3B PE = 1 SV = 1 | 2.60E+07 | -0.15 | -0.13 | -0.02 |
| Q15717 | ELAV-like protein 1 OS = Homo sapiens GN = ELAVL1 PE = 1 SV = 2 | 1.70E+07 | -0.46 | -0.09 | -0.37 |
| Q4LE36 | ACLY variant protein (Fragment) OS = Homo sapiens GN = ACLY variant protein PE = 2 SV = 1 | 6.80E+07 | #DIV/0! | #DIV/0! | -0.23 |
| Q14554 | Protein disulfide-isomerase A5 OS = Homo sapiens GN = PDIA5 PE = 1 SV = 1 | | #DIV/0! | #DIV/0! | -0.18 |
| Q93084 | Sarcoplasmic/endoplasmic reticulum calcium ATPase 3 OS = Homo sapiens GN = ATP2A3 PE = 1 SV = 2 | | #DIV/0! | #DIV/0! | -0.46 |
| B4E290 | cDNA FLJ50039, highly similar to Homo sapiens solute carrier family 25, member 24, transcript variant 1, mRNA OS= | 5.80E+07 | -0.24 | 0.22 | 0.25 |
| P17302 | Gap junction alpha-1 protein OS = Homo sapiens GN = GJA1 PE = 1 SV = 2 | 3.00E+07 | -0.53 | -0.78 | -0.27 |
| A0A0A0MSG | Four and a half LIM domains protein 2 OS = Homo sapiens GN = FHL2 PE = 1 SV = 1 | | #DIV/0! | #NUM! | -0.31 |
| Q96GT9 | X antigen family member 2 OS = Homo sapiens GN = XAGE2 PE = 1 SV = 1 | | #DIV/0! | -0.04 | -0.41 |
| M0R0R2 | 40S ribosomal protein S5 OS = Homo sapiens GN = RPS5 PE = 1 SV = 1 | 1.10E+08 | -0.31 | -0.22 | -0.18 |
| P02747 | Complement C1q subcomponent subunit C OS = Homo sapiens GN = C1QC PE = 1 SV = 3 | 6.70E+07 | -0.52 | -0.28 | -0.02 |
| Q00765 | Receptor expression-enhancing protein 5 OS = Homo sapiens GN = REEP5 PE = 1 SV = 3 | 7.80E+07 | -0.7 | -0.23 | -1.69 |
| P39023 | 60S ribosomal protein L3 OS = Homo sapiens GN = RPL3 PE = 1 SV = 2 | 1.00E+08 | -0.41 | 0.1 | -0.02 |
| O15143 | Actin-related protein 2/3 complex subunit 1B OS = Homo sapiens GN = ARPC1B PE = 1 SV = 3 | 2.50E+07 | -1.53 | 0.16 | -0.45 |
| A0A024R944 | Serpin peptidase inhibitor, clade C (Antithrombin), member 1, isoform CRA_a OS = Homo sapiens GN = SERPINC1 PE = 3 | 7.80E+07 | #NUM! | 0.28 | -0.35 |
| A0A024R8N2 | Integrin beta OS = Homo sapiens GN = ITGB4 PE = 3 SV = 1 | 5.50E+07 | -0.51 | -0.06 | -0.84 |
| P04899 | Guanine nucleotide-binding protein G(i) subunit alpha-2 OS = Homo sapiens GN = GNAI2 PE = 1 SV = 3 | 7.00E+07 | -0.47 | -0.12 | -0.01 |
| P06703 | Protein S100-A6 Os = Homo sapiens GN = S100A6 PE = 1 SV = 1 | 5.60E+08 | -0.62 | 0.22 | #DIV/0! |
| Q9Y4K0 | Lysyl oxidase homolog 2 OS = Homo sapiens GN = LOxL2 PE = 1 SV = 1 | 1.10E+08 | -0.46 | -0.44 | #DIV/0! |
| B7Z6Q5 | Beta-galactosidase OS = Homo sapiens PE = 2 SV = 1 | | #DIV/0! | #DIV/0! | #DIV/0! |
| Q9NZN4 | EH domain containing protein 2 OS = Homo sapiens GN = EHD2 PE = 1 SV = 1 | 3.20E+08 | -0.46 | #DIV/0! | -0.5 |
| Q9BRP8 | Partner of Y14 and mago OS = Homo sapiens GN = WIBG PE = 1 SV = 1 | | #DIV/0! | -0.29 | #DIV/0! |
| B3RFR9 | Hydroxysteroid (17-beta) dehydrogenase 1 isoform OS = Homo sapiens GN = TXNDC12 PE = 1 SV = 1 | | -0.79 | #DIV/0! | -0.09 |
| O95881 | Thioredoxin domain-containing protein 12 OS = Homo sapiens GN = PH = 2 SV = 1 | 9.20E+07 | -0.51 | #DIV/0! | -0.58 |
| P26373 | 60S ribosomal protein L13 OS = Homo sapiens GN = RPL13 PE = 1 SV = 4 | | #DIV/0! | #DIV/0! | -0.45 |
| Q16270 | Insulin-like growth factor-binding protein 7 OS = Homo sapiens GN = IGFBP7 PE = 1 SV = 1 | 4.20E+07 | #DIV/0! | #DIV/0! | #DIV/0! |
| P05198 | Eukaryotic translation initiation factor 2 subunit 1 OS = Homo sapiens GN = EIF2S1 PE = 1 SV = 3 | 6.90E+07 | #DIV/0! | #NUM! | -0.4 |
| A0A024R3D8 | Acetyltransferase component of pyruvate dehydrogenase complex OS = Homo sapiens GN = DLAT PE = 3 SV = 1 | | #DIV/0! | 0.78 | -0.49 |
| Q5U000 | Cathepsin Z OS = Homo sapiens PE = 2 SV = 1 | | 0.38 | 0.03 | #DIV/0! |
| O14818 | Proteasome subunit alpha type-7 OS = Homo sapiens GN = PSMA7 PE = 1 SV = 1 | | -0.46 | #DIV/0! | #DIV/0! |
| A0A024R8L7 | Acyl coenzyme A oxidase OS = Homo sapiens GN = ACOX1 PE = 3 SV = 1 | 6.00E+07 | -0.18 | #NUM! | 0.25 |
| P26447 | Protein S100-A4 OS = Homo sapiens GN = S100A4 PE = 1 SV = 1 | 9.00E+08 | -0.16 | #DIV/0! | #DIV/0! |
| P0DME0 | Protein SETSIP OS = Homo sapiens GN = SETSIP PE = 1 SV = 1 | | | | |
| P05164 | Myeloperoxidase OS = Homo sapiens GN = MPO PE = 1 SV = 1 | | | | |
| P36551 | Oxygen-dependent coproporphyrinogen-III oxidase, mitochondrial OS = Homo sapiens GN = CPOX PE = 1 SV = 3 | | | | |
| A0A024R2M | Oxidative-stress responsive 1, isoform CRA_a OS = Homo sapiens GN = OXSR1 PE = 4 SV = 1 | | | | |
| Q2TBJ1 | Inverted formin-2 OS = Homo sapiens GN = INF2 PE = 1 SV = 2 | 1.40E+07 | | | |
| P27144 | Adenylate kinase 4, mitochondrial OS = Homo sapiens GN = AK4 PE = 1 SV = 1 | | | | |

APPENDIX A-continued

| ID | Description | Value | Col4 | Col5 | Col6 |
|---|---|---|---|---|---|
| E9PI68 | Signal peptidase complex subunit 2 OS = Homo sapiens GN = SPCS2 PE = 1 SV = 1 | | #DIV/0! | #DIV/0! | #DIV/0! |
| A8K2N0 | cDNA FLJ77835, highly similar to Homo sapiens complement component 1, s subcomponent (C1S), transcript variant | | #DIV/0! | #DIV/0! | #DIV/0! |
| Q13596 | Sorting nexin-1 OS = Homo sapiens GN = SNX1 PE = 1 SV = 3 | | #DIV/0! | #DIV/0! | #DIV/0! |
| L7N2F9 | Uncharacterized protein (Fragment) OS = Homo sapiens PE = 4 SV = 1 | 3.10E+07 | #DIV/0! | #DIV/0! | −0.01 |
| P50502 | Hsc70-interacting protein OS = Homo sapiens GN = ST13 PE = 1 SV = 2 | | −0.33 | −0.31 | #DIV/0! |
| P39060 | Collagen alpha-1(XVIII) chain OS = Homo sapiens GN = COL18A1 PE = 1 SV = 5 | | −0.49 | #NUM! | −0.35 |
| E9LUH4 | Mutant methyl CpG binding protein 2 variant 1 OS = Homo sapiens GN = MECP2 PE = 2 SV = 1 | 5.40E+07 | #DIV/0! | #DIV/0! | −0.08 |
| V9HW37 | Epididymis secretory protein Li 69 OS = Homo sapiens GN = HEL-S-69 PE = 1 SV = 1 | 2.40E+07 | #DIV/0! | #DIV/0! | −0.4 |
| B2R4F3 | cDNA, FLJ92068, highly similar to Homo sapiens Rho GDP dissociation inhibitor (GDI) beta (ARHGDIB), mRNA OS = Ho | | #DIV/0! | #DIV/0! | −1.17 |
| A0A024R6Z0 | Dynein, cytoplasmic 1, light intermediate chain 2, isoform CRA_a OS = Homo sapiens GN = DYNC1LI2 PE = 4 SV = 1 | 2.30E+08 | −0.73 | −0.33 | −0.01 |
| Q59E85 | Caveolin (Fragment) OS = Homo sapiens PE = 2 SV = 1 | 3.10E+08 | −1.26 | −0.09 | −0.04 |
| E5KLJ5 | Dynamin-like 120 kDa protein, mitochondrial OS = Homo sapiens GN = OPA1 PE = 1 SV = 1 | 4.40E+07 | −0.16 | −0.15 | −0.42 |
| Q59EF6 | Calpain 2, large [catalytic] subunit variant (Fragment) OS = Homo sapiens PE = 2 SV = 1 | 6.10E+07 | −0.68 | −0.65 | −0.44 |
| P05109 | Protein S100-A8 OS = Homo sapiens GN = S100A8 PE = 1 SV = 1 | 1.30E+08 | −0.61 | −0.19 | #DIV/0! |
| O15173 | Membrane-associated progesterone receptor component 2 OS = Homo sapiens GN = PGRMC2 PE = 1 SV = 1 | 2.20E+08 | −0.29 | #NUM! | #DIV/0! |
| Q59EP1 | Annexin (Fragment) OS = Homo sapiens PE = 2 SV = 1 | | −0.43 | #NUM! | 0.26 |
| Q08211 | ATP-dependent RNA helicase A OS = Homo sapiens GN = DHX9 PE = 1 SV = 4 | 1.10E+07 | 0.26 | 0 | −0.07 |
| B4DZF2 | cDNA FLJ59571, highly similar to Eukaryotic translation initiation factor 4gamma 2 OS = Homo sapiens PE = 2 SV = 1 | 1.90E+07 | −0.66 | −0.59 | −0.07 |
| B2RD79 | Ubiquitin carboxyl-terminal hydrolase OS = Homo sapiens PE = 2 SV = 1 | 2.10E+07 | −0.33 | −0.16 | −0.17 |
| P08754 | Guanine nucleotide-binding protein G(k) subunit alpha OS = Homo sapiens GN = GNAI3 PE = 1 SV = 3 | 2.50E+08 | −0.65 | −0.56 | −0.09 |
| Q9Y5M8 | Signal recognition particle receptor subunit beta OS = Homo sapiens GN = SRPRB PE = 1 SV = 3 | 4.40E+07 | −0.42 | #NUM! | −0.37 |
| P02649 | Apolipoprotein E OS = Homo sapiens GN = APOE PE = 1 SV = 1 | 1.70E+08 | −0.37 | 0 | −0.15 |
| P63096 | Guanine nucleotide-binding protein G(i) subunit alpha-1 OS = Homo sapiens GN = GNAI1 PE = 1 SV = 2 | 9.60E+07 | −0.37 | −0.22 | −0.2 |
| Q00325 | Phosphate carrier protein, mitochondrial OS = Homo sapiens GN = SLC25A3 PE = 1 SV = 2 | 8.20E+07 | −0.36 | −0.17 | #DIV/0! |
| P52209 | 6-phosphogluconate dehydrogenase, decarboxylating OS = Homo sapiens GN = PGD PE = 1 SV = 3 | | −0.72 | #NUM! | −0.29 |
| A8K8F6 | cDNA FLJ78417, highly similar to Homo sapiens low density lipoprotein receptor-related protein associated protein 1 | 3.90E+07 | −0.37 | −0.08 | −0.8 |
| P35268 | 60S ribosomal protein L22 OS = Homo sapiens GN = RPL22 PE = 1 SV = 2 | 9.50E+07 | −1.05 | −0.25 | #DIV/0! |
| P62906 | 60S ribosomal protein L10a OS = Homo sapiens GN = RPL10A PE = 1 SV = 2 | | #DIV/0! | #DIV/0! | −0.45 |
| B7Z8Q2 | cDNA FLJ55606, highly similar to Alpha-2-HS-glycoprotein OS = Homo sapiens PE = 2 SV = 1 | 9.60E+07 | −0.72 | −0.27 | #DIV/0! |
| B4DPZ4 | cDNA FLJ60782, highly similar to Rho-GTPase-activating protein 1 OS = Homo sapiens PE = 2 SV = 1 | | −0.72 | #NUM! | #DIV/0! |
| H0YMV8 | 40S ribosomal protein S27 OS = Homo sapiens GN = RPS27L PE = 1 SV = 1 | | −0.2 | −0.24 | 0.04 |
| A2KBB9 | Anti-(ED-B) scFv (Fragment) OS = Homo sapiens PE = 2 SV = 1 | 1.10E+08 | #DIV/0! | #DIV/0! | −0.39 |
| Q14520 | Hyaluronan-binding protein 2 OS = Homo sapiens GN = HABP2 PE = 1 SV = 1 | 3.20E+07 | #DIV/0! | #DIV/0! | #DIV/0! |
| B7Z268 | Single-stranded DNA binding protein 1, isoform CRA_c OS = Homo sapiens GN = SSBP1 PE = 2 SV = 1 | | #DIV/0! | −0.5 | −0.43 |
| P12110 | Collagen alpha-2(VI) chain OS = Homo sapiens GN = COL6A2 PE = 1 SV = 4 | 3.80E+07 | −0.93 | −0.05 | −0.67 |
| A0A024R233 | Tight junction protein 2 (Zona occludens 2), isoform CRA_a OS = Homo sapiens GN = TJP2 PE = 4 SV = 1 | 8.80E+07 | −0.71 | 0 | −0.34 |
| P62851 | 40S ribosomal protein S25 OS = Homo sapiens GN = RPS25 PE = 1 SV = 1 | 1.60E+08 | −0.34 | −0.14 | −0.09 |
| Q02978 | Mitochondrial 2-oxoglutarate/malate carrier protein OS = Homo sapiens GN = SLC25A11 PE = 1 SV = 3 | 4.40E+07 | −0.23 | #NUM! | #DIV/0! |
| Q5TDH0 | Protein DDI1 homolog 2 OS = Homo sapiens GN = DDI2 PE = 1 SV = 1 | | −0.73 | #DIV/0! | #DIV/0! |
| P22059 | Oxysterol-binding protein 1 OS = Homo sapiens GN = OSBP PE = 1 SV = 1 | | | | |
| P22830 | Ferrochelatase, mitochondrial OS = Homo sapiens GN = FECH PE = 1 SV = 2 | | | | |
| A0A024RAZ7 | Heterogeneous nuclear ribonucleoprotein A1, isoform CRA_b OS = Homo sapiens GN = HNRPA1 PE = 4 SV = 1 | | | | |
| Q9BXP8 | Pappalysin-2 OS = Homo sapiens GN = PAPPA2 PE = 1 SV = 1 | | | | |
| O00232 | 26S proteasome non-ATPase regulatory subunit 12 OS = Homo sapiens GN = PSMD12 PE = 1 SV = 1 | | | | |
| Q08431 | Lactadherin OS = Homo sapiens GN = MFGE8 PE = 1 SV = 2 | | | | |
| B4DLJ5 | cDNA FLJ55716, highly similar to Desmocollin-2 OS = Homo sapiens PE = 2 SV = 1 | | | | |
| Q5GF9 | Full-length cDNA 5-PRIME end of clone CS0DF013YM24 of Fetal brain of Homo sapiens (Human) variant (Fragment) | | | | |
| B3KXY9 | Hexokinase OS = Homo sapiens PE = 2 SV = 1 | | | | |
| P28838 | Cytosol aminopeptidase OS = Homo sapiens GN = LAP3 PE = 1 SV = 3 | | | | |
| Q9NZU5 | LIM and cysteine-rich domains protein 1 OS = Homo sapiens GN = LMCD1 PE = 1 SV = 1 | | | | |
| U3KQ56 | Glyoxylate reductase/hydroxypyruvate reductase OS = Homo sapiens GN = GRHPR PE = 1 SV = 1 | | | | |
| A0A0A6YYJ8 | Putative RNA-binding protein Luc7-like 2 OS = Homo sapiens GN = LUC7L2 PE = 4 SV = 1 | | | | |
| P50479 | PDZ and LIM domain protein 4 OS = Homo sapiens GN = PDLIM4 PE = 1 SV = 2 | | | | |

APPENDIX A-continued

| | | | | | | |
|---|---|---|---|---|---|---|
| B4DKQ5 | cDNA FLJ54710, highly similar to Target of Myb protein 1 OS = Homo sapiens PE = 2 SV = 1 | | #DIV/0! | #DIV/0! | #DIV/0! | #DIV/0! |
| Q6FGH9 | DNCL1 protein OS = Homo sapiens GN = DNCL1 PE = 2 SV = 1 | 8.30E+07 | −0.77 | −0.19 | −0.58 |
| Q8NCA5 | Protein FAM98A OS = Homo sapiens GN = FAM98A PE = 1 SV = 1 | | #DIV/0! | #DIV/0! | #DIV/0! |
| P43034 | Platelet-activating factor acetylhydrolase IB subunit alpha OS = Homo sapiens GN = PAFAH1B1 PE = 1 SV = 2 | | #DIV/0! | #DIV/0! | #DIV/0! |
| A0A0A0MSV | Tapasin OS = Homo sapiens GN = TAPBP PE = 1 SV = 1 | 2.50E+07 | −0.17 | −0.42 | 0.26 |
| B5BUB5 | Autoantigen La (Fragment) OS = Homo sapiens GN = SSB PE = 2 SV = 2 | | #DIV/0! | #DIV/0! | #DIV/0! |
| B3KS98 | Eukaryotic translation initiation factor 3 subunit H OS = Homo sapiens GN = EIF3H PE = 1 SV = 1 | | #DIV/0! | #DIV/0! | #DIV/0! |
| D0W033 | MHC class I antigen (Fragment) OS = Homo sapiens GN = HLA-A PE = 3 SV = 1 | | #DIV/0! | #DIV/0! | #DIV/0! |
| Q9BUS0 | ZYX protein (Fragment) OS = Homo sapiens GN = ZYX PE = 2 SV = 2 | | −0.54 | #NUM! | #DIV/0! |
| P58546 | Myotrophin OS = Homo sapiens GN = MTPN PE = 1 SV = 2 | | #DIV/0! | #DIV/0! | #DIV/0! |
| B2R829 | cDNA FLJ93711, highly similar to Homo sapiens myeloid cell nuclear differentiation antigen (MNDA), mRNA OS = Hom | | −0.5 | 0.09 | −0.76 |
| Q9UBS4 | DnaJ homolog subfamily B member 11 OS = Homo sapiens GN = DNAJB11 PE = 1 SV = 1 | 6.30E+07 | −0.67 | #DIV/0! | −0.6 |
| H0YAC1 | Tripartite motif-containing 29, isoform CRA_a OS = Homo sapiens GN = TRIM29 PE = 4 SV = 1 | 7.10E+07 | #DIV/0! | #DIV/0! | #DIV/0! |
| J3KNQ4 | Plasma kallikrein (Fragment) OS = Homo sapiens GN = KLKB1 PE = 1 SV = 1 | | #DIV/0! | #DIV/0! | #DIV/0! |
| Q13219 | Alpha-parvin (Fragment) OS = Homo sapiens GN = PARVA PE = 1 SV = 1 | 2.80E+07 | −0.35 | −0.39 | 0.04 |
| Q1O471 | Pappalysin-1 OS = Homo sapiens GN = PAPPA PE = 1 SV = 1 | | #DIV/0! | #DIV/0! | #DIV/0! |
| Q59ER5 | Polypeptide N-acetylgalactosaminyltransferase 2 OS = Homo sapiens GN = GALNT2 PE = 1 SV = 1 | | #DIV/0! | #DIV/0! | #DIV/0! |
| A8K401 | WD repeat-containing protein 1 isoform 1 variant (Fragment) OS = Homo sapiens PE = 2 SV = 1 | 8.00E+07 | −0.72 | −0.14 | −0.58 |
| A0A024RDE8 | Prohibitin, isoform CRA_a OS = Homo sapiens GN = PHB PE = 2 SV = 1 | 1.70E+07 | −0.54 | −0.08 | −0.08 |
| P23634 | PDZ and LIM domain 5, isoform CRA_c OS = Homo sapiens GN = PDLIM5 PE = 4 SV = 1 | 4.80E+07 | −0.7 | −0.32 | −0.38 |
| A8K7Q1 | Plasma membrane calcium-transporting ATPase 4 OS = Homo sapiens GN = ATP2B4 PE = 1 SV = 2 | 3.10E+07 | −0.33 | −0.16 | −0.17 |
| P62195 | 26S protease regulatory subunit 8 OS = Homo sapiens GN = PSMC5 PE = 1 SV = 1 | | #DIV/0! | #DIV/0! | #DIV/0! |
| B2R7C7 | Alkaline phosphatase OS = Homo sapiens PE = 2 SV = 1 | | −1.24 | #NUM! | #DIV/0! |
| A0A087X117 | Nodal modulator 1 OS = Homo sapiens GN = NOMO1 PE = 1 SV = 1 | | −0.59 | #NUM! | #DIV/0! |
| B2RDG0 | Proteasome subunit alpha type OS = Homo sapiens PE = 2 SV = 1 | 2.00E+07 | −0.71 | −0.11 | −0.12 |
| L7RXH5 | Mitogen-activated protein kinase OS = Homo sapiens GN = MAPK3 PE = 2 SV = 1 | | −0.49 | −0.21 | −0.7 |
| O75533 | Splicing factor 3B subunit 1 OS = Homo sapiens GN = SF3B1 PE = 1 SV = 3 | 1.10E+07 | #DIV/0! | #DIV/0! | #DIV/0! |
| Q5STZ8 | ATP-binding cassette sub-family F member 1 (Fragment) OS = Homo sapiens GN = ABCF1 PE = 1 SV = 1 | | #DIV/0! | #DIV/0! | #DIV/0! |
| Q13185 | Chromobox protein homolog 3 OS = Homo sapiens GN = CBX3 PE = 1 SV = 4 | | #DIV/0! | #DIV/0! | #DIV/0! |
| O15400 | Syntaxin-7 OS = Homo sapiens GN = STX7 PE = 1 SV = 4 | 4.40E+07 | −0.82 | −0.14 | −0.68 |
| Q53H88 | Dynactin 2 variant (Fragment) OS = Homo sapiens PE = 2 SV = 1 | 3.10E+07 | #DIV/0! | #DIV/0! | #DIV/0! |
| B4E1Z4 | Uncharacterized protein OS = Homo sapiens PE = 1 SV = 1 | | −0.54 | #NUM! | #DIV/0! |
| P24043 | Laminin subunit alpha-2 OS = Homo sapiens GN = LAMA2 PE = 1 SV = 4 | 5.90E+07 | −0.54 | −0.11 | −0.43 |
| P49821 | NADH dehydrogenase [ubiquinone] flavoprotein 1, mitochondrial OS = Homo sapiens GN = NDUFV1 PE = 1 SV = 4 | 6.90E+07 | −0.64 | −0.34 | −0.31 |
| P08559 | Pyruvate dehydrogenase E1 component subunit alpha, somatic form, mitochondrial OS = Homo sapiens GN = PDHA1P | 1.20E+08 | −0.58 | 0.04 | −0.62 |
| Q9H444 | Charged multivesicular body protein 4b OS = Homo sapiens GN = CHMP4B PE = 1 SV = 1 | 2.50E+07 | −0.29 | −0.33 | 0.05 |
| P26038 | Moesin OS = Homo sapiens GN = MSN PE = 1 SV = 3 | 5.80E+07 | −1.05 | −0.21 | −0.84 |
| G3V3D1 | Epididymal secretory protein E1 (Fragment) OS = Homo sapiens GN = NPC2 PE = 1 SV = 1 | | #DIV/0! | #NUM! | #DIV/0! |
| P05108 | Cholesterol side chain cleavage enzyme, mitochondrial OS = Homo sapiens GN = CYP11A1 PE = 1 SV = 2 | | #DIV/0! | #DIV/0! | #DIV/0! |
| Q96KG9 | N-terminal kinase-like protein OS = Homo sapiens GN = SCYL1 PE = 1 SV = 1 | | #DIV/0! | #DIV/0! | #DIV/0! |
| P51888 | Prolargin OS = Homo sapiens GN = PRELP PE = 1 SV = 1 | 7.30E+07 | −0.07 | 0.56 | −0.63 |
| Q8TDJ5 | Tyrosine-protein kinase receptor OS = Homo sapiens GN = TFG/ALK fusion PE = 2 SV = 1 | | #NUM! | −0.67 | #NUM! |
| A8K4W2 | cDNA FLJ78635, highly similar to Homo sapiens ATP synthase, H+ transporting, mitochondrial F0 complex, subunit b, | 9.10E+07 | #DIV/0! | #DIV/0! | −0.96 |
| Q92621 | Nuclear pore complex protein Nup205 OS = Homo sapiens GN = NUP205 PE = 1 SV = 3 | | | | |
| A0A024R994 | Copine III, isoform CRA_a OS = Homo sapiens GN = CPNE3 PE = 4 SV = 1 | | | | |
| Q5U043 | 5-(hydroxymethyl)glutathione dehydrogenase OS = Homo sapiens GN = CPNE3 PE = 2 SV = 1 | | | | |
| Q01844 | RNA binding protein EWS (Fragment) OS = Homo sapiens GN = EWSR1 PE = 1 SV = 1 | | | | |
| A0A024R9N6 | EH-domain containing 4, isoform CRA_a OS = Homo sapiens GN = EHD4 PE = 4 SV = 1 | | | | |
| A0A024R9D7 | 2,4-dienoyl CoA reductase 1, mitochondrial, isoform CRA_b OS = Homo sapiens GN = DECR1 PE = 4 SV = 1 | | | | |
| P17936 | Insulin-like growth factor binding protein 3 OS = Homo sapiens GN = IGFBP3 PE = 1 SV = 2 | | | | |
| Q7L5L3 | Glycerophosphodiester phosphodiesterase domain-containing protein 3 OS = Homo sapiens GN = GDPD3 PE = 2 SV = 3 | | | | |
| Q8TF42 | Ubiquitin associated and SH3 domain-containing protein 3 OS = Homo sapiens GN = UBASH3B PE1 SV = 2 | | | | |

APPENDIX A-continued

| | | | | |
|---|---|---|---|---|
| P52943 | Cysteine-rich protein 2 OS = Homo sapiens GN = CRIP2 PE = 1 SV = 1 | 5.50E+07 | #DIV/0! | −0.09 |
| A0A024R7M | Transmembrane emp24 protein transport domain containing 9, isoform CRA_a OS = Homo sapiens GN = TMED9 PE = 3 | 1.30E+08 | −0.59 | 0.07 | −0.67 |
| P62277 | 40S ribosomal protein S13 OS = Homo sapiens GN = RPS13 PE = 1 SV = 2 | | | | −0.24 |
| O75367 | Core histone macro-H2A1 OS = Homo sapiens GN = H2AFY PE = 1 SV = 4 | 1.90E+08 | −0.28 | −0.04 | 0.23 |
| Q9H9B4 | Sideroflexin-1 OS = Homo sapiens GN = SFXN1 PE = 1 SV = 4 | 1.60E+07 | −0.48 | −0.02 | −0.46 |
| P22695 | Cytochrome b-c1 complex subunit 2, mitochondrial OS = Homo sapiens GN = UQCRC2 PE = 1 SV = 3 | 4.00E+07 | −0.63 | −0.53 | −0.09 |
| A2NB46 | Cold agglutinin FS-2 L-chain (Fragment) OS = Homo sapiens PE = 2 SV = 1 | 4.10E+07 | −0.28 | −0.16 | −0.11 |
| P09497 | Clathrin light chain B OS = Homo sapiens GN = CLTB PE = 1 SV = 1 | 1.30E+08 | −0.79 | −0.6 | −0.19 |
| P10620 | Microsomal glutathione S-transferase 1 OS = Homo sapiens GN = MGST1 PE = 1 SV = 1 | 1.70E+08 | #DIV/0! | #DIV/0! | #DIV/0! |
| P42166 | Lamina-associated polypeptide 2, isoform alpha OS = Homo sapiens GN = TMPO PE = 1 SV = 1 | | #DIV/0! | #DIV/0! | −0.86 |
| P19827 | Inter-alpha-trypsin inhibitor heavy chain H1 OS = Homo sapiens GN = ITIH1 PE = 1 SV = 3 | 1.20E+07 | −0.29 | −0.51 | 0.22 |
| B2R673 | cDNA, FLJ92818, highly similar to Homo sapiens pyruvate dehydrogenase complex, component X (PDHX), mRNA OS= | | #DIV/0! | #DIV/0! | #DIV/0! |
| Q96QR8 | Transcriptional activator protein Pur-beta OS = Homo sapiens GN = PURB PE = 1 SV = 3 | 3.90E+07 | #DIV/0! | #DIV/0! | 0.02 |
| Q15363 | Transmembrane emp24 domain-containing protein 2 OS = Homo sapiens GN = TMED2 PE = 1 SV = 1 | 1.90E+08 | −1.93 | −0.08 | −1.85 |
| P07954 | Fumarate hydratase, mitochondrial OS = Homo sapiens GN = FH PE = 1 SV = 3 | 4.30E+07 | 0.28 | 0.63 | −0.35 |
| Q8TC12 | Retinol dehydrogenase 11 OS = Homo sapiens GN = RDH11 PE = 1 SV = 2 | | #DIV/0! | #DIV/0! | #DIV/0! |
| Q32P28 | Prolyl 3-hydroxylase 1 OS = Homo sapiens GN = P3H1 PE = 1 SV = 2 | | #DIV/0! | #DIV/0! | #DIV/0! |
| Q9U70 | N-acetyl-D-glucosamine kinase OS = Homo sapiens GN = NAGK PE = 1 SV = 4 | | #DIV/0! | #DIV/0! | #DIV/0! |
| A0A024R883 | ATPase, H+ transporting, lysosomal 13 kDa, V1 subunit G1, isoform CRA_a OS = Homo sapiens GN = ATP6V1G1 PE = 4 SV | | #DIV/0! | #DIV/0! | #DIV/0! |
| Q6P988 | Palmitoleoyl-protein carboxylesterase NOTUM OS = Homo sapiens GN = NOTUM PE = 1 SV = 1 | | #DIV/0! | #DIV/0! | #DIV/0! |
| P07814 | Bifunctional glutamate/proline-tRNA ligase OS = Homo sapiens GN = EPRS PE = 1 SV = 5 | | #DIV/0! | #DIV/0! | #DIV/0! |
| Q9NV17 | ATPase family AAA domain-containing protein 3A OS = Homo sapiens GN = ATAD3A PE = 1 SV = 2 | 9.50E+07 | −1.14 | −0.28 | −0.86 |
| B4E1U9 | cDNA FLJ54776, highly similar to Cell division control protein 42 homolog OS = Homo sapiens PE = 2 SV = 1 | | #DIV/0! | #DIV/0! | #DIV/0! |
| Q9H4A6 | Golgi phosphoprotein 3 OS = Homo sapiens GN = GOLPH3 PE = 1 SV = 1 | 4.50E+07 | −1.03 | −0.25 | −0.78 |
| Q9NRN7 | L-aminoadipate-semialdehyde dehydrogenase-phosphopantetheinyl transferase OS = Homo sapiens GN = AASDHPPT | 2.10E+08 | −0.3 | −0.02 | −0.28 |
| A6NFX8 | ADP-sugar pyrophosphatase OS = Homo sapiens GN = NUDT5 PE = 1 SV = 1 | | #NUM! | #NUM! | −0.59 |
| Q59E89 | DnaJ (Hsp40) homolog, subfamily B, member 4 variant (Fragment) OS = Homo sapiens PE = 2 SV = 1 | 3.00E+07 | −0.3 | #NUM! | −0.68 |
| A8K132 | cDNA FLJ75476, highly similar to Homo sapiens glutaminase (GLS), mRNA OS = Homo sapiens PE = 2 SV = 1 | 1.80E+07 | | | |
| P12268 | Inosine-5′-monophosphate dehydrogenase 2 OS = Homo sapiens GN = IMPDH2 PE = 1 SV = 2 | | #DIV/0! | #NUM! | #DIV/0! |
| P62854 | 40S ribosomal protein S26 OS = Homo sapiens GN = RPS26 PE = 1 SV = 3 | | −0.71 | #NUM! | #DIV/0! |
| Q9UBI6 | Guanine nucleotide-binding protein G(I)/G(S)/G(O) subunit gamma-12 OS = Homo sapiens GN = GNG12 PE = 1 SV = 3 | | −0.73 | −0.37 | −0.36 |
| P62913 | 60S ribosomal protein L11 OS = Homo sapiens GN = RPL11 PE = 1 SV = 2 | | #DIV/0! | #DIV/0! | #DIV/0! |
| Q12846 | Syntaxin-4 OS = Homo sapiens GN = STX4 PE = 1 SV = 2 | | #DIV/0! | #DIV/0! | #DIV/0! |
| A0A024RDS2 | Periostin, osteoblast specific factor, isoform CRA_c OS = Homo sapiens GN = POSTN PE = 4 SV = 1 | 8.50E+07 | #DIV/0! | #DIV/0! | #DIV/0! |
| B7Z2P5 | cDNA FLJ56478, highly similar to Homo sapiens COBL-like 1 (COBLL1), mRNA OS = Homo sapiens PE = 2 SV = 1 | 2.90E+07 | #DIV/0! | #DIV/0! | −0.91 |
| P61151 | Serine/threonine-protein phosphatase 2A 55 kDa regulatory subunit B alpha isoform OS = Homo sapiens GN = PPP2R2 | | #DIV/0! | #DIV/0! | #DIV/0! |
| Q13344 | Fus-like protein (Fragment) OS = Homo sapiens PE = 2 SV = 1 | | #DIV/0! | #DIV/0! | −0.68 |
| Q53HB7 | Diablo isoform 1 variant (Fragment) OS = Homo sapiens PE = 2 SV = 1 | | #DIV/0! | #DIV/0! | −0.15 |
| Q9BU40 | Chordin-like protein 1 OS = Homo sapiens GN = CHRDL1 PE = 2 SV = 1 | 2.20E+07 | −1.39 | #NUM! | #DIV/0! |
| P53992 | Protein transport protein Sec24C OS = Homo sapiens GN = SEC24C PE = 1 SV = 1 | | −0.11 | 0 | −0.11 |
| Q8N1B4 | Vacuolar protein sorting-associated protein 52 homolog OS = Homo sapiens GN = VPS52 PE = 1 SV = 3 | | #DIV/0! | #DIV/0! | #DIV/0! |
| Q6P5V6 | SNX5 protein (Fragment) OS = Homo sapiens GN = SNX5 PE = 2 SV = 1 | | #DIV/0! | #DIV/0! | #DIV/0! |
| Q8WVX7 | Ribosomal protein S19 (Fragment) OS = Homo sapiens PE = 2 SV = 1 | 5.80E+07 | −0.26 | −0.11 | −0.15 |
| P53582 | Methionine aminopeptidase 1 OS = Homo sapiens GN = METAP1 PE = 1 SV = 2 | | #DIV/0! | #DIV/0! | #DIV/0! |
| P17980 | 26S protease regulatory subunit 6A OS = Homo sapiens GN = PSMC3 PE = 1 SV = 3 | 6.90E+07 | −0.21 | 0.63 | −0.85 |
| Q15459 | Splicing factor 3A subunit 1 OS = Homo sapiens GN = SF3A1 PE = 1 SV = 1 | | #DIV/0! | #DIV/0! | −0.11 |

APPENDIX A-continued

| ID | Description | Value | Col4 | Col5 | Col6 |
|---|---|---|---|---|---|
| A0A024RDJ1 | DC2 protein, isoform CRA_a OS = Homo sapiens GN = DC2 PE = 4 SV = 1 | 5.70E+07 | -1.35 | -0.14 | -1.21 |
| P55060 | Exportin-2 OS = Homo sapiens GN = CSE1L PE = 1 SV = 3 | | #DIV/0! | #DIV/0! | #DIV/0! |
| B5BTZ8 | Small nuclear ribonucleoprotein polypeptide B" OS = Homo sapiens GN = SNRPB2 PE = 2 SV = 1 | | #DIV/0! | #DIV/0! | #DIV/0! |
| A0A024QZT4 | Serpin peptidase inhibitor, clade B (Ovalbumin), member 9, isoform CRA_a OS = Homo sapiens GN = SERPINB9 PE = 3 SV | | #DIV/0! | #DIV/0! | #DIV/0! |
| Q32MZ4 | Leucine-rich repeat flightless-interacting protein 1 OS = Homo sapiens GN = LRRFIP1 PE = 1 SV = 2 | | #DIV/0! | #DIV/0! | #DIV/0! |
| P12270 | Nucleoprotein TPR OS = Homo sapiens GN = TPR PE = 1 SV = 3 | 6.20E+06 | -0.26 | -0.51 | 0.25 |
| A0A024RAI1 | ARP3 actin-related protein 3 homolog (Yeast), isoform CRA_a OS = Homo sapiens GN = ACTR3 PE = 3 SV = 1 | | #DIV/0! | #NUM! | #DIV/0! |
| P55884 | Eukaryotic translation initiation factor 3 subunit B OS = Homo sapiens GN = EIF3B PE = 1 SV = 1 | | #DIV/0! | #DIV/0! | #DIV/0! |
| Q99426 | Tubulin-folding cofactor B OS = Homo sapiens GN = TBCB PE = 1 SV = 2 | | #DIV/0! | #DIV/0! | #DIV/0! |
| A0A068LKQ0 | Ig heavy chain variable region (Fragment) OS = Homo sapiens PE = 4 SV = 1 | | #DIV/0! | #DIV/0! | #DIV/0! |
| Q9GZU2 | Paternally-expressed gene 3 protein OS = Homo sapiens GN = PEG3 PE = 1 SV = 1 | | #DIV/0! | #DIV/0! | #DIV/0! |
| A0A0B4J2D5 | Protein LOC102724023 OS = Homo sapiens GN = LOC102724023 PE = 4 SV = 1 | 3.20E+07 | -0.44 | -0.41 | -0.03 |
| Q59EC0 | Adenosine deaminase, RNA-specific isoform ADAR-a variant (Fragment) OS = Homo sapiens PE = 2 SV = 1 | | #DIV/0! | #DIV/0! | #DIV/0! |
| Q9UHG3 | Prenylcysteine oxidase 1 OS = Homo sapiens GN = PCYOX1 PE = 1 SV = 3 | 7.10E+07 | -0.43 | -0.19 | -0.24 |
| Q9NZZ3 | Charged multivesicular body protein 5 OS = Homo sapiens GN = CHMP5 PE = 1 SV = 1 | | #DIV/0! | #DIV/0! | #DIV/0! |
| A0A024QZS4 | Peptidyl-prolyl cis-trans isomerase OS = Homo sapiens GN = PPIF PE = 3 SV = 1 | | #NUM! | #NUM! | #NUM! |
| B3KY04 | cDNA FLJ46506 fis, clone THYMU3030752, highly similar to BTB/POZ domain-containing protein KCTD12 OS = Homo s | | #DIV/0! | #DIV/0! | #DIV/0! |
| Q4LE33 | TNC variant protein (Fragment) OS = Homo sapiens GN = TNC variant protein PE = 2 SV = 1 | 8.60E+05 | -0.68 | -1.53 | 0.85 |
| Q4LE58 | EIF4G1 variant protein (Fragment) OS = Homo sapiens GN = EIF4G1 variant protein PE = 2 SV = 1 | 4.40E+06 | #NUM! | -0.1 | #NUM! |
| P02743 | Serum amyloid P-component OS = Homo sapiens GN = APCS PE = 1 SV = 1 | 9.40E+07 | #DIV/0! | #NUM! | -0.67 |
| Q14444 | Caprin-1 OS = Homo sapiens GN = CAPRIN1 PE = 1 SV = 2 | | #DIV/0! | #DIV/0! | #DIV/0! |
| P27695 | DNA-(apurinic or apyrimidinic site) lyase OS = Homo sapiens GN = APEX1 PE = 1 SV = 2 | | #DIV/0! | #DIV/0! | -0.05 |
| Q14TF0 | Glutamate-cysteine ligase OS = Homo sapiens GN = GCLC PE = 2 SV = 1 | | #DIV/0! | #DIV/0! | -0.31 |
| A8K2Y2 | cDNA FLJ78120, highly similar to Homo sapiens eukaryotic translation initiation factor 2, subunit 3 gamma, 52 kDa (El | | -0.04 | #DIV/0! | #DIV/0! |
| Q9UBC2 | Epidermal growth factor receptor substrate 15-like 1 OS = Homo sapiens GN = EPS15L1 PE = 1 SV = 1 | | #DIV/0! | #DIV/0! | -3.09 |
| A0A087WY3 | YTH domain-containing family protein 3 OS = Homo sapiens GN = YTHDF3 PE = 1 SV = 1 | | #DIV/0! | -0.07 | #DIV/0! |
| P21281 | V-type proton ATPase subunit B, brain isoform OS = Homo sapiens GN = ATP6V1B2 PE = 1 SV = 3 | | -1 | -0.42 | -0.58 |
| P18065 | Insulin-like growth factor-binding protein 2 OS = Homo sapiens GN = IGFBP2 PE = 1 SV = 2 | 7.80E+06 | #DIV/0! | #NUM! | #DIV/0! |
| J3KPF3 | 4F2 cell-surface antigen heavy chain OS = Homo sapiens GN = SLC3A2 PE = 1 SV = 1 | 7.70E+07 | -0.97 | #DIV/0! | #DIV/0! |
| C1PHA2 | Kinesin-like protein OS = Homo sapiens GN = KIF5B-ALK PE = 2 SV = 1 | | #DIV/0! | #DIV/0! | #DIV/0! |
| Q96TA1 | Niban-like protein 1 OS = Homo sapiens GN = FAM129B PE = 1 SV = 1 | | #DIV/0! | #DIV/0! | #DIV/0! |
| B2RSW3 | cDNA FLJ92658, highly similar to Homo sapiens poly (ADP-ribose) polymerase family, member 1 (PARP1), mRNA OS | 1.20E+08 | #DIV/0! | #DIV/0! | #DIV/0! |
| B72AC8 | 60S ribosomal protein L31 OS = Homo sapiens GN = RPL31 PE = 1 SV = 1 | | -3.16 | #DIV/0! | #DIV/0! |
| B2R8I2 | cDNA, FLJ93914, highly similar to Homo sapiens histidine-rich glycoprotein (HRG), mRNA OS = Homo sapiens PE = 2 SV | 4.20E+07 | -1 | -0.42 | #DIV/0! |
| P51149 | Ras-related protein Rab-7a OS = Homo sapiens GN = RAB7A PE = 1 SV = 1 | | #DIV/0! | #DIV/0! | #DIV/0! |
| B3KUY2 | Prostaglandin E synthase 3 (Cytosolic), isoform CRA_c OS = Homo sapiens GN = PTGES3 PE = 2 SV = 1 | | #DIV/0! | #DIV/0! | #DIV/0! |
| A0A087X2I1 | 26S protease regulatory subunit 10B OS = Homo sapiens GN = PSMC6 PE = 1 SV = 1 | | -0.94 | #DIV/0! | #DIV/0! |
| O76003 | Glutaredoxin-3 OS = Homo sapiens GN = GLRX3 PE = 1 SV = 2 | | #DIV/0! | #DIV/0! | #DIV/0! |
| P12273 | Prolactin-inducible protein OS = Homo sapiens GN = PIP PE = 1 SV = 1 | 2.90E+07 | #DIV/0! | #DIV/0! | -1.02 |
| K7ELC2 | 40S ribosomal protein S15 OS = Homo sapiens GN = RPS15 PE = 1 SV = 1 | 4.80E+07 | -0.3 | -0.22 | -0.08 |
| P05579 | Methionine aminopeptidase 2 OS = Homo sapiens GN = METAP2 PE = 1 SV = 1 | | #DIV/0! | #DIV/0! | #DIV/0! |
| Q9Y3A6 | Transmembrane emp24 domain-containing protein 5 OS = Homo sapiens GN = TMED5 PE = 1 SV = 1 | 4.70E+07 | -1.02 | -0.01 | -1.01 |
| Q03591 | Complement factor H-related protein 1 OS = Homo sapiens GN = CFHR1 PE = 1 SV = 1 | | #DIV/0! | #DIV/0! | #DIV/0! |
| B4DWB5 | cDNA FLJ53931, highly similar to Bifunctional 3'-phosphoadenosine5'-phosphosulfate synthetase 2 OS = Homo sapien | | #DIV/0! | #NUM! | #NUM! |
| P22413 | Ectonucleotide pyrophosphatase/phosphodiesterase family member 1 OS = Homo sapiens GN = ENPP1 PE = 1 SV = 2 | | -0.94 | #DIV/0! | #DIV/0! |
| Q9BXP5 | Serrate RNA effector molecule homolog OS = Homo sapiens GN = SRRT PE = 1 SV = 1 | | #DIV/0! | #DIV/0! | #DIV/0! |
| A0A024R2A3 | HCG1979072, isoform CRA_b OS = Homo sapiens GN = hCG_1979072 PE = 4 SV = 1 | | #DIV/0! | #DIV/0! | #DIV/0! |
| A0A024RBF6 | HCG26523, isoform CRA_b OS = Homo sapiens GN = hCG_26523 PE = 4 SV = 1 | | -0.3 | -0.22 | -0.08 |
| Q9UGM3 | Deleted in malignant brain tumors 1 protein OS = Homo sapiens GN = DMBT1 PE = 1 SV = 2 | | #DIV/0! | #DIV/0! | #DIV/0! |
| B2R6S5 | UMP-CMP kinase OS = Homo sapiens GN = CMPK PE = 2 SV = 1 | | -0.64 | -0.01 | -1.01 |
| Q5T1J5 | Putative coiled-coil-helix-coiled-coil-helix domain-containing protein CHCHD2P9, mitochondrial OS = Homo sapiens G | | #DIV/0! | #NUM! | #DIV/0! |
| A8K761 | NADH dehydrogenase (Ubiquinone) 1 beta subcomplex, 10, 22 kDa, isoform CRA_b OS = Homo sapiens GN = NDUFB10 | | -0.91 | #DIV/0! | #DIV/0! |
| Q13409 | Cytoplasmic dynein 1 intermediate chain 2 OS = Homo sapiens GN = DYNC1I2 PE = 1 SV = 3 | | #DIV/0! | #DIV/0! | #DIV/0! |

APPENDIX A-continued

| ID | Description | Value1 | Value2 | Value3 | Value4 |
|---|---|---|---|---|---|
| A8K0G3 | AP complex subunit beta OS = Homo sapiens PE = 2 SV = 1 | 3.10E+07 | −0.62 | −0.21 | −0.41 |
| B3KXB8 | cDNA FLJ45106 fis, clone BRAWH303293, highly similar to Synaptopodin OS = Homo sapiens PE = 2 SV = 1 | | −0.59 | #NUM! | #DIV/0! |
| P14868 | Aspartate-tRNA ligase, cytoplasmic OS = Homo sapiens GN = DARS PE = 1 SV = 2 | | −0.3 | #NUM! | #DIV/0! |
| Q9UNA0 | A disintegrin and metalloproteinase with thrombospondin motifs 5 OS = Homo sapiens GN = ADAMTS5 PE = 1 SV = 2 | | −1.79 | #NUM! | #DIV/0! |
| P61956 | Small ubiquitin-related modifier 2 OS = Homo sapiens GN = SUMO2 PE = 1 SV = 3 | | −0.6 | #NUM! | #DIV/0! |
| A0A024RAM | Microtubule-associated protein 1B, isoform CRA_b OS = Homo sapiens GN = MAP1B PE = 4 SV = 1 | | −0.58 | #NUM! | #DIV/0! |
| P35221 | Catenin alpha-1 OS = Homo sapiens GN = CTNNA1 PE = 1 SV = 1 | | | #DIV/0! | #DIV/0! |
| P00492 | Hypoxanthine-guanine phosphoribosyltransferase OS = Homo sapiens GN = HPRT1 PE = 1 SV = 2 | | | #DIV/0! | #DIV/0! |
| A43652 | Afamin OS = Homo sapiens GN = AFM PE = 1 SV = 1 | | | #DIV/0! | #DIV/0! |
| A0A024RBB7 | Nucleosome assembly protein 1-like 1, isoform CRA_a OS = Homo sapiens GN = NAP1L1 PE = 3 SV = 1 | | #NUM! | #NUM! | #DIV/0! |
| B4DNE1 | cDNA FLJ52708, highly similar to Basigin OS = Homo sapiens PE = 2 SV = 1 | 2.40E+07 | −0.3 | −0.45 | 0.15 |
| P31930 | Cytochrome b-c1 complex subunit 1, mitochondrial OS = Homo sapiens GN = UQCRC1 PE = 1 SV = 3 | 5.10E+07 | −0.18 | 0.01 | −0.19 |
| B3KXW5 | cDNA FLJ46199 fis, clone TEST4007965, highly similar to AP-1 complex subunit gamma-1 OS = Homo sapiens PE = 2 SV | 7.30E+06 | #DIV/0! | #NUM! | #NUM! |
| Q32Q14 | NDUFA7 protein (Fragment) OS = Homo sapiens GN = NDUFA7 PE = 2 SV = 1 | 4.90E+07 | #DIV/0! | #DIV/0! | −0.83 |
| Q5TBU5 | HCG1773630 OS = Homo sapiens GN = hCG_1773630 PE = 2 SV = 1 | 1.00E+08 | −0.71 | 0.08 | −0.8 |
| P05387 | 60S acidic ribosomal protein P2 OS = Homo sapiens GN = RPLP2 PE = 1 SV = 1 | | −0.71 | #DIV/0! | #DIV/0! |
| O43491 | Band 4.1-like protein 2 OS = Homo sapiens GN = EPB41L2 PE = 1 SV = 1 | | −0.36 | #DIV/0! | #DIV/0! |
| Q9NPJ3 | Acyl-coenzyme A thioesterase 13 OS = Homo sapiens GN = ACOT13 PE = 1 SV = 1 | 4.30E+07 | −0.18 | #DIV/0! | −0.38 |
| E5KMI6 | Lon protease homolog, mitochondrial OS = Homo sapiens GN = LONP1 PE = 3 SV = 1 | | −0.18 | #DIV/0! | #DIV/0! |
| Q8P253 | Vacuolar protein sorting-associated protein 18 homolog OS = Homo sapiens GN = VPS18 PE = 1 SV = 2 | 2.70E+07 | −0.18 | −0.05 | −0.13 |
| A0A0A0MSE | Hydroxyacyl-coenzyme A dehydrogenase, mitochondrial OS = Homo sapiens GN = HADH PE = 1 SV = 1 | | #DIV/0! | #DIV/0! | #DIV/0! |
| P02760 | Protein AMBP OS = Homo sapiens GM = AMBP PE = 1 SV = 1 | | #DIV/0! | #DIV/0! | #DIV/0! |
| O43818 | U3 small nucleolar RNA-interacting protein 2 OS = Homo sapiens GN = RRP9 PE = 1 SV = 1 | | #DIV/0! | #DIV/0! | #DIV/0! |
| Q92530 | Proteasome inhibitor PI31 subunit OS = Homo sapiens GN = PSMF1 PE = 1 SV = 1 | | #DIV/0! | #DIV/0! | #DIV/0! |
| A0A024R2Q4 | Ribosomal protein L15 OS = Homo sapiens GN = RPL15 PE = 3 SV = 1 | 9.80E+07 | −0.18 | −0.09 | −0.09 |
| G3V1L9 | Tight junction protein 1 (Zona occludens 1), isoform CRA_a OS = Homo sapiens GN = TJP1 PE = 1 SV = 1 | | #DIV/0! | #DIV/0! | #DIV/0! |
| A0A024R8D5 | HCG30600, isoform CRA_a OS = Homo sapiens GN = hCG_30600 PE = 4 SV = 1 | 5.20E+08 | −0.21 | 0.02 | −0.22 |
| P54819 | Adenylate kinase 2, mitochondrial OS = Homo sapiens GN = AK2 PE = 1 SV = 2 | 7.20E+07 | −0.64 | −0.14 | −0.5 |
| P33316 | Deoxyuridine 5′-triphosphate nucleotidohydrolase, mitochondrial OS = Homo sapiens GN = DUT PE = 1 SV = 4 | | #DIV/0! | #DIV/0! | #DIV/0! |
| O00231 | 26S proteasome non-ATPase regulatory subunit 11 OS = Homo sapiens GN = PSMD11 PE = 1 SV = 3 | | −0.72 | #NUM! | #DIV/0! |
| Q16706 | Alpha-mannosidase 2 OS = Homo sapiens GN = MAN2A1 PE = 1 SV = 2 | | #DIV/0! | #DIV/0! | #DIV/0! |
| P14174 | Macrophage migration inhibitory factor OS = Homo sapiens GN = MIF PE = 1 SV = 4 | 1.30E+08 | −0.88 | −0.38 | −0.5 |
| A8MUS3 | 60S ribosomal protein L23a OS = Homo sapiens GN = RPL23A PE = 1 SV = 1 | 9.60E+07 | −0.36 | −0.22 | −0.14 |
| Q9Y2W1 | Thyroid hormone receptor-associated protein 3 OS = Homo sapiens GN = THRAP3 PE = 1 SV = 2 | | −0.37 | #DIV/0! | #DIV/0! |
| B5BU01 | Eukaryotic translation initiation factor 2 beta OS = Homo sapiens GN = EIF2S2 PE = 2 SV = 1 | | −0.93 | #NUM! | #DIV/0! |
| A4D1B5 | Gamma-secretase-activating protein OS = Homo sapiens GN = GSAP PE = 1 SV = 3 | | #DIV/0! | #DIV/0! | #DIV/0! |
| B7Z6C2 | cDNA FLJ50663, highly similar to Phosphoglucomutase-1 (EC 5.4.2.2) OS = Homo sapiens PE = 2 SV = 1 | | #DIV/0! | #DIV/0! | #DIV/0! |
| P46939 | Utrophin OS = Homo sapiens GN = UTRN PE = 1 SV = 2 | | #DIV/0! | #DIV/0! | #DIV/0! |
| D3DPK5 | SH3 domain binding glutamic acid-rich protein like 3, isoform CRA_a (Fragment) OS = Homo sapiens GN = SH3BGRL3 P | | #DIV/0! | #DIV/0! | #DIV/0! |
| B2R9F3 | cDNA FLJ94363, highly similar to Homo sapiens transporter 1, ATP-binding cassette, sub-family B(MDR/TAP) (TAP1) | | #DIV/0! | #DIV/0! | #DIV/0! |
| P07738 | Bisphosphoglycerate mutase OS = Homo sapiens GN = BPGM PE = 1 SV = 2 | | #DIV/0! | #DIV/0! | #DIV/0! |
| Q16822 | Phosphoenolpyruvate carboxykinase [GTP], mitochondrial OS = Homo sapiens GN = PCK2 PE = 1 SV = 3 | | #DIV/0! | #DIV/0! | #DIV/0! |
| Q8N9N5 | Protein BANP OS = Homo sapiens GN = BANP PE = 1 SV = 1 | | #DIV/0! | #DIV/0! | #DIV/0! |
| A8K517 | Ribosomal protein S23, isoform CRA_a OS = Homo sapiens GN = RPS23 PE = 2 SV = 1 | 8.40E+07 | −0.91 | −0.19 | −0.72 |
| P62318 | Small nuclear ribonucleoprotein Sm D3 OS = Homo sapiens GN = SNRPD3 PE = 1 SV = 1 | | −0.46 | #NUM! | #DIV/0! |
| P49458 | Signal recognition particle 9 kDa protein OS = Homo sapiens GN = SRP9 PE = 1 SV = 2 | | #DIV/0! | #DIV/0! | #DIV/0! |
| Q8TCS8 | Polyribonucleotide nucleotidyltransferase 1, mitochondrial OS = Homo sapiens GN = PNPT1 PE = 1 SV = 2 | | −0.09 | #NUM! | #DIV/0! |
| P35998 | 26S protease regulatory subunit 7 OS = Homo sapiens GN = PSMC2 PE = 1 SV = 3 | | −0.21 | #NUM! | #DIV/0! |
| O00151 | PDZ and LIM domain protein 1 OS = Homo sapiens GN = PDLIM1 PE = 1 SV = 4 | | −0.49 | −0.8 | 0.31 |
| B7Z7F0 | cDNA FLJ56420, highly similar to Aspartyl aminopeptidase (EC 3.4.11.21) OS = Homo sapiens PE = 2 SV = 1 | 1.90E+07 | | #DIV/0! | #DIV/0! |
| B5BUB1 | RuvB-like 1 (Fragment) OS = Homo sapiens GN = RUVBL1 PE = 2 SV = 1 | | #DIV/0! | #DIV/0! | #DIV/0! |
| P31153 | S-adenosylmethionine synthase isoform type-2 OS = Homo sapiens GN = MAT2A PE = 1 SV = 1 | | #DIV/0! | #DIV/0! | #DIV/0! |
| B2R983 | cDNA, FLJ94267, highly similar to Homo sapiens glutathione S-transferase omega 1 (GSTO1), mRNA OS = Homo sapie | 1.90E+07 | −0.81 | −0.68 | −0.13 |

APPENDIX A-continued

| ID | Description | Value1 | Value2 | Value3 | Value4 |
|---|---|---|---|---|---|
| M0QXF9 | Branched-chain-amino-acid aminotransferase (Fragment) OS = Homo sapiens GN = BCAT2 PE = 1 SV = 1 | | #DIV/0! | #DIV/0! | #DIV/0! |
| A0A024R718 | Pre-B-cell colony enhancing factor 1, isoform CRA_a OS = Homo sapiens GN = PBEF1 PE = 4 SV = 1 | 1.80E+07 | −0.35 | −0.35 | 0 |
| Q4LE40 | C14orf159 variant protein (Fragment) OS = Homo sapiens GN = C14orf159 variant protein PE = 2 SV = 1 | | #DIV/0! | #DIV/0! | #DIV/0! |
| A8K646 | cDNA FLJ75699, highly similar to Homo sapiens osteoclast stimulating factor 1 (OSTF1), mRNA OS = Homo sapiens PE | | #DIV/0! | #DIV/0! | #DIV/0! |
| A4D2P0 | Ras-related C3 botulinum toxin substrate 1 (Rho family, small GTP binding protein Rac1) OS = Homo sapiens GN = RAC | 7.10E+07 | −1.09 | −0.35 | −0.74 |
| P09110 | 3-ketoacyl-CoA thiolase, peroxisomal OS = Homo sapiens GN = ACAA1 PE = 1 SV = 2 | | #NUM! | #NUM! | #NUM! |
| E7EPT4 | NADH dehydrogenase [ubiquinone] flavoprotein 2, mitochondrial OS = Homo sapiens GN = NDUFV2 PE = 1 SV = 1 | 1.00E+08 | −0.56 | 0.02 | −1.48 |
| P00734 | Prothrombin OS = Homo sapiens GN = F2 PE = 1 SV = 2 | | −1.46 | #DIV/0! | #DIV/0! |
| A8K455 | S-adenosylmethionine synthase OS = Homo sapiens PE = 2 SV = 1 | | #DIV/0! | #DIV/0! | #DIV/0! |
| B3KM95 | Phosphatidate cytidylyltransferase OS = Homo sapiens PE = 2 SV = 1 | 1.10E+08 | −0.86 | −0.37 | −0.49 |
| B4DI63 | cDNA FLJ59205, highly similar to Mimecan OS = Homo sapiens PE = 2 SV = 1 | 2.60E+07 | −0.53 | −0.23 | −0.3 |
| A8K525 | cDNA FLJ76817, highly similar to Homo sapiens non-POU domain containing, octamer-binding (NONO), mRNA OS = H | 8.70E+07 | −0.45 | −0.1 | −0.35 |
| P18085 | ADP-ribosylation factor 4 OS = Homo sapiens GN = ARF4 PE = 1 SV = 3 | | #DIV/0! | #DIV/0! | #DIV/0! |
| U3KQV3 | Uncharacterized protein (Fragment) OS = Homo sapiens PE = 4 SV = 5 | | #DIV/0! | #DIV/0! | #DIV/0! |
| P60468 | Protein transport protein Sec61 subunit beta OS = Homo sapiens GN = SEC61B PE = 1 SV = 2 | | #DIV/0! | #DIV/0! | #DIV/0! |
| A8K2W3 | cDNA FLJ78516 OS = Homo sapiens PE = 2 SV = 1 | | #DIV/0! | #DIV/0! | #DIV/0! |
| A0A024RB01 | Integrin, alpha 5 (Fibronectin receptor, alpha polypeptide), isoform CRA_b OS = Homo sapiens GN = ITGA5 PE = 3 SV = 1 | 3.90E+07 | −0.51 | −0.09 | −0.41 |
| P35606 | Coatomer subunit beta' OS = Homo sapiens GN = COPB2 PE = 1 SV = 2 | 3.50E+07 | −0.2 | 0.03 | −0.22 |
| O43143 | Pre-mRNA-splicing factor ATP-dependent RNA helicase DHX15 OS = Homo sapiens GN = DHX15 PE = 1 SV = 2 | | #DIV/0! | #DIV/0! | #DIV/0! |
| Q16881 | Thioredoxin reductase 1, cytoplasmic OS = Homo sapiens GN = TXNRD1 PE = 1 SV = 3 | | #DIV/0! | #DIV/0! | #DIV/0! |
| A0A024R5C5 | Pyruvate carboxylase OS = Homo sapiens GN = PC PE = 4 SV = 1 | 1.40E+07 | −0.86 | −0.71 | −0.15 |
| B2R5M8 | Isocitrate dehydrogenase [NADP] OS = Homo sapiens PE = 2 SV = 1 | | #DIV/0! | #DIV/0! | #DIV/0! |
| B2R7S3 | cDNA, FLJ93580, highly similar to Homo sapiens TRAF family member-associated NFKB activator (TANK), transcript v | | #DIV/0! | #DIV/0! | #DIV/0! |
| P02790 | Hemopexin OS = Homo sapiens GN = HPX PE = 1 SV = 2 | 6.50E+07 | −0.57 | −0.33 | −0.23 |
| K7ER00 | Phenylalanine-tRNA ligase alpha subunit OS = Homo sapiens GN = FARSA PE = 1 SV = 1 | | #DIV/0! | #DIV/0! | #DIV/0! |
| P15121 | Aldose reductase OS = Homo sapiens GN = AKR1B1 PE = 1 SV = 3 | | #DIV/0! | #DIV/0! | #DIV/0! |
| B2RBH2 | cDNA, FLJ95508, highly similar to Homo sapiens 5'-nucleotidase, ecto (CD73) (NT5E), mRNA OS = Homo sapiens PE = 2 | | −1.16 | #NUM! | #DIV/0! |
| A0A0A0MQS | Laminin subunit alpha-4 OS = Homo sapiens GN = LAMA4 PE = 1 SV = 1 | | −0.89 | #NUM! | #DIV/0! |
| B3KUL5 | Oxysterol-binding protein OS = Homo sapiens PE = 2 SV = 2 | | #DIV/0! | #DIV/0! | #DIV/0! |
| P53539 | Protein fosB OS = Homo sapiens GN = FOSB PE = 2 SV = 1 | | #DIV/0! | #DIV/0! | #DIV/0! |
| A8K878 | Mesencephalic astrocyte-derived neurotrophic factor OS = Homo sapiens GN = MANF PE = 1 SV = 1 | 2.70E+07 | −0.4 | −0.15 | −0.26 |
| B7ZKJ8 | ITIH4 protein OS = Homo sapiens GN = ITIH4 PE = 1 SV = 1 | | 0.09 | −0.21 | #DIV/0! |
| P18077 | 60S ribosomal protein L35a OS = Homo sapiens GN = RPL35A PE = 1 SV = 1 | 6.50E+07 | −0.82 | −0.19 | −0.64 |
| A0A087WZE | High mobility group nucleosome-binding domain containing protein 3 OS = Homo sapiens GN = HMGN3 PE = 1 SV = 1 | | #DIV/0! | #DIV/0! | #DIV/0! |
| V9HWD3 | Epididymis luminal protein 117 OS = Homo sapiens GN = HEL117 PE = 2 SV = 1 | | #DIV/0! | #DIV/0! | #DIV/0! |
| Q14203 | Dynactin subunit 1 OS = Homo sapiens GN = DCTN1 PE = 1 SV = 3 | | #DIV/0! | #DIV/0! | #DIV/0! |
| V9HW44 | Epididymis secretory protein Li 303 OS = Homo sapiens GN = HEL-S-303 PE = 2 SV = 1 | | −0.83 | #DIV/0! | #DIV/0! |
| O95758 | Polypyrimidine tract-binding protein 3 OS = Homo sapiens GN = PTBP3 PE = 1 SV = 2 | 6.60E+07 | #DIV/0! | #DIV/0! | #DIV/0! |
| H3BN98 | Uncharacterized protein (Fragment) OS = Homo sapiens PE = 4 SV = 1 | | #DIV/0! | #NUM! | −0.25 |
| Q6ZTQ4 | Cadherin-related family member 3 OS = Homo sapiens GN = CDHR3 PE = 1 SV = 1 | 1.40E+07 | #DIV/0! | #DIV/0! | #DIV/0! |
| Q724W1 | L-xylulose reductase OS = Homo sapiens GN = DCXR PE = 1 SV = 2 | 1.60E+07 | −0.75 | −0.59 | −0.16 |
| P50402 | Emerin OS = Homo sapiens GN = EMD PE = 1 SV = 1 | 6.80E+07 | −0.38 | −0.21 | −0.17 |
| P08697 | Alpha-2-antiplasmin OS = Homo sapiens GN = SERPINF2 PE = 1 SV = 3 | 2.80E+07 | −0.36 | −0.23 | −0.12 |
| J3KN66 | Torsin-1A-interacting protein 1 OS = Homo sapiens GN = TOR1AIP1 PE = 1 SV = 1 | | #DIV/0! | #DIV/0! | #DIV/0! |
| Q16610 | Extracellular matrix protein 1 OS = Homo sapiens GN = ECM1 PPE = 1 SVPE = 1 | 6.80E+07 | −0.96 | −0.51 | −0.45 |
| B7Z9B8 | cDNA FLJ56912, highly similar to Fibulin-2 OS = Homo sapiens PE = 2 SV = 1 | 4.40E+07 | −1.97 | −0.47 | −1.5 |
| Q9UEY8 | Gamma-adducin OS = Homo sapiens GN = ADD3 PE = 1 SV = 1 | | #DIV/0! | #DIV/0! | #DIV/0! |
| Q6ZU43 | cDNA FLJ4007 fis, clone TESTI4023762 OS = Homo sapiens PE = 2 SV = 1 | | #DIV/0! | #DIV/0! | #DIV/0! |
| Q5HYL6 | Putative uncharacterized protein DKFZp686E1899 OS = Homo sapiens GN = DKFZp686E1899 PE = 2 SV = 1 | 2.40E+07 | #DIV/0! | −0.16 | #DIV/0! |
| Q53GF0 | Cytidine 5'-monophosphate N-acetylneuraminic acid synthetase variant (Fragment) OS = Homo sapiens PE = 2 SV = 1 | | #NUM! | #NUM! | #NUM! |
| O75947 | ATP synthase subunit d, mitochondrial OS = Homo sapiens GN = ATP5H PE = 1 SV = 3 | 8.30E+07 | −0.64 | −0.19 | −0.44 |
| Q9Y230 | RuvB-like 2 OS = Homo sapiens GN = RUVBL2 PE = 1 SV = 3 | | #DIV/0! | #DIV/0! | #DIV/0! |
| Q6YN16 | Hydroxysteroid dehydrogenase-like protein 2 OS = Homo sapiens GN = HSDL2 PE = 1 SV = 1 | | #DIV/0! | #DIV/0! | #DIV/0! |

APPENDIX A-continued

| ID | Description | Val1 | Val2 | Val3 |
|---|---|---|---|---|
| B7ZLH8 | EVPL protein OS = Homo sapiens GN = EVPL PE = 2 SV = 1 | 1.40E+08 | #DIV/0! | -1.29 |
| Q70UQ0 | Inhibitor of nuclear factor kappa-B kinase-interacting protein OS = Homo sapiens GN = IKBIP PE = 1 SV = 1 | | #DIV/0! | #DIV/0! |
| B4DUT8 | Calponin OS = Homo sapiens GN = CNN2 PE = 1 SV = 1 | | #DIV/0! | #DIV/0! |
| Q62MU0 | Delta-aminolevulinic acid dehydratase OS = Homo sapiens PE = 2 SV = 1 | | #DIV/0! | #DIV/0! |
| D3DSQ1 | N-acylsphingosine amidohydrolase (Acid ceramidase) 1, isoform CRA_c OS = Homo sapiens GN = ASAH1 PE = 4 SV = 1 | | #DIV/0! | #DIV/0! |
| P26641 | Elongation factor 1-gamma OS = Homo sapiens GN = EEF1G PE = 1 SV = 3 | 7.70E+07 | -0.38 | -0.37 |
| P21912 | Succinate dehydrogenase [ubiquinone] iron-sulfur subunit, mitochondrial OS = Homo sapiens GN = SDHB PE = 1 SV = 3 | 1.40E+07 | -0.38 | 0.23 |
| O43175 | D-3-phosphoglycerate dehydrogenase OS = Homo sapiens GN = PHGDH PE = 1 SV = 4 | | #DIV/0! | #DIV/0! |
| Q59ED7 | Putative uncharacterized protein (Fragment) OS = Homo sapiens PE = 2 SV = 1 | 2.50E+07 | -1 | -0.36 |
| B4DNC2 | cDNA FLJ51906, highly similar to Heat-shock protein beta-6 OS = Homo sapiens PE = 2 SV = 1 | | #DIV/0! | #DIV/0! |
| O15511 | Actin-related protein 2/3 complex subunit 5 OS = Homo sapiens GN = ARPC5 PE = 1 SV = 3 | | #DIV/0! | #DIV/0! |
| P50213 | Isocitrate dehydrogenase [NAD] subunit alpha, mitochondrial OS = Homo sapiens GN = IDH3A PE = 1 SV = 1 | | #DIV/0! | #DIV/0! |
| A0A0A6YYG9 | Protein ARPC4-TTLL3 OS = Homo sapiens GN = ARPC4-TTLL3 PE = 4 SV = 1 | | #DIV/0! | #DIV/0! |
| O00629 | Importin subunit alpha-3 OS = Homo sapiens GN = KPNA4 PE = 1 SV = 1 | | #DIV/0! | #DIV/0! |
| H7BY55 | Complement decay-accelerating factor OS = Homo sapiens GN = CD55 PE = 1 SV = 2 | | #DIV/0! | #DIV/0! |
| A0A024R046 | High mobility group nucleosomal binding domain 4, isoform CRA_a OS = Homo sapiens GN = HMGN4 PE = 4 SV = 1 | | #DIV/0! | #DIV/0! |
| P40763 | Signal transducer and activator of transcription 3 OS = Homo sapiens GN = STAT3 PE = 1 SV = 2 | | #DIV/0! | #DIV/0! |
| B2R7B5 | cDNA, FLJ93365, highly similar to Homo sapiens KH domain containing, RNA binding, signal transduction associated | 6.00E+07 | -0.06 | -0.02 | -0.04 |
| A6QKW0 | SHINC3 OS = Homo sapiens GN = SHINC3 PE = 2 SV = 1 | 1.90E+07 | #DIV/0! | #DIV/0! | -0.72 |
| M0QYN0 | Myeloid-derived growth factor OS = Homo sapiens GN = MYDGF PE = 1 SV = 1 | 3.70E+07 | 0.26 | 0.04 | 0.22 |
| A8K3H8 | cDNA FLJ77680, highly similar to Homo sapiens protein phosphatase 2 (formerly 2A), regulatory subunit A (PR 65), al | 7.50E+07 | -0.46 | 0.03 | -0.49 |
| O75832 | 26S proteasome non-ATPase regulatory subunit 10 OS = Homo sapiens GN = PSMD10 PE = 1 SV = 1 | | #DIV/0! | #DIV/0! | #DIV/0! |
| Q9Y3U8 | 60S ribosomal protein L36 OS = Homo sapiens GN = RPL36 PE = 1 SV = 3 | 1.10E+08 | -0.56 | -0.04 | -0.52 |
| Q15435 | Protein phosphatase 1 regulatory subunit 7 OS = Homo sapiens GN = PPP1R7 PE = 1 SV = 1 | | #DIV/0! | #DIV/0! | #DIV/0! |
| Q32MA0 | Dual specificity phosphatase 16 OS = Homo sapiens GN = DUSP16 PE = 2 SV = 1 | | #DIV/0! | #DIV/0! | #DIV/0! |
| D3DYC4 | Nestin, isoform CRA_c OS = Homo sapiens GN = NES PE = 3 SV = 1 | | #DIV/0! | #DIV/0! | #DIV/0! |
| A5PLM9 | Cathepsin L1 OS = Homo sapiens GN = CTSL1 PE = 2 SV = 1 | | #DIV/0! | #DIV/0! | #DIV/0! |
| Q6NUK7 | Non-specific protein-tyrosine kinase (Fragment) OS = Homo sapiens GN = LYN PE = 2 SV = 1 | 8.30E+06 | -0.29 | -1.12 | 0.54 |
| P08246 | Neutrophil elastase OS = Homo sapiens GN = ELANE PE = 1 SV = 1 | | -0.58 | #DIV/0! | #DIV/0! |
| Q9NWH2 | Transmembrane protein 242 OS = Homo sapiens GN = TMEM242 PE = 1 SV = 1 | | #DIV/0! | #DIV/0! | #DIV/0! |
| P11717 | Cation-independent mannose-6-phosphate receptor OS = Homo sapiens GN = IGF2R PE = 1 SV = 3 | | #DIV/0! | #DIV/0! | #DIV/0! |
| A8K6K7 | cDNA FLJ76881, highly similar to Homo sapiens glycogen synthase 1 (muscle) (GYS1), mRNA OS = Homo sapiens PE = 2 | | #DIV/0! | #NUM! | #NUM! |
| P42677 | 40S ribosomal protein S27 OS = Homo sapiens GN = RPS27 PE = 1 SV = 3 | | -0.18 | -0.17 | -1.1 |
| Q9H0B8 | Cysteine-rich secretory protein LCCL domain-containing 2 OS = Homo sapiens GN = CRISPLD2 PE = 2 SV = 1 | 6.70E+07 | #NUM! | -0.38 | #DIV/0! |
| P61163 | Alpha-centractin OS = Homo sapiens GN = ACTR1A PE = 1 SV = 1 | 1.20E+08 | #DIV/0! | #DIV/0! | #DIV/0! |
| Q72AI7 | LIM and senescent cell antigen-like-containing domain protein 2 OS = Homo sapiens GN = LIMS2 PE = 1 SV = 1 | | -1.48 | #DIV/0! | #DIV/0! |
| E7EMB3 | Calmodulin OS = Homo sapiens GN = CALM2 PE = 1 SV = 1 | | #DIV/0! | #DIV/0! | #DIV/0! |
| Q15437 | Protein transport protein Sec23B OS = Homo sapiens GN = SEC23B PE = 1 SV = 2 | | #DIV/0! | #DIV/0! | #DIV/0! |
| E7D7X9 | Pyrroline-5-carboxylate reductase OS = Homo sapiens PE = 2 SV = 1 | 1.10E+07 | -0.18 | -0.04 | -0.62 |
| A0A024RB87 | RAP1B, member of RAS oncogene family, isoform CRA_a OS = Homo sapiens GN = RAP1B PE = 4 SV = 1 | 1.00E+08 | -0.66 | -0.04 | #DIV/0! |
| E9PIR9 | Absent in melanoma 1-like protein OS = Homo sapiens GN = AIM1L PE = 1 SV = 1 | | 0.17 | #NUM! | 0.4 |
| Q68DE3 | Basic helix-loop-helix domain-containing protein KIAA2018 OS = Homo sapiens GN = KIAA2018 PE = 1 SV = 3 | | -0.52 | #NUM! | #DIV/0! |
| A0A024RD93 | Phosphoribosylaminoimidazole carboxylase, phosphoribosylaminoimidazole succinocarboxamide synthetase, isofor | | -0.22 | #NUM! | #DIV/0! |
| P36542 | ATP synthase subunit gamma, mitochondrial OS = Homo sapiens GN = ATP5C1 PE = 1 SV = 1 | | 0.29 | #NUM! | #DIV/0! |
| Q5M9N0 | Coiled-coil domain-containing protein 158 OS = Homo sapiens GN = CCDC158 PE = 1 SV = 2 | 1.30E+07 | -0.1 | -0.12 | |
| P54920 | Alpha-soluble NSF attachment protein OS = Homo sapiens GN = NAPA PE = 1 SV = 3 | | | | |
| Q9H1B7 | Interferon regulatory factor 2-binding protein-like OS = Homo sapiens GN = IRF2BPL PE = 1 SV = 1 | | | | |
| Q14247 | Src substrate cortactin OS = Homo sapiens GN = CTTN PE = 1 SV = 2 | | | | |
| F4ZW62 | NF45 OS = Homo sapiens PE = 1 SV = 1 | | | | |
| Q9Y3E8 | CGI-150 protein OS = Homo sapiens PE = 2 SV = 1 | | | | |
| Q9Y2896 | Golgi apparatus protein 1 OS = Homo sapiens GN = GLG1 PE = 1 SV = 2 | | | | |
| A0A024RB16 | Family with sequence similarity 62 (C2 domain containing), member A, isoform CRA_a OS = Homo sapiens GN = FAM62 | | | | |
| A8K2L6 | Annexin OS = Homo sapiens PE = 2 SV = 1 | | | | |

APPENDIX A-continued

| ID | Description | Col3 | Col4 | Col5 |
|---|---|---|---|---|
| Q96D15 | Reticulocalbin-3 OS = Homo sapiens GN = RCN3 PE = 1 SV = 1 | | −0.16 | #DIV/0! |
| P54886 | Delta-1-pyrroline-5-carboxylate synthase OS = Homo sapiens GN = ALDH18A1 PE = 1 SV = 2 | | | #DIV/0! |
| Q9UFN0 | Protein NipSnap homolog 3A OS = Homo sapiens GN = NIPSNAP3A PE = 1 SV = 2 | | | #DIV/0! |
| B2RB70 | Neurocalcin delta, isoform CRA_a OS = Homo sapiens GN = NCALD PE = 2 SV = 1 | | | #DIV/0! |
| Q59FB9 | Toll interacting protein variant (Fragment) OS = Homo sapiens PE = 2 SV = 1 | 2.30E+07 | −0.12 | −0.84 |
| P23508 | Colorectal mutant cancer protein OS = Homo sapiens GN = MCC PE = 1 SV = 1 | | −0.96 | #DIV/0! |
| Q9Y446 | Plakophilin-3 OS = Homo sapiens GN = PKP3 PE = 1 SV = 1 | 9.70E+07 | #DIV/0! | −0.73 |
| A8K566 | cDNA FLJ78246, highly similar to Homo sapiens splicing factor 3a, subunit 3, 60 kDa (SF3A3), mRNA OS = Homo sapien | | #DIV/0! | #DIV/0! |
| B4E2A6 | cDNA FLJ55508, highly similar to 5adl/unc-84-like protein 2 OS = Homo sapiens PE = 2 SV = 1 | | #DIV/0! | #DIV/0! |
| A0A0A0MTJ9 | Neutral cholesterol ester hydrolase 1 OS = Homo sapiens GN = NCEH1 PE = 1 SV = 1 | | #DIV/0! | #DIV/0! |
| B3KQC9 | cDNA FLJ90240 fis, clone NT2RM2001126, highly similar to Multiple PDZ domain protein OS = Homo sapiens PE = 2 SV = | | #DIV/0! | #DIV/0! |
| L7UUZ7 | Integrin beta OS = Homo sapiens GN = ITGB3 PE = 1 SV = 1 | | #DIV/0! | #DIV/0! |
| Q59G75 | Isoleucyl-tRNA synthetase, cytoplasmic variant (Fragment) OS = Homo sapiens GN = HEL-S-74 PE = 2 SV = 1 | | −0.74 | #DIV/0! |
| Q13242 | Serine/arginine-rich splicing factor 9 OS = Homo sapiens GN = SRSF9 PE = 1 SV = 1 | | −0.48 | #DIV/0! |
| F8VW96 | Cysteine and glycine-rich protein 2 OS = Homo sapiens GN = CSRP2 PE = 1 SV = 1 | | #NUM! | 0.07 |
| A0A087WW6 | 26S proteasome non-ATPase regulatory subunit 1 OS = Homo sapiens GN = PSMD1 PE = 1 SV = 1 | | #DIV/0! | −0.04 |
| V9HW62 | Lactoylglutathione lyase OS = Homo sapiens GN = HEL-S-74 PE = 2 SV = 1 | | #DIV/0! | −0.07 |
| K7ELC7 | 60S ribosomal protein L27 (Fragment) OS = Homo sapiens GN = RPL27 PE = 1 SV = 1 | 2.80E+07 | #DIV/0! | HDIV/0! |
| P62280 | 40S ribosomal protein S11 OS = Homo sapiens GN = RPS11 PE = 1 SV = 3 | 8.30E+07 | #DIV/0! | HDIV/0! |
| P26885 | Peptidyl-prolyl cis-trans isomerase FKBP2 OS = Homo sapiens GN = FKBP2 PE = 1 SV = 2 | 7.20E+07 | #DIV/0! | #DIV/0! |
| Q6UVK1 | Chondroitin sulfate proteoglycan 4 OS = Homo sapiens GN = CSPG4 PE = 1 SV = 2 | | #DIV/0! | #DIV/0! |
| B5ME19 | Eukaryotic translation initiation factor 3 subunit C-like protein OS = Homo sapiens GN = EIF3CL PE = 3 SV = 1 | | #DIV/0! | #DIV/0! |
| Q13151 | Heterogeneous nuclear ribonucleoprotein A0 OS = Homo sapiens GN = HNRNPA0 PE = 1 SV = 1 | | #DIV/0! | #DIV/0! |
| M0QYS1 | 60S ribosomal protein L13a (Fragment) OS = Homo sapiens GN = RPL13A PE = 1 SV = 2 | 5.80E+07 | −0.96 | −0.68 |
| Q96K75 | Zinc finger protein 514 OS = Homo sapiens GN = ZNF514 PE = 1 SV = 1 | | #DIV/0! | #DIV/0! |
| B4DMN1 | cDNA FLJ61136, highly similar to Ras-related protein Rab-11A OS = Homo sapiens PE = 2 SV = 1 | 1.30E+08 | −0.82 | −0.73 |
| A0A024RAD5 | Dolichyl-diphosphooligosaccharide-protein glycosyltransferase 48 kDa subunit OS = Homo sapiens GN = DDOST PE = 3 | 1.20E+08 | #DIV/0! | −0.65 |
| A0A024QYR8 | Dinucleotide oxidase disulfide thiol exchanger 2 superfamily member 2 OS = Homo sapiens GN = TM9SF2 PE = 2 SV = 1 | 8.90E+06 | 0.21 | 0.61 |
| O00154 | Cytosolic acyl coenzyme A thioester hydrolase OS = Homo sapiens GN = ACOT7 PE = 1 SV = 3 | 4.50E+07 | −0.39 | 0.04 |
| A0A0A0MTH | Integrin-linked protein kinase OS = Homo sapiens GN = ILK PE = 1 SV = 1 | | #DIV/0! | #DIV/0! |
| A8K644 | Splicing factor, arginine/serine-rich 4, isoform CRA_b OS = Homo sapiens GN = SFRS4 PE = 2 SV = 1 | | −0.93 | −0.28 |
| Q59EI9 | ADP,ATP carrier protein, liver isoform T2 variant (Fragment) OS = Homo sapiens GN = SEC13 PE = 1 SV = 1 | 1.00E+08 | 0.11 | −0.18 |
| Q53HV2 | Chaperonn containing TCP1, suhunit 7 (Eta) variant (Fragment) OS = Homo sapiens GN = SCCPDH PE = 1 SV = 1 | 1.80E+07 | −0.55 | −0.11 |
| A0A024RAR8 | ADP-ribosylation factor 6 OS = Homo sapiens GN = ARF6 PE = 1 SV = 2 | | −0.02 | −0.18 |
| Q9Y305 | Acyl-coenzyme A thioesterase 9, mitochondrial OS = Homo sapiens GN = ACOT9 PE = 1 SV = 1 | 2.20E+07 | −0.8 | −0.43 |
| V9HWD8 | Epididymis secretory sperm binding protein Li 163pA OS = Homo sapiens GN = HEL-S-163pA PE = 2 SV = 1 | 3.90E+07 | −1.2 | 0.16 |
| Q16658 | Type 1 tumor necrosis factor receptor shedding aminopeptidase regulator, isoform CRA_a OS = Homo sapiens GN = AR | | −0.72 | −0.09 |
| P13073 | Fascin OS = Homo sapiens GN = FSCN1 PE = 1 SV = 3 | | #NUM! | −0.31 |
| P04275 | von Willebrand factor OS = Homo sapiens GN = VWF PE = 1 SV = 4 | 1.20E+08 | −0.66 | −0.28 |
| E9PR17 | Alternative protein CSF2RB OS = Homo sapiens GN = CSF2RB PE = 4 SV = 1 | 1.30E+08 | −0.77 | −0.38 |
| L0R5A1 | Cytochrome c oxidase subunit 4 isoform 1, mitochondrial OS = Homo sapiens GN = COX4I1 PE = 1 SV = 1 | | −0.12 | −0.65 |
| P50570 | Dynamin-2 OS = Homo sapiens GN = DNM2 PE = 1 SV = 2 | | #DIV/0! | #DIV/0! |
| A6NMB1 | Sialic acid-binding Ig-like lectin 16 OS = Homo sapiens GN = SIGLEC16 PE = 2 SV = 3 | | −0.38 | #DIV/0! |
| P06727 | Apolipoprotein A-IV OS = Homo sapiens GN = APOA4 PE = 1 SV = 3 | | #DIV/0! | #DIV/0! |
| Q5T9B7 | Adenylate kinase isoenzyme 1 OS = Homo sapiens GN = AK1 PE = 1 SV = 1 | | −0.8 | #NUM! |
| A8K3H0 | cDNA FLJ75548, highly similar to Homo sapiens microfibrillar associated protein 5 (MFAP5), mRNA OS = Homo sapien | 2.00E+08 | −0.74 | 0.1 |
| Q9UGM5 | Fetuin-B OS = Homo sapiens GN = FETUB PE = 1 SV = 2 | | #DIV/0! | #DIV/0! |
| Q0D2Q6 | Phosphoglycerate mutase 1 (Brain) OS = Homo sapiens GN = PGAM1 PE = 2 SV = 1 | 1.10E+08 | #DIV/0! | −0.84 |
| P55001 | Microfibrillar-associated protein 2 OS = Homo sapiens GN = MFAP2 PE = 2 SV = 1 | 3.10E+07 | #DIV/0! | −0.74 |

APPENDIX A-continued

| ID | Description | | | | |
|---|---|---|---|---|---|
| Q86V15 | Zinc finger protein castor homolog 1 OS = Homo sapiens GN = CASZ1 PE = 1 SV = 4 | | #DIV/0! | #DIV/0! | #DIV/0! |
| Q92743 | Serine protease HTRA1 OS = Homo sapiens GN = HTRA1 PE = 1 SV = 1 | 9.80E+07 | #DIV/0! | -0.15 | #NUM! |
| A8K5K0 | cDNA FLJ78309, highly similar to Homo sapiens heterogeneous nuclear ribonucleoprotein U-like 1 (HNRPUL1), trans 1 | | #DIV/0! | #DIV/0! | #DIV/0! |
| Q15008 | 26S proteasome non-ATPase regulatory subunit 6 OS = Homo sapiens GN = PSMD6 PE = 1 SV = 1 | | #DIV/0! | #DIV/0! | #DIV/0! |
| P00387 | NADH-cytochrome b5 reductase 3 OS = Homo sapiens GN = CYB5R3 PE = 1 SV = 3 | 1.60E+08 | -1.02 | -0.23 | -0.79 |
| Q14165 | Malectin OS = Homo sapiens GN = MLEC PE = 1 SV = 1 | 2.30E+07 | -0.3 | -0.02 | -0.28 |
| O75822 | Eukaryotic translation initiation factor 3 subunit J OS = Homo sapiens GN = EIF3J PE = 1 SV = 2 | | #DIV/0! | #DIV/0! | #DIV/0! |
| A0A075B6Z2 | Protein TRAJ56 (Fragment) OS = Homo sapiens GN = TRAJ56 PE = 4 SV = 1 | | #DIV/0! | #DIV/0! | #DIV/0! |
| A8K586 | AP-3 complex subunit beta OS = Homo sapiens PE = 2 SV = 1 | | #DIV/0! | #DIV/0! | #DIV/0! |
| B2R7P8 | cDNA, FLJ93545, highly similar to Homo sapiens 5-aminoimidazole-4-carboxamide ribonucleotide formyltransferase/ | 2.50E+07 | #NUM! | -0.52 | -0.77 |
| E9PGN7 | Plasma protease C1 inhibitor OS = Homo sapiens GN = SERPING1 PE = 1 SV = 1 | 2.00E+07 | #NUM! | #DIV/0! | #DIV/0! |
| O60493 | Sorting nexin-3 OS = Homo sapiens GN = SNX3 PE = 1 SV = 3 | | #DIV/0! | #DIV/0! | #DIV/0! |
| A0A024R758 | Uncharacterized protein OS = Homo sapiens GN = NAG6 PE = 4 SV = 1 | | #DIV/0! | #DIV/0! | #DIV/0! |
| A0A0A6YYL6 | Protein RPL17-C18orf32 OS = Homo sapiens GN = RPL17-C18orf32 PE = 3 SV = 1 | 8.40E+07 | 0.18 | 0.11 | 0.07 |
| Q12841 | Follistatin-related protein 1 OS = Homo sapiens GN = FSTL1 PE = 1 SV = 1 | | #DIV/0! | #DIV/0! | #DIV/0! |
| A8K8Z4 | cDNA FLJ78071, highly similar to Human MHC class III complement component C6 mRNA OS = Homo sapiens PE = 2 SV | | #DIV/0! | #DIV/0! | #DIV/0! |
| O94973 | AP-2 complex subunit alpha-2 OS = Homo sapiens GN = AP2A2 PE = 1 SV = 2 | | #DIV/0! | #DIV/0! | #DIV/0! |
| Q9Y2V2 | Calcium-regulated heat stable protein 1 OS = Homo sapiens GN = CARHSP1 PE = 1 SV = 2 | | -1.2 | #NUM! | #NUM! |
| U6A3P2 | Mutant hemoglobin alpha 2 globin chain (Fragment) OS = Homo sapiens GN = HBA2 PE = 3 SV = 1 | 9.60E+07 | #NUM! | -1.06 | #NUM! |
| P68032 | Actin, alpha cardiac muscle 1 OS = Homo sapiens GN = ACTC1 PE = 1 SV = 1 | | #NUM! | #NUM! | #NUM! |
| A8K2I0 | cDNA FLJ78504, highly similar to Homo sapiens keratin 6A (KRT6A), mRNA OS = Homo sapiens PE = 2 SV = 1 | 2.40E+09 | #NUM! | 0.27 | #NUM! |
| B4DUV1 | Fibulin-1 OS = Homo sapiens PE = 2 SV = 1 | | #NUM! | -0.28 | #NUM! |
| Q53H26 | Transferrin variant (Fragment) OS = Homo sapiens PE = 2 SV = 1 | 3.20E+08 | #NUM! | #NUM! | #NUM! |
| Q6MZV7 | Putative uncharacterized protein DKFZp686C11235 OS = Homo sapiens GN = DKFZp686C11235 PE = 2 SV = 1 | | #NUM! | -0.02 | #NUM! |
| Q8IV28 | NID2 protein OS = Homo sapiens GN = NID2 PE = 2 SV = 1 | 8.30E+07 | #NUM! | #NUM! | #NUM! |
| Q6P5S8 | IGK@ protein OS = Homo sapiens GN = IGK@ PE = 1 SV = 1 | 7.10E+07 | #NUM! | 0.85 | #NUM! |
| P68366 | Tubulin alpha-4A chain OS = Homo sapiens GN = TUBA4A PE = 1 SV = 1 | 9.40E+07 | #NUM! | -0.23 | #NUM! |
| A7BI36 | p180/ribosome receptor OS = Homo sapiens GN = RRBP1 PE = 2 SV = 2 | 2.00E+08 | #NUM! | -0.48 | #NUM! |
| D3GKD8 | A-gamma globin Osilo variant OS = Homo sapiens GN = HBG1 PE = 3 SV = 1 | 2.40E+08 | #NUM! | -0.03 | #NUM! |
| Q59EJ3 | Heat shock 70 kDa protein 1A variant (Fragment) OS = Homo sapiens PE = 2 SV = 1 | 2.80E+08 | #NUM! | -0.22 | #NUM! |
| Q6N093 | Putative uncharacterized protein DKFZp686I04196 (Fragment) OS = Homo sapiens GN = DKFZp686I04196 PE = 2 SV = 1 | | #NUM! | -0.2 | #NUM! |
| P68104 | Elongation factor 1-alpha 1 OS = Homo sapiens GN = EEF1A1 PE = 1 SV = 1 | 6.30E+08 | #NUM! | 0.04 | #NUM! |
| B2R6L0 | cDNA, FLJ93005, highly similar to Homo sapiens tubulin, beta polypeptide (TUBB), mRNA OS = Homo sapiens PE = 2 SV = 1 | | #NUM! | #NUM! | #DIV/0! |
| P06899 | Histone H2B type 1-J OS = Homo sapiens GN = HIST1H2BJ PE = 1 SV = 3 | 1.50E+08 | #NUM! | 0.32 | #DIV/0! |
| Q5XKE5 | Keratin, type II cytoskeletal 79 OS = Homo sapiens GN = KRT79 PE = 1 SV = 2 | 1.60E+08 | #NUM! | -0.18 | #DIV/0! |
| A8K3B0 | cDNA FLJ77877, highly similar to Human ENO2 neuron specific (gamma) enolase OS = Homo sapiens PE = 2 SV = 1 | | #NUM! | -4.03 | #DIV/0! |
| Q2M2I5 | Keratin, type I cytoskeletal 24 OS = Homo sapiens GN = KRT24 PE = 1 SV = 1 | 6.40E+05 | #NUM! | 0.85 | #DIV/0! |
| P02511 | Alpha-crystallin B chain OS = Homo sapiens GN = CRYAB PE = 1 SV = 2 | 2.10E+09 | #NUM! | -0.89 | #NUM! |
| V9HWH9 | Protein S100 OS = Homo sapiens GN = HEL-S-43 PE = 2 SV = 1 | 6.90E+07 | #NUM! | -0.28 | #NUM! |
| A6NMH8 | Tetraspanin 4 (Fragment) OS = Homo sapiens GN = CD81 PE = 1 SV = 1 | 5.10E+08 | #NUM! | -0.2 | #NUM! |
| E7EQR4 | Ezrin OS = Homo sapiens GN = EZR PE = 1 SV = 1 | 8.80E+07 | #NUM! | 0.32 | #NUM! |
| P0C0S5 | Histone H2A.Z OS = Homo sapiens GN = H2AFZ PE = 1 SV = 2 | 1.50E+08 | #NUM! | -0.18 | #DIV/0! |
| B8XPJ8 | Membrane bound catechol-O-methyltransferase OS = Homo sapiens GN = COMT PE = 2 SV = 1 | 1.30E+08 | #NUM! | -0.06 | #NUM! |
| X5D2L1 | Hydroxysteroid 11-beta dehydrogenase 1 isoform A (Fragment) OS = Homo sapiens GN = HSD11B1 PE = 2 SV = 1 | 2.20E+07 | #NUM! | -1.06 | #NUM! |
| P05120 | Plasminogen activator inhibitor 2 OS = Homo sapiens GN = SERPINB2 PE = 1 SV = 2 | 1.00E+08 | #NUM! | 0.48 | #NUM! |
| Q9Y4G6 | Talin-2 OS = Homo sapiens GN = TLN2 PE = 1 SV = 4 | | #NUM! | #NUM! | #DIV/0! |
| H6VRG2 | Keratin 1 OS = Homo sapiens GN = KRT1 PE = 3 SV = 1 | 1.30E+08 | #NUM! | 0 | #DIV/0! |
| B7Z6L0 | Annexin OS = Homo sapiens PE = 2 SV = 1 | | #NUM! | #NUM! | #NUM! |
| D6REI5 | Guanine nucleotide-binding protein subunit beta-2-like 1 (Fragment) OS = Homo sapiens GN = GNB2L1 PE = 1 SV = 1 | | #NUM! | #NUM! | #NUM! |
| A0A087X1U6 | Epiplakin OS = Homo sapiens GN = EPPK1 PE = 1 SV = 1 | 1.70E+08 | #NUM! | 0.77 | #NUM! |
| Q53G35 | Phosphoglycerate mutase (Fragment) OS = Homo sapiens PE = 2 SV = 1 | | #NUM! | #NUM! | #NUM! |
| Q16891 | MICOS complex subunit MIC60 OS = Homo sapiens GN = IMMT PE = 1 SV = 1 | 4.70E+07 | #NUM! | -0.37 | #NUM! |
| B2R4M6 | Protein S100 OS = Homo sapiens PE = 2 SV = 1 | 7.90E+07 | #NUM! | -0.42 | #NUM! |

APPENDIX A-continued

| ID | Description | | | | |
|---|---|---|---|---|---|
| D9YZV4 | Tropomyosin 1 (Alpha) isoform 1 OS = Homo sapiens GN = TPM1 PE = 3 SV = 1 | | #DIV/0! | #DIV/0! | #DIV/0! |
| Q72Y4 | GTP:AMP phosphotransferase AK3, mitochondrial OS = Homo sapiens GN = AK3 PE = 2 SV = 1 | | #NUM! | #NUM! | #NUM! |
| P49368 | T-complex protein 1 subunit gamma OS = Homo sapiens GN = CCT3 PE = 1 SV = 4 | 2.90E+07 | #NUM! | -0.18 | #DIV/0! |
| H9ZY12 | Thioredoxin OS = Homo sapiens GN = TXN PE = 2 SV = 1 | 9.60E+07 | #NUM! | -0.25 | #DIV/0! |
| M0QXB4 | Coatomer protein complex, subunit epsilon, isoform CRA_g OS = Homo sapiens GN = COPE PE = 1 SV = 1 | 4.20E+07 | #NUM! | -0.03 | #DIV/0! |
| Q8IUE6 | Histone H2A type 2-B OS = Homo sapiens GN = HIST2H2AB PE = 1 SV = 3 | 1.00E+08 | #NUM! | -0.18 | #DIV/0! |
| A0A024R056 | Guanine nucleotide binding protein (G protein), beta polypeptide 1, isoform CRA_a OS = Homo sapiens GN = GNB1 PE = 4 SV = 1 | 3.30E+07 | #NUM! | -0.43 | #DIV/0! |
| A0A0D9SF53 | ATP-dependent RNA helicase DDX3X OS = Homo sapiens GN = DDX3X PE = 1 SV = 1 | 2.90E+07 | #NUM! | -0.5 | #DIV/0! |
| P62244 | 40S ribosomal protein S15a OS = Homo sapiens GN = RPS15A PE = 1 SV = 2 | | #NUM! | #NUM! | #NUM! |
| Q07960 | Rho GTPase-activating protein 1 OS = Homo sapiens GN = ARHGAP1 PE = 1 SV = 1 | 3.10E+07 | #NUM! | -0.04 | #DIV/0! |
| P27169 | Serum paraoxonase/arylesterase 1 OS = Homo sapiens GN = PON1 PE = 1 SV = 3 | | #NUM! | #NUM! | #NUM! |
| H7BY58 | Protein-L-isoaspartate O-methyltransferase OS = Homo sapiens GN = PCMT1 PE = 1 SV = 1 | | #NUM! | #NUM! | #NUM! |
| Q6DD88 | Atlastin-3 OS = Homo sapiens GN = ATL3 PE = 1 SV = 1 | 2.80E+07 | #NUM! | -0.3 | #DIV/0! |
| A0A024R1K7 | Tyrosine 3-monooxygenase/tryptophan 5-monooxygenase activation protein, eta polypeptide, isoform CRA_b OS = Homo sapien | | #NUM! | #NUM! | #NUM! |
| A0A024R9Q1 | Thrombospondin 1, isoform CRA_a OS = Homo sapiens GN = THBS1 PE = 1 SV = 1 | 1.50E+08 | #NUM! | 0.26 | #DIV/0! |
| V9HWI3 | Cathepsin D (Lysosomal aspartyl peptidase), isoform CRA_a OS = Homo sapiens GN = HEL-S-130P PE = 2 SV = 1 | 4.10E+07 | #NUM! | -0.28 | #DIV/0! |
| A0A024R498 | Serpin peptidase inhibitor, clade E (Nexin, plasminogen activator inhibitor type 1), member 2, isoform CRA_b OS = Homo sapiens | 1.40E+08 | #NUM! | 0 | #DIV/0! |
| P48059 | LIM and senescent cell antigen-like-containing domain protein 1 OS = Homo sapiens GN = LIMS1 PE = 1 SV = 4 | | #NUM! | #NUM! | #NUM! |
| Q72K6 | Endoplasmic reticulum metallopeptidase 1 OS = Homo sapiens GN = ERMP1 PE = 1 SV = 2 | | #NUM! | #NUM! | #NUM! |
| O95782 | Serpin B6 OS = Homo sapiens GN = SERPINB6 PE = 1 SV = 1 | 4.80E+07 | #NUM! | -0.14 | #DIV/0! |
| A8KTT4 | AP-2 complex subunit alpha-1 OS = Homo sapiens GN = AP2A1 PE = 1 SV = 3 | 3.60E+07 | #NUM! | -0.03 | #DIV/0! |
| Q13425 | Beta-2-syntrophin OS = Homo sapiens GN = SNTB2 PE = 1 SV = 1 | 4.40E+07 | #NUM! | -0.44 | #DIV/0! |
| C7DJS2 | Glutathione S-transferase pi (Fragment) OS = Homo sapiens GN = GSTP1 PE = 2 SV = 1 | 5.90E+07 | #NUM! | 0.05 | #DIV/0! |
| E9PCR7 | 2-oxoglutarate dehydrogenase, mitochondrial OS = Homo sapiens GN = OGDH PE = 1 SV = 1 | | #NUM! | #NUM! | #NUM! |
| Q13724 | Mannosyl-oligosaccharide glucosidase OS = Homo sapiens GN = MOGS PE = 1 SV = 5 | 6.90E+07 | #NUM! | -0.07 | #DIV/0! |
| P61626 | Lysozyme C OS = Homo sapiens GN = LYZ PE = 1 SV = 1 | 7.80E+07 | #NUM! | -0.06 | #DIV/0! |
| B2RDE8 | cDNA, FLJ96580, highly similar to Homo sapiens hepatoma-derived growth factor (high-mobility group protein 1-like) (HDGF), m | 2.80E+07 | #NUM! | -0.17 | #DIV/0! |
| A8K6A6 | cDNA FLJ78619, highly similar to Homo sapiens melanoma cell adhesion molecule (MCAM), mRNA OS = Homo sapiens PE = 2 SV = 1 | 2.40E+07 | #NUM! | -0.19 | #DIV/0! |
| Q86UE4 | Protein LYRIC OS = Homo sapiens GN = MTDH PE = 1 SV = 2 | | #NUM! | #NUM! | #NUM! |
| B2R8R5 | cDNA, FLJ94025, highly similar to Homo sapiens tripartite motif-containing 28 (TRIM28), mRNA OS = Homo sapiens PE = 2 SV = 1 | 3.30E+07 | #NUM! | 0.14 | #DIV/0! |
| P08311 | Cathepsin G OS = Homo sapiens GN = CTSG PE = 1 SV = 2 | 1.20E+07 | #NUM! | -0.32 | #DIV/0! |
| Q08380 | Galectin-3-binding protein OS = Homo sapiens GN = LGALS3BP PE = 1 SV = 1 | 2.70E+07 | #NUM! | -0.2 | #DIV/0! |
| P15153 | Ras-related C3 botulinum toxin substrate 2 OS = Homo sapiens GN = RAC2 PE = 1 SV = 1 | | #DIV/0! | #DIV/0! | #DIV/0! |
| Q86YZ3 | Hornerin OS = Homo sapiens GN = HRNR PE = 1 SV = 1 | | #NUM! | -0.1 | #DIV/0! |
| A0A087WYO | Thrombospondin type-1 domain-containing protein 7A OS = Homo sapiens GN = THSD7A PE = 1 SV = 1 | | #NUM! | #NUM! | #NUM! |
| A0A024QZN7 | Chromosome 10 open reading frame 70, isoform CRA_b OS = Homo sapiens GN = C10orf70 PE = 4 SV = 1 | | #NUM! | #NUM! | #NUM! |
| Q9NQC3 | Reticulon-4 OS = Homo sapiens GN = RTN4 PE = 1 SV = 2 | 2.00E+07 | #NUM! | -0.9 | #DIV/0! |
| P68431 | Histone H3.1 OS = Homo sapiens GN = HIST1H3A PE = 1 SV = 2 | | #NUM! | #NUM! | #NUM! |
| Q5UOI6 | H. sapiens ras-related Hrab1A protein OS = Homo sapiens GN = RAB1A PE = 1 SV = 1 | 9.80E+07 | #NUM! | -0.47 | #DIV/0! |
| Q5JR05 | Rho-related GTP-binding protein RhoC OS = Homo sapiens GN = RHOC PE = 3 SV = 1 | | #NUM! | #NUM! | #NUM! |
| Q2F838 | Eukaryotic translation elongation factor 1 gamma (Fragment) OS = Homo sapiens PE = 2 SV = 1 | | #DIV/0! | #DIV/0! | #DIV/0! |
| Q9POLO | Vesicle-associated membrane protein-associated protein A OS = Homo sapiens GN = VAPA PE = 1 SV = 3 | 7.30E+07 | #NUM! | -0.1 | #DIV/0! |
| E9PNQ8 | Thy-1 membrane glycoprotein (Fragment) OS = Homo sapiens GN = THY1 PE = 1 SV = 1 | | #NUM! | #NUM! | #NUM! |
| A0A024QZJ8 | Leucine rich repeat containing 54, isoform CRA_a OS = Homo sapiens GN = LRRC54 PE = 4 SV = 1 | | #NUM! | #NUM! | #NUM! |
| P78527 | DNA-dependent protein kinase catalytic subunit OS = Homo sapiens GN = PRKDC PE = 1 SV = 3 | 1.10E+07 | #NUM! | -0.28 | #DIV/0! |
| B4DUP2 | cDNA FLJ56155, highly similar to UTP-glucose-1-phosphate uridylyltransferase 2 (EC 2.7.7.9) OS = Homo sapiens PE = 2 SV = 1 | 6.30E+07 | #NUM! | -0.12 | #DIV/0! |
| Q96QK1 | Vacuolar protein sorting-associated protein 35 OS = Homo sapiens GN = VPS35 PE = 1 SV = 2 | | #NUM! | #NUM! | #NUM! |
| J9R021 | Eukaryotic translation initiation factor 3 subunit A OS = Homo sapiens GN = eIF3a PE = 2 SV = 1 | | #NUM! | #NUM! | #NUM! |
| O94788 | Retinal dehydrogenase 2 OS = Homo sapiens GN = ALDH1A2 PE = 1 SV = 1 | | #NUM! | #NUM! | #NUM! |
| B3KNX0 | cDNA FLJ30621 fis, clone CTONG2001681, highly similar to Complement C1s subcomponent (EC 3.4.21.42) OS = Homo sapiens PE | | #NUM! | #NUM! | #NUM! |
| P16615 | Sarcoplasmic/endoplasmic reticulum calcium ATPase 2 OS = Homo sapiens GN = ATP2A2 PE = 1 SV = 1 | 5.20E+07 | #NUM! | -0.33 | #NUM! |

APPENDIX A-continued

| ID | Description | Val1 | Val2 | Val3 | Val4 |
|---|---|---|---|---|---|
| A0A0C4DGV | Semaphorin-3B OS = Homo sapiens GN = SEMA3B PE = 1 SV = 1 | | #NUM! | #NUM! | #DIV/0! |
| B4DNB9 | cDNA FLJ53069, highly similar to AP-2 complex subunit mu-1 OS = Homo sapiens PE = 2 SV = 1 | | #NUM! | #NUM! | #DIV/0! |
| P61604 | 10 kDa heat shock protein, mitochondrial OS = Homo sapiens GN = HSPE1 PE = 1 SV = 2 | | #NUM! | #NUM! | #DIV/0! |
| P20618 | Proteasome subunit beta type-1 OS = Homo sapiens GN = PSMB1 PE = 1 SV = 2 | 6.40E+07 | #NUM! | 0.51 | #DIV/0! |
| O76024 | Wolframin OS = Homo sapiens GN = WFS1 PE = 1 SV = 2 | | #NUM! | -0.18 | #DIV/0! |
| H0YKD8 | 60S ribosomal protein L28 OS = Homo sapiens GN = RPL28 PE = 1 SV = 1 | 7.30E+07 | #NUM! | 0.06 | #DIV/0! |
| J3QRS3 | Myosin regulatory light chain 12A OS = Homo sapiens GN = MYL12A PE = 1 SV = 1 | 1.10E+08 | #NUM! | #NUM! | #DIV/0! |
| Q09028 | Histone-binding protein RBBP4 OS = Homo sapiens GN = RBBP4 PE = 1 SV = 3 | | #NUM! | -0.2 | #DIV/0! |
| I3L504 | Eukaryotic translation initiation factor 5A-1 OS = Homo sapiens GN = EIF5A PE = 1 SV = 1 | 8.20E+07 | #NUM! | -0.25 | #DIV/0! |
| A0A024R845 | RAB14, member RAS oncogene family, isoform CRA_a OS = Homo sapiens GN = RAB14 PE = 3 SV = 1 | 4.90E+07 | #NUM! | #NUM! | #DIV/0! |
| A0A0A0MQT | Retinol binding protein 1, cellular OS = Homo sapiens GN = RBP1 PE = 1 SV = 1 | | #NUM! | #NUM! | #DIV/0! |
| H0Y166 | Dehydrogenase/reductase SDR family member 7 (Fragment) OS = Homo sapiens GN = DHRS7 PE = 1 SV = 1 | | #NUM! | #NUM! | #DIV/0! |
| B1AP13 | Complement decay-accelerating factor OS = Homo sapiens GN = CD55 PE = 1 SV = 1 | | #NUM! | #NUM! | #DIV/0! |
| Q6ZMJ2 | Scavenger receptor class A member 5 OS = Homo sapiens GN = SCARA5 PE = 2 SV = 1 | | #NUM! | #NUM! | #DIV/0! |
| I1W660 | Dickkopf-like protein 1 OS = Homo sapiens GN = DKK1 PE = 2 SV = 1 | | #NUM! | #NUM! | #DIV/0! |
| P26599 | Polypyrimidine tract-binding protein 1 OS = Homo sapiens GN = PTBP1 PE = 1 SV = 1 | 9.70E+07 | #NUM! | -0.01 | #DIV/0! |
| A0A024R035 | Complement component 9, isoform CRA_a OS = Homo sapiens GN = C9 PE = 4 SV = 1 | 9.90E+07 | #NUM! | 0.07 | #DIV/0! |
| P22352 | Glutathione peroxidase 3 OS = Homo sapiens GN = GPX3 PE = 1 SV = 2 | | #NUM! | #NUM! | #DIV/0! |
| A0A0A0MTS | Glucose-6-phosphate isomerase (Fragment) OS = Homo sapiens GN = GPI PE = 1 SV = 1 | 2.70E+07 | #NUM! | -0.31 | #DIV/0! |
| A5PLK9 | Metalloendopeptidase OS = Homo sapiens GN = BMP1 PE = 2 SV = 1 | | #NUM! | #NUM! | #DIV/0! |
| P11177 | Pyruvate dehydrogenase E1 component subunit beta, mitochondrial OS = Homo sapiens GN = PDHB PE = 1 SV = 3 | | #NUM! | #NUM! | #DIV/0! |
| A2RUM7 | Ribosomal protein L5 OS = Homo sapiens GN = RPL5 PE = 2 SV = 1 | 8.50E+07 | #NUM! | 0.04 | #DIV/0! |
| B4E1J8 | cDNA FLJ56285, highly similar to ADP-ribosylation factor-like protein 8B OS = Homo sapiens PE = 2 SV = 1 | 2.00E+07 | #NUM! | -0.62 | #DIV/0! |
| P22692 | Insulin-like growth factor-binding protein 4 OS = Homo sapiens GN = IGFBP4 PE = 1 SV = 2 | | #NUM! | #NUM! | #DIV/0! |
| D3DP46 | Signal peptidase complex subunit 3 homolog (S. cerevisiae), isoform CRA_a OS = Homo sapiens GN = SPCS3 PE = 4 SV = 1 | 3.90E+07 | #NUM! | -0.14 | #DIV/0! |
| B4DKM6 | cDNA FLJ54305, highly similar to Serum paraoxonase/arylesterase 2 (EC 3.1.1.2) OS = Homo sapiens PE = 2 SV = 1 | 3.00E+07 | #NUM! | -0.31 | #DIV/0! |
| P36405 | ADP-ribosylation factor-like protein 3 OS = Homo sapiens GN = ARL3 PE = 1 SV = 2 | | #NUM! | #NUM! | #DIV/0! |
| B2R6F3 | Splicing factor arginine/serine-rich 3 OS = Homo sapiens GN = SFRS3 PE = 2 SV = 1 | | #NUM! | #NUM! | #DIV/0! |
| Q9UMS4 | Pre-mRNA-processing factor 19 OS = Homo sapiens GN = PRPF19 PE = 1 SV = 1 | | #NUM! | #NUM! | #DIV/0! |
| P26368 | Splicing factor U2AF 65 kDa subunit OS = Homo sapiens GN = U2AF2 PE = 1 SV = 4 | | #NUM! | #NUM! | #DIV/0! |
| B4E0X1 | Beta-2-microglobulin OS = Homo sapiens PE = 2 SV = 1 | | #NUM! | #NUM! | #DIV/0! |
| Q6DK41 | Protein Wnt (Fragment) OS = Homo sapiens GN = WNT5A PE = 2 SV = 2 | | #NUM! | #NUM! | #DIV/0! |
| Q5JWF2 | Guanine nucleotide-binding protein G(s) subunit alpha isoforms XLas OS = Homo sapiens GN = GNAS PE = 1 SV = 2 | 2.00E+07 | #NUM! | 0.22 | #DIV/0! |
| O00764 | Pyridoxal kinase OS = Homo sapiens GN = PDXK PE = 1 SV = 1 | 7.80E+07 | #NUM! | 0.57 | #DIV/0! |
| P32320 | Cytidine deaminase OS = Homo sapiens GN = CDA PE = 1 SV = 2 | | #NUM! | #NUM! | #DIV/0! |
| Q53GL6 | RNA binding protein (Autoantigenic, hnRNP-associated with lethal yellow) long isoform variant (Fragment) OS = Homo sapiens G | | #NUM! | #NUM! | #DIV/0! |
| B3KS79 | cDNA FLJ35730 fis, done TESTI2003131, highly similar to ALPHA-1-ANTICHYMOTRYPSIN OS = Homo sapiens PE = 2 SV = 1 | 1.60E+07 | #NUM! | -0.21 | #DIV/0! |
| Q96CS3 | FAS-associated factor 2 OS = Homo sapiens GN = FAF2 PE = 1 SV = 2 | | #NUM! | #NUM! | #DIV/0! |
| A1L0T0 | Acetolactate synthase-like protein OS = Homo sapiens GN = ILVBL PE = 1 SV = 1 | 5.70E+07 | #NUM! | 0.08 | #DIV/0! |
| Q6IP11 | Ribosomal protein L29 OS = Homo sapiens GN = RPL29 PE = 2 SV = 1 | 1.40E+08 | #NUM! | -0.27 | #DIV/0! |
| A5YM53 | ITGAV protein OS = Homo sapiens GN = ITGAV PE = 2 SV = 1 | 1.40E+07 | #NUM! | 0 | #DIV/0! |
| A8K6C9 | cDNA FLJ78037, highly similar to Homo sapiens insulin-like growth factor 2 (somatomedin A), mRNA OS = Homo sapiens PE = 2 SV = 1 | | #NUM! | #NUM! | #DIV/0! |
| A8K3I0 | cDNA FLJ78437, highly similar to Homo sapiens cartilage oligomeric matrix protein (COMP), mRNA OS = Homo sapiens PE = 2 SV = 1 | | #NUM! | #NUM! | #DIV/0! |
| C7EXL7 | MHC class I antigen OS = Homo sapiens GN = HLA-Cw PE = 3 SV = 1 | 2.70E+07 | #NUM! | -0.89 | #DIV/0! |
| A0A024RAF7 | Endothelin converting enzyme 1, isoform CRA_b OS = Homo sapiens GN = ECE1 PE = 4 SV = 1 | | #NUM! | #NUM! | #DIV/0! |
| H3BS72 | Very-long-chain (3R)-3-hydroxyacyl-CoA dehydratase 3 OS = Homo sapiens GN = HACD3 PE = 1 SV = 1 | | #NUM! | #NUM! | #DIV/0! |
| Q9NYL4 | Peptidyl-prolyl cis-trans isomerase FKBP11 OS = Homo sapiens GN = FKBP11 PE = 1 SV = 1 | 2.50E+07 | #NUM! | -0.43 | #DIV/0! |
| A8K769 | cDNA FLJ77721, highly similar to Homo sapiens secretory carrier membrane protein 2 (SCAMP2), mRNA OS = Homo sapiens PE = 2 | | #NUM! | #NUM! | #DIV/0! |
| A0A024QZJ7 | Coiled-coil domain containing 6, isoform CRA_a OS = Homo sapiens GN = CCDC6 PE = 4 SV = 1 | | #NUM! | #NUM! | #DIV/0! |
| Q6ZY3 | KN motif and ankyrin repeat domain-containing protein 2 OS = Homo sapiens GN = KANK2 PE = 1 SV = 1 | | #NUM! | #NUM! | #DIV/0! |
| P42224 | Signal transducer and activator of transcription 1-alpha/beta OS = Homo sapiens GN = STAT1 PE = 1 SV = 2 | 8.70E+06 | #NUM! | -0.32 | #DIV/0! |
| O75462 | Cytokine receptor-like factor 1 OS = Homo sapiens GN = CRLF1 PE = 1 SV = 1 | | #NUM! | #NUM! | #DIV/0! |

APPENDIX A-continued

| ID | Description | Value1 | Value2 | Value3 |
|---|---|---|---|---|
| A4D2Q0 | Unc-84 homolog A (C. elegans) OS = Homo sapiens GN = UNC84A PE = 4 SV = 1 | 1.00E+07 | #NUM! | -0.08 | #NUM! |
| Q9UHX1 | PolyU(U)-binding-splicing factor PUF60 OS = Homo sapiens GN = PUF60 PE = 1 SV = 1 | | #NUM! | #NUM! | #DIV/0! |
| Q13666 | 40S ribosomal protein S21 OS = Homo sapiens PE = 2 SV = 1 | 1.30E+07 | #NUM! | -0.35 | #NUM! |
| P09466 | Glycodelin OS = Homo sapiens GN = PAEP PE = 1 SV = 2 | | #NUM! | #DIV/0! | #DIV/0! |
| A0A024RAN2 | Calpastatin, isoform CRA_a OS = Homo sapiens GN = CAST PE = 4 SV = 1 | 7.10E+07 | #NUM! | -0.04 | #NUM! |
| P27105 | Erythrocyte band 7 integral membrane protein OS = Homo sapiens GN = STOM PE = 1 SV = 3 | | #NUM! | #NUM! | #DIV/0! |
| C9JF17 | Apolipoprotein D (Fragment) OS = Homo sapiens GN = APOD PE = 1 SV = 1 | | #NUM! | #NUM! | #DIV/0! |
| Q9HDC9 | Adipocyte plasma membrane-associated protein OS = Homo sapiens GN = APMAP PE = 1 SV = 2 | 3.50E+07 | #NUM! | -0.96 | #NUM! |
| Q96RG5 | Insulin receptor substrate 2 insertion mutant (Fragment) OS = Homo sapiens GN = IRS2 PE = 4 SV = 1 | | #NUM! | #DIV/0! | #DIV/0! |
| P62847 | 40S ribosomal protein S24 OS = Homo sapiens GN = RPS24 PE = 1 SV = 1 | 5.20E+07 | #NUM! | -0.23 | #NUM! |
| P62081 | 40S ribosomal protein S7 OS = Homo sapiens GN = RPS7 PE = 1 SV = 1 | | #NUM! | #NUM! | #DIV/0! |
| Q9HAV7 | GrpE protein homolog 1, mitochondrial OS = Homo sapiens GN = GRPEL1 PE = 1 SV = 2 | | #NUM! | #NUM! | #DIV/0! |
| Q96PD5 | N-acetylmuramoyl-L-alanine amidase OS = Homo sapiens GN = PGLYRP2 PE = 1 SV = 1 | | #DIV/0! | #DIV/0! | #DIV/0! |
| H3BNX8 | Cytochrome c oxidase subunit 5A, mitochondrial OS = Homo sapiens GN = COX5A PE = 1 SV = 1 | 2.10E+07 | #NUM! | -0.46 | #NUM! |
| P24310 | Cytochrome c oxidase subunit 7A1, mitochondrial OS = Homo sapiens GN = COX7A1 PE = 1 SV = 2 | | #NUM! | #NUM! | #DIV/0! |
| Q7L4Q3 | Glutathione peroxidase OS = Homo sapiens GN = GPX1 PE = 2 SV = 1 | 2.50E+07 | #NUM! | -0.11 | #NUM! |
| A8K4A5 | cDNA FLJ77482, highly similar to Human atrial natriuretic peptide clearance receptor (ANP C-receptor) mRNA OS = Homo sapiens | | #NUM! | #NUM! | #DIV/0! |
| A0A024R0V4 | Vasodilator-stimulated phosphoprotein, isoform CRA_a OS = Homo sapiens GN = VASP PE = 4 SV = 1 | 3.20E+07 | #NUM! | -0.03 | #NUM! |
| P35610 | Sterol O-acyltransferase 1 OS = Homo sapiens GN = SOAT1 PE = 1 SV = 3 | | #NUM! | #NUM! | #DIV/0! |
| Q96M3 | Probable carboxypeptidase X1 OS = Homo sapiens GN = CPXM1 PE = 2 SV = 2 | | #NUM! | #NUM! | #DIV/0! |
| B2RDI5 | cDNA, FLJ96627, highly similar to Homo sapiens calpain 1, (mu/l) large subunit (CAPN1), mRNA | 4.00E+07 | #NUM! | 0.15 | #NUM! |
| Q13201 | Multimerin-1 OS = Homo sapiens GN = MMRN1 PE = 1 SV = 3 | | #DIV/0! | #DIV/0! | #DIV/0! |
| O14907 | Tax1-binding protein 3 OS = Homo sapiens GN = TAX1BP3 PE = 1 SV = 2 | | #NUM! | -0.41 | #NUM! |
| Q6SZC8 | Single-chain Fv (Fragment) OS = Homo sapiens GN = scFv PE = 2 SV = 1 | | #NUM! | -0.3 | #NUM! |
| Q59G88 | Coronin (Fragment) OS = Homo sapiens PE = 3 SV = 1 | | #NUM! | #NUM! | #DIV/0! |
| Q14696 | LDLR chaperone MESD OS = Homo sapiens GN = MESDC2 PE = 1 SV = 2 | 1.00E+07 | #NUM! | 0.15 | #NUM! |
| Q8TAA3 | Proteasome subunit alpha type-7-like OS = Homo sapiens GN = PSMA8 PE = 2 SV = 3 | 9.10E+06 | #NUM! | -0.21 | #NUM! |
| Q9H2P1 | DC16 OS = Homo sapiens PE = 2 SV = 1 | 2.00E+07 | #NUM! | -0.29 | #NUM! |
| A0A0B4J1S4 | 15 kDa selenoprotein OS = Homo sapiens GN = SEP15 PE = 1 SV = 1 | 8.70E+07 | #NUM! | #NUM! | #DIV/0! |
| F8W727 | 60S ribosomal protein L32 OS = Homo sapiens GN = RPL32 PE = 1 SV = 1 | 6.10E+07 | #NUM! | #NUM! | #DIV/0! |
| P11279 | Lysosome-associated membrane glycoprotein 1 OS = Homo sapiens GN = LAMP1 PE = 1 SV = 3 | | #NUM! | #NUM! | #DIV/0! |
| O43488 | Aflatoxin B1 aldehyde reductase member 2 OS = Homo sapiens GN = AKR7A2 PE = 1 SV = 3 | | #NUM! | #NUM! | #DIV/0! |
| A0A024R118 | Methyltransferase like 7A, isoform CRA_a OS = Homo sapiens GN = METTL7A PE = 4 SV = 1 | 1.60E+07 | #NUM! | -0.4 | #NUM! |
| A0A024QZK8 | Heterogeneous nuclear ribonucleoprotein H3 (2H9), isoform CRA_a OS = Homo sapiens GN = HNRPH3 | | #NUM! | #NUM! | #DIV/0! |
| B3KM21 | Family with sequence similarity 36, member A, isoform CRA_a OS = Homo sapiens GN = FAM36A PE = 2 SV = 1 | | #NUM! | #NUM! | #DIV/0! |
| Q53HQ0 | Flotillin 1 variant (Fragment) OS = Homo sapiens PE = 2 SV = 1 | | #NUM! | #NUM! | #DIV/0! |
| A0A087WYF | MICOS complex subunit MIC27 OS = Homo sapiens GN = APOOL PE = 1 SV = 1 | | #NUM! | #NUM! | #DIV/0! |
| Q9BRX8 | Redox-regulatory protein FAM213A OS = Homo sapiens GN = FAM213A PE = 1 SV = 3 | 5.80E+07 | #NUM! | -0.32 | #NUM! |
| B7Z8W8 | Reticulon OS = Homo sapiens PE = 2 SV = 1 | | #NUM! | #NUM! | #DIV/0! |
| Q6IAX6 | 3'-phosphoadenosine 5'-phosphosulfate synthase 1 OS = Homo sapiens GN = PAPSS1 PE = 2 SV = 1 | | #NUM! | #NUM! | #DIV/0! |
| Q76L A1 | CSTB protein OS = Homo sapiens GN = CSTB PE = 2 SV = 1 | 4.20E+07 | #NUM! | -0.23 | #NUM! |
| F8VVA7 | Coatomer subunit zeta-1 OS = Homo sapiens GN = CPZ1 PE = 1 SV = 1 | | #NUM! | #NUM! | #DIV/0! |
| B3KN29 | cDNA FLJ13371 fis, clone PLACE1000656, highly similar to PRA1 family protein 2 OS = Homo sapiens | | #NUM! | #NUM! | #DIV/0! |
| B4DW13 | HCG23341, isoform CRA_d OS = Homo sapiens GN = hCG_23341 PE = 2 SV = 1 | | #NUM! | #NUM! | #DIV/0! |
| F8WA42 | Sulfatase-modifying factor 2 OS = Homo sapiens GN = SUMF2 PE = 1 SV = 1 | 2.20E+07 | #NUM! | -0.12 | #NUM! |
| A4D2D2 | Procollagen C-endopeptidase enhancer OS = Homo sapiens GN = PCOLCE PE = 4 SV = 1 | 1.90E+07 | #NUM! | -0.57 | #NUM! |
| Q13283 | Ras GTPase-activating protein-binding protein 1 OS = Homo sapiens GN = G3BP1 PE = 1 SV = 1 | | #NUM! | #NUM! | #DIV/0! |
| Q9NX40 | OCIA domain-containing protein 1 OS = Homo sapiens GN = OCIAD1 PE = 1 SV = 1 | | #NUM! | #NUM! | #DIV/0! |
| P59665 | Neutrophil defensin 1 OS = Homo sapiens GN = DEFA1 PE = 1 SV = 1 | | #NUM! | #NUM! | #DIV/0! |
| A8K4K9 | cDNA FLJ76169 OS = Homo sapiens PE = 2 SV = 1 | | #NUM! | #NUM! | #DIV/0! |
| J3KQ48 | Peptidyl-tRNA hydrolase 2, mitochondrial OS = Homo sapiens GN = PTRH2 PE = 1 SV = 1 | | #NUM! | #NUM! | #DIV/0! |
| D3DR22 | Hydroxysteroid (17-beta) dehydrogenase 12, isoform CRA_a OS = Homo sapiens GN = HSD17B12 PE = 3 SV = 1 | | #NUM! | #NUM! | #DIV/0! |
| P35914 | Hydroxymethylglutaryl-CoA lyase, mitochondrial OS = Homo sapiens GN = HMGCL PE = 1 SV = 2 | | #NUM! | #NUM! | #DIV/0! |

APPENDIX A-continued

| ID | Description | Val1 | Val2 | Val3 | Val4 |
|---|---|---|---|---|---|
| B2RDT8 | cDNA, FLJ96764, highly similar to Homo sapiens sorting nexin 8 (SNX8), mRNA OS = Homo sapiens | | #DIV/0! | #DIV/0! | #DIV/0! |
| P26006 | Integrin alpha-3 OS = Homo sapiens GN = ITGA3 PE = 1 SV = 5 | 7.90E+07 | #DIV/0! | −0.22 | #DIV/0! |
| A8MU27 | Small ubiquitin-related modifier 3 OS = Homo sapiens GN = SUM03 PE = 1 SV = 1 | | #NUM! | #NUM! | #NUM! |
| Q969X5 | Endoplasmic reticulum-Golgi intermediate compartment protein 1 OS = Homo sapiens GN = ERGIC1 | 9.10E+07 | #DIV/0! | #DIV/0! | #DIV/0! |
| E7EMK3 | Flotillin-2 OS = Homo sapiens GN = FLOT2 PE = 1 | | #NUM! | #NUM! | #NUM! |
| P61160 | Actin-related protein 2 OS = Homo sapiens GN = ACTR2 PE = 1 SV = 1 | | #NUM! | #NUM! | #NUM! |
| B1AHD1 | NHP2-like protein 1 OS = Homo sapiens GN = NHP2L1 PE = 1 SV = 1 | | #NUM! | #NUM! | #NUM! |
| F8VV71 | Ubiquitin-conjugating enzyme E2 N OS = Homo sapiens GN = UBE2N PE = 1 SV = 1 | | #DIV/0! | #DIV/0! | #DIV/0! |
| Q9BY32 | Inosine triphosphate pyrophosphatase OS = Homo sapiens GN = ITPA PE = 1 SV = 2 | | #NUM! | #NUM! | #NUM! |
| Q16629 | Serine/arginine-rich splicing factor 7 OS = Homo sapiens GN = SRSF7 PE = 1 SV = 1 | 5.00E+07 | #DIV/0! | −0.16 | #DIV/0! |
| Q9BW30 | Tubulin polymerization-promoting protein family member 3 OS = Homo sapiens GN = TPPP3 PE = 1 SV = 1 | 1.30E+08 | #NUM! | 0.19 | #NUM! |
| Q59E93 | Membrane alanine aminopeptidase variant (Fragment) OS = Homo sapiens PE = 2 SV = 1 | | #NUM! | #NUM! | #NUM! |
| Q5VV89 | Microsomal glutathione S-transferase 3 OS = Homo sapiens GN = MGST3 PE = 1 SV = 1 | 7.40E+07 | #NUM! | −0.49 | #NUM! |
| Q9Y3Y2 | Chromatin target of PRMT1 protein OS = Homo sapiens GN = CHTOP PE = 1 SV = 2 | | #NUM! | #NUM! | #NUM! |
| B2R4D5 | Actin-related protein 2/3 complex subunit 3 OS = Homo sapiens PE = 2 SV = 1 | 4.20E+07 | #NUM! | −0.23 | #NUM! |
| H7BXI1 | Extended synaptotagmin-2 (Fragment) OS = Homo sapiens GN = ESYT2 PE = 1 SV = 1 | | #DIV/0! | #NUM! | #NUM! |
| Q32Q10 | RSU1 protein (Fragment) OS = Homo sapiens GN = RSU1 PE = 2 SV = 1 | | #NUM! | #NUM! | #NUM! |
| J3KTL2 | Serine/arginine-rich splicing factor 1 OS = Homo sapiens GN = SRSF1 PE = 1 SV = 1 | 3.20E+07 | #DIV/0! | #DIV/0! | #DIV/0! |
| G3V5Z7 | Proteasome subunit alpha type OS = Homo sapiens GN = PSMA6 PE = 1 SV = 1 | | #NUM! | #NUM! | #NUM! |
| P84157 | Matrix-remodeling-associated protein 7 OS = Homo sapiens GN = MXRA7 PE = 1 SV = 1 | | #NUM! | #NUM! | #NUM! |
| A0A024QZF2 | Related RAS viral (R-ras) oncogene homolog, isoform CRA_a OS = Homo sapiens GN = RRAS PE = 4 SV = 1 | | #NUM! | −0.4 | #NUM! |
| A0A024R866 | Ribosomal protein L35, isoform CRA_a OS = Homo sapiens GN = RPL35 PE = 3 SV = 1 | 7.60E+07 | #DIV/0! | #DIV/0! | #DIV/0! |
| B3KQQ9 | cDNA PSEC0048 fis, clone NT2RP2000028, highly similar to Serine protease 23 OS = Homo sapiens | | #NUM! | #NUM! | #NUM! |
| Q8WUY3 | Protein prune homolog 2 OS = Homo sapiens GN = PRUNE2 PE = 1 SV = 3 | | #NUM! | #NUM! | #NUM! |
| Q9UNL2 | Translocon-associated protein subunit gamma OS = Homo sapiens GN = SSR3 PE = 1 SV = 1 | | #NUM! | #NUM! | #NUM! |
| A0A087WX7 | Chorionic somatomammotropin hormone 2 OS = Homo sapiens GN = CSH2 PE = 3 SV = 1 | | #NUM! | #NUM! | #NUM! |
| Q96IY4 | Carboxypeptidase B2 OS = Homo sapiens GN = CPB2 PE = 1 SV = 2 | | #NUM! | #NUM! | #NUM! |
| X6R8A1 | Carboxypeptidase OS = Homo sapiens GN = CTSA PE = 1 SV = 1 | | #NUM! | #NUM! | #NUM! |
| P23497 | Nuclear autoantigen Sp-100 OS = Homo sapiens GN = SP100 PE = 1 SV = 3 | 8.30E+07 | #NUM! | −0.16 | #NUM! |
| Q96IJ7 | Protein disulfide-isomerase TMX3 OS = Homo sapiens GN = TMX3 PE = 1 SV = 2 | | #NUM! | #NUM! | #NUM! |
| P25789 | Proteasome subunit alpha type-4 OS = Homo sapiens GN = PSMA4 PE = 1 SV = 1 | 2.10E+07 | #NUM! | 0.07 | #NUM! |
| A0A024RDR0 | High-mobility group box 1, isoform CRA_a OS = Homo sapiens GN = HMGB1 PE = 4 SV = 1 | | #NUM! | #NUM! | #NUM! |
| V9GYM3 | Apolipoprotein A-II OS = Homo sapiens GN = APDA2 PE = 1 SV = 1 | | #NUM! | #NUM! | #NUM! |
| P49207 | 60S ribosomal protein L34 OS = Homo sapiens GN = RPL34 PE = 1 SV = 3 | | #NUM! | #NUM! | #NUM! |
| P46063 | ATP-dependent DNA helicase Q1 OS = Homo sapiens GN = RECQL PE = 1 SV = 3 | | #NUM! | #NUM! | #NUM! |
| Q92520 | Protein FAM3C OS = Homo sapiens GN = FAM3C PE = 1 SV = 1 | | #NUM! | #NUM! | #NUM! |
| A4D1W8 | Ependymin related protein 1 (Zebrafish), isoform CRA_b OS = Homo sapiens GN = UCC1 PE = 4 SV = 1 | 1.30E+08 | #NUM! | 0.07 | #NUM! |
| D3DQ70 | SERPINE1 mRNA binding protein 1, isoform CRA_d OS = Homo sapiens GN = SERBP1 PE = 4 SV = 1 | | #NUM! | #NUM! | #NUM! |
| B4DNR4 | cDNA FLJ52338, highly similar to Calpain-9 (EC 3.4.22.—) OS = Homo sapiens PE = 2 SV = 1 | | #NUM! | #NUM! | #NUM! |
| P26583 | High mobility group protein B2 OS = Homo sapiens GN = HMGB2 PE = 1 SV = 2 | | #NUM! | #NUM! | #NUM! |
| P28066 | Proteasome subunit alpha type-5 OS = Homo sapiens GN = PSMA5 PE = 1 SV = 3 | | #NUM! | #NUM! | #NUM! |
| B2RDQ3 | cDNA, FLJ96718, highly similar to Homo sapiens splicing factor, arginine/serine-rich 10 | | #NUM! | #NUM! | #NUM! |
| Q14213 | interleukin-27 subunit beta OS = Homo sapiens GN = EBI3 PE = 1 SV = 2 | | #NUM! | #NUM! | #NUM! |
| P24158 | Myeloblastin OS = Homo sapiens GN = PRTN3 PE = 1 SV = 3 | | #NUM! | #NUM! | #NUM! |
| Q99715 | Collagen alpha-1(XII) chain OS = Homo sapiens GN = COL12A1 PE = 1 SV = 2 | 4.50E+07 | #NUM! | 0.24 | #NUM! |
| P27487 | Dipeptidyl peptidase 4 OS = Homo sapiens GN = DPP4 PE = 1 SV = 2 | 1.00E+08 | #NUM! | 0.8 | #NUM! |
| O14498 | Immunoglobulin superfamily containing leucine-rich repeat protein OS = Homo sapiens GN = ISLR | | #NUM! | #NUM! | #NUM! |
| Q8IW90 | MTCH1 protein (Fragment) OS = Homo sapiens GN = MTCH1 PE = 2 SV = 1 | | #NUM! | #NUM! | #NUM! |
| F8WCF6 | Protein ARPC4-TTLL3 OS = Homo sapiens GN = ARPC4-TTLL3 PE = 4 SV = 1 | 7.10E+07 | #NUM! | −0.06 | #NUM! |
| A0A0C4DGQ | Calpain small subunit 1 OS = Homo sapiens GN = CAPNS1 PE = 1 SV = 1 | 4.90E+07 | #DIV/0! | #DIV/0! | #DIV/0! |
| P11233 | Ras-related protein Ral-A OS = Homo sapiens GN = RALA PE = 1 SV = 1 | 1.50E+07 | #NUM! | −0.24 | #NUM! |
| O43181 | NADH dehydrogenase [ubiquinone] iron-sulfur protein 4, mitochondrial OS = Homo sapiens GN = NDUFS4 | | #NUM! | #NUM! | #NUM! |
| A0A087X1L7 | Left-right determination factor 2 OS = Homo sapiens GN = LEFTY2 PE = 1 SV = 1 | | #NUM! | #NUM! | #NUM! |

APPENDIX A-continued

| ID | Description | Val1 | Val2 | Val3 |
|---|---|---|---|---|
| P0C7P4 | Putative cytochrome b-c1 complex subunit Rieske-like protein 1 OS = Homo sapiens GN = UQCRFS1P1 | 3.20E+07 | #NUM! | 0.36 |
| P54727 | UV excision repair protein RAD23 homolog B OS = Homo sapiens GN = RAD23B PE = 1 SV = 1 | | #NUM! | #NUM! |
| Q510G2 | Prolactin OS = Homo sapiens GN = PRL PE = 1 SV = 1 | | #NUM! | #DIV/0! |
| E5KNY5 | Leucine-rich PPR-motif containing OS = Homo sapiens GN = LRPPRC PE = 4 SV = 1 | | #NUM! | #NUM! |
| A4PBF7 | TATA box binding protein (TBP)-associated factor 4B OS = Homo sapiens GN = taf4b PE = 2 SV = 1 | | #NUM! | #NUM! |
| P10768 | S-formylglutathione hydrolase OS = Homo sapiens GN = ESD PE = 1 SV = 2 | | #NUM! | #NUM! |
| Q59G70 | Mannosyl (Alpha-1,3-)-glycoprotein beta-1,2-N-acetylglucosaminyltransferase variant (Fragment) | | #DIV/0! | #DIV/0! |
| Q59FZ8 | Nebulette non-muscle isoform variant (Fragment) OS = Homo sapiens PE = 2 SV = 1 | 4.70E+07 | #NUM! | −0.33 |
| A8MYS5 | Post-GPI attachment to proteins factor 2 OS = Homo sapiens GN = PGAP2 PE = 4 SV = 2 | | #NUM! | #NUM! |
| Q727H5 | Transmembrane emp24 domain-containing protein 4 OS = Homo sapiens GN = TMED4 PE = 1 SV = 1 | 3.40E+07 | #NUM! | −0.09 |
| P02458 | Collagen alpha-1(II) chain OS = Homo sapiens GN = COL2A1 PE = 1 SV = 3 | 1.50E+09 | #NUM! | −0.08 |
| Q14258 | E3 ubiquitin/ISG15 ligase TRIM25 OS = Homo sapiens GN = TRIM25 PE = 1 SV = 2 | 2.10E+08 | #NUM! | 0.18 |
| J3KQN4 | 60S ribosomal protein L36a OS = Homo sapiens GN = RPL36A PE = 3 SV = 1 | | #NUM! | #NUM! |
| Q92626 | Peroxidasin homolog OS = Homo sapiens GN = PXDN PE = 1 SV = 2 | | #DIV/0! | #DIV/0! |
| Q14019 | Coactosin-like protein OS = Homo sapiens GN = COTL1 PE = 1 SV = 3 | 2.60E+07 | #NUM! | −0.12 |
| B2R761 | cDNA, FLJ93299, highly similar to Homo sapiens sterol carrier protein 2 (SCP2), mRNA | 2.80E+07 | #NUM! | −0.07 |
| P05161 | Ubiquitin-like protein ISG15 OS = Homo sapiens GN = ISG15 PE = 1 SV = 5 | | #NUM! | #NUM! |
| A8K103 | cDNA FLJ75454, highly similar to Homo sapiens arrestin, beta 1 (ARRB1), transcript variant 1 | 1.10E+08 | #NUM! | #NUM! |
| Q13421 | Mesothelin OS = Homo sapiens GN = MSLN PE = 1 SV = 2 | 3.40E+07 | #NUM! | 1.07 |
| Q96FQ6 | Protein S100-A16 OS = Homo sapiens GN = S100A16 PE = 1 SV = 1 | 1.90E+07 | #NUM! | −0.18 |
| P10155 | 60 kDa SS-A/Ro ribonucleoprotein OS = Homo sapiens GN = TROVE2 PE = 1 SV = 2 | | #NUM! | #NUM! |
| P56199 | Integrin alpha-1 OS = Homo sapiens GN = ITGA1 PE = 1 SV = 2 | | #NUM! | #NUM! |
| A0A024R8U5 | Splicing factor, arginine/serine-rich 2, isoform CRA_a OS = Homo sapiens GN = SFRS2 PE = 4 SV = 1 | 1.10E+08 | #NUM! | −0.04 |
| A6XNE2 | Complement factor D preproprotein OS = Homo sapiens GN = AEBP1 PE = 1 SV = 1 | 4.60E+07 | #NUM! | −0.06 |
| Q9BUD6 | Spondin-2 OS = Homo sapiens GN = SPON2 PE = 1 SV = 3 | | #DIV/0! | #DIV/0! |
| K7ERQ8 | Uncharacterized protein (Fragment) OS = Homo sapiens PE = 3 SV = 1 | 1.40E+08 | #NUM! | −0.27 |
| Q14151 | Scaffold attachment factor B2 OS = Homo sapiens GN = SAFB2 PE = 1 SV = 1 | | #NUM! | #NUM! |
| A4D1G5 | 40S ribosomal protein S27 OS = Homo sapiens GN = LOC392748 PE = 3 SV = 1 | 3.90E+07 | #NUM! | 0.1 |
| B2R679 | cDNA, FLJ92825, highly similar to Homo sapiens SARIa gene homolog 1 (S. cerevisiae) (SARA1) | 4.70E+07 | #NUM! | 0.27 |
| Q8IUX7 | Adipocyte enhancer-binding protein 1 OS = Homo sapiens GN = AEBP1 PE = 1 SV = 1 | | #DIV/0! | #DIV/0! |
| Q9BTV4 | Transmembrane protein 43 OS = Homo sapiens GN = TMEM43 PE = 1 SV = 1 | 6.40E+07 | #NUM! | −0.24 |
| P46776 | 60S ribosomal protein L27a OS = Homo sapiens GN = RPL27A PE = 1 SV = 2 | | #NUM! | #NUM! |
| P23526 | Adenosylhomocysteinase OS = Homo sapiens GN = AHCY PE = 1 SV = 4 | | #NUM! | #NUM! |
| A8K7E0 | cDNA FLJ76911, highly similar to Homo sapiens biglycan (BGN), mRNA OS = Homo sapiens PE = 2 SV = 1 | | #NUM! | #NUM! |
| A0A024QYT5 | Serpin peptidase inhibitor, clade E (Nexin, plasminogen activator inhibitor type 1), member 1 | | #NUM! | #NUM! |
| A6NEL0 | Non-histone chromosomal protein HMG-14 OS = Homo sapiens GN = HMGN1 PE = 1 SV = 1 | | #NUM! | #NUM! |
| B1AJZ9 | Forkhead-associated domain-containing protein 1 OS = Homo sapiens GN = FHAD1 PE = 2 SV = 2 | | #NUM! | #NUM! |
| P61960 | Ubiquitin-fold modifier 1 OS = Homo sapiens GN = UFM1 PE = 1 SV = 1 | | #NUM! | #NUM! |
| O43615 | Mitochondrial import inner membrane translocase subunit TIM44 OS = Homo sapiens GN = TIMM44 | | #DIV/0! | #DIV/0! |
| Q14683 | Structural maintenance of chromosomes protein 1A OS = Homo sapiens GN = SMC1A PE = 1 SV = 2 | 2.30E+08 | #NUM! | −0.73 |
| P30626 | Sorcin OS = Homo sapiens GN = SRI PE = 1 SV = 1 | 3.20E+07 | #NUM! | −0.01 |
| P61254 | 60S ribosomal protein L26 OS = Homo sapiens GN = RPL26 PE = 1 SV = 1 | 8.30E+07 | #NUM! | #NUM! |
| A0A024R6J9 | Serpin peptidase inhibitor, clade A (Alpha-1 antiproteinase, antitrypsin), member 4, isoform CRA | | #NUM! | #NUM! |
| D4QEZ8 | Short-chain acyl-CoA dehydrogenase OS = Homo sapiens GN = ACADS PE = 2 SV = 1 | | #NUM! | #NUM! |
| H9STE0 | Cytochrome c oxidase subunit 2 OS = Homo sapiens GN = COX2 PE = 3 SV = 1 | 2.70E+07 | #NUM! | −0.36 |
| Q99442 | Translocation protein SEC62 OS = Homo sapiens GN = SEC62 PE = 1 SV = 1 | | #DIV/0! | #DIV/0! |
| Q59EG8 | Proteasome 26S non-ATPase subunit 2 variant (Fragment) OS = Homo sapiens PE = 2 SV = 1 | | #NUM! | #NUM! |
| P50238 | Cysteine-rich protein 1 OS = Homo sapiens GN = CRIP1 PE = 1 SV = 3 | | #NUM! | #NUM! |
| P15531 | Nucleoside diphosphate kinase A OS = Homo sapiens GN = NME1 PE = 1 SV = 1 | 4.80E+07 | #NUM! | −0.32 |
| Q01638 | Interleukin-1 receptor-like 1 OS = Homo sapiens GN = IL1RL1 PE = 1 SV = 4 | | #DIV/0! | #DIV/0! |
| P14550 | Alcohol dehydrogenase [NADP(+)] OS = Homo sapiens GN = AKR1A1 PE = 1 SV = 3 | | #NUM! | #NUM! |
| B7Z6S9 | Glucosylceramidase OS = Homo sapiens PE = 2 SV = 1 | | #NUM! | #NUM! |
| B7Z8X5 | cDNA FLJ61541, highly similar to Homo sapiens PDZ and LIM domain 5 (PDLIM5), transcript variant 2 | | #NUM! | #NUM! |

APPENDIX A-continued

| ID | Description | Col3 | Col4 | Col5 |
|---|---|---|---|---|
| Q9HCU0 | Endosialin OS = Homo sapiens GN = CD248 PE = 1 SV = 1 | #NUM! | #NUM! | #DIV/0! |
| Q96JY6 | PDZ and LIM domain protein 2 OS = Homo sapiens GN = PDLIM2 PE = 1 SV = 1 | #NUM! | #NUM! | #DIV/0! |
| P51970 | NADH dehydrogenase [ubiquinone] 1 alpha subcomplex subunit 8 OS = Homo sapiens GN = NDUFA8 | 2.00E+07 | −0.26 | #DIV/0! |
| P00167 | Cytochrome b5 OS = Homo sapiens GN = CYB5A PE = 1 SV = 2 | #NUM! | #NUM! | #DIV/0! |
| B2RBF9 | Protocadherin gamma-A12 OS = Homo sapiens GN = PCDHGA12 PE = 2 SV = 1 | #DIV/0! | #DIV/0! | #DIV/0! |
| Q15019 | cDNA, FLJ95487, highly similar to Homo sapiens peptidyl arginine deiminase, type 1 (PADI1) | 6.30E+07 | −0.16 | #DIV/0! |
| A0A024RAM | Septin-2 OS = Homo sapiens GN = SEPT2 PE = 1 SV = 1 | #NUM! | #NUM! | #DIV/0! |
| O43681 | Glutaredoxin (Thioltransferase), isoform CRA_c OS = Homo sapiens GN = GLRX PE = 4 SV = 1 | #NUM! | #NUM! | #DIV/0! |
| P01591 | ATPase ASNA1 OS = Homo sapiens GN = ASNA1 PE = 1 SV = 2 | #NUM! | #NUM! | #DIV/0! |
| A8K6K4 | Immunoglobulin J chain OS = Homo sapiens GN = JCHAIN PE = 1 SV = 1 | #NUM! | #NUM! | #DIV/0! |
| Q9BUT1 | cDNA FLJ77565, highly similar to Homo sapiens interleukin 1 receptor accessory protein (IL1RAP) | #NUM! | #NUM! | #DIV/0! |
| A0A075B716 | 3-hydroxybutyrate dehydrogenase type 2 OS = Homo sapiens GN = BDH2 PE = 1 SV = 2 | #NUM! | #NUM! | #DIV/0! |
| Q59GK9 | 40S ribosomal protein S17 OS = Homo sapiens GN = RPS17 PE = 1 SV = 1 | #NUM! | #NUM! | #DIV/0! |
| A8MT02 | Ribosomal protein L21 variant (Fragment) OS = Homo sapiens PE = 2 SV = 1 | 1.30E+07 | −1.16 | #DIV/0! |
| P01031 | Small nuclear ribonucleoprotein-associated proteins B and B' OS = Homo sapiens GN = SNRPB PE = 1 SV = 3 | #NUM! | #NUM! | #DIV/0! |
| X6R2S6 | Complement C5 OS = Homo sapiens GN = C5 PE = 1 SV = 4 | #NUM! | #NUM! | #DIV/0! |
| Q6SA08 | Signal peptidase complex subunit 1 OS = Homo sapiens GN = SPCS1 PE = 1 SV = 1 | #NUM! | #NUM! | #DIV/0! |
| A6NFQ7 | Testis-specific serine/threonine-protein kinase 4 OS = Homo sapiens GN = TSSK4 PE = 1 SV = 1 | 2.90E+07 | 0.05 | #DIV/0! |
| H0YET1 | Divergent paired-related homeobox protein OS = Homo sapiens GN = DPRX PE = 3 SV = 1 | #DIV/0! | #DIV/0! | #DIV/0! |
| Q14498 | Liprin-beta-2 (Fragment) OS = Homo sapiens GN = PPFIBP2 PE = 1 SV = 1 | #DIV/0! | #DIV/0! | #DIV/0! |
| O95428 | RNA-binding protein 39 OS = Homo sapiens GN = RBM39 PE = 1 SV = 2 | #DIV/0! | #DIV/0! | #DIV/0! |
| E9PB61 | Papilin OS = Homo sapiens GN = PAPLN PE = 2 SV = 4 | #DIV/0! | #DIV/0! | #DIV/0! |
| Q9BSL1 | THO complex subunit 4 OS = Homo sapiens GN = ALYREF PE = 1 SV = 1 | #NUM! | #NUM! | #DIV/0! |
| Q9Y6C9 | Ubiquitin-associated domain-containing protein 1 OS = Homo sapiens GN = UBAC1 PE = 1 SV = 1 | #NUM! | #NUM! | #DIV/0! |
| A0A024R8J2 | Mitochondrial carrier homolog 2 OS = Homo sapiens GN = MTCH2 PE = 1 SV = 1 | #DIV/0! | #DIV/0! | #DIV/0! |
| B4DPP6 | Protein tyrosine phosphatase type IVA, member 1, isoform CRA_a OS = Homo sapiens GN = PTP4A1 | 3.40E+10 | #DIV/0! | #DIV/0! |
| B3KY79 | cDNA FLJ54371, highly similar to Serum albumin OS = Homo sapiens PE = 2 SV = 1 | 1.40E+08 | #DIV/0! | #DIV/0! |
| A8K3K1 | cDNA FLJ46620 fis, clone TLUNG2000654, highly similar to Keratin, type II cytoskeletal 7 | 2.40E+09 | #DIV/0! | #DIV/0! |
| Q6GMX6 | cDNA FLJ78096, highly similar to Homo sapiens actin, alpha, cardiac muscle (ACTC), mRNA | 1.00E+09 | #DIV/0! | #DIV/0! |
| F5H5D3 | IGH@ protein OS = Homo sapiens GN = IGH@ PE = 1 SV = 1 | 5.60E+08 | #DIV/0! | #DIV/0! |
| Q8TCD0 | Tubulin alpha-1C chain OS = Homo sapiens GN = TUBA1C PE = 1 SV = 1 | 9.10E+08 | #DIV/0! | #DIV/0! |
| Q9NSB2 | Uncharacterized protein OS = Homo sapiens PE = 1 SV = 1 | | #NUM! | #DIV/0! |
| P19013 | Keratin, type II cuticular Hb4 OS = Homo sapiens GN = KRT84 PE = 2 SV = 2 | 3.50E+07 | #NUM! | #DIV/0! |
| B2ZZ89 | Keratin, type II cytoskeletal 4 OS = Homo sapiens GN = KRT4 PE = 1 SV = 4 | 9.90E+07 | #NUM! | #DIV/0! |
| B3KML9 | Epididymis luminal protein 102 OS = Homo sapiens GN = SPTBN1 PE = 2 SV = 1 | 1.80E+08 | #NUM! | #DIV/0! |
| P50454 | cDNA FLJ11352 fis, clone HEMBA1000020, highly similar to Tubulin beta-2C chain OS = Homo sapiens | 2.80E+08 | #NUM! | #DIV/0! |
| Q71UF1 | Serpin H1 OS = Homo sapiens GN = SERPINH1 PE = 1 SV = 2 | 1.60E+08 | #NUM! | #DIV/0! |
| E7EPZ9 | Aconitase OS = Homo sapiens GN = ACO2 PE = 4 SV = 1 | 1.10E+08 | #NUM! | #DIV/0! |
| P61981 | Tenascin-X OS = Homo sapiens GN = TNXB PE = 1 SV = 1 | 6.00E+07 | #NUM! | #DIV/0! |
| Q9BUF5 | 14-3-3 protein gamma OS = Homo sapiens GN = YWHAG PE = 1 SV = 2 | 2.20E+07 | #NUM! | #DIV/0! |
| P05187 | Tubulin beta-6 chain OS = Homo sapiens GN = TUBB6 PE = 1 SV = 1 | 1.00E+08 | #NUM! | #DIV/0! |
| O95171 | Alkaline phosphatase, placental type OS = Homo sapiens GN = ALPP PE = 1 SV = 1 | 5.80E+07 | #NUM! | #DIV/0! |
| T2F9S8 | Sciellin OS = Homo sapiens GN = SCEL PE = 1 SV = 2 | 1.60E+08 | #NUM! | #DIV/0! |
| A8K7F6 | DNA-directed RNA polymerase II subunit RPB11-b2 OS = Homo sapiens GN = POLR2J3 PE = 2 SV = 1 | 6.30E+07 | #NUM! | #DIV/0! |
| D3DRA2 | cDNA FLJ78244, highly similar to Homo sapiens eukaryotic translation initiation factor 4A, isoform 1 | 6.70E+07 | #NUM! | #DIV/0! |
| P08134 | Collagen, type XVII, alpha 1, isoform CRA_b OS = Homo sapiens GN = COL17A1 PE = 2 SV = 1 | 5.10E+07 | #NUM! | #DIV/0! |
| O75841 | Rho-related GTP-binding protein RhoC OS = Homo sapiens GN = RHOC PE = 1 SV = 1 | 4.20E+07 | #NUM! | #DIV/0! |
| A0A024R8W | Uroplakin-1b OS = Homo sapiens GN = UPK1B PE = 2 SV = 5 | | #NUM! | #DIV/0! |
| H0Y449 | DEAD (Asp-Glu-Ala-Asp) box polypeptide 48, isoform CRA_a OS = Homo sapiens GN = DDX48 PE = 3 SV = 1 | 6.60E+06 | #NUM! | #DIV/0! |
| H0Y300 | Nuclease-sensitive element-binding protein 1 (Fragment) OS = Homo sapiens GN = YBX1 PE = 1 SV = 1 | 3.30E+07 | #NUM! | #DIV/0! |
| A4D0U5 | Haptoglobin OS = Homo sapiens GN = HP PE = 1 SV = 1 | 3.40E+07 | #NUM! | #DIV/0! |
| B7Z2B0 | Testis derived transcript (3 LIM domains) OS = Homo sapiens GN = TES PE = 4 SV = 1 | 4.30E+07 | #NUM! | #DIV/0! |
| | cDNA FLJ53470, highly similar to Calcium/calmodulin-dependent protein kinase type II delta chain | | | |

APPENDIX A-continued

| ID | Description | Value | | |
|---|---|---|---|---|
| Q92599 | Septin-8 OS = Homo sapiens GN = SEPT8 PE = 1 SV = 4 | 3.30E+07 | #DIV/0! | #NUM! |
| Q53GR7 | Solute carrier family 25, member 13 (Citrin) variant (Fragment) OS = Homo sapiens PE = 2 SV = 1 | 3.60E+07 | #DIV/0! | #NUM! |
| A0A024R4N0 | HCG1640809, isoform CRA_b OS = Homo sapiens GN = hCG_1640809 PE = 4 SV = 1 | 3.40E+07 | #DIV/0! | #NUM! |
| A4D2J9 | Calcium/calmodulin-dependent protein kinase (CaM kinase) II beta OS = Homo sapiens GN = CAMK2B | 2.10E+07 | #DIV/0! | #NUM! |
| P23434 | Glycine cleavage system H protein, mitochondrial OS = Homo sapiens GN = GCSH PE = 1 SV = 2 | 2.30E+07 | #DIV/0! | #NUM! |
| A8K2U0 | Alpha-2-macroglobulin-like protein 1 OS = Homo sapiens GN = A2ML1 PE = 1 SV = 3 | 3.00E+07 | #DIV/0! | #NUM! |
| P00739 | Haptoglobin-related protein OS = Homo sapiens GN = HPR PE = 2 SV = 2 | 2.50E+07 | #DIV/0! | #NUM! |
| F5H423 | Uncharacterized protein OS = Homo sapiens PE = 3 SV = 1 | 2.50E+07 | #DIV/0! | #NUM! |
| D6NKH9 | L-lactate dehydrogenase OS = Homo sapiens PE = 2 SV = 1 | 4.90E+05 | #DIV/0! | #NUM! |
| Q6DEN2 | DPYSL3 protein OS = Homo sapiens GN = DPYSL3 PE = 2 SV = 1 | 2.20E+07 | #DIV/0! | #NUM! |
| O15231 | Zinc finger protein 185 OS = Homo sapiens GN = ZNF185 PE = 1 SV = 3 | 3.70E+07 | #DIV/0! | #NUM! |
| Q8WXI7 | Mucin-16 OS = Homo sapiens GN = MUC16 PE = 1 SV = 2 | 2.00E+07 | #DIV/0! | #NUM! |
| S4R3N1 | Protein HSPE1-MOB4 OS = Homo sapiens GN = HSPE1-MOB4 PE = 3 SV = 1 | 8.80E+07 | #DIV/0! | #NUM! |
| A0A0A0MT2 | Sodium/potassium-transporting ATPase subunit alpha-3 OS = Homo sapiens GN = ATP1A3 PE = 1 SV = 1 | 8.80E+06 | #DIV/0! | #NUM! |
| P02763 | Alpha-1-acid glycoprotein 1 OS = Homo sapiens GN = ORM1 PE = 1 SV = 1 | 3.70E+07 | #DIV/0! | #NUM! |
| B0YIW2 | Apolipoprotein C-III OS = Homo sapiens GN = APOC3 PE = 1 SV = 1 | | #DIV/0! | #NUM! |
| B2R4A2 | Cytochrome b-c1 complex subunit 7 OS = Homo sapiens PE = 2 SV = 1 | 2.20E+07 | #DIV/0! | #NUM! |
| A8K2N5 | Integrin beta OS = Homo sapiens PE = 2 SV = 1 | 2.10E+07 | #DIV/0! | #NUM! |
| B4DYN5 | Succinate dehydrogenase [ubiquinone] flavoprotein subunit, mitochondrial OS = Homo sapiens | 4.00E+07 | #DIV/0! | #NUM! |
| P07357 | Complement component C8 alpha chain OS = Homo sapiens GN = C8A PE = 1 SV = 2 | | #DIV/0! | #NUM! |
| Q8TA92 | Similar to AFG3 ATPase family gene 3-like 2 (Yeast) (Fragment) OS = Homo sapiens PE = 2 SV = 1 | 6.00E+06 | #DIV/0! | #NUM! |
| A0A024R8Q1 | Glucosidase, alpha acid (Pompe disease, glycogen storage disease type II), isoform CRA_a GN = GAA | 1.10E+07 | #DIV/0! | #NUM! |
| B4E2S3 | cDNA FLJ56561 OS = Homo sapiens PE = 2 SV = 1 | 1.80E+07 | #DIV/0! | #NUM! |
| Q9BZZ5 | Apoptosis inhibitor 5 OS = Homo sapiens GN = API5 PE = 1 SV = 3 | 6.60E+05 | #DIV/0! | #NUM! |
| Q9H3N1 | Thioredoxin-related transmembrane protein 1 OS = Homo sapiens GN = TMX1 PE = 1 SV = 1 | 3.50E+07 | #DIV/0! | #NUM! |
| H3BNC9 | Uncharacterized protein (Fragment) OS = Homo sapiens PE = 4 SV = 1 | 6.60E+07 | #DIV/0! | #NUM! |
| A8K2U2 | Hexokinase OS = Homo sapiens PE = 2 SV = 1 | 3.40E+07 | #DIV/0! | #NUM! |
| O15144 | Actin-related protein 2/3 complex subunit 2 OS = Homo sapiens GN = ARPC2 PE = 1 SV = 1 | | #DIV/0! | #NUM! |
| P54136 | Arginine-tRNA ligase, cytoplasmic OS = Homo sapiens GN = RARS PE = 1 SV = 2 | 7.40E+06 | #DIV/0! | #NUM! |
| Q9BYG4 | Protein PBDC1 OS = Homo sapiens GN = PBDC1 PE = 1 SV = 1 | 7.20E+05 | #DIV/0! | #NUM! |
| Q14108 | Lysosome membrane protein 2 OS = Homo sapiens GN = SCARB2 PE = 1 SV = 2 | | #DIV/0! | #NUM! |
| P10606 | Cytochrome c oxidase subunit 5B, mitochondrial OS = Homo sapiens GN = COX5B PE = 1 SV = 1 | 3.40E+07 | #DIV/0! | #NUM! |
| Q9NSF4 | Isoleucine-tRNA ligase, mitochondrial OS = Homo sapiens GN = IARS2 PE = 1 SV = 2 | 3.10E+07 | #DIV/0! | #NUM! |
| A0A024R259 | KIAA0427, isoform CRA_a OS = Homo sapiens GN = KIAA0427 PE = 4 SV = 1 | 1.60E+07 | #DIV/0! | #NUM! |
| Q71V07 | Signal recognition particle subunit SRP72 OS = Homo sapiens PE = 2 SV = 1 | 1.10E+07 | #DIV/0! | #NUM! |
| Q8WWI1 | LIM domain only protein 7 OS = Homo sapiens GN = LMO7 PE = 1 SV = 3 | 2.00E+07 | #DIV/0! | #NUM! |
| Q8WXV6 | Plectin isoform 1a (Fragment) OS = Homo sapiens GN = PLEC1 PE = 2 SV = 1 | | #DIV/0! | #NUM! |
| Q6P587 | Acylpyruvase FAHD1, mitochondrial OS = Homo sapiens GN = FAHD1 PE = 1 SV = 2 | 3.20E+07 | #DIV/0! | #NUM! |
| J3KNL6 | Protein transport protein Sec16A OS = Homo sapiens GN = SEC16A PE = 1 SV = 1 | | #DIV/0! | #NUM! |
| O75694 | Nuclear pore complex protein Nup155 OS = Homo sapiens GN = NUP155 PE = 1 SV = 1 | 1.30E+07 | #DIV/0! | #NUM! |
| Q53G34 | Mitochondrial carrier homolog 2 variant (Fragment) OS = Homo sapiens PE = 2 SV = 1 | 8.90E+06 | #DIV/0! | #NUM! |
| P0CE67 | Putative uncharacterized protein C3orf79 OS = Homo sapiens GN = C3orf79 PE = 4 SV = 1 | 1.20E+08 | #DIV/0! | #NUM! |
| G8ILH6 | Tetraspanin (Fragment) OS = Homo sapiens GN = CD9 PE = 1 SV = 1 | 1.80E+08 | #DIV/0! | #NUM! |
| B4DS05 | cDNA FLJ59403, highly similar to Nucleosome assembly protein 1-like 4 OS = Homo sapiens PE = 2 SV = 1 | 1.30E+07 | #DIV/0! | #NUM! |
| Q9NT15 | Phosphatidylinositide phosphatase SAC1 OS = Homo sapiens GN = SACM1L PE = 1 SV = 2 | 2.20E+07 | #DIV/0! | #NUM! |
| Q96T51 | RUN and FYVE domain-containing protein 1 OS = Homo sapiens GN = RUFY1 PE = 1 SV = 2 | 1.00E+07 | #DIV/0! | #NUM! |
| S4R347 | Formin-binding protein 1-like OS = Homo sapiens GN = FNBP1L PE = 1 SV = 1 | 9.10E+07 | #DIV/0! | #NUM! |
| Q13085 | Acetyl-CoA carboxylase 1 OS = Homo sapiens GN = ACACA PE = 1 SV = 2 | | #DIV/0! | #NUM! |
| A0A087WX15 | Cadherin-1 OS = Homo sapiens GN = CDH1 PE = 1 SV = 1 | | #DIV/0! | #NUM! |
| K4PZ75 | Ig superfamily receptor LNIR OS = Homo sapiens GN = LNIR PE = 2 SV = 1 | 7.60E+06 | #DIV/0! | #NUM! |
| B3KTJ9 | cDNA FLJ38393 fis, clone FEBRA2007212 OS = Homo sapiens PE = 2 SV = 1 | 1.90E+07 | #DIV/0! | #NUM! |
| B2R856 | Acyl-coenzyme A oxidase OS = Homo sapiens PE = 2 SV = 1 | 7.50E+06 | #DIV/0! | #NUM! |
| Q6N0B1 | Succinyl-CoA ligase subunit beta (Fragment) OS = Homo sapiens GN = DKFZp686D0880 PE = 2 SV = 1 | 3.10E+07 | #DIV/0! | #NUM! |

APPENDIX A-continued

| ID | Description | Value | | |
|---|---|---|---|---|
| E9PLN8 | Uncharacterized protein (Fragment) OS = Homo sapiens PE = 4 SV = 1 | 3.50E+07 | #DIV/0! | #NUM! |
| Q6IPX4 | 40S ribosomal protein S16 OS = Homo sapiens GN = RPS16 PE = 1 SV = 1 | 1.40E+08 | #DIV/0! | #NUM! |
| Q53FN7 | BZW1 protein variant (Fragment) OS = Homo sapiens PE = 2 SV = 1 | 1.30E+07 | #DIV/0! | #NUM! |
| Q9H6S3 | Epidermal growth factor receptor kinase substrate 8-like protein 2 OS = Homo sapiens GN = EPS8L2 | 1.20E+07 | #DIV/0! | #NUM! |
| D6REX3 | Protein transport protein Sec31A OS = Homo sapiens GN = SEC31A PE = 1 SV = 1 | 2.70E+07 | #DIV/0! | #NUM! |
| P61513 | 60S ribosomal protein L37a OS = Homo sapiens GN = RPL37A PE = 1 SV = 2 | 2.80E+07 | #DIV/0! | #NUM! |
| Q9UBC9 | Small proline-rich protein 3 OS = Homo sapiens GN = SPRR3 PE = 1 SV = 2 | 8.60E+07 | #DIV/0! | #NUM! |
| Q53FR4 | Vacuolar protein sorting 35 variant (Fragment) OS = Homo sapiens PE = 2 SV = 1 | 4.80E+07 | #DIV/0! | #NUM! |
| A8K2Q6 | Peptidyl-prolyl cis-trans isomerase OS = Homo sapiens PE = 2 SV = 1 | 2.20E+07 | #DIV/0! | #NUM! |
| Q96M27 | Protein PRRC1 OS = Homo sapiens GN = PRRC1 PE = 1 SV = 1 | 2.00E+07 | #DIV/0! | #NUM! |
| Q13835 | Plakophilin-1 OS = Homo sapiens GN = PKP1 PE = 1 SV = 2 | 6.70E+07 | #DIV/0! | #NUM! |
| P16152 | Carbonyl reductase [NADPH] 1 OS = Homo sapiens GN = CBR1 PE = 1 SV = 3 | 2.30E+07 | #DIV/0! | #NUM! |
| C9JZQ1 | Translocon-associated protein subunit alpha OS = Homo sapiens GN = SSR1 PE = 1 SV = 1 | 2.30E+07 | #DIV/0! | #NUM! |
| Q9BSJ2 | Gamma-tubulin complex component 2 OS = Homo sapiens GN = TUBGCP2 PE = 1 SV = 2 | 1.30E+06 | #DIV/0! | #NUM! |
| S4R435 | Protein RPS10-NUDT3 (Fragment) OS = Homo sapiens GN = RPS10-NUDT3 PE = 3 SV = 1 | 4.80E+07 | #DIV/0! | #NUM! |
| L8ECD6 | Alternative protein PMEL OS = Homo sapiens GN = PMEL PE = 4 SV = 1 | 1.00E+09 | #DIV/0! | #NUM! |
| A8K5T7 | cDNA FLJ75365, highly similar to Homo sapiens SUGT1B (SUGT1) mRNA OS = Homo sapiens PE = 2 SV = 1 | | #DIV/0! | #DIV/0! |
| A0A024RDT1 | Mitochondrial translational release factor 1, isoform CRA_a OS = Homo sapiens GN = MTRF1 PE = 4 SV = 1 | 1.90E+07 | #DIV/0! | #NUM! |
| H0Y368 | Dolichol-phosphate mannosyltransferase subunit 1 (Fragment) OS = Homo sapiens GN = DPM1 PE = 1 SV = 1 | 2.40E+07 | #DIV/0! | #NUM! |
| Q6ZP37 | CDNA FLJ26554 fis, clone LNF01773, highly similar to Galactokinase OS = Homo sapiens PE = 2 SV = 1 | 3.70E+07 | #DIV/0! | #NUM! |
| B4DT31 | cDNA FLJ53425, highly similar to Far upstream element-binding protein 1 OS = Homo sapiens PE = 2 SV = 1 | 3.30E+07 | #DIV/0! | #NUM! |
| B3KXM2 | Serine/threonine-protein phosphatase OS = Homo sapiens PE = 2 SV = 1 | | #DIV/0! | #DIV/0! |
| Q16651 | Prostasin OS = Homo sapiens GN = PRSS8 PE = 1 SV = 1 | 1.40E+07 | #DIV/0! | #NUM! |
| Q12904 | Aminoacyl tRNA synthase complex-interacting multifunctional protein 1 OS = Homo sapiens GN = AIMP1 | 5.90E+07 | #DIV/0! | #NUM! |
| P56381 | ATP synthase subunit epsilon, mitochondrial OS = Homo sapiens GN = ATP5E PE = 1 SV = 2 | 1.30E+08 | #DIV/0! | #NUM! |
| K7EQE8 | Derlin-2 (Fragment) OS = Homo sapiens GN = DERL2 PE = 1 SV = 1 | 1.70E+07 | #DIV/0! | #NUM! |
| O00161 | Synaptosomal-associated protein 23 OS = Homo sapiens GN = SNAP23 PE = 1 SV = 1 | 1.70E+07 | #DIV/0! | #NUM! |
| B0YIW6 | Archain 1, isoform CRA_a OS = Homo sapiens GN = ARCN1 PE = 1 SV = 1 | | #DIV/0! | #DIV/0! |
| Q8IWZ3 | Ankyrin repeat and KH domain-containing protein 1 OS = Homo sapiens GN = ANKHD1 PE = 1 SV = 1 | 1.40E+07 | #DIV/0! | #NUM! |
| B4DX78 | cDNA FLJ54484, highly similar to ATP-dependent RNA helicase DDX39 (EC 3.6.1.—) OS = Homo sapiens | 1.70E+07 | #DIV/0! | #NUM! |
| P51571 | Translocon-associated protein subunit delta OS = Homo sapiens GN = SSR4 PE = 1 SV = 1 | 1.10E+08 | #DIV/0! | #NUM! |
| Q5T655 | Cilia- and flagella-associated protein 58 OS = Homo sapiens GN = CFAP58 PE = 1 SV = 1 | 1.40E+06 | #DIV/0! | #NUM! |
| Q8NHY2 | E3 ubiquitin-protein ligase RFWD2 OS = Homo sapiens GN = RFWD2 PE = 1 SV = 3 | 5.60E+08 | #DIV/0! | #NUM! |
| Q15788 | Nuclear receptor coactivator 1 OS = Homo sapiens GN = NCOA1 PE = 1 SV = 3 | 1.90E+07 | #DIV/0! | #NUM! |
| P67812 | Signal peptidase complex catalytic subunit SEC11A OS = Homo sapiens GN = SEC11A PE = 1 SV = 1 | 4.80E+06 | #DIV/0! | #NUM! |
| P49792 | E3 SUMO-protein ligase RanBP2 OS = Homo sapiens GN = RANBP2 PE = 1 SV = 2 | | #DIV/0! | #DIV/0! |
| A0A0G2JPZ2 | Taste receptor type 2 OS = Homo sapiens GN = TAS2R42 PE = 3 SV = 1 | | #DIV/0! | #DIV/0! |
| P02746 | Complement C1q subcomponent subunit B OS = Homo sapiens GN = C1QB PE = 1 SV = 3 | 9.00E+06 | #DIV/0! | #NUM! |
| Q9HBA9 | Putative N-acetylated-alpha-linked acidic dipeptidase OS = Homo sapiens GN = FOLH1B PE = 2 SV = 1 | 1.40E+08 | #DIV/0! | #NUM! |
| P21817 | Ryanodine receptor 1 OS = Homo sapiens GN = RYR1 PE = 1 SV = 3 | 2.10E+08 | #DIV/0! | #NUM! |
| Q9Y3S1 | Serine/threonine-protein kinase WNK2 OS = Homo sapiens GN = WNK2 PE = 1 SV = 4 | 1.20E+08 | #DIV/0! | #NUM! |
| P46937 | Transcriptional coactivator YAP1 OS = Homo sapiens GN = YAP1 PE = 1 SV = 2 | | #DIV/0! | #DIV/0! |
| A0A0C4DGX5 | Ras-related protein Rab-25 OS = Homo sapiens GN = RAB25 PE = 1 SV = 1 | 5.70E+06 | #DIV/0! | #NUM! |
| Q0P5U8 | FLJ90650 protein OS = Homo sapiens GN = FLJ90650 PE = 1 SV = 1 | 3.60E+07 | #DIV/0! | #NUM! |
| Q7RTY8 | Transmembrane protease serine 7 OS = Homo sapiens GN = TMPRSS7 PE = 2 SV = 3 | 2.10E+08 | #DIV/0! | #NUM! |
| Q96DA0 | Zymogen granule protein 16 homolog B OS = Homo sapiens GN = ZG16B PE = 1 SV = 3 | 1.80E+05 | #DIV/0! | #NUM! |
| A0A087WXU | Extended synaptotagmin-2 OS = Homo sapiens GN = ESYT2 PE = 1 SV = 1 | 6.50E+07 | #DIV/0! | #NUM! |
| | | 1.40E+07 | #DIV/0! | #NUM! |

We claim:

1. A method of preparing an amniotic composition comprising cells from an amniotic membrane comprising:
   mincing the amniotic membrane in a cryopreservation solution;
   cryopreserving the minced amniotic membrane in the cryopreservation solution;
   homogenizing the frozen cryopreserved minced amniotic membrane and cryopreservation solution to form a tissue cell suspension solution;
   filtering the tissue cell suspension solution to remove large particles;
   centrifuging the filtered tissue cell suspension solution to produce a pellet and a supernatant, wherein the centrifuging at least partially separates the cells from the extracellular material and the cryopreservation solution; and
   resuspending the pellet in a cell resuspension solution to form the amniotic composition, wherein the concentration of viable cells in the amniotic composition is at least about 2.7 million cells per milliliter.

2. The method of claim 1, wherein the amniotic composition further comprises growth factors derived from the amniotic membrane.

3. The method of claim 1, wherein the amniotic composition is subjected to a second cryopreservation process, wherein the amniotic composition is stored at −18° C. for at least six months during which the viability of the cells in the amniotic composition remains substantially the same.

4. The method of claim 1, wherein the cryopreservation solution comprises about 8% DMSO and about 92% saline.

5. The method of claim 1, wherein cryopreservation comprises gradually freezing the minced amniotic membrane at a controlled rate until −80° C. is reached.

6. The method of claim 5, further comprising storing the cryopreserved minced amniotic membrane in liquid nitrogen.

7. The method of claim 1, wherein the amniotic composition is sterile.

8. The method of claim 1, wherein the filtering removes large particulates in the tissue cell suspension solution which are larger than about 200 µm.

9. The method of claim 1, wherein the cell solution comprises at least one of phosphate buffered saline and saline.

10. The method of claim 1, wherein the filtered cell suspension solution is centrifuged at a relative centrifugal force of about 235×g.

11. The method of claim 10, wherein the filtered cell suspension solution is centrifuged in a 50 mL conical tube.

12. The method of claim 1, wherein the amniotic composition solution is flowable through a needle of at least 22 gauge.

13. The method of claim 1, wherein the frozen minced amniotic membrane is homogenized in a Dounce.

14. A method of preparing an amniotic composition comprising cells from an amniotic membrane in a placenta comprising: receiving the placenta;
   isolating the amniotic membrane from the placenta;
   mincing the amniotic membrane in a cryopreservation solution;
   cryopreserving the minced amniotic membrane in the cryopreservation solution;
   homogenizing the frozen cryopreserved minced amniotic membrane and cryopreservation solution to form a tissue cell suspension solution;
   filtering the tissue cell suspension solution through a filter of having a pore size of about 200 µm;
   centrifuging the filtered tissue cell suspension solution at a relative centrifugal force of about 235×g to produce a pellet comprising the cells and a supernatant; and
   suspending the pellet in a cell suspension resuspension solution to form the amniotic composition, wherein the concentration of viable cells in the amniotic composition is at least 2.7 million cells per milliliter of the suspension solution.

15. The method of claim 14, wherein the frozen minced amniotic membrane is first homogenized in a 50 mL Dounce with a large clearance pestle followed by a small clearance pestle.

16. The method of claim 14, wherein the cryopreservation solution comprises approximately 8% DMSO and about 92% saline.

17. The method of claim 14, wherein cryopreservation comprises gradually freezing the minced amniotic membrane in a rate-controlled freezer initially at 4° C. until −80° C. is reached after at least 10 hours.

18. The method of claim 14, wherein the amniotic composition is stored at −18° C. for at least six months during which the viability of the cells in the cell solution remains substantially the same.

19. The method of claim 14, wherein the cell suspension solution comprises at least one of phosphate buffered saline and saline.

20. The method of claim 14, wherein the amniotic composition comprises growth factors derived from the amniotic membrane.

21. A method of treatment with an amniotic composition comprising cells from an amniotic membrane in a placenta comprising:
   delivering the amniotic composition comprising the cells to the wound site, wherein the cell solution is prepared by:
      mincing the amniotic membrane in a cryopreservation solution;
      cryopreserving the minced amniotic membrane in the cryopreservation solution;
      homogenizing the cryopreserved minced amniotic membrane and cryopreservation solution to form a cell suspension solution;
      filtering the cell suspension solution through a filter of having a pore size of about 200 um;
      centrifuging the filtered cell suspension solution at a relative centrifugal force of about 235×g to produce a pellet comprising the cells and a supernatant;
      resuspending the pellet in a resuspension solution to form the amniotic composition, wherein:
      the concentration of viable cells in the an amniotic composition is at least 2.7 million cells per milliliter of the suspension solution; and
      the amniotic composition comprises growth factors derived from the amniotic membrane.

* * * * *